US005625126A

United States Patent [19]
Lonberg et al.

[11] Patent Number: 5,625,126
[45] Date of Patent: Apr. 29, 1997

[54] TRANSGENIC NON-HUMAN ANIMALS FOR PRODUCING HETEROLOGOUS ANTIBODIES

[75] Inventors: Nils Lonberg, Redwood City; Robert M. Kay, San Francisco, both of Calif.

[73] Assignee: GenPharm International, Inc., Palo Alto, Calif.

[21] Appl. No.: 352,322

[22] Filed: Dec. 7, 1994

Related U.S. Application Data

[63] Continuation-in-part of Ser. No. 209,741, Mar. 9, 1994, which is a continuation-in-part of Ser. No. 165,699, Dec. 10, 1993, which is a continuation-in-part of Ser. No. 161,739, Dec. 3, 1993, which is a continuation-in-part of Ser. No. 155,301, Nov. 18, 1993, abandoned, which is a continuation-in-part of Ser. No. 96,762, Jul. 22, 1993, which is a continuation-in-part of Ser. No. 53,131, Apr. 26, 1993, which is a continuation-in-part of Ser. No. 990,860, Dec. 16, 1992, Pat. No. 5,545,806, which is a continuation-in-part of Ser. No. 904,068, Jun. 23, 1992, which is a continuation-in-part of Ser. No. 853,408, Mar. 18, 1992, which is a continuation-in-part of Ser. No. 834,539, Feb. 5, 1992, Pat. No. 5,633,425, which is a continuation-in-part of Ser. No. 810,279, Dec. 17, 1991, Pat. No. 5,569,825, which is a continuation-in-part of Ser. No. 575,962, Aug. 31, 1990, abandoned, which is a continuation-in-part of Ser. No. 574,748, Aug. 29, 1990, abandoned.

[51] Int. Cl.$^6$ .......................... C12N 15/00; C07H 21/02; C07H 21/04
[52] U.S. Cl. .......................... 800/2; 435/172.3; 536/23.1; 536/23.5; 536/23.53; 800/DIG. 1; 800/DIG. 4
[58] Field of Search .......................... 800/2; 435/172.3, 435/172.2; 536/23.1

[56] References Cited

U.S. PATENT DOCUMENTS

| | | | |
|---|---|---|---|
| 4,204,244 | 5/1980 | Fell et al. | |
| 5,175,384 | 12/1992 | Krimpenfort et al. | 800/2 |
| 5,434,340 | 7/1995 | Krimpenfort et al. | 800/2 |

FOREIGN PATENT DOCUMENTS

| | | |
|---|---|---|
| 0315062 | 5/1989 | European Pat. Off. |
| WO90/04036 | 4/1990 | WIPO |
| WO90/12878 | 11/1990 | WIPO |
| WO91/00906 | 1/1991 | WIPO |
| WO91/10741 | 7/1991 | WIPO |
| WO92/03918 | 3/1992 | WIPO |

OTHER PUBLICATIONS

Alt et al., Immunoglobulin genes in transgenic mice, TIG – Aug. 1985.
Berman et. al., Content and organization of the human Ig $V_H$ locus: definition of three new $V_H$ families and linkage to the Ig $C_H$ locus, The EMBO J. 7:727–738 (1988).
Berton et. al., Synthesis of germ–line γ1 immunoglobulin heavy–chain transcripts in resting B cells: Induction by interleukin 4 and inhibition by interferon γ, Proc. Natl. Acad. Sci. (U.S.A) 86:2829–2833 (1989).
Bollag et al., Homologous recombination in mammalian cells, Annu. Rev. Genet. 23:199–225 (1989).
Bruggemann et al., Human antibody production in transgenic mice: expression from 100 kb of the human IgH locus, Eur. J. Immunol. 21:1323–1326 (1991).
Bruggemann et al., A repertoire of monoclonal antibodies with human heavy chains from transgenic mice, Proc. Natl. Acad. Sci. USA 86:6709–6713 (1989).
Bucchini et al., Rearrangement of a chicken immunoglobulin gene occurs in the lymphoid lineage of transgenic mice, Nature 326:409–411 (1987).
Capecchi, The new mouse genetics: Altering the genome by gene targeting, TIG 5:70–76 (1989).
Capecchi, Altering the genome by homologous recombination, Science 244:1288–1292 (1989).
Coffman et. al., T cell activity that enhances polyclonal IgE production and its inhibition by interferon–γ, J. Immunol. 136:949–954 (1986).
Coffman et al., A mouse T cell product that preferentially enhances IgA production, J. Immunol. 139:3685–3690 (1987).
Doetschman et al., Targetted correction of a mutant HPRT gene in mouse embryonic stem cells, Nature 330:576–578 (1987).
Durdik et al., Isotype switching by a microinjected μ immunoglobulin heavy chain gene in transgenic mice, Proc. Natl. Acad. Sci. USA 86:2346–2350 (1989).
Esser and Radbruch, Rapid induction of transcription of unrearranged Sγ1 switch regions in activated murine B cells by interleukin 4, The EMBO J. 8:483–488 (1989).
Ferrier et al., Separate elements control DJ and VDJ rearrangement in a transgenic recombination substrate, The EMBO J. 9:117–125 (1990).
Forni, extensive splenic B cell activation in IgM–transgenic mice, Eur. J. Immunol. 20:983–989 (1990).
Gerstein et al., Isotype switching of an immunoglobulin heavy chain transgene occurs by dna recombination between different chromosomes, Cell 63:537–548 (1990).
Goodhardt et al., Rearrangement and expression of rabbit immunoglobulin κ light chain gene in transgenic mice, Proc. Natl. Acad. Sci. (U.S.A.) 84:4229–4233 (1987).
Gordon, Transgenic mice in immunology, The Mount Sinai Journal of Medicine 53:223–231 (1986).
Hagman et al., Inhibition of immunoglobulin gene rearrangement by the expression of a λ2 transgene, J. Exp. Med. 169:1911–1929 (1989).
Ichihard et al., Organization of human immunoglobulin heavy chain diversity gene loci, The EMBO J. 7:4141–4150 (1988).
Iglesias et al., Expression of immunoglobulin delta chain causes allelic exclusion in transgenic mice, Nature 330:482–484 (1987).

(List continued on next page.)

*Primary Examiner*—Suzanne E. Ziska
*Attorney, Agent, or Firm*—Townsend and Townsend and Crew LLP

[57] ABSTRACT

The invention relates to transgenic non-human animals capable of producing heterologous antibodies and methods for producing human sequence antibodies which bind to human antigens with substantial affinity.

5 Claims, 89 Drawing Sheets

OTHER PUBLICATIONS

James and Bell, Human monoclonal antibody production current status and future prospects, J. of Immunol. Methods 100:5–40 (1987).

Jasin and Berg, Homologous integration in mammalian cells without target gene selection, Genes & Development 2:1353–1363 (1988).

Kenny et al., Alternation of the B cell surface phenotype, immune response to phosphocholine and the B cell repertoire in M167 α plus κ transgenic mice, J. of Immunol. 142:4466–4474 (1989).

Jung et al., Shutdown of class switching recombination by deletion of a switch region control element, Science 259:984–987 (1993).

Kitamura et al., A B cell–deficient mouse by targeted disruption of the membrane exon of the immunoglobulin μ chain gene, Nature 350:423–426 (1991).

Koller and Smithies, Inactivating the $β_2$–microgobulin locus in mouse embryonic stem cells by homologous recombination, Proc. Natl. Acad. Sci. USA 86:8932–8935 (1989).

Lin et al., Recombination in mouse L cells between DNA introduced into cells and homologous chromosomal sequences, Proc. Natl. Acad. Sci. USA 82:1391–1395 (1985).

Linton et al., Primary antibody–forming cells secondary B cells are generated from separate precursor cell subpopulations, Cell 59:1049–1059 (1989).

Lo et al., Expression of mouse IgA by transgenic mice, pigs and sheep, Eur. J. Immunol. 21:1001–1006 (1991).

Lorenz et al., Physical map of the human immunoglobulin k locus and its implications for the mechanisms of $V_κ$–$J_κ$ rearrangement, Nucl. Acids Res. 15:9667–9676 (1987).

Lutzker and Alt, Structure and expression of germ line immunoglobulin γ2b transcripts, Mol. Cell Biol. 8:1849–1852 (1988).

Mansour et al., Disruption of the proto–oncogene int–2 in mouse embryo–derived stem cells: a general strategy for targeting mutations to non–selectable genes, Nature 336:348–352 (1988).

Mills et.al., Sequences of human immunoglobulin switch regions: implications for recombination and transcription, Nucl. Acids. Res. 18:7305–7316 (1991).

Mills et al., DNase I hypersensitive sites in the chromatin of human μ immunoglobulin heavy–chain genes, Nature 306:809–812 (1983).

Mowatt et. al., DNA sequence of the murine γ1 switch segment reveals novel structural elements, J.Immunol. 136:2674–2683 (1986).

Muller et al., Membrane–bound IgM Obstructs B cell development in transgenic mice, Eur. J. Immunol. 19:923–928 (1989).

Murray & Szostak, Construction of artificial chromosomes in yeast, Nature 305:189–193 (1983).

Neuberger et al., Isotype exclusion and transgene down–reglation in immunogloublin–λ transgenic mice, Nature 338:350–352 (1989).

Nikaido et al., Nucleotide sequences of switch regions of immunoglobulin C and C genes and their comparison, J. Biol. Chem. 257:7322–7329 (1982).

Nikaido et al., Switch region of immunoglobulin Cμ gene is composed of simple tandem repetitive sequences, Nature 292:845–848 (1981).

Nussenzweig et al., A human immunoglobulin gene reduces the incidence of lymphomas in c–Myc–bearing transgenic mice, Nature 336:446–450 (1988).

Nussenzweig et al., Allelic exclusion in transgenic mice carrying mutant human IgM genesJ. Exp. Med. 167:1969 (1988).

Oettinger et al., RAG–1 and RAG–2, adjacent genes that synergistically activate V(D)J recombination, Science 248:1517–1523 (1990).

Petters, transgenic mice in immunological research, Vet. Immunol. Imunopath. 17:267–278 (1987).

Rabbits et. al., Human immunoglobulin heavy chain genes: evolutionary comparisons of Cμ, Cδ and Cγ genes and associated switch sequences, Nucl. Acids Res. 9:4509–4524 (1981).

Rath et al., Quantitative analysis of idiotypic mimicry and allelic exclusion in mice with a μ Ig Transgene, J. of Immunol. 143:2074–2080 (1989).

Rath et al., B cell abnormalities induced by a μ ig transgene extend to L chain isotype usage, J. of Immunol. 146:2841 (1991).

Ravetch et al., Evolutionary approach to the question of immunoglobulin heavy chain switching: Evidence from cloned human and mouse genes, Proc. Natl. Acad. Sci. (U.S.A.) 77:6734–6738 (1980).

Reid et al., A single DNA response element can confer inducibility by both α– and γ–interferons, Proc. Natl. Acad. Sci. (U.S.A.) 86:840–844 (1989).

Ritchie et al., Allelic exclusion and control of endogenous immunoglobulin gene rearrangement in κ transgenic mice, Nature 312:517–520 (1984).

Rothman et al., Structure and expression of germline immunoglobulin γ3 heavy chain gene transcripts: implications for mitogen and lymphokine directed class–switching, Intl. Immunol. 2:621–627 (1990).

Rusconi et al., Transmission and expression of a specific pair of rearranged immunoglobulin μ and κ genes in a transgenic mouse line, Nature 314:330–334 (1985).

Sato et al., Physical linkage of a variable region segment and the joining region segment of the human immunoglobulin heavy chain locus, Biochem. Biophys. Res. Comm. 154:264–271 (1988).

Sevidy and Sharp, Positive genetic selection for gene disruption in mammalian cells by homologous recombination, Proc. Natl. Acad. Sci. USA 86:227–231 (1989).

Shimizu et al., Trans–splicing as a possible molecular mechanism for the multiple isotype expression of the immunoglobulin gene, J. Exp. Med. 173:1385–1393 (1991).

Shimizu et al., Immunoglobulin double–isotype expression by trans–mRNA in a human immunoglobulin transgenic mouse, Proc. Natl. Acad. Sci. USA 86:8020–8023 (1989).

Sideras et. al., Production of sterile transcripts of Cγ genes in an IgM–producing human neoplastic B cell line that switches to IgG–producing cells, Intl. Immunol. 1: 631–642 (1989).

Siebenlist et al., Human immunoglobulin D segments encoded in tandem multigenic families, Nature 294:631–635 (1981).

Smithies et al., Insertion of DNA sequences into the human chromosomal β–globulin locus by homologous recombination, Nature 317:230–234 (1985).

Snapper et. al., Interferon–γ and B cell stimulatory factor–1 reciprocally regulate Ig isotype production, Science 236:944–947 (1987).

Song et al., Accurate modification of a chromosomal plasmid by homologous recombination in human cells, Proc. Natl. Acad. Sci. USA 84:6820–6824 (1987).

Soriano et al., Targeted disruption of the c–src proto–oncogene leads to osteopetrosis in mice, Cell 64:693–702 (1991).

Stavnezer et al., Immunoglobulin heavy–chain switching may be directed by prior induction of transcripts from constant–region genes, Proc. Natl. Acad Sci. (U.S.A.) 85:7704–7708 (1988).

Storb, Immunoglobulin gene analysis in transgenic mice, in Immunoglobulin Genes, Academic Press Limited, pp. 303–326 (1989).

Storb et al., Expression, allelic exclusion and somatic mutation of mouse immunoglobulin kappa genes, Immunological Reviews 89:85–102 (1986).

Szurek et al., Complete nucleotide sequence of the murine γ3 switch region and analysis of switch recombination in two γ3–expressing hybridfomas, J. Immunol. 135:620–626 (1985).

Tahara et al., HLA antibody responses in HLA class I transgenic mice, Immunogenetics 32:351–360 (1990).

Taussig et al., Regulation of immunoglobulin gene rearrangement and expression, immunology today 10:143–146 (1989).

Thomas and Capecchi, Site–directed mutagenesis by gene targeting in mouse embryo–derived stem cells, Cell 51:503–512 (1987).

Thomas et al., High frequency targeting of genes to specific sites in the mammalian genome, Cell 44:419–428 (1986).

Uhlmann and Peyman, Antisense Oligonucleotides: A new therapeutic principle, Chemical Reviews 90:544–584 (1990).

Weaver et al., A transgenic immunoglobulin Mu gene prevents rearragement of endogenous genes, Cell 42:117–127 (1985).

Yamamura et al., Cell–type–specific and regulated expression of a human λ1 heavy–chain immunoglobulin gene in transgenic mice, Proc. Natl. Acad. Sci. USA 83:2152–2156 (1986).

Yancopoulos and Alt, Regulation of the assembly and expression of variable–region genes, Ann. Rev. Immunol. 4:339–368 (1986).

Yancopoulos and Alt, Developmentally controlled and tissue–specific expression of unrearranged $V_H$ gene segments, Cell 40:271–281 (1985).

Yasui et al., Class switch from μ to δ is mediated by homologous recombination between $\sigma_\mu$ and $\epsilon_\mu$ sequences in human immunoglobulin gene loci, Eur. J. Immunol. 19:1399–1403 (1989).

Zijlstra et al., Germ–line transmission of a disrupted $\beta_2$–microglobulin gene produced by homologous recombination in embryonic stem cells, Nature 342:435–438 (1989).

Zimmer and Gruss, Production of chimaeric mice containing embryonic stem (ES) cells carrying a homoeobox Hox 1.1 allele mutated by homologous recombination, Nature 338:150–153 (1989).

Buttin, Exogenous Ig gene rearrangement in transgenic mice: a new strategy for human monoclonal antibody production? TIG – vol. 3, No. 8 (Aug. 1987).

Green et al., Antigen–specific human monoclonal antibodies from mice engineered with human Ig heavy and light chain YACs, Nature Genetics 7:13–21 (1994).

Hofker et al., Complete physical map of the human immunoglobulin heavy chain constant region gene complex, Proc. Natl. Acad. Sci. USA 86:5567–5571 (1989).

Humphries et al., A new human immunoglobulin $V_H$ family prefernetially rearranged in immature B–cell tumours, Nature 331:446–449 (1988).

Jaenisch, Transgenic Animals, Science 240:1468–1474 (1988).

Jakobovits et al., Analysis of homozygous mutant chimeric mice: Deletion of the immunoglobulin heavy–chain joining region blocks B–cell development and antibody production, Proc. Natl. Acad. Sci. USA 90:2551–2555 (1993).

Lonberg et al., Antigen–specific human antibodies from mice comprising four distinct genetic modifications, Nature 368:856–859 (1994).

Miller et al., Structural alterations in J regions of mouse immunoglobulin λ genes are associated with differential gene expression, Nature 295:428–430 (1982).

Morrison, Success in specification, Nature 368:812–813 (1994).

Pettersson et al., A second B cell–specific enhancer 3' of the immunoglobulin heavy–chain locus, Nature 344:165–168 (1990).

Scangos and Bieberich, Gene transfer into mice, Advances in Genetics 24: 285–322 (1987).

Stites et al., *Basic & Clinical Immunology*, p. 50 (1984).

Tanaka et al., An antisense oligonucleotide complementary to a sequence in Iγ2b Increase γ2b germline transcrips, stimulates B cell DNA synthesis, and inhibits immunoglobulin secretion, The Journal of Experimental Medicine 175:597–607 (1992).

Taki et al., Targeted insertion of a variable region gene into the immunoglobulin heavy chain locus, Science 262:1268–1271 (1993).

Taylor et al., Human immunoglobulin transgenes undergo rearrangement, somatic mutation and class switching in mice that lack endogenous IgM, International Immunology 6:579–591 (1994).

Vlasov et al., Arrest of immunoglobulin G mRNA translation in vitro with an alkylating antisense oligonucleotide derivative, Chemical Abstracts, p. 28, 112:229433X (1990).

Weiss, Mice making human–like antibodies, The Washington Post, Apr. 28, 1994.

M. Neuberger (1996) *Nature Biotechnology* 14:826. Generating high–avidity human Mabs in mice.

D. Fishwild et al. (1996) *Nature Biotechnology* 14:845. High–avidity human IgGκ monoclonal antibodies from a novel strain of minilocus transgenic mice.

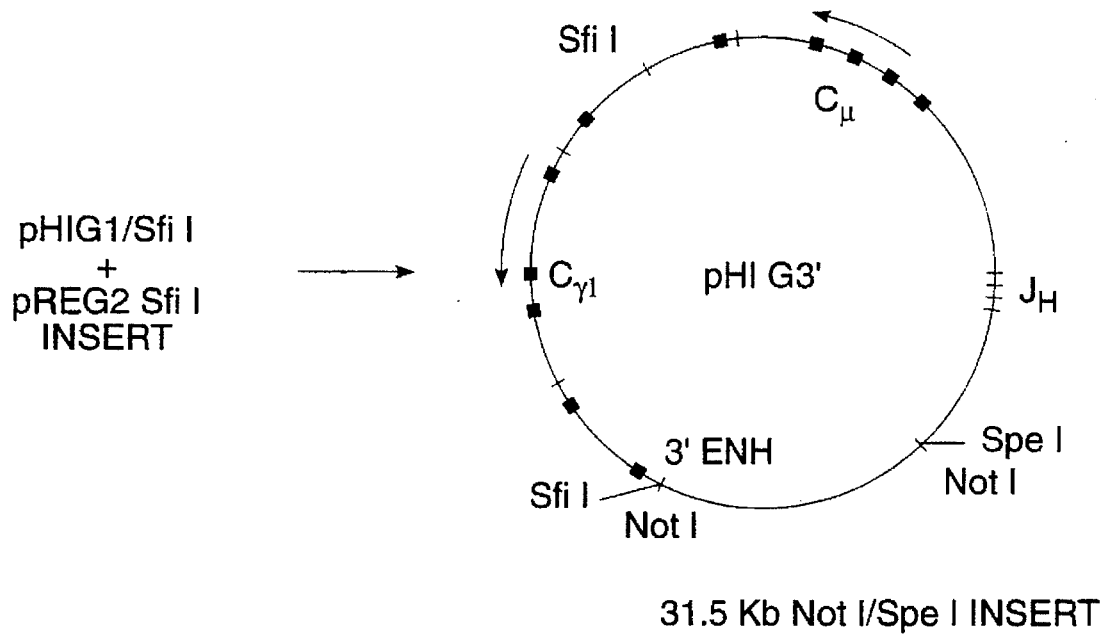
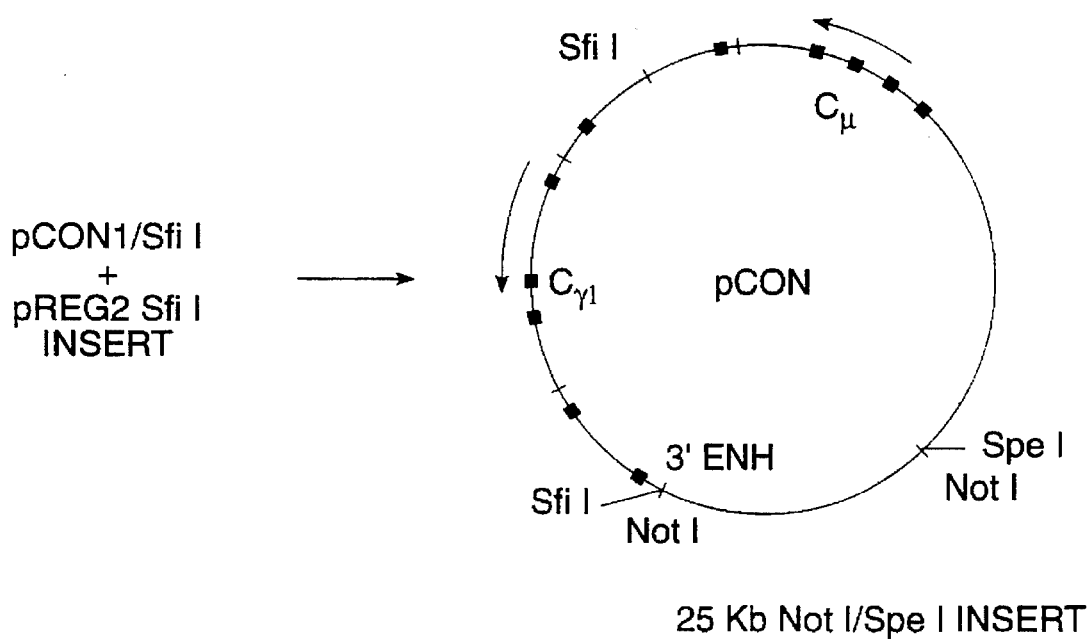
FIG. 12

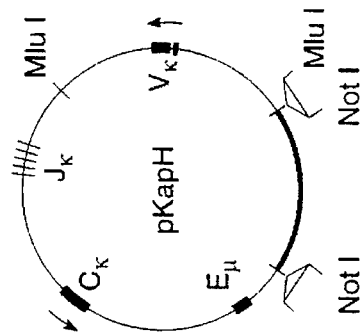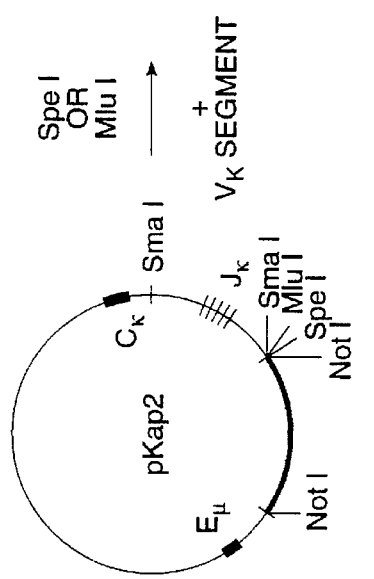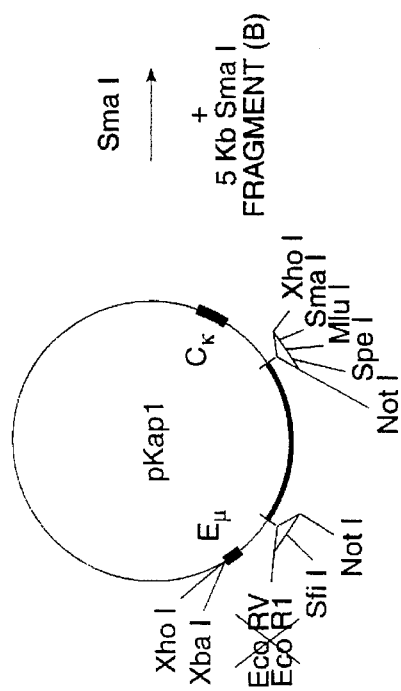
FIG. 17

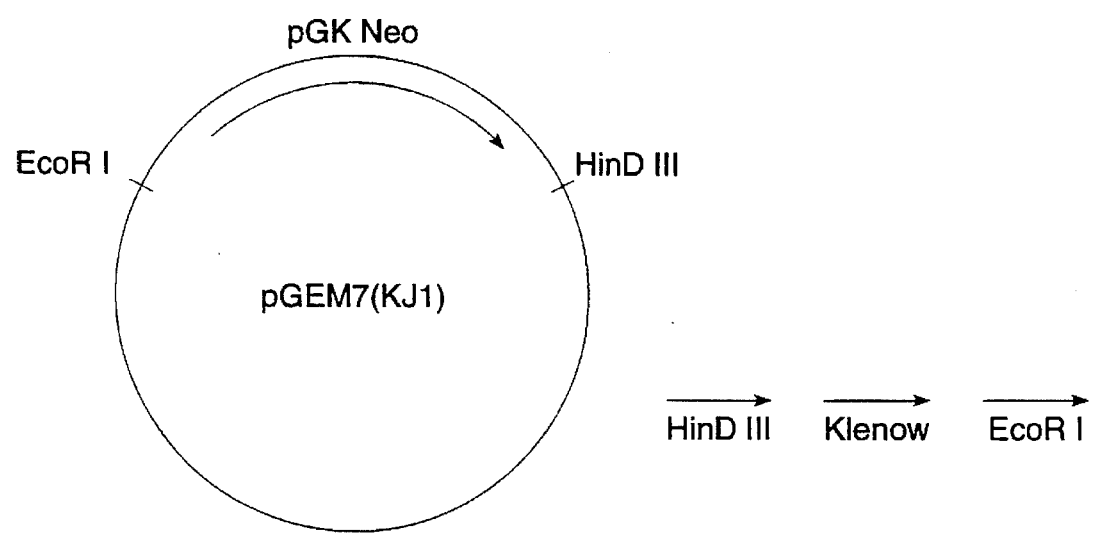
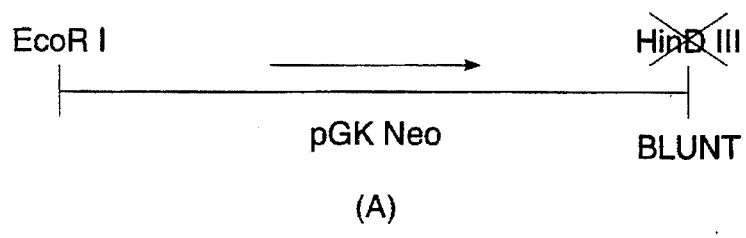
(A)
*FIG. 18B*

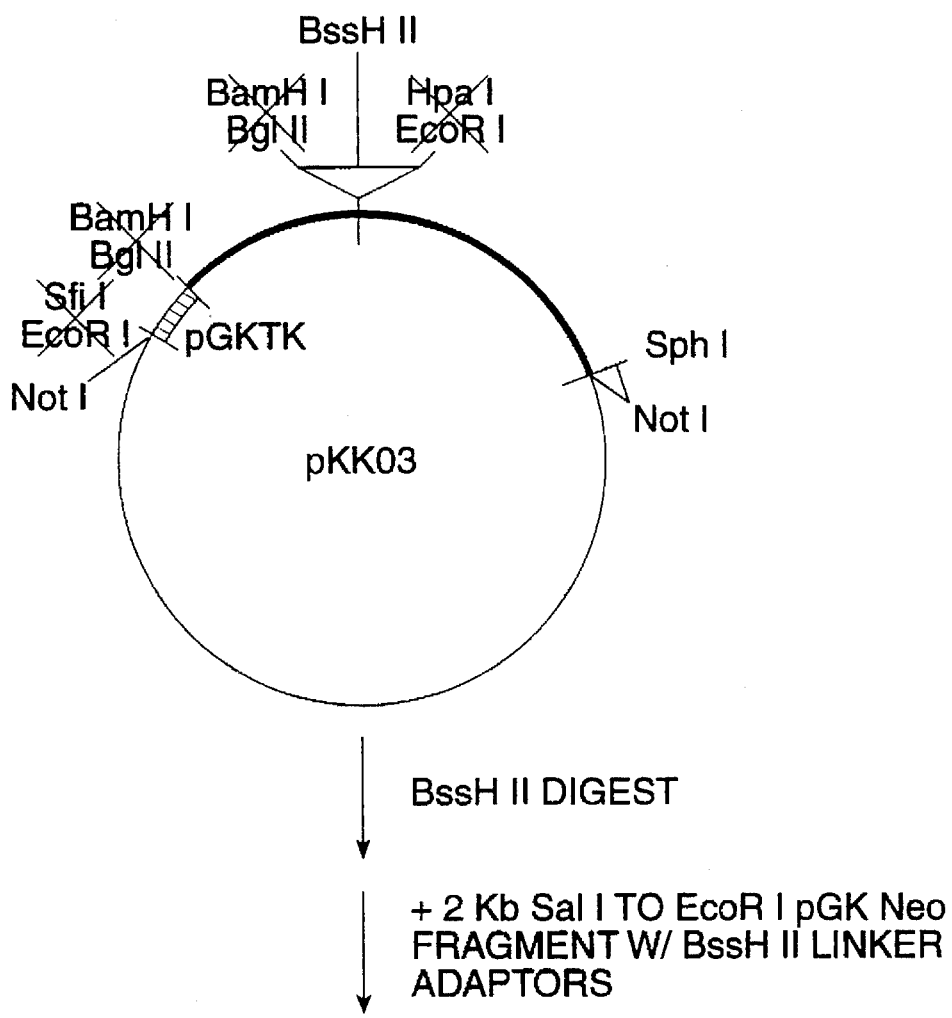
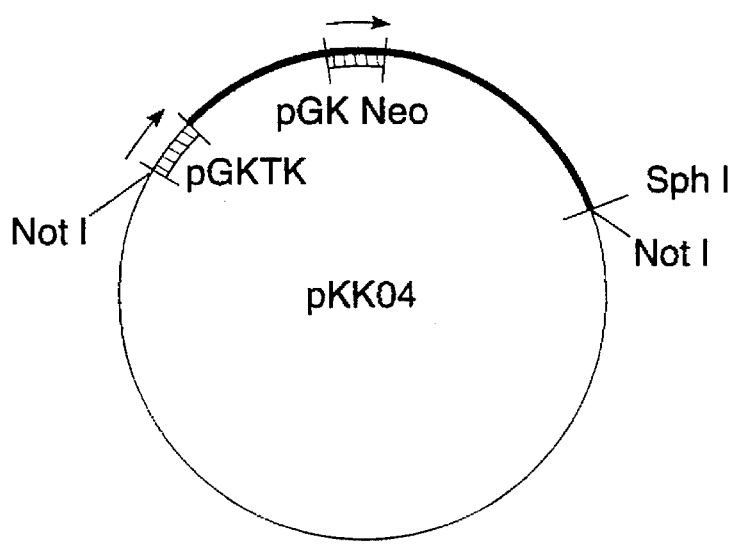
FIG. 19C

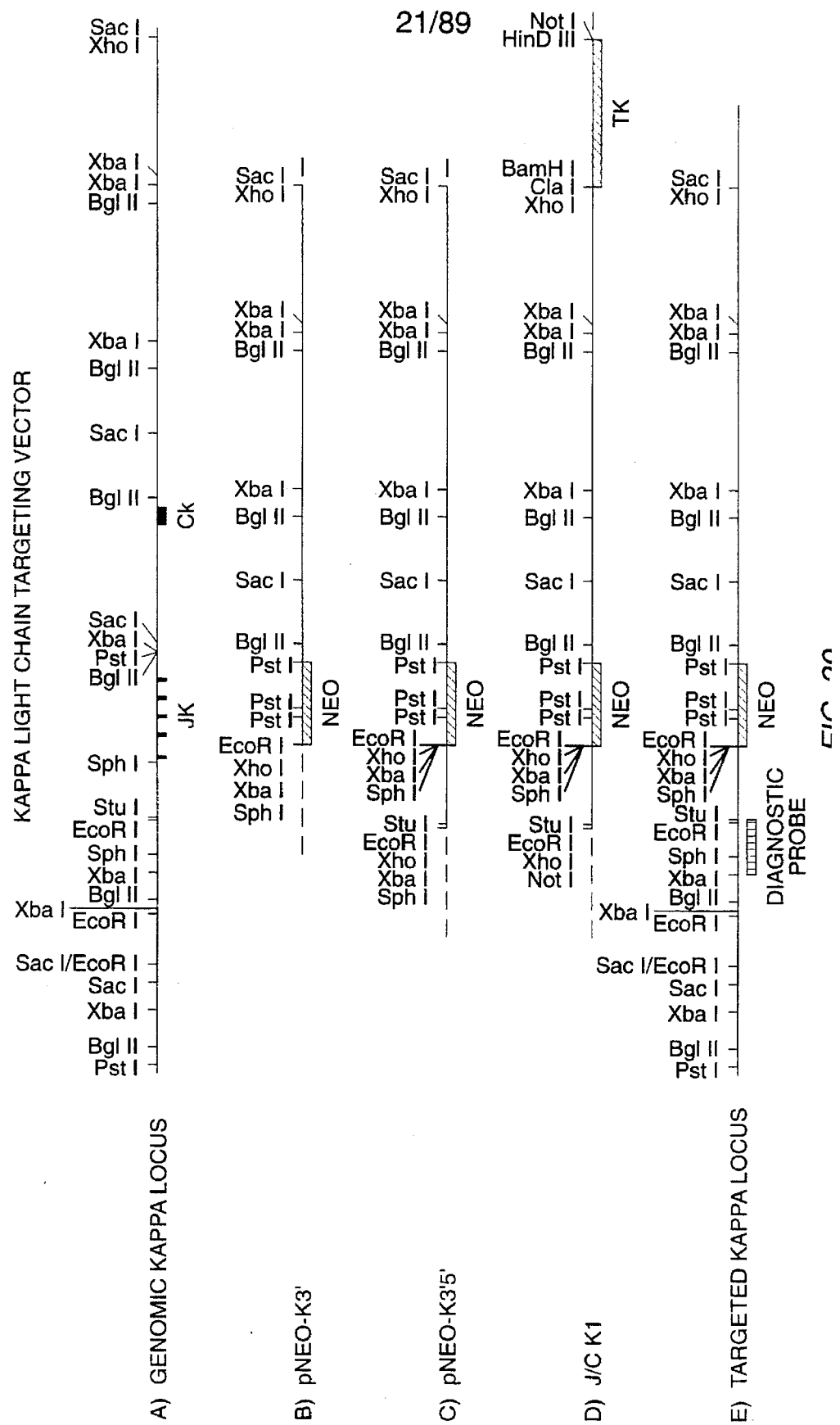

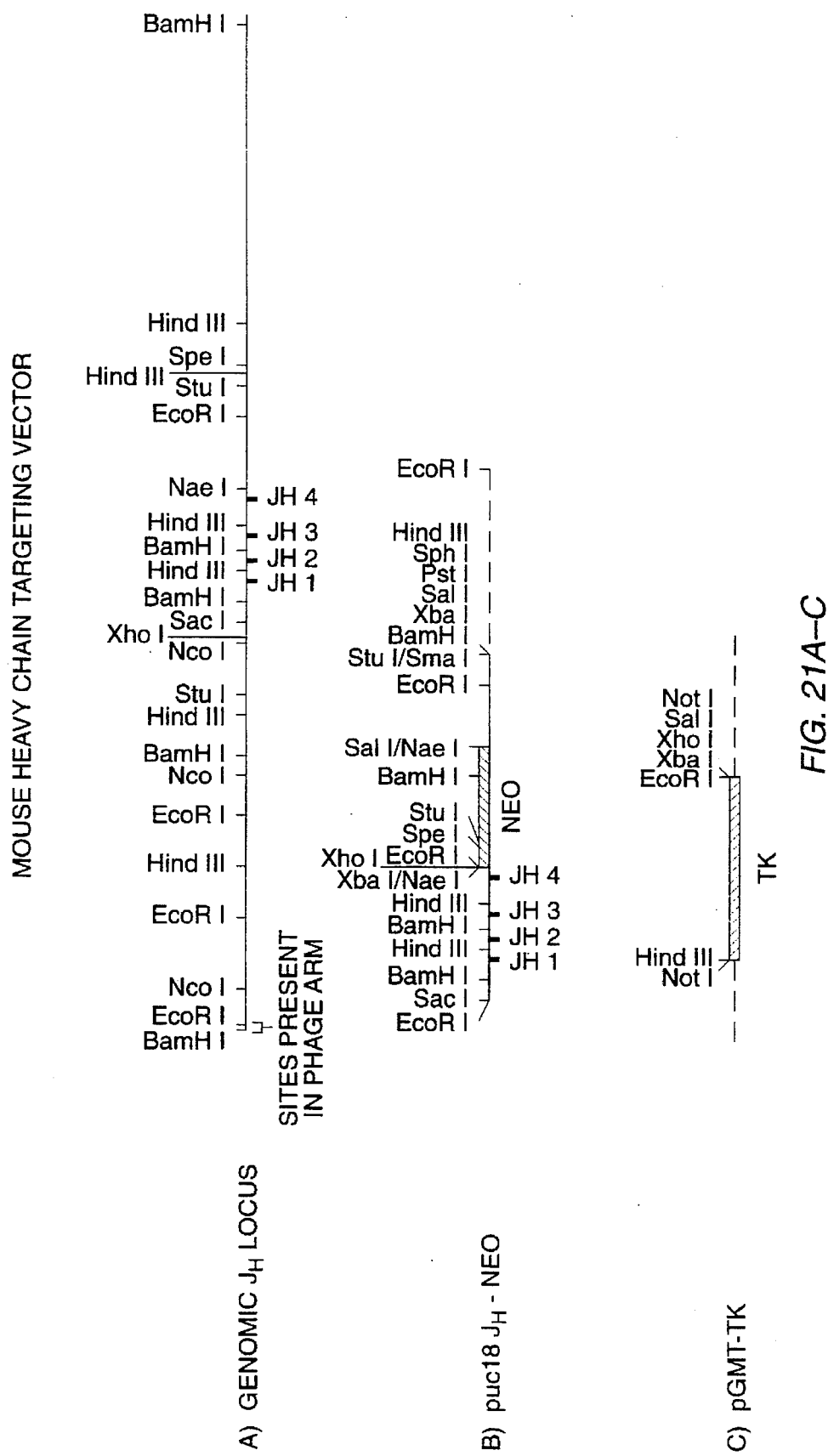
FIG. 21A-C

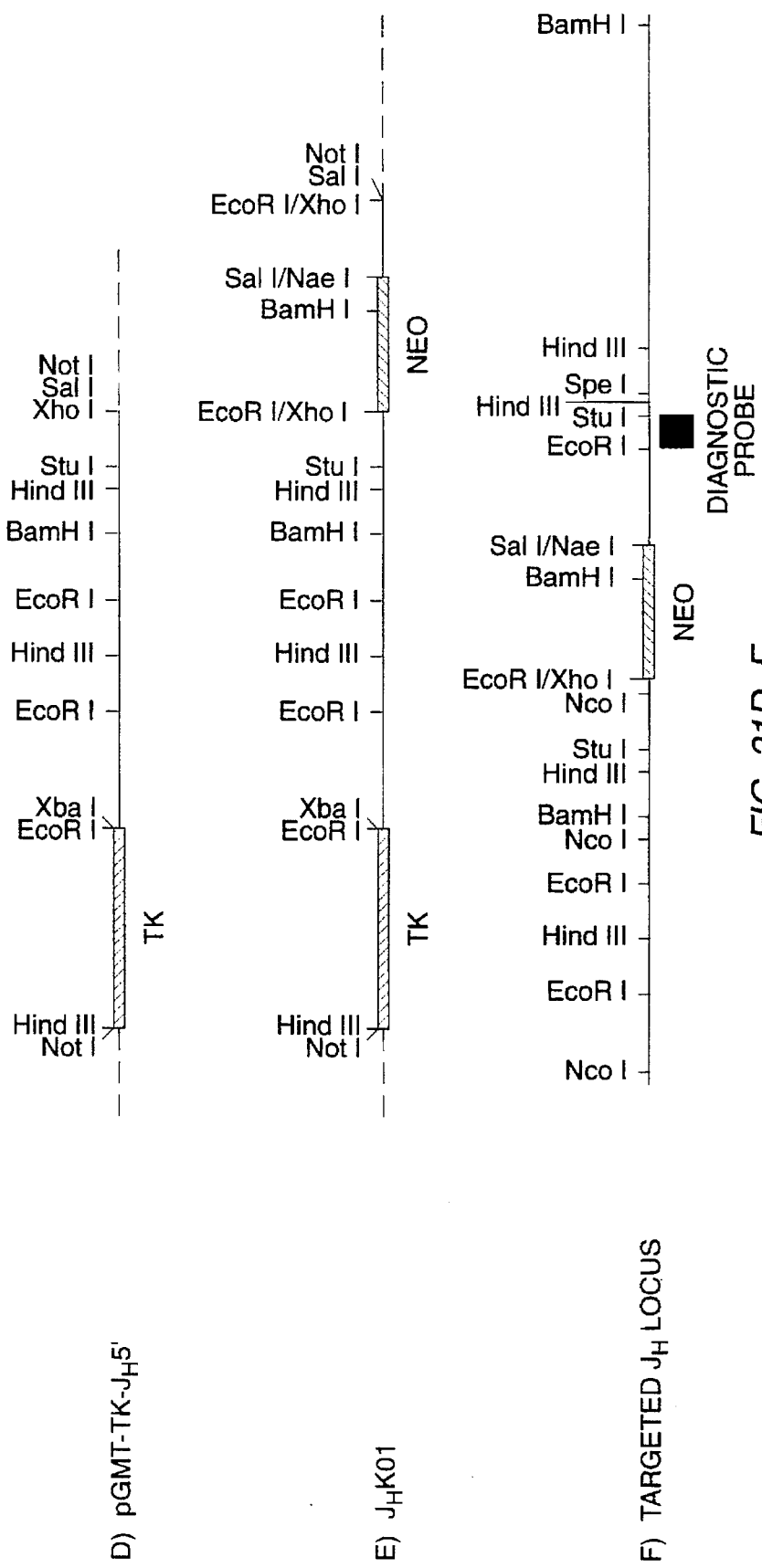
FIG. 21D-F

SYNTHETIC HEAVY CHAIN VARIABLE REGION

FIG. 40

```
TTTTCTGGCC  TGACAACCAG  GGTGGCGCAG  GATGCTCAGT  GCAGAGAGGA       50

AGAAGCAGGT  GGTCTCTGCA  GCTGGAAGCT  CAGCTCCCAC  CCAGCTGCTT      100

TGCATGTCCC  TCCCAGCTGC  CCTACCTTCC  AGAGCCATA TCAAT GCCTG       150

TGTCAGAGCC  CTGGGGAGGA  ACTGCTCAGT  TAGGACCCAG  AGGGAACCAT      200
                                                          Me
GGAAGCCCCA  GCTCAGCTTC  TCTTCCTCCT  GCTACTCTGG  CTCCCAGgtg      250
tGluAlaPro  AlaGlnLeuL  euPheLeuLe  uLeuLeuTrp  LeuPro
aggggggaacc  atgaggtggt  tttgcacatt  agtgaaaact  cttgccacct     300
ctgctcagca  agaaatataa  ttaaaattca  aagtatatca  acaattttgg      350
ctctactcaa  agacagttgg  tttgatcttg  attacatgag  tgcatttctg      400
ttttatttcc  aatttcagAT  ACCACCGGAG  AAATTGTGTT  GACACAGTCT      450
            Asp  ThrThrGlyG  luIleValLe  uThrGlnSer
CCAGCCACCC  TGTCTTTGTC  TCCAGGGGAA  AGAGCCACCC  TCTCCTGCAG      500
ProAlaThrL  euSerLeuSe  rProGlyGlu  ArgAlaThrL  euSerCysAr
GGCCAGTCAG  AGTGTTAGCA  GCTACTTAGC  CTGGTACCAA  CAGAAACCTG      550
gAlaSerGln  SerValSerS  erTyrLeuAl  aTrpTyrGln  GlnLysProG
GCCAGGCTCC  CAGGCTCCTC  ATCTATGATG  CATCCAACAG  GGCCACTGGC      600
lyGlnAlaPr  oArgLeuLeu  IleTyrAspA  laSerAsnAr  gAlaThrGly
ATCCCAGCCA  GGTTCAGTGG  CAGTGGGTCT  GGGACAGACT  TCACTCTCAC      650
IleProAlaA  rgPheSerGl  ySerGlySer  GlyThrAspP  heThrLeuTh
CATCAGCAGC  CTAGAGCCTG  AAGATTTTGC  AGTTTATTAC  TGTCAGCAGC      700
rIleSerSer  LeuGluProG  luAspPheAl  aValTyrTyr  CysGlnGlnA
GTAGCAACTG  GCCTCCCACA  GTGATTCCAC  ATGAAACAAA  AACCCCAACA      750
rgSerAsnTr  pPro
AGACCATCAG  TGTTTACTAG  ATTATTATAC  CAGCTGCTTC  CTTTACAGAC      800

AGCTAGTGGG  GT                                                  812
```

*FIG. 41*

```
AGGGCGGCGC AGATGCTCAG TGCAGAGAGA AGAAACAGGT GGTCTCTGCA    50

GCTGGAAGCT CAGCTCCCAC CCCAGCTGCT TTGCATGTCC CTCCCAGCTG   100

CCCTACCTTC CAGAGCCAT ATCAATGCCT GGGTCAGAGC TCTGGGGAGG    150

AACTGCTCAG TTAGGACCCA GACGGAACCA TGGAAGCCCC AGCGCAGCTT   200
                                 M etGluAlaPr oAlaGlnLeu
CTCTTCCTCC TGCTACTCTG GCTCACAGgt gaggggaata tgaggtgtct   250
LeuPheLeuL euLeuLeuTr pLeuThr
ttgcacatca gtgaaaactc ctgccacctc tgctcagcaa gaaatataat   300
taaaattcaa aatagatcaa caattttggc tctactcaaa gacagtgggt   350
ttgattttga ttacatgagt gcatttctgt tttatttcca atttcagATA   400
                                                  AspT
CCACCGGAGA AATTGTGTTG ACACAGTCTC CAGCCACCCT GTCTTTGTCT   450
hrThrGlyGl uIleValLeu ThrGlnSerP roAlaThrLe uSerLeuSer
CCAGGGGAAA GAGCCACCCT CTCCTGCAGG GCCAGTCAGG GTGTTAGCAG   500
ProGlyGluA rgAlaThrLe uSerCysArg AlaSerGlnG lyValSerSe
CTACTTAGCC TGGTACCAGC AGAAACCTGG CCAGGCTCCC AGGCTCCTCA   550
rTyrLeuAla TrpTyrGlnG lnLysProGl yGlnAlaPro ArgLeuLeuI
TCTATGATGC ATCCAACAGG GCCACTGGCA TCCCAGCCAG GTTCAGTGGC   600
leTyrAspAl aSerAsnArg AlaThrGlyI leProAlaAr gPheSerGly
AGTGGGCCTG GGACAGACTT CACTCTCACC ATCAGCAGCC TAGAGCCTGA   650
SerGlyProG lyThrAspPh eThrLeuThr IleSerSerL euGluProGl
AGATTTTGCA GTTTATTACT GTCAGCAGCG TAGCAACTGG CATCCCACAG   700
uAspPheAla ValTyrTyrC ysGlnGlnAr gSerAsnTrp His
TGATTCCACA TGAAACAAAA ACCCCAACAA GACCATCAGT GTTTACTAGA   750

TTATTATACC AGCTGCTTCC TTTACAGACA GCTAGTGGGG TGGCCACTCA   800

GTGTTAGCAT CTCAGCTCTA TTTGGCCATT TTGGAGTTCA AGTTGTCAAG   850

TCCAAAATTA CTTATGTTAG TCCATTGCAT CATACCATTT CAGTGTGGCT   900
```

*FIG. 42*

```
CCGCCCCAGC TGCTTTGCAT GTCCCTCCCA GCCGCCCTGC AGTCCAGAGC    50

CCATATCAAT GCCTGGGTCA GAGCTCTGGA GAAGAGCTGC TCAGTTAGGA   100

ACCCCAGAGG GAACCATGGA AACCCCAGCG CAGCTTCTCT TCCTCCTGCT   150
                MetGl uThrProAla GlnLeuLeuP heLeuLeuLe
ACTCTGGCTC CCAGgtgagg ggaacatggg atggttttgc atgtcagtga   200
uLeuTrpLeu Pro
aaaccctctc aagtcctgtt acctggcaac tctgctcagt caatacaata   250
attaaagctc aatataaagc aataattctg gctcttctgg gaagacaatg   300
ggtttgattt agattacatg ggtgactttt ctgttttatt tccaatctca   350
gATACCACCG GAGAAATTGT GTTGACGCAG TCTCCAGGCA CCCTGTCTTT   400
AspThrThrG lyGluIleVa lLeuThrGln SerProGlyT hrLeuSerLe
GTCTCCAGGG GAAAGAGCCA CCCTCTCCTG CAGGGCCAGT CAGAGTGTTA   450
uSerProGly GluArgAlaT hrLeuSerCy sArgAlaSer GlnSerValS
GCAGCAGCTA CTTAGCCTGG TACCAGCAGA AACCTGGCCA GGCTCCCAGG   500
erSerSerTy rLeuAlaTrp TyrGlnGlnL ysProGlyGl nAlaProArg
CTCCTCATCT ATGGTGCATC CAGCAGGGCC ACTGGCATCC CAGACAGGTT   550
LeuLeuIleT yrGlyAlaSe rSerArgAla ThrGlyIleP roAspArgPh
CAGTGGCAGT GGGTCTGGGA CAGACTTCAC TCTCACCATC AGCAGACTGG   600
eSerGlySer GlySerGlyT hrAspPheTh rLeuThrIle SerArgLeuG
AGCCTGAAGA TTTTGCAGTG TATTACTGTC AGCAGTATGG TAGCTCACCT   650
luProGluAs pPheAlaVal TyrTyrCysG lnGlnTyrGl ySerSerPro
CCCACAGTGA TTCAGCTTGA ACAAAAACC TCTGCAAGAC CTTCATTGTT   700

TACTAGATTA TACCAGCTGC TTCCTTTACA GATAGCTGCT GCAATGACAA   750

CTCAATTTAG CATCTCTCTC TGCTTGGGCA TTTTGGGGAT CTTAAAAAAG   800

TAATCCCTTG ATATATTTTT GACTCTGATT CCTGCATTTT TCCTCAGACC   850

AAGATGGACA GCCAGGTTTA AGCACAGTTT CACAGTAATG GCCACTGGAT   900
```

FIG. 43

```
AAACACATTC TCTGCAGACA AATTTGAGCT ACCTTGATCT TACCTGGACA    50

GGTGGGGACA CTGAGCTGGT GCTGAGTTAC TCAGATGCGC CAGCTCTGCA   100

GCTGTGCCCA GCCTGCCCCA TCCCCTGCTC ATTTGCATGT TCCCAGAGCA   150

CAACCTCCTG CCCTGAAGCC TTATTAATAG GCTGGTCAGA CTTTGTGCAG   200

GAATCAGACC CAGTCAGGAC ACAGCATGGA CATGAGGGTC CTCGCTCAGC   250
                                 MetAs pMetArgVal LeuAlaGlnL
TCCTGGGGCT CCTGCTGCTC TGTTTCCCAG gtaaggatgg agaacactag   300
euLeuGlyLe uLeuLeuLeu CysPhePro
cagtttactc agcccagggt gctcagtact gctttactat tcagggaaat   350
tctcttacaa catgattaat tgtgtggaca tttgttttta tgtttccaat   400
ctcagGTGCC AGATGTGACA TCCAGATGAC CCAGTCTCCA TCCTCACTGT   450
      GlyAla ArgCysAspI leGlnMetTh rGlnSerPro SerSerLeuS
CTGCATCTGT AGGAGACAGA GTCACCATCA CTTGTCGGGC GAGTCAGGGT   500
erAlaSerVa lGlyAspArg ValThrIleT hrCysArgAl aSerGlnGly
ATTAGCAGCT GGTTAGCCTG GTATCAGCAG AAACCAGAGA AAGCCCCTAA   550
IleSerSerT rpLeuAlaTr pTyrGlnGln LysProGluL ysAlaProLy
GTCCCTGATC TATGCTGCAT CCAGTTTGCA AAGTGGGGTC CCATCAAGGT   600
sSerLeuIle TyrAlaAlaS erSerLeuGl nSerGlyVal ProSerArgP
TCAGCGGCAG TGGATCTGGG ACAGATTTCA CTCTCACCAT CAGCAGCCTG   650
heSerGlySe rGlySerGly ThrAspPheT hrLeuThrIl eSerSerLeu
CAGCCTGAAG ATTTTGCAAC TTATTACTGC AACAGTATA ATAGTTACCC    700
GlnProGluA spPheAlaTh rTyrTyrCys GlnGlnTyrA snSerTyrPr
ACCCACAGTG TTACACACCC AAACATAAAC CCCCAGGGAA GCAGATGTGT   750
o
GAGGCTGGGC TGCCCCAGCT GCTTCTCCTG ATGCCTCCAT CAGCTGAGAG   800

TGTTCCTCAG ATGCAGCCAC ACTCTGATGG TGTTGGTAGA TGGGGAC      847
```

*FIG. 44*

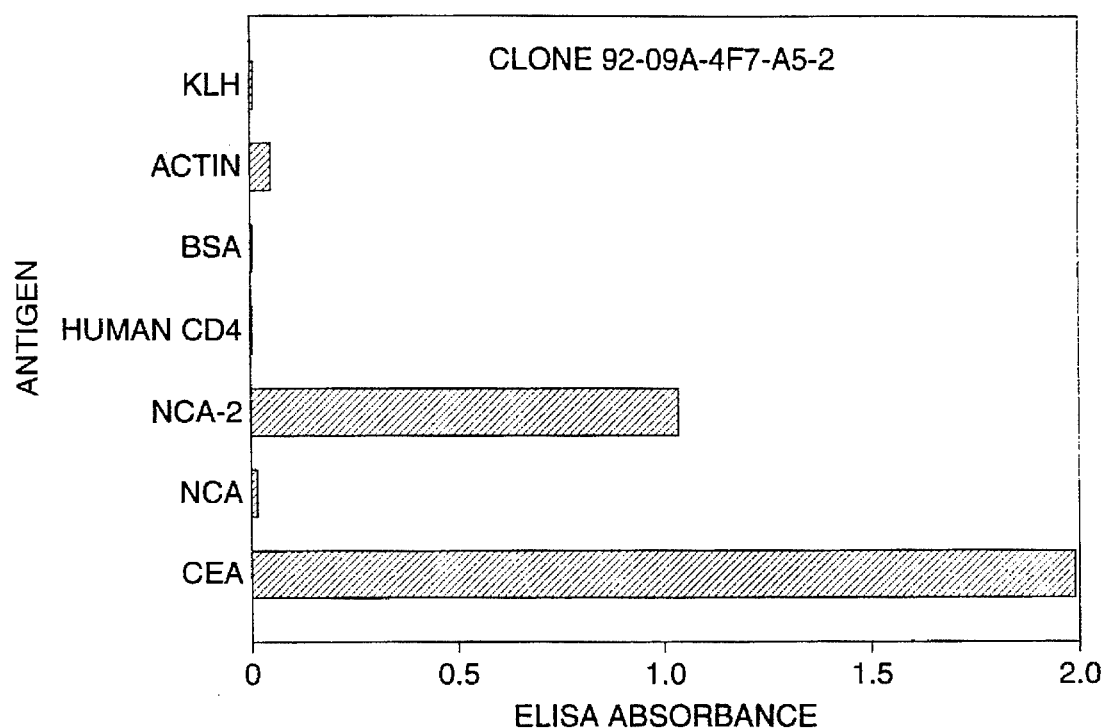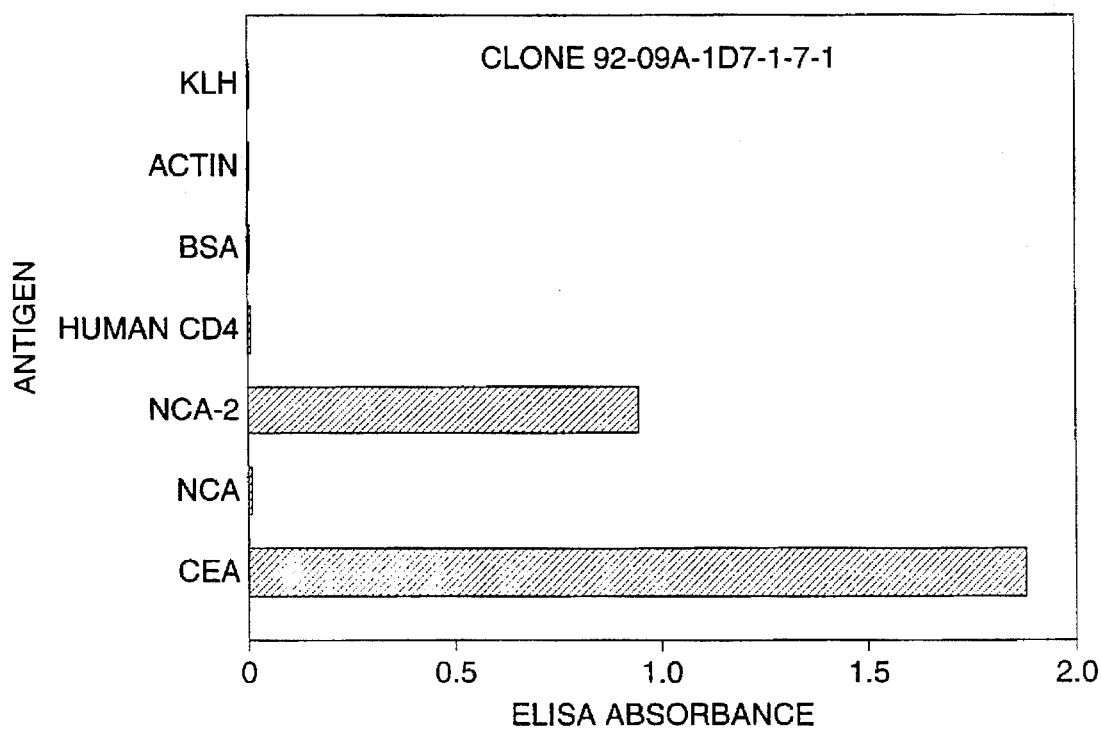
FIG. 46

|     |         |    | VH251 | HUMAN<br>n D n | J | MOUSE<br>Cγ |
|-----|---------|----|-------|----------------|---|-------------|
| 5   | DXP'1 J6 | G1 | GCCTCGGACACCGCCATGTATTACTGTGtGAGA | cattTATGGTTCGGGGAGTTAcg | CGGTgTGgACGTCTGGGGCCAAGGGACCACGGTCACCGTCTCCTCAG | CCAAAACGACACCCCCATCTGTCTATCCACT |
| 7   | DHQ52 J3 | G1 | GCCTCGGACACCGCCATGTATTACTGTGTGAGA | cACTGGGcattggat | GCTCTTGATgtCTGGGGCCAAGgGACCACGGTCACCGTCTTCTTCAG | CCAAAACGACACCCCCATCAGTCTATCCACT |
| 2   | DHQ52 J3 | G2b | GCCTCGGACACCGCCATGTATTACTGTGCGAGA | ACTGGGATgat | GCTTTTGATATCTGGGCCAAGGGACAATGGTCACCGTCTCTTCAG | CCAAAACACACCCCCATCAGTCTATCCACT |
| 3   | D? J3 | G2b | GaCTCGGACACCGCCATGTATTACTGTGCGAGA | caggggagagat | GCTTTAGATATCTGGGCCAAGGGACAATGGTCACCGTCTCTTCAG | CCAAAACAACACCCCCATCAGTCTATCCACT |
| 4   | DXP'1 J4 | G2b | GCCTCGGACACCGCCATGTATTAtTGTGtGAGA | catagggACTATatTTCGgGGAGTTATTttcc | TGACTACTGGGGCCAGGGAACCCTGGTCACCGTCTCCTCAG | CCAAAACAACACCCCCATCAGTCTATCCACT |
| 10  | DHQ52 J3 | G2b | GCCTCGGACACCGCCATGTATTACTGTGCGAGA | ACTGGgAtgat | GCTTTTGATATCTGGGCCAAGGGACCACGGTCACCGTCTCTTCAG | CCAAAACAACACCCCCATCAGTCTATCCACT |
| 1   | D? J3 | G3 | GCCTCGGACACCGCCATGTATTACTGTGCGAGA | catgggtctatg | GATATCTGGGCCAAGGACAATGGTCACCGTCTCTTCAG | CTACAACAAGCCCATCTGTCTATCCCTT |
| 6   | DHQ52 J4 | G3 | GCCTCGGACACCGCCATGTATTACTGTGCGAGA | gagggcgtcACTGGGGAtcg | TTTGACTAcTGGGGCCAGGGACCCTGGTCACCGTCTCCTCAG | CTACAACAAGCCCATCTGTCTATCCCTT |
| 8   | DIR2 J3 | G3 | GCCTCGGACACCGCCATGTATTACTGTGCGAGA | agggACcCCctgat | GCTTTTGATATCTGGGCCAAGGGACAATGGTCACCGTCTCTTCAG | CTACAACAGCCCATCTGTCTATCCCTT |
| 9   | DIR2r J6 | G3 | GCCTCGGACACCGCCATGTATTACTGTGCGAGA | cgtGGGCCT | TACTACTACTACGGTATGGACGTCTGGGGCCAAGGGACCACGGTCACCGTCTCCTCAG | CTACAACAGCCCATCTGTCTATCCCTT |

*FIG. 47*

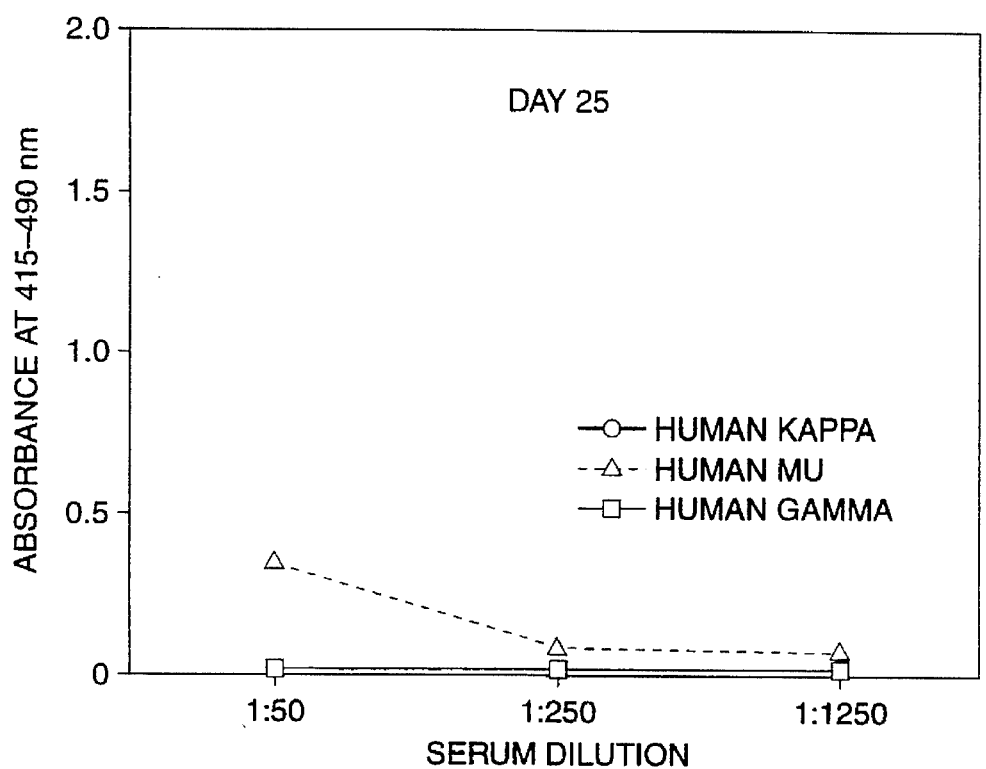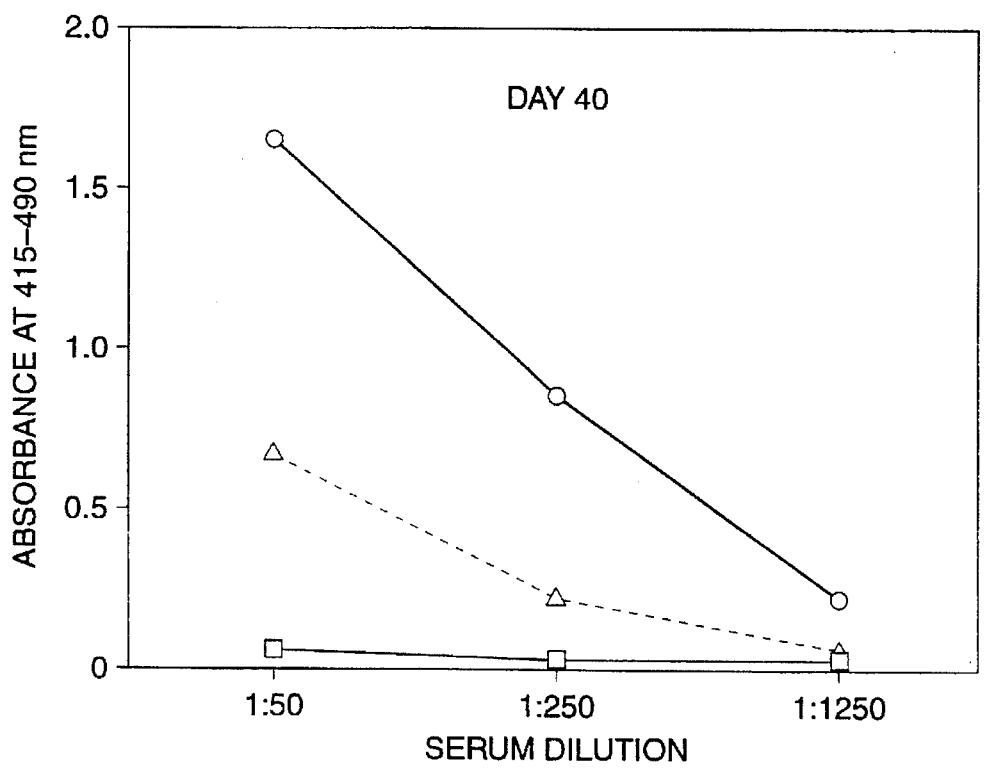
FIG. 48

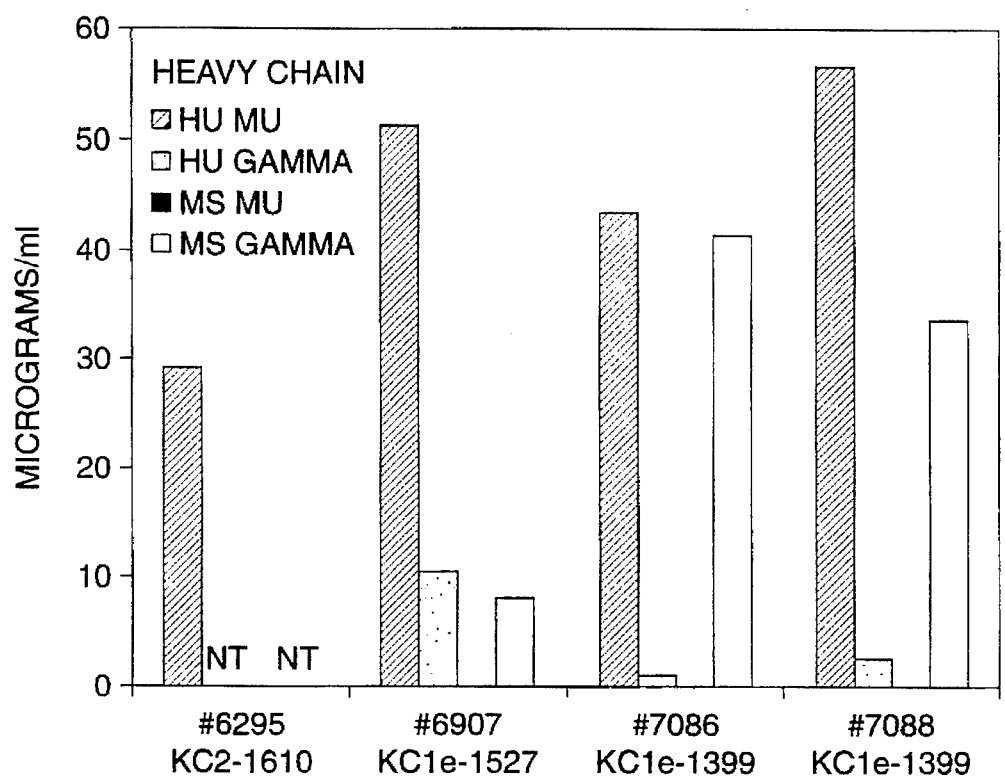
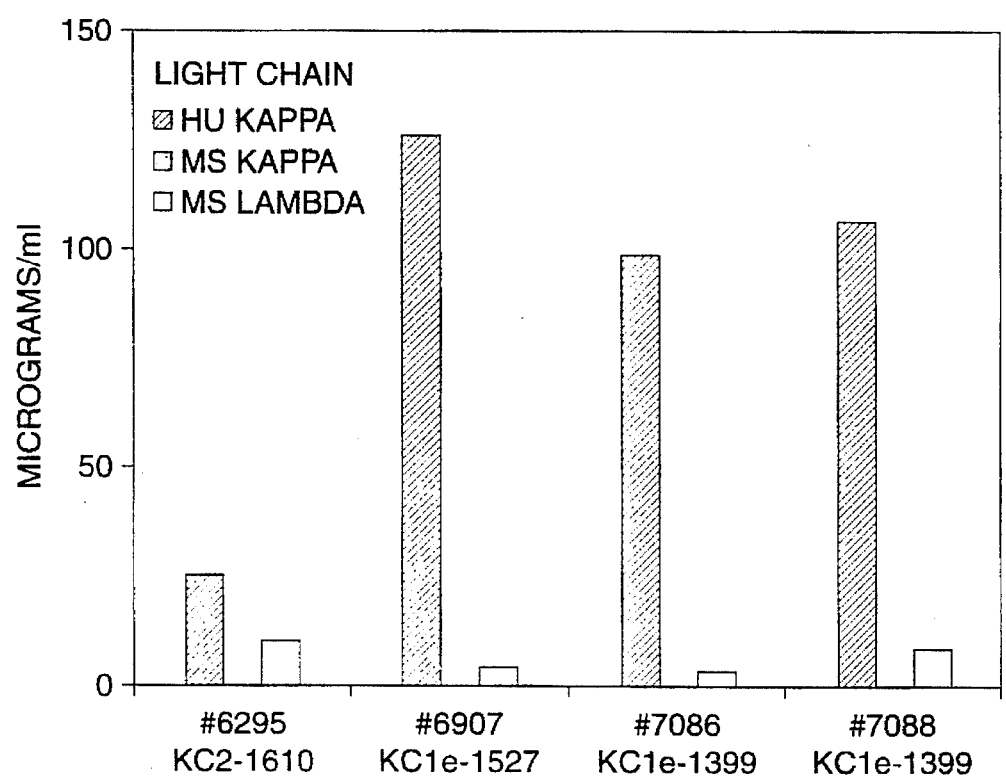
FIG. 53

LIGHT CHAIN MINILOCI
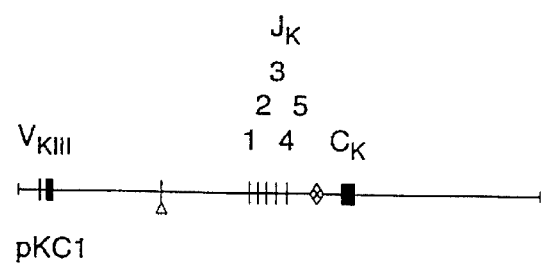
pKC1
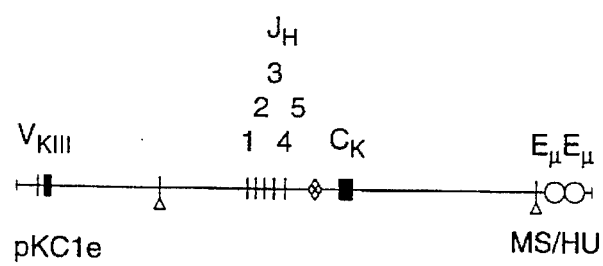
pKC1e
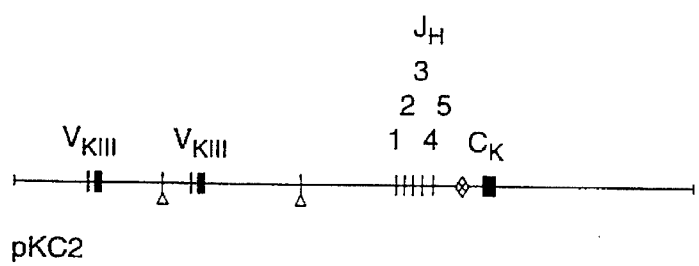
pKC2
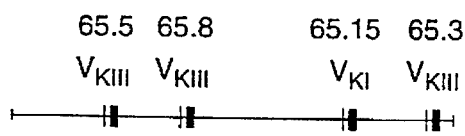
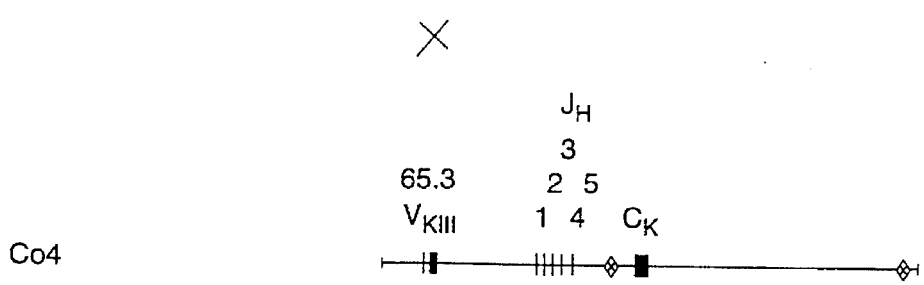
Co4
FIG. 57A

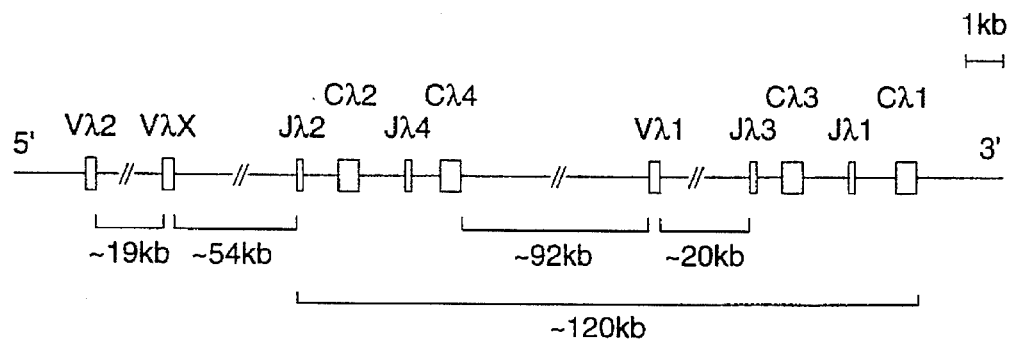
FIG. 58
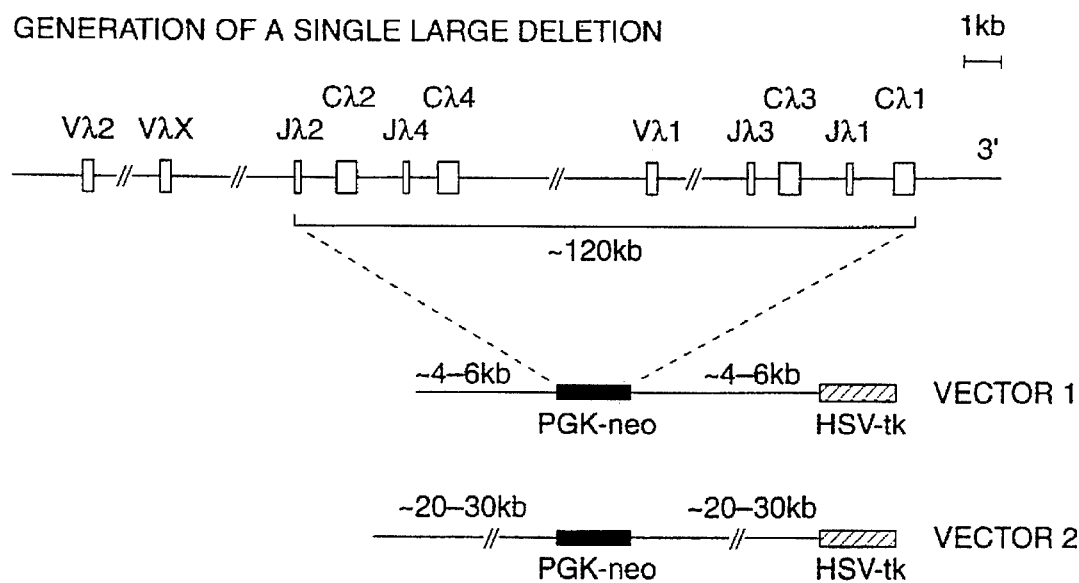
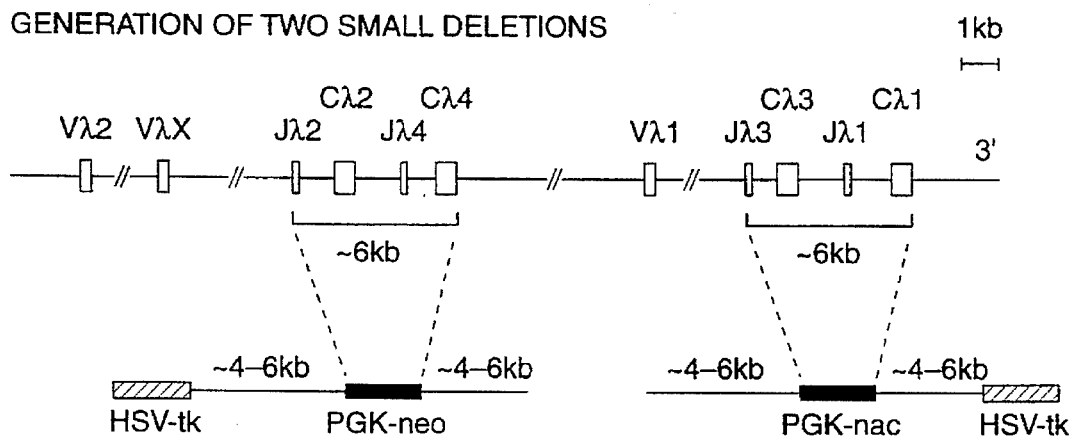
FIG. 59

CGAGAGGGGCGGGGGGAAGACTACTATCCCAGGCAGGTTTTAGGTTCCAGAGTCTGCGAG
AAATCCCACCATCTACCCACTGACACTCCCACCAGTCCTGTGCAGTGATCCCGTGATAAT
CGGCTGCCTGATTCACGATTACTTCCCTTTCGGCACGATGAATGTGACCTGGGGAAAGAG
TGGGAAGGATATAACCACCGTGAACTTTCCACCTGCCCTCGCCTCTGGGGGACGGTACAC
CATGAGCAGCCAGTTAACCCTGCCAGCTGTCGAGTGCCCAGAAGGAGAGTCCGTGAAATG
TTCCGTGCAACATGACTCTAACCCCGTCCAAGAATTGGATGTGAATTGCTCTGGTAAAGA
ACGTTAGGGGGTCAGCTAGGGGTGGGATAAGTCCTACCTTATCTAGATCCATATATCCCT
CTGATGCACACCCTCACAGGAATCCCTCAGAAACCTCCACTATGGGGATTGGGGGAAGGA
AGCGTAAACAGGTCTAGAAGGAGCTGGAGGCCTCAGAACATCCAGAAACGGGGACAGCAA
AGGAGACAAGGAGAATATACTGATTTGCTAGGACATCTTCTGTTACAGGTCCTACTCCTC
CTCCTCCTATTACTATTCCTTCCTGCCAGCCCAGCCTGTCACTGCAGCGGCCAGCTCTTG
AGGACCTGCTCCTGGGTTCAGATGCCAGCATCACATGTACTCTGAATGGCCTGAGAAATC
CTGAGGGAGCTGCTTTCACCTGGGAGCCCTCCACTGGGAAGGATGCAGTGCAGAAGAAAG
CTGCGCAGAATTCCTGCGGCTGCTACAGTGTGTCCAGCGTCCTGCCTGGCTGTGCTGAGC
GCTGGAACAGTGGCGCATCATTCAAGTGCACAGTTACCCATCCTGAGTCTGGCACCTTAA
CTGGCACAATTGCCAAAGTCACAGGTGAGCTCAGATGCATACCAGGACATTGTATGACGT
TCCCTGCTCACATGCCTGCTTTCTTCCTATAATACAGATGCTCAACTAACTGCTCATGTC
CTTATATCACAGAGGGAAATTGGAGCTATCTGAGGAACTGCCCAGAAGGGAAGGGCAGAG
GGGTCTTGCTCTCCTTGTCTGAGCCATAACTCTTCTTTCTACCTTCCAGTGAACACCTTC
CCACCCCAGGTCCACCTGCTACCGCCGCCGTCGGAGGAGCTGGCCCTGAATGAGCTCTTG
TCCCTGACATGCCTGGTGCGAGCTTTCAACCCTAAAGAAGTGCTGGTGCGATGGCTGCAT
GGAAATGAGGAGCTGTCCCCAGAAAGCTACCTAGTGTTTGAGCCCCTAAAGGAGCCAGGC
GAGGGAGCCACCACCTACCTGGTGACAAGCGTGTTGCGTGTATCAGCTGAAACCTGGAAA
CAGGGTGACCAGTACTCCTGCATGGTGGGCCACGAGGCCTTGCCCATGAACTTCACCCAG
AAGACCATCGACCGTCTGTCGGGTAAACCCACCAATGTCAGCGTGTCTGTGATCATGTCA
GAGGGAGATGGCATCTGCTACTGAGCCACCCTGCCTGTCCCTACTCCTAGAATAAACTCT
GTGCTCATCCAAAGTATCCCTGCACTTCCACCCAGTGCCTGTCCACCACCCTGGGGTCTA
CGAAACACAGGGAGGGGTCAGGGCCCAGGGAGGGAGAAATACCACCACCTAAGC

FIG. 61

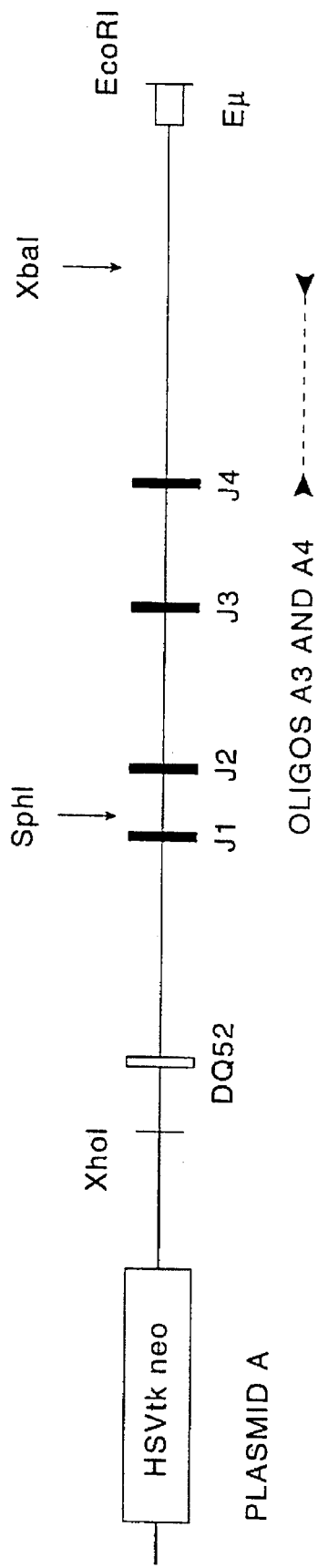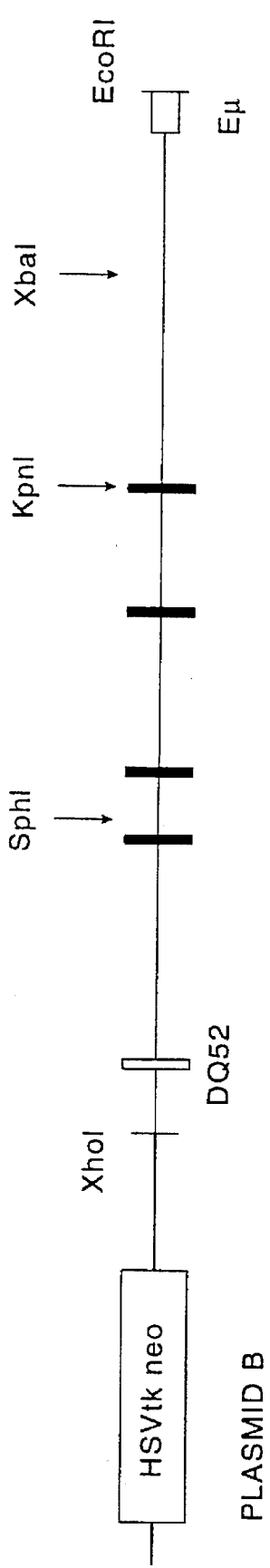
FIG. 62

```
              V_H251                       N D N                    J                              C_γ        mouse γ1
2357.t5  DXP'1 J6
gcctcggacaccgccatgtattactgtTgaga CATTtatggttcggggagttaCg    cggtGtgAacgtctggggccaagggaccacggtctccttcag  ccaaaacgacaccccatctgtctatccac 2357.t7  DHQ52 J3
gcctcggacaccgccatgtattactgtgcgaga CactgggCATTGGAT           gctCttgatGtctggggccaagggacaatgtCtcaccgtctcttcag ccaaaacgacaccccatctgtctatccac
                                                                                                              mouse γ2b
2357.t2  DHQ52 J3
gcctcggacaccgccatgtattactgtgcgaga actggggaTGAT              gcttttgatatctggggccaagggacaatggtcaccgtctcttcag  ccaaaacaacacccccatcagtctatccac 2357.t3  D? J3
gActcggacaccgccatgtattactgtgcgaga CAGGGAGAGAT               gctttagatatctggggccaagggacaatgtcaccgtctcttcag   ccaaaacaacacccccatcagtctatccac 2357.t4  DXP'1 J4
gcctcggacaccgccatgtattaTtgtgTgaga CATAGGGactataTTtcggggagttattTTCC  tgactactggggccagggaaccctgtcaccgtctcctcag ccaaaacaacacccccatcagtctatccac 2357.t1  D? J3
gcctcggacaccgccatgtattactgtgcgaga actggggaTGAT              gcttttgatatctggggccaagggacaatgtcaccgtctcttcag ccaaaacaacacccccatcagtctatccac
                                                                                                               mouse γ3
2357.t6  DHQ52 J4
gcctcggacaccgccatgtattactgtgcgaga CATGGGTCTATG              gatatctggggccaagggacaatggtcaccgtctcttcag    ctacaacaacagcccccatctgtctatccct 2357.t8  DIR2 J3
gcctcggacaccgccatgtattactgtgcgaga GAGAGCGGTCactgggaTCG      tttgactaTtggggccagggaacctgtcaccgtctcctcag   ctacaacaacagccccatctgtctatccct 2357.t9  DIR2R J6
gcctcggacaccgccatgtattactgtgcgaga AGGgaccccCTGAT            gcttttgatatctggggccaagggacaatgtcaccgtctcttcag ctacaacaacagccccatctgtctatccct
                                                                                                                mouse
gcctcggacaccgccatgtattactgtgcgaga CGggggcct                 tactactactacggtatggacgtctggggccaagggaccacggtcaccgtctcctcag ctacaacaacagcccccatctgtctatccct human
```

```
                        20                    30                    40                 50    52 a 53           60
         TCTCTGAAGATCCCTGTAAGGGTTCTGGATACAGCTTTACCAGCTACTGGATCGGCTGGGTGCGCCAGATGCCCGGGAAAGGCCTGAGTGGATGGGGATCATTATCCTGTGACTCTGATACCAGATACAGCCCGTCCTTCCAAGGCCAGGTC
VH251.GL
J2
3204.sp28  .........................CGT.........................................................................................................................
J3
3204.ln10  ...............................G.....................................................................................................................
J4
3204.ln3   ..................................G...........................A.....................................................................................
3204.ln7   ..............................A..C..G..........................A.....................................................................................
3204.ln8   ...............................G...............................A.....................................................................................
3204.ln14  ...............................G.....................................................................................................................
3204.ln15  ...............................G................................A....................................................................................
3204.sp22  ..............................T.................................A....................................................................................
3204.sp26  ..............................G..................................A.................C.................................................................
3204.sp27  ..............................T......................................................................................................................
3204.sp30  ..............................G.................................A....................................................................................
J5
3204.sp19  ...................T.....................................................................................G..........................................
J6
3204.sp20  .........................T.T.G..A...G....................................................CA....................................C.G.T................
                                        ──── CDR I ────                                                    ──── CDR II ────
```

RPA-T4/2C11-8
12:BDPHARMCOMP004\FL2-H\FL2-HEIGHT
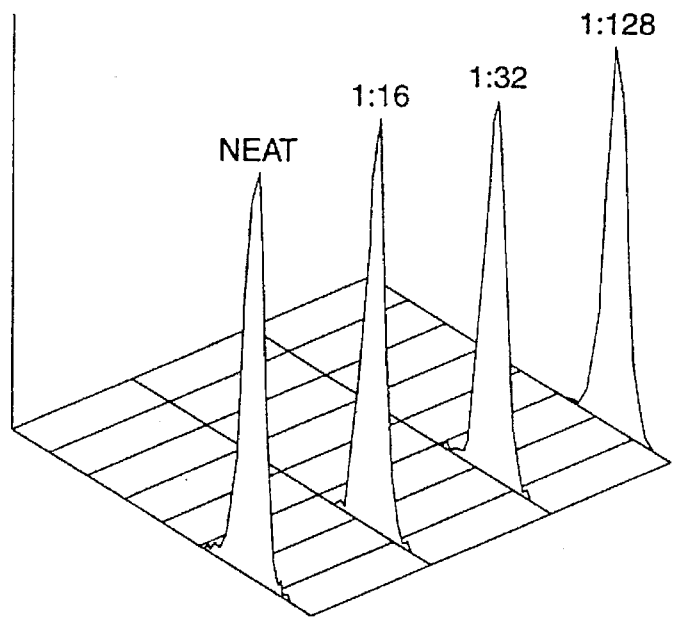
Leu-3a/2C11-8
12:BDPHARMCOMP025\FL2-H\FL2-HEIGHT
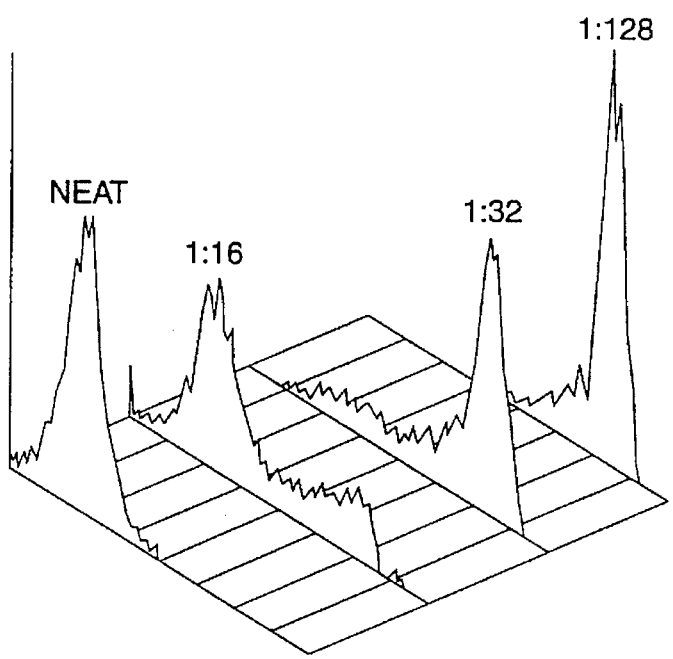
FIG. 75 pGP2b sequence:

```
AATTAGCggccgctgtcgacaagcttcgaattcagtatcgatgtggtacctggatcctcgagtgcGGCCGCAGTATGCAA
AAAAAAGCCCGCTCATTAGGCGGGCTCTTGGCAGAACATATCCATCGCGTCCGCCATCTCCAGCAGCCGCACGCGGCGCA
TCTCGGGCAGCGTTGGGTCCTGGCCACGGGTGCGCATGATCGTGCTCCTGTCGTTGAGGACCCGGCTAGGCTGGCGGGGT
TGCCTTACTGGTTAGCAGAATGAATCACCGATACGCGAGCGAACGTGAAGCGACTGCTGCTGCAAAACGTCTGCGACCTG
AGCAACAACATGAATGGTCTTCGGTTTCCGTGTTTCGTAAAGTCTGGAAACGCGGAAGTCAGCGCCCTGCACCATTATGT
TCCGGATCTGCATCGCAGGATGCTGCTGGCTACCCTGTGGAACACCTACATCTGTATTAACGAAGCGCTGGCATTGACCC
TGAGTGATTTTTCTCTGGTCCCGCCGCATCCATACCGCCAGTTGTTTACCCTCACAACGTTCCAGTAACCGGGCATGTTC
ATCATCAGTAACCCGTATCGTGAGCATCCTCTCTCGTTTCATCGGTATCATTACCCCCATGAACAGAAATTCCCCCTTAC
ACGGAGGCATCAAGTGACCAAACAGGAAAAAACCGCCCTTAACATGGCCCGCTTTATCAGAAGCCAGACATTAACGCTTC
TGGAGAAACTCAACGAGCTGGACGCGGATGAACAGGCAGACATCTGTGAATCGCTTCACGACCACGCTGATGAGCTTTAC
CGCAGCTGCCTCGCGCGTTTCGGTGATGACGGTGAAAACCTCTGACACATGCAGCTCCCGGAGACGGTCACAGCTTGTCT
GTAAGCGGATGCCGGGAGCAGACAAGCCCGTCAGGGCGCGTCAGCGGGTGTTGGCGGGTGTCGGGGCGCAGCCATGACCC
AGTCACGTAGCGATAGCGGAGTGTATACTGGCTTAACTATGCGGCATCAGAGCAGATTGTACTGAGAGTGCACCATATGC
GGTGTGAAATACCGCACAGATGCGTAAGGAGAAAATACCGCATCAGGCGCTCTTCCGCTTCCTCGCTCACTGACTCGCTG
CGCTCGGTCGTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGTTTTTCCATA
GGCTCCGCCCCCCTGACGAGCATCACAAAAATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGAGTCCAACCCGGTAAGA
CACGACTTATCGCCACTGGCAGCAGCCAggcgcgccttggcctaagaggccaCTGGTAACAGGATTAGCAGAGCGAGGTA
TGTAGGCGGTGCTACAGAGTTCTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGCTGCAGGCATCGTGGTGTCACGCTCGTCGTT
TGGTATGGCTTCATTCAGCTCCGGTTCCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACTCATGGTTATGGCAGCACTGCATAAT
TCTCTTACTGTCATGCCATCCGTAAGATGCTTTTCTGTGACTGGTGAGTACTCAACCAAGTCATTCTGAGAATAGTGTAT
GCGGCGACCGAGTTGCTCTTGCCCGGCGTCAACACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGTGCA
CCCAACTGATCTTCAGCATCTTTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCGCGCACATTTCCCCGAAAAGTG
CCACCTGACGTCTAAGAAACCATTATTATCATGACATTAACCTATAAAAATAGGCGTATCACGAGGCCCTTTCGTCTTCA
AG
```

FIG. 77A

TRANSGENIC NON-HUMAN ANIMALS FOR PRODUCING HETEROLOGOUS ANTIBODIES

CROSS-REFERENCE TO RELATED APPLICATION

This application is a continuation-in-part of U.S. Ser. No. 08/209,741 filed Mar. 9, 1994, which is a continuation-in-part of U.S. Ser. No. 08/165,699 filed Dec. 10, 1993, which is a continuation-in-part os U.S. Ser. No. 08/161,739 filed Dec. 3, 1993, which is a continuation-in-part of U.S. Ser. No. 08/155,301 filed Nov. 18, 1993, now abandoned, which is a continuation-in-part of U.S. Ser. No. 08/096,762 filed Jul. 22, 1993, which is a continuation-in-part of U.S. Ser. No. 08/053,131 filed Apr. 26, 1993, which is a continuation-in-part of U.S. Ser. No. 07/990,860 filed Dec. 16, 1992, now U.S. Pat. No. 5,545,806 which is a continuation-in-part of U.S. Ser. No. 07/904,068 filed Jun. 23, 1992, which is a continuation-in-part of U.S. Ser. No. 07/853,408 filed Mar. 18, 1992, which is a continuation-in-part of U.S. Ser. No. 07/834,539, filed Feb. 5, 1992, now U.S. Pat. No. 5,633,425, which is a continuation in part of Ser. No. 07/810,279 filed Dec. 17, 1991, now U.S. Pat. No. 5,569,825 which is a continuation-in-part of U.S. Ser. No. 07/575,962 filed Aug. 31, 1990 now abandoned, which is a continuation-in-part of U.S. Ser. No. 07/574,748 filed Aug. 29, 1990 now abandoned. This application claims foreign priority benefits under Title 35, United States Code, Section 119, to PCT Application No. PCT/US91/06185 (which corresponds to U.S. Ser. No. 07/834,539 filed Feb. 5, 1992) to PCT Application No. PCT/US92/10983, and to PCT Application No. PCT/US94/04580.

TECHNICAL FIELD

The invention relates to transgenic non-human animals capable of producing heterologous antibodies, transgenes used to produce such transgenic animals, transgenes capable of functionally rearranging a heterologous D gene in V-D-J recombination, immortalized B-cells capable of producing heterologous antibodies, methods and transgenes for producing heterologous antibodies of multiple isotypes, methods and transgenes for producing heterologous antibodies wherein a variable region sequence comprises somatic mutation as compared to germline rearranged variable region sequences, transgenic nonhuman animals which produce antibodies having a human primary sequence and which bind to human antigens, hybridomas made from B cells of such transgenic animals, and monclonal antibodies expressed by such hybridomas.

BACKGROUND OF THE INVENTION

One of the major impediments facing the development of in vivo therapeutic and diagnostic applications for monoclonal antibodies in humans is the intrinsic immunogenicity of non-human immunoglobulins. For example, when immunocompetent human patients are administered therapeutic doses of rodent monoclonal antibodies, the patients produce antibodies against the rodent immunoglobulin sequences; these human anti-mouse antibodies (HAMA) neutralize the therapeutic antibodies and can cause acute toxicity. Hence, it is desirable to produce human immunoglobulins that are reactive with specific human antigens that are promising therapeutic and/or diagnostic targets. However, producing human immunoglobulins that bind specifically with human antigens is problematic.

The present technology for generating monoclonal antibodies involves pre-exposing, or priming, an animal (usually a rat or mouse) with antigen, harvesting B-cells from that animal, and generating a library of hybridoma clones. By screening a hybridoma population for antigen binding specificity (idiotype) and also screening for immunoglobulin class (isotype), it is possible to select hybridoma clones that secrete the desired antibody.

However, when present methods for generating monoclonal antibodies are applied for the purpose of generating human antibodies that have binding specificities for human antigens, obtaining B-lymphocytes which produce human immunoglobulins a serious obstacle, since humans will typically not make immune responses against self-antigens.

Hence, present methods of generating human monoclonal antibodies that are specifically reactive with human antigens are clearly insufficient. It is evident that the same limitations on generating monoclonal antibodies to authentic self antigens apply where non-human species are used as the source of B-cells for making the hybridoma.

The construction of transgenic animals harboring a functional heterologous immunoglobulin transgene are a method by which antibodies reactive with self antigens may be produced. However, in order to obtain expression of therapeutically useful antibodies, or hybridoma clones producing such antibodies, the transgenic animal must produce transgenic B cells that are capable of maturing through the B lymphocyte development pathway. Such maturation requires the presence of surface IgM on the transgenic B cells, however isotypes other than IgM are desired for therapeutic uses. Thus, there is a need for transgenes and animals harboring such transgenes that are able to undergo functional V-D-J rearrangement to generate recombinational diversity and junctional diversity. Further, such transgenes and transgenic animals preferably include cis-acting sequences that facilitate isotype switching from a first isotype that is required for B cell maturation to a subsequent isotype that has superior therapeutic utility.

A number of experiments have reported the use of transfected cell lines to determine the specific DNA sequences required for Ig gene rearrangement (reviewed by Lewis and Gellert (1989), *Cell*, 59, 585–588). Such reports have identified putative sequences and concluded that the accessibility of these sequences to the recombinase enzymes used for rearrangement is modulated by transcription (Yancopoulos and Alt (1985), *Cell*, 40, 271–281). The sequences for V(D)J joining are reportedly a highly conserved, near-palindromic heptamer and a less well conserved AT-rich nanomer separated by a spacer of either 12 or 23 bp (Tonegawa (1983), *Nature*, 302, 575–581; Hesse, et al. (1989), *Genes in Dev.*, 3, 1053–1061). Efficient recombination reportedly occurs only between sites containing recombination signal sequences with different length spacer regions.

Ig gene rearrangement, though studied in tissue culture cells, has not been extensively examined in transgenic mice. Only a handful of reports have been published describing rearrangement test constructs introduced into mice [Buchini, et al. (1987), *Nature*, 326, 409–411 (unrearranged chicken λ transgene); Goodhart, et al. (1987), *Proc. Natl. Acad. Sci. USA*, 84, 4229–4233) (unrearranged rabbit κ gene); and Bruggemann, et al. (1989), *Proc. Natl. Acad. Sci. USA*, 86, 6709–6713 (hybrid mouse-human heavy chain)]. The results of such experiments, however, have been variable, in some cases, producing incomplete or minimal rearrangement of the transgene.

Further, a variety of biological functions of antibody molecules are exerted by the Fc portion of molecules, such as the interaction with mast cells or basophils through Fcε, and binding of complement by Fcμ or Fcγ, it further is desirable to generate a functional diversity of antibodies of a given specificity by variation of isotype.

Although transgenic animals have been generated that incorporate transgenes encoding one or more chains of a heterologous antibody, there have been no reports of heterologous transgenes that undergo successful isotype switching. Transgenic animals that cannot switch isotypes are limited to producing heterologous antibodies of a single isotype, and more specifically are limited to producing an isotype that is essential for B cell maturation, such as IgM and possibly IgD, which may be of limited therapeutic utility. Thus, there is a need for heterologous immunoglobulin transgenes and transgenic animals that are capable of switching from an isotype needed for B cell development to an isotype that has a desired characteristic for therapeutic use.

Based on the foregoing, it is clear that a need exists for methods of efficiently producing heterologous antibodies, e.g. antibodies encoded by genetic sequences of a first species that are produced in a second species. More particularly, there is a need in the art for heterologous immunoglobulin transgenes and transgenic animals that are capable of undergoing functional V-D-J gene rearrangement that incorporates all or a portion of a D gene segment which contributes to recombinational diversity. Further, there is a need in the art for transgenes and transgenic animals that can support V-D-J recombination and isotype switching so that (1) functional B cell development may occur, and (2) therapeutically useful heterologous antibodies may be produced. There is also a need for a source of B cells which can be used to make hybridomas that produce monoclonal antibodies for therapeutic or diagnostic use in the particular species for which they are designed. A heterologous immunoglobulin transgene capable of functional V-D-J recombination and/or capable of isotype switching could fulfill these needs.

In accordance with the foregoing object transgenic nonhuman animals are provided which are capable of producing a heterologous antibody, such as a human antibody.

Further, it is an object to provide B-cells from such transgenic animals which are capable of expressing heterologous antibodies wherein such B-cells are immortalized to provide a source of a monoclonal antibody specific for a particular antigen.

In accordance with this foregoing object, it is a further object of the invention to provide hybridoma cells that are capable of producing such heterologous monoclonal antibodies.

Still further, it is an object herein to provide heterologous unrearranged and rearranged immunoglobulin heavy and light chain transgenes useful for producing the aforementioned non-human transgenic animals.

Still further, it is an object herein to provide methods to disrupt endogenous immunoglobulin loci in the transgenic animals.

Still further, it is an object herein to provide methods to induce heterologous antibody production in the aforementioned transgenic non-human animal.

A further object of the invention is to provide methods to generate an immunoglobulin variable region gene segment repertoire that is used to construct one or more transgenes of the invention.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

Transgenic nonhuman animals are provided which are capable of producing a heterologous antibody, such as a human antibody. Such heterologous antibodies may be of various isotypes, including: IgG1, IgG2, IgG3, IgG4, IgM, IgA1, IgA2, IgA$_{sec}$, IgD, of IgE. In order for such transgenic nonhuman animals to make an immune response, it is necessary for the transgenic B cells and pre-B cells to produce surface-bound immunoglobulin, particularly of the IgM (or possibly IgD) isotype, in order to effectuate B cell development and antigen-stimulated maturation. Such expression of an IgM (or IgD) surface-bound immunoglobulin is only required during the antigen-stimulated maturation phase of B cell development, and mature B cells may produce other isotypes, although only a single switched isotype may be produced at a time.

Typically, a cell of the B-cell lineage will produce only a single isotype at a time, although cis or trans alternative RNA splicing, such as occurs naturally with the $\mu_s$ (secreted μ) and $\mu_M$ (membrane-bound μ) forms, and the μ and δ immunoglobulin chains, may lead to the contemporaneous expression of multiple isotypes by a single cell. Therefore, in order to produce heterologous antibodies of multiple isotypes, specifically the therapeutically useful IgG, IgA, and IgE isotypes, it is necessary that isotype switching occur. Such isotype switching may be classical class-switching or may result from one or more non-classical isotype switching mechanisms.

The invention provides heterologous immunoglobulin transgenes and transgenic nonhuman animals harboring such transgenes, wherein the transgenic animal is capable of producing heterologous antibodies of multiple isotypes by undergoing isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ sequences (δ-associated deletion). Alternative non-classical switching mechanisms, such as intertransgene and/or interchromosomal recombination, among others, may occur and effectuate isotype switching. Such transgenes and transgenic nonhuman animals produce a first immunoglobulin isotype that is necessary for antigen-stimulated B cell maturation and can switch to encode and produce one or more subsequent heterologous isotypes that have therapeutic and/or diagnostic utility. Transgenic nonhuman animals of the invention are thus able to produce, in one embodiment, IgG, IgA, and/or IgE antibodies that are encoded by human immunoglobulin genetic sequences and which also bind specific human antigens with high affinity.

The invention also encompasses B-cells from such transgenic animals that are capable of expressing heterologous antibodies of various isotypes, wherein such B-cells are immortalized to provide a source of a monoclonal antibody specific for a particular antigen. Hybridoma cells that are derived from such B-cells can serve as one source of such heterologous monoclonal antibodies.

The invention provides heterologous unrearranged and rearranged immunoglobulin heavy and light chain transgenes capable of undergoing isotype switching in vivo in the aforementioned non-human transgenic animals or in explanted lymphocytes of the B-cell lineage from such transgenic animals. Such isotype switching may occur spontaneously or be induced by treatment of the transgenic animal or explanted B-lineage lymphocytes with agents that promote isotype switching, such as T-cell-derived lymphokines (e.g., IL-4 and IFN$_\gamma$).

Still further, the invention includes methods to induce heterologous antibody production in the aforementioned transgenic non-human animal, wherein such antibodies may be of various isotypes. These methods include producing an antigen-stimulated immune response in a transgenic nonhuman animal for the generation of heterologous antibodies, particularly heterologous antibodies of a switched isotype (i.e., IgG, IgA, and IgE).

This invention provides methods whereby the transgene contains sequences that effectuate isotype switching, so that the heterologous immunoglobulins produced in the transgenic animal and monoclonal antibody clones derived from the B-cells of said animal may be of various isotypes.

This invention further provides methods that facilitate isotype switching of the transgene, so that switching between particular isotypes may occur at much higher or lower frequencies or in different temporal orders than typically occurs in germline immunoglobulin loci. Switch regions may be grafted from various $C_H$ genes and ligated to other $C_H$ genes in a transgene construct; such grafted switch sequences will typically function independently of the associated $C_H$ gene so that switching in the transgene construct will typically be a function of the origin of the associated switch regions. Alternatively, or in combination with switch sequences, δ-associated deletion sequences may be linked to various $C_H$ genes to effect non-classical switching by deletion of sequences between two δ-associated deletion sequences. Thus, a transgene may be constructed so that a particular $C_H$ gene is linked to a different switch sequence and thereby is switched to more frequently than occurs when the naturally associated switch region is used.

This invention also provides methods to determine whether isotype switching of transgene sequences has occurred in a transgenic animal containing an immunoglobulin transgene.

The invention provides immunoglobulin transgene constructs and methods for producing immunoglobulin transgene constructs, some of which contain a subset of germline immunoglobulin loci sequences (which may include deletions). The invention includes a specific method for facilitated cloning and construction of immunoglobulin transgenes, involving a vector that employs unique XhoI and SalI restriction sites flanked by two unique NotI sites. This method exploits the complementary termini of XhoI and SalI restrictions sites and is useful for creating large constructs by ordered concatemerization of restriction fragments in a vector.

The transgenes of the invention include a heavy chain transgene comprising DNA encoding at least one variable gene segment, one diversity gene segment, one joining gene segment and one constant region gene segment. The immunoglobulin light chain transgene comprises DNA encoding at least one variable gene segment, one joining gene segment and one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes permit recombination of the gene segments (functional rearrangement) and expression of the resultant rearranged immunoglobulin heavy and/or light chains within the transgenic non-human animal when said animal is exposed to antigen.

In one aspect of the invention, heterologous heavy and light immunoglobulin transgenes comprise relatively large fragments of unrearranged heterologous DNA. Such fragments typically comprise a substantial portion of the C, J (and in the case of heavy chain, D) segments from a heterologous immunoglobulin locus. In addition, such fragments also comprise a substantial portion of the variable gene segments.

In one embodiment, such transgene constructs comprise regulatory sequences, e.g. promoters, enhancers, class switch regions, recombination signals and the like, corresponding to sequences derived from the heterologous DNA. Alternatively, such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse.

In a method of the invention, a transgenic non-human animal containing germline unrearranged light and heavy immunoglobulin transgenes—that undergo VDJ joining during D-cell differentiation—is contacted with an antigen to induce production of a heterologous antibody in a secondary repertoire B-cell.

Also included in the invention are vectors and methods to disrupt the endogenous immunoglobulin loci in the non-human animal to be used in the invention. Such vectors and methods utilize a transgene, preferably positive-negative selection vector, which is constructed such that it targets the functional disruption of a class of gene segments encoding a heavy and/or light immunoglobulin chain endogenous to the non-human animal used in the invention. Such endogenous gene segments include diversity, joining and constant region gene segments. In this aspect of the invention, the positive-negative selection vector is contacted with at least one embryonic stem cell of a non-human animal after which cells are selected wherein the positive-negative selection vector has integrated into the genome of the non-human animal by way of homologous recombination. After transplantation, the resultant transgenic non-human animal is substantially incapable of mounting an immunoglobulin-mediated immune response as a result of homologous integration of the vector into chromosomal DNA. Such immune deficient non-human animals may thereafter be used for study of immune deficiencies or used as the recipient of heterologous immunoglobulin heavy and light chain transgenes.

The invention also provides vectors, methods, and compositions useful for suppressing the expression of one or more species of immunoglobulin chain(s), without disrupting an endogenous immunoglobulin locus. Such methods are useful for suppressing expression of one or more endogenous immunoglobulin chains while permitting the expression of one or more transgene-encoded immunoglobulin chains. Unlike genetic disruption of an endogenous immunoglobulin chain locus, suppression of immunoglobulin chain expression does not require the time-consuming breeding that is needed to establish transgenic animals homozygous for a disrupted Ig locus. An additional advantage of suppression as compared to engognous Ig gene disruption is that, in certain embodiments, chain suppression is reversible within an individual animal. For example, Ig chain suppression may be accomplished with: (1) transgenes encoding and expressing antisense RNA that specifically hybridizes to an endogenous Ig chain gene sequence, (2) antisense oligonucleotides that specifically hybridize to an endogenous Ig chain gene sequence, and (3) immunoglobulins that bind specifically to an endogenous Ig chain polypeptide.

The invention provides transgenic non-human animals comprising: a homozygous pair of functionally disrupted endogenous heavy chain alleles, a homozygous pair of functionally disrupted endogenous light chain alleles, at least one copy of a heterologous immunoglobulin heavy chain transgene, and at least one copy of a heterologous immunoglobulin heavy chain transgene, wherein said animal makes an antibody response following immunization with an antigen, such as a human antigen (e.g., CD4). The invention also provides such a transgenic non-human animal wherein said functionally disrupted endogenous heavy chain allele is a $J_H$ region homologous recombination knockout, said functionally disrupted endogenous light chain allele is a $J_\kappa$ region homologous recombination knockout, said heterologous immunoglobulin heavy chain transgene is the HC1 or HC2 human minigene transgene, said heterologous light chain transgene is the KC2 or KC1e human κ transgene, and wherein said antigen is a human antigen.

The invention also provides various embodiments for suppressing, ablating, and/or functionally disrupting the endogenous nonhuman immunoglobulin loci.

The invention also provides transgenic mice expressing both human sequence heavy chains and chimeric heavy chains comprising a human sequence heavy chain variable region and a murine sequence heavy chain constant region. Such chimeric heavy chains are generally produced by trans-switching between a functionally rearranged human transgene and an endogenous murine heavy chain constant region (e.g., γ1, γ2a, γ2b, γ3). Antibodies comprising such chimeric heavy chains, typically in combination with a transgene-encoded human sequence light chain or endogenous murine light chain, are formed in response to immunization with a predetermined antigen. The transgenic mice of these embodiments can comprise B cells which produce (express) a human sequence heavy chain at a first timepoint and trans-switch to produce (express) a chimeric heavy chain composed of a human variable region and a murine constant region (e.g., γ1, γ2a, γ2b, γ3) at a second (subsequent) timepoint; such human sequence and chimeric heavy chains are incorporated into functional antibodies with light chains; such antibodies are present in the serum of such transgenic mice. Thus, to restate: the transgenic mice of these embodiments can comprise B cells which express a human sequence heavy chain and subsequently switch (via trans-switching or cis-switching) to express a chimeric or isotype-switched heavy chain composed of a human variable region and a alternative constant region (e.g., murine γ1, γ2a, γ2b, γ3; human γ, α, ε); such human sequence and chimeric or isotype-switched heavy chains are incorporated into functional antibodies with light chains (human or mouse); such antibodies are present in the serum of such transgenic mice.

The invention also provides a method for generating a large transgene, said method comprising:

introducing into a mammalian cell at least three polynucleotide species; a first polynucleotide species having a recombinogenic region of sequence identity shared with a second polynucleotide species, a second polynucleotide species having a recombinogenic region of sequence identity shared with a first polynucleotide species and a recombinogenic region of sequence identity shared with a third polynucleotide species, and a third polynucleotide species having a recombinogenic region of sequence identity shared with said second polynucleotide species.

Recombinogenic regions are regions of substantial sequence identity sufficient to generate homologous recombination in vivo in a mammalian cell (e.g., ES cell), and preferably also in non-mammalian eukaryotic cells (e.g., Saccharaomyces and other yeast or fungal cells). Typically, recombinogenic regions are at least 50 to 100000 nucleotides long or longer, preferably 500 nucleotides to 10000 nucleotides long, and are often 80–100 percent identical, frequently 95–100 percent identical, often isogenic.

The references discussed herein are provided solely for their disclosure prior to the filing date of the present application. Nothing herein is to be construed as an admission that the inventors are not entitled to antedate such disclosure by virtue of prior invention.

BRIEF DESCRIPTION OF THE FIGURES

FIG. 12 depicts the construction of pHIG3' and PCON.

FIG. 17 depicts the construction of pKapH.

FIGS. 18A through 18D depict the construction of a positive–negative selection vector for functionally disrupting the endogenous heavy chain immunoglobulin locus of mouse.

FIGS. 19A through 19C depict the construction of a positive–negative selection vector for functionally disrupting the endogenous immunoglobulin light chain loci in mouse.

FIGS. 20A through 20E depict the structure of a kappa light chain targeting vector.

FIGS. 21A through 21F depict the structure of a mouse heavy chain targeting vector.

FIG. 40 shows aligned variable region sequences of 23 randomly-chosen cDNAs generated from mRNA obtained from lymphoid tissue of HC1 transgenic mice immunized with human carcinoembryonic antigen (CEA) as compared to the germline transgene sequence (top line); on each line nucleotide changes relative to germline sequence are shown. The regions corresponding to heavy chain CDR1, CDR2, and CDR3 are indicated. Non-germline encoded nucleotides are shown in capital letters.

FIG. 41 show the nucleotide sequence of a human DNA fragment, designated vk65.3, containing a $V_\kappa$ gene segment; the deduced amino acid sequences of the $V_\kappa$ coding regions are also shown; splicing and recombination signal sequences (heptamer/nonamer) are shown boxed.

FIG. 42 show the nucleotide sequence of a human DNA fragment, designated vk65.5, containing a $V_\kappa$ gene segment; the deduced amino acid sequences of the $V_\kappa$ coding regions are also shown; splicing and recombination signal sequences (heptamer/nonamer) are shown boxed.

FIG. 43 show the nucleotide sequence of a human DNA fragment, designated vk65.8, containing a $V_\kappa$ gene segment; the deduced amino acid sequences of the $V_\kappa$ coding regions are also shown; splicing and recombination signal sequences (heptamer/nonamer) are shown boxed.

FIG. 44 show the nucleotide sequence of a human DNA fragment, designated vk65.15, containing a $V_\kappa$ gene segment; the deduced amino acid sequences of the $V_\kappa$ coding regions are also shown; splicing and recombination signal sequences (heptamer/nonamer) are shown boxed.

FIG. 46 shows ELISA results for monoclonal antibodies reactive with CEA and non-CEA antigens showing the specificity of antigen binding.

FIG. 47 shows the DNA sequences of 10 cDNAs amplified by PCR to amplify transcripts having a human VDJ and a murine constant region sequence.

FIG. 48 shows ELISA results for various dilutions of serum obtained from mice bearing both a human heavy chain minilocus transgene and a human κ minilocus transgene; the mouse was immunized with human CD4 and the data shown represents antibodies reactive with human CD4 and possessing human κ, human µ, or human γ epitopes, respectively.

FIG. 53 shows the amounts of human µ, human γ, human κ, mouse µ, mouse γ, mouse κ, and mouse λ chains in the serum of unimmunized 0011 mice.

FIG. 58 shows a schematic representation of inactivation of the murine λ locus by homologous gene targeting.

FIG. 59 schematically shows the structure of a homologous recombination targeting transgene for deleting genes, such as heavy chain constant region genes.

129. Structural genes are shown by closed boxes in the top line; second and third lines show restriction sites with symbols indicated.

FIG. 61 shows a nucleotide sequence of mouse heavy chain locus α constant region gene.

FIG. 62 shows the construction of a frameshift vector (plasmid B) for introducing a two bp frameshift into the murine heavy chain locus $J_4$ gene.

Figure 63:
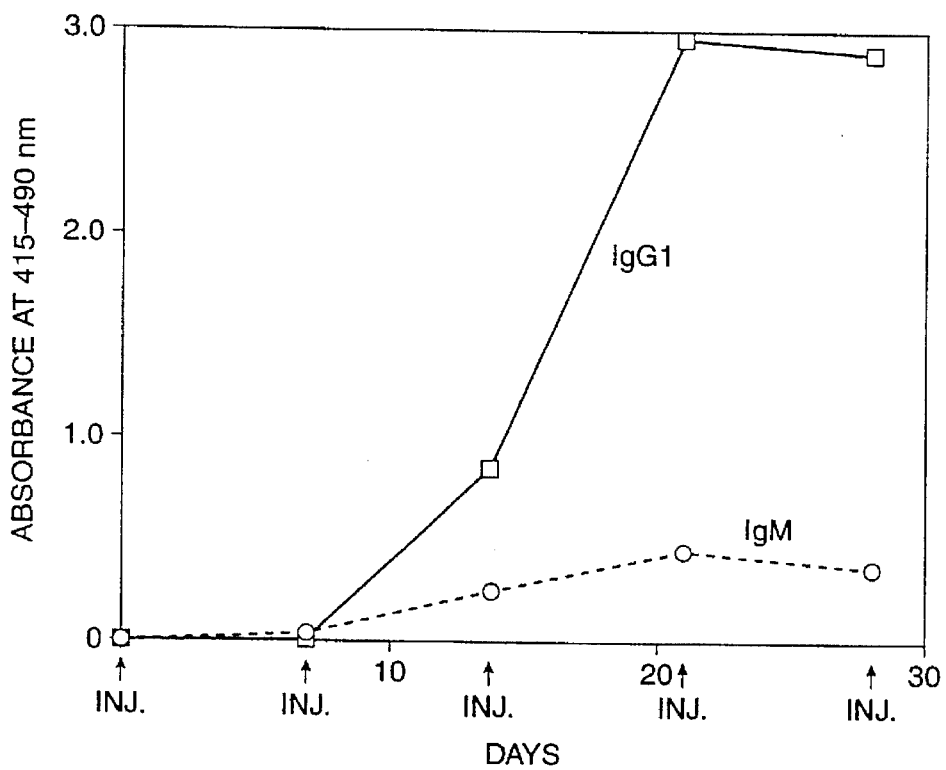

FIG. 63 shows isotype specific response of transgenic animals during hyperimmunization. The relative levels of reactive human µ and γ1 are indicated by a colorimetric ELISA assay (y-axis). We immunized three 7–10 week old male HC1 line 57 transgenic animals (#1991, #2356, #2357), in a homozygous JHD background, by intraperitoneal injections of CEA in Freund's adjuvant. The figure depicts binding of 250 fold dilutions of pooled serum (collected prior to each injection) to CEA coated microtiter wells.

Figure 64A:
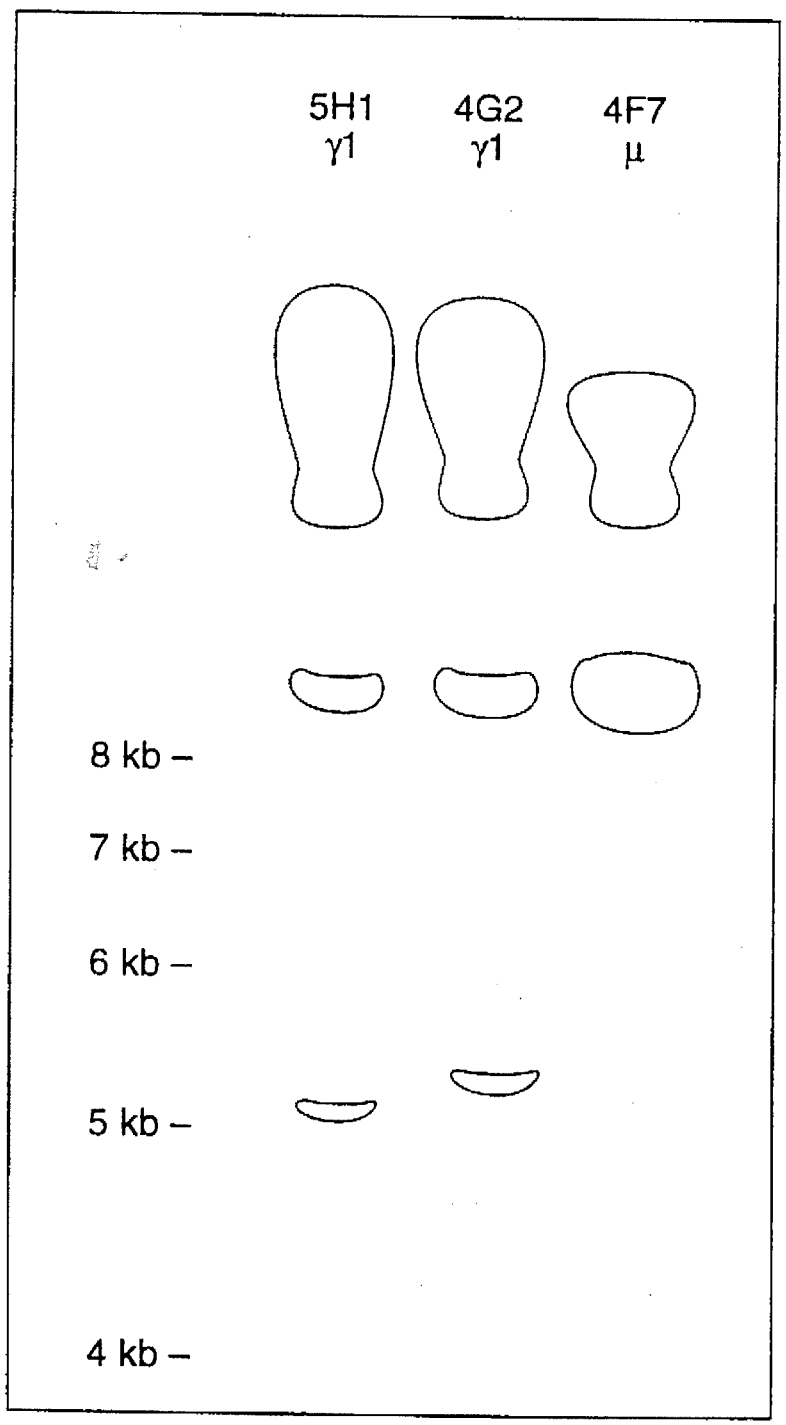
Figure 64B:
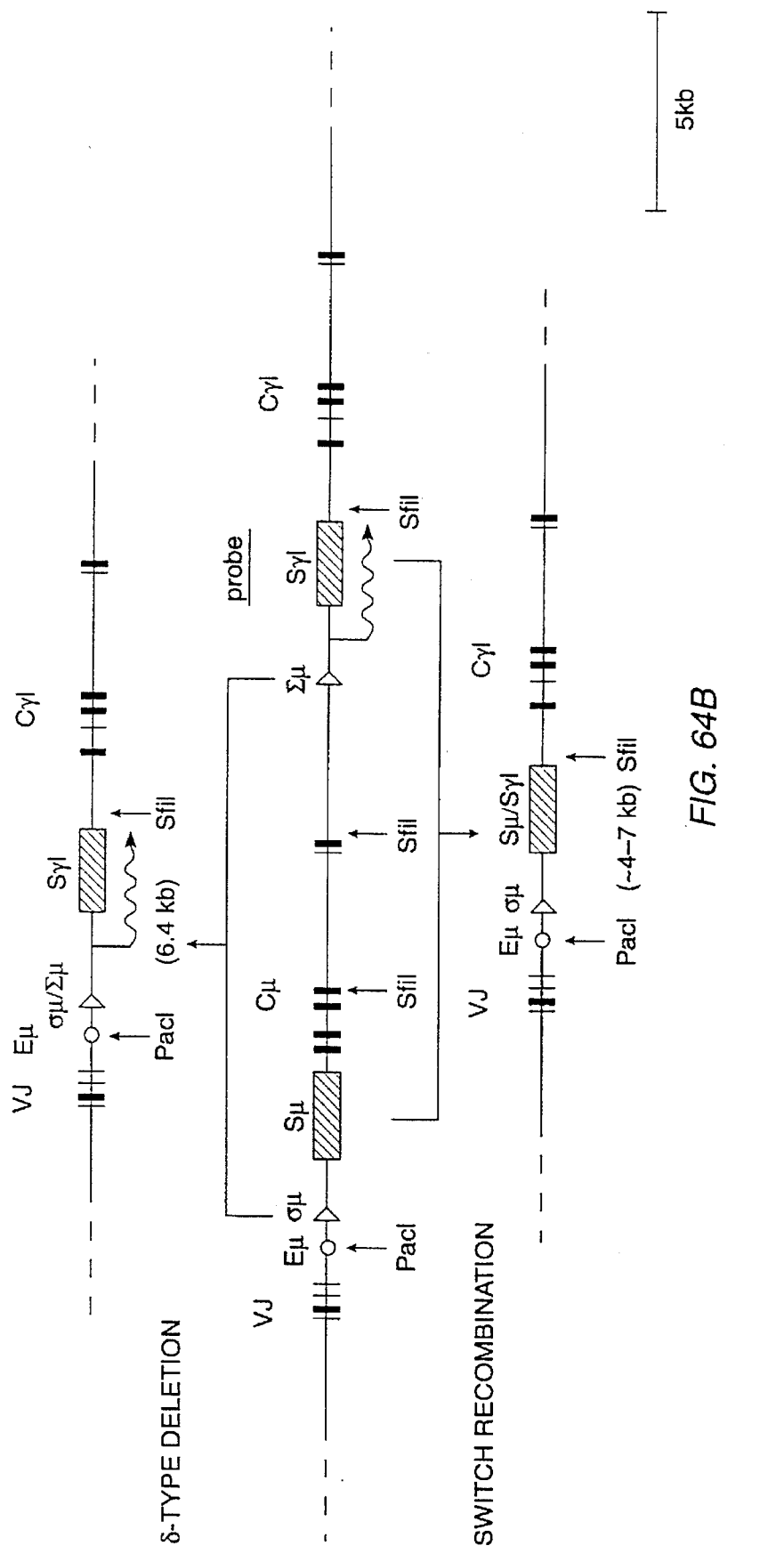

FIG. 64A and 64B show expression of transgene encoded γ1 isotype mediated by class switch recombination. The genomic structure of integrated transgenes in two different human γ1 expressing hybridomas is consistent with recombination between the µ and γ1 switch regions. FIG. 64A shows a Southern blot of PacI/SfiI digested DNA isolated from three transgene expressing hybridomas. From left to right: clone 92-09A-5H1-5, human γ1$^+$/µ$^-$; clone 92-90A-4G2-2, human γ1$^+$/µ$^-$; clone 92-09A-4F7-A5-2, human γ1$^-$, µ$^+$. All three hybridomas are derived from a 7 month old male mouse hemizygous for the HC1-57 integration, and homozygous for the JHD disruption (mouse #1991). The blot is hybridized with a probe derived from a 2.3 kb BglII/SfiI DNA fragment spanning the 3' half of the human γ1 switch region. No switch product is found in the µ expressing hybridoma, while the two γ1 expressing hybridomas, 92-09A-5H1-5 and 92-09A-4G2-2, contain switch products resulting in PacI/SfiI fragments of 5.1 and 5.3 kb respectively, FIG. 64B is a diagram of two possible deletional mechanisms by which a class switch from µ to γ1 can occur. The human µ gene is flanked by 400 bp direct repeats (σµ and Σµ) which can recombine to delete µ. Class switching by this mechanism will always generate a 6.4 kb PacI/SfiI fragment, while class switching by recombination between the µ and the γ1 switch regions will generate a PacI/SfiI fragment between 4 and 7 kb, with size variation between individual switch events. The two γ1 expressing hybridomas examined in FIG. 64A appear to have undergone recombination between the µ and γ1 switch regions.

FIG. 65 shows chimeric human/mouse immunoglobulin heavy chains generated by trans-switching. cDNA clones of trans-switch products were generated by reverse transcription and PCR amplification of a mixture of spleen and lymph node RNA isolated from a hyperimmunized HC1 transgenic-JHD mouse (#2357; see legend to FIG. 63 for description of animal and immunization schedule). The partial nucleotide sequence of 10 randomly picked clones is shown. Lower case letters indicate germline encoded, capital letters indicate nucleotides that cannot be assigned to known germline sequences; these may be somatic mutations, N nucleotides, or truncated D segments. Both face type indicates mouse γ sequences.

Figure 66A.1:
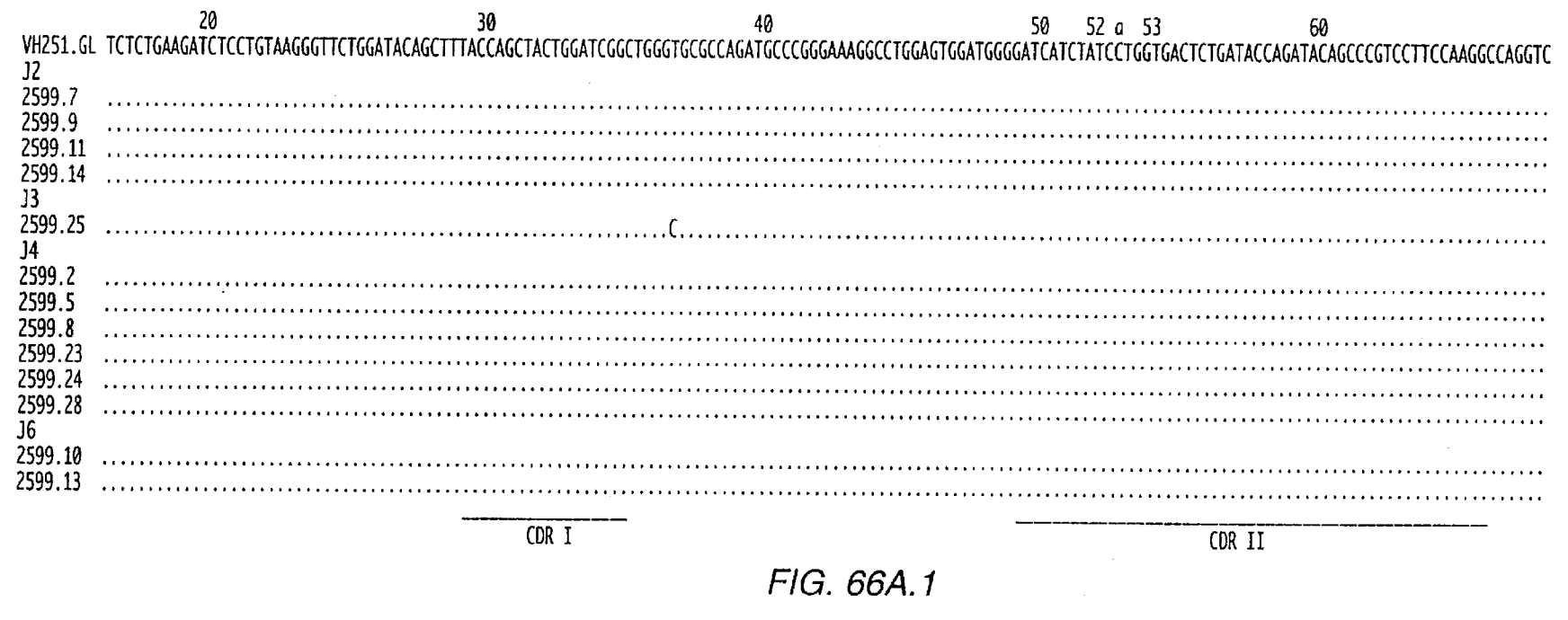
Figure 66A.2:
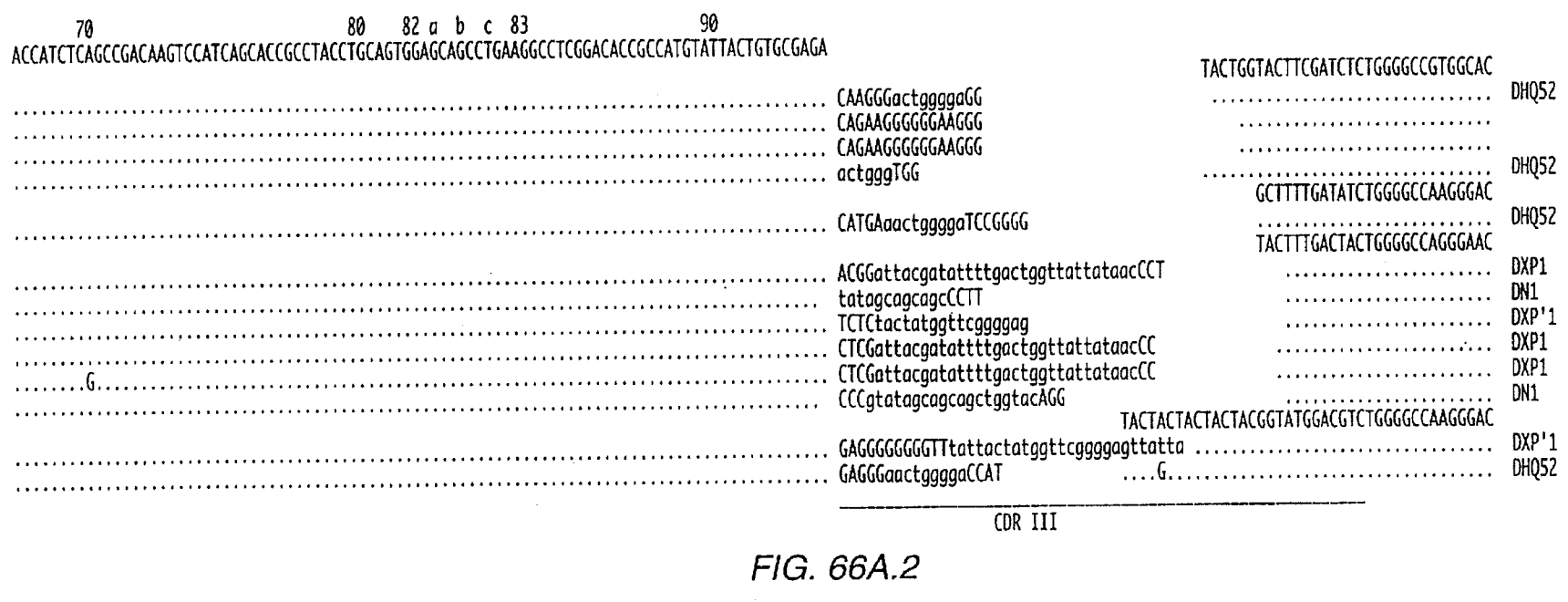
Figure 66B.2:
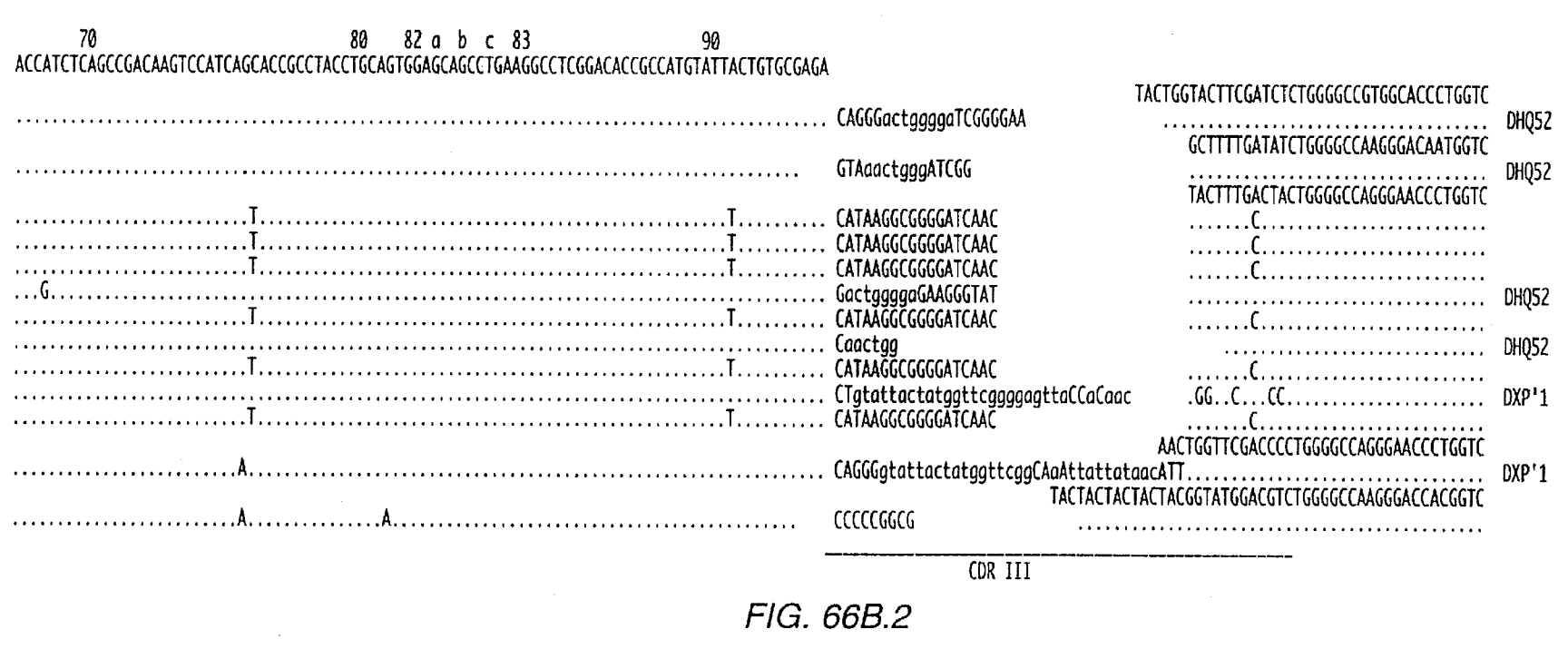

FIGS. 66A and 66B show that the rearranged VH251 transgene undergoes somatic mutation in a hyperimmunized. The partial nucleotide sequence of IgG heavy chain variable region cDNA clones from CH1 line 26 mice exhibiting FIG. 66A primary and FIG. 66B secondary responses to antigen. Germline sequence is shown at the top; nucleotide changes from germline are given for each clone. A period indicates identity with germline sequence, capital letters indicate no identified germline origin. The sequences are grouped according to J segment usage. The germline sequence of each of the J segments if shown. Lower case letters within CDR3 sequences indicate identity to known D segment included in the HC1 transgene. The assigned D segments are indicated at the end of each sequence. Unassigned sequences could be derived from N region addition or somatic mutation; or in some cases they are simply too short to distinguish random N nucleotides from known D segments. FIG. 66A primary response: 13 randomly picked VH251-γ1 cDNA clones. A 4 week old female HC1 line 26-JHD mouse (#2599) was given a single injection of KLH and complete Freunds adjuvant; spleen cell RNA was isolated 5 days later. The overall frequency of somatic mutations within the V segment is 0.06% (2/3,198 bp). FIG. 66B secondary response: 13 randomly picked VH251-γ1 cDNA clones. A 2 month old female HC1 line 26-JHD mouse (#3204) was given 3 injections of HEL and Freunds adjuvant over one month (a primary injection with complete adjuvant and boosts with incomplete at one week and 3 weeks); spleen and lymph node RNA was isolated 4 months later. The overall frequency of somatic mutations within the V segment is 1.6% (52/3,198 bp).

Figure 67A:
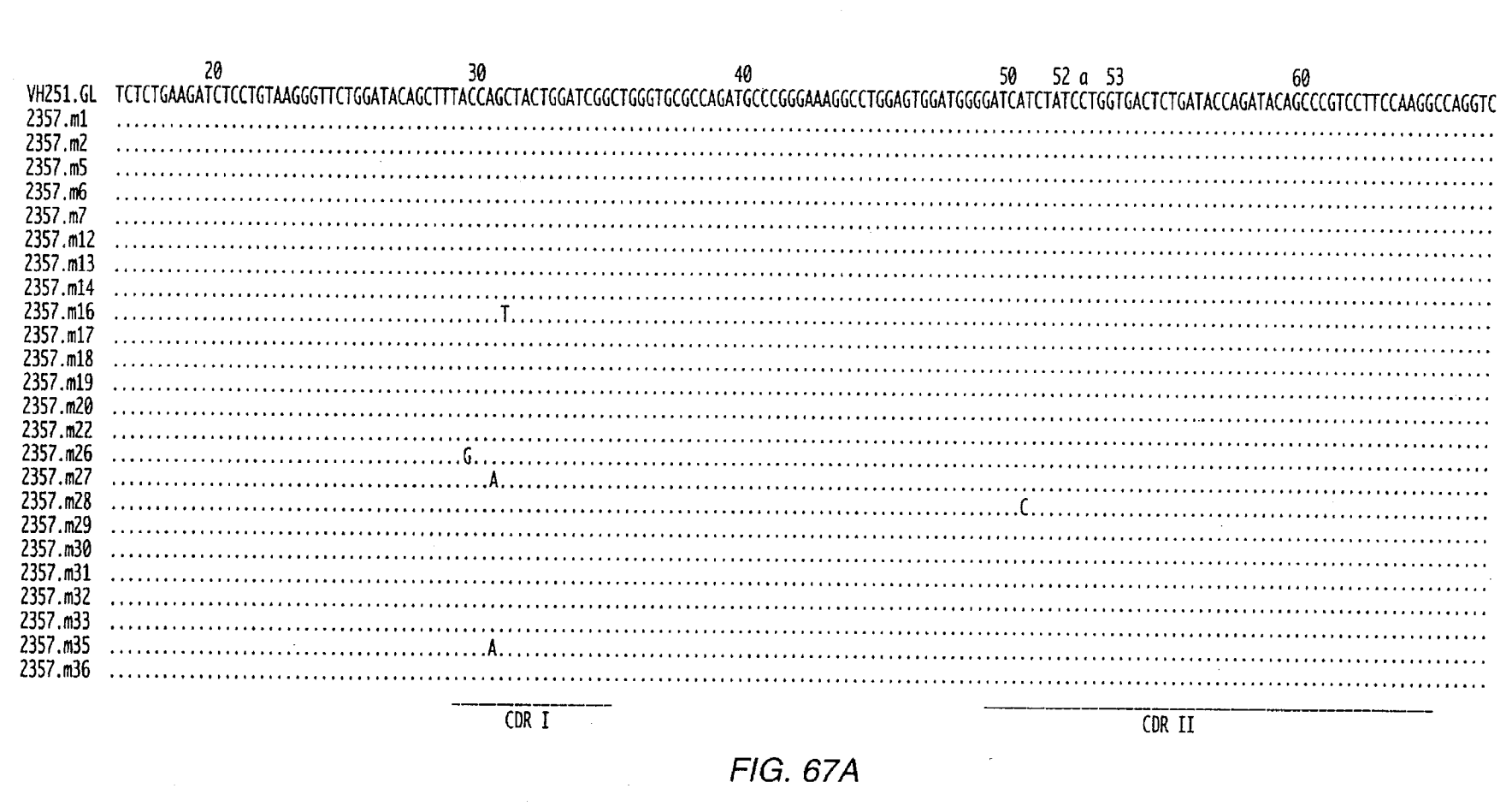
Figure 67B.1:
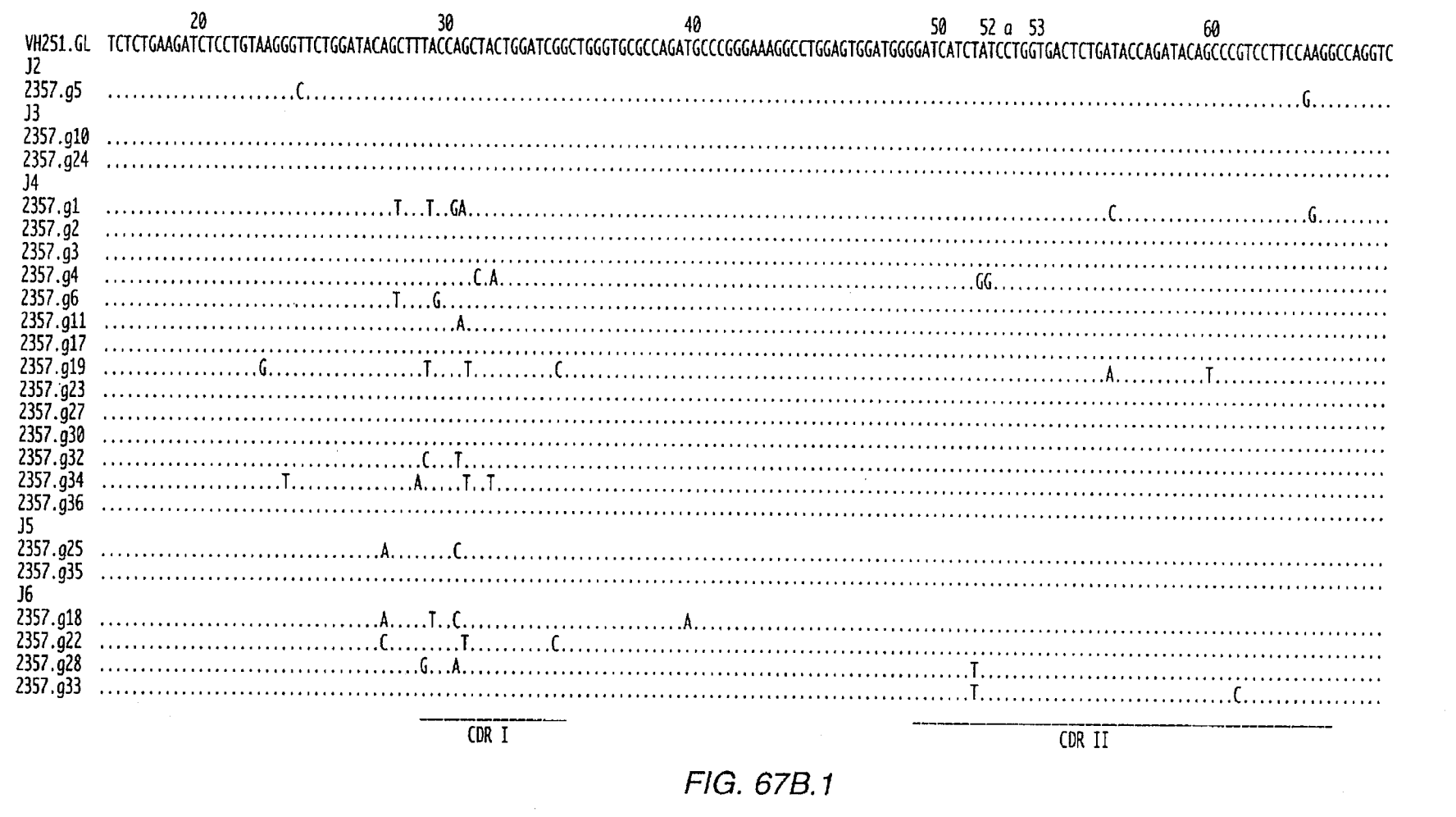
Figure 67B.2:
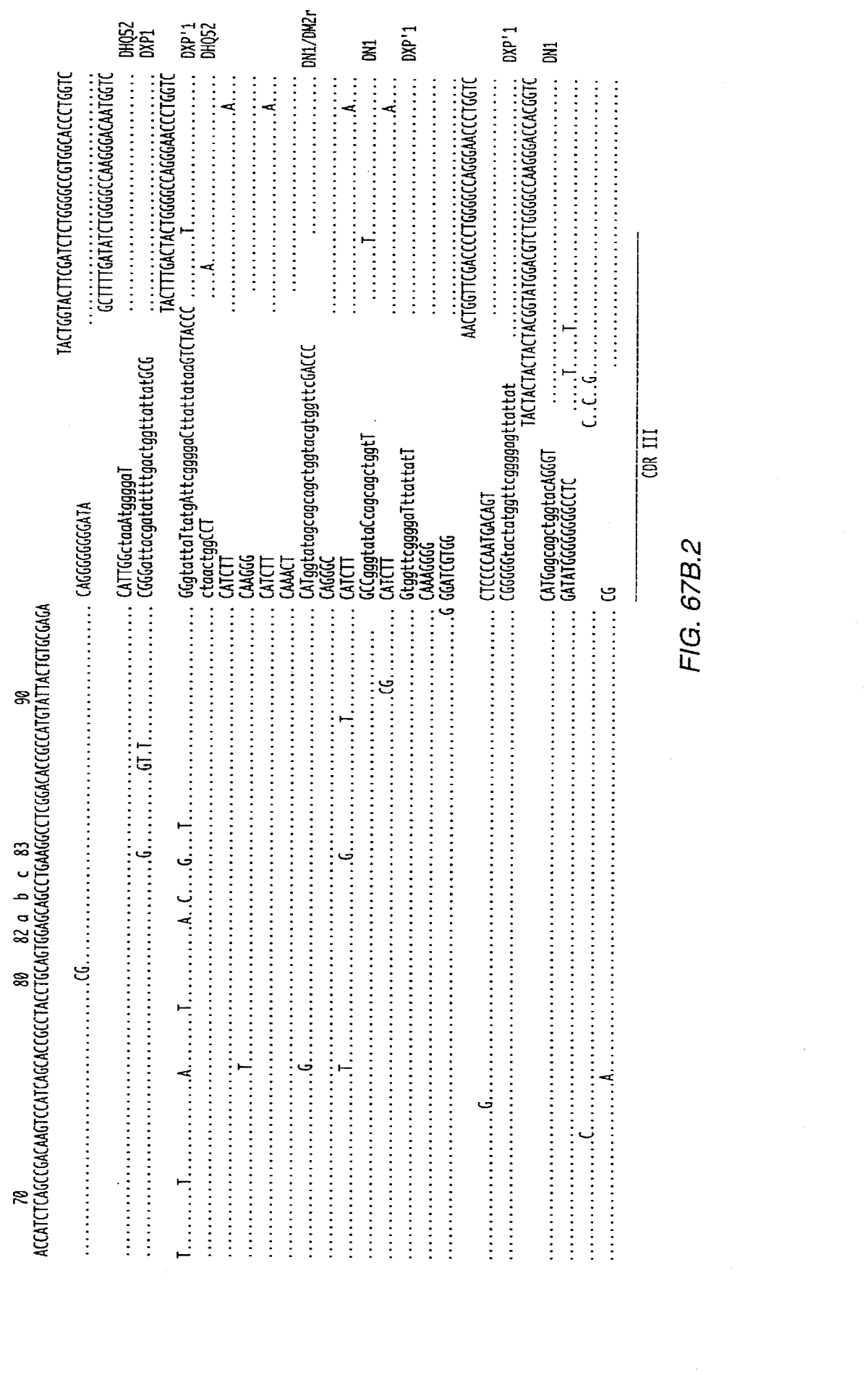

FIGS. 67A and 67B show that extensive somatic mutation is confined to γ1 sequences: somatic mutation and class switching occur within the same population of B cells. Partial nucleotide sequence of VH251 cDNA clones isolated from spleen and lymph node cells of HC1 line 57 transgenic-JHD mouse (#2357) hyperimmunized against CEA (see FIG. 63 for immunization schedule). FIG. 67A: IgM: 23 randomly picked VH251-µ cDNA clones. Nucleotide sequence of 156 bp segment including CDRs 1 and 2 surrounding residues. The overall level of somatic mutation is 0.1% (5/3,744 bp). FIG. 67B: IgG: 23 randomly picked VH251-γ1 cDNA clones. Nucleotide sequence of segment including CDRs 1 through 3 and surrounding residues. The overall frequency of somatic mutation within the V segment is 1.1% (65/5,658 bp). For comparison with the µ sequences in FIG. 67A: the mutation frequency for first 156 nucleotides is 1.1% (41/3,588 bp). See legend to FIGS. 66A and 66B for explanation of symbols.

Figure 68A:
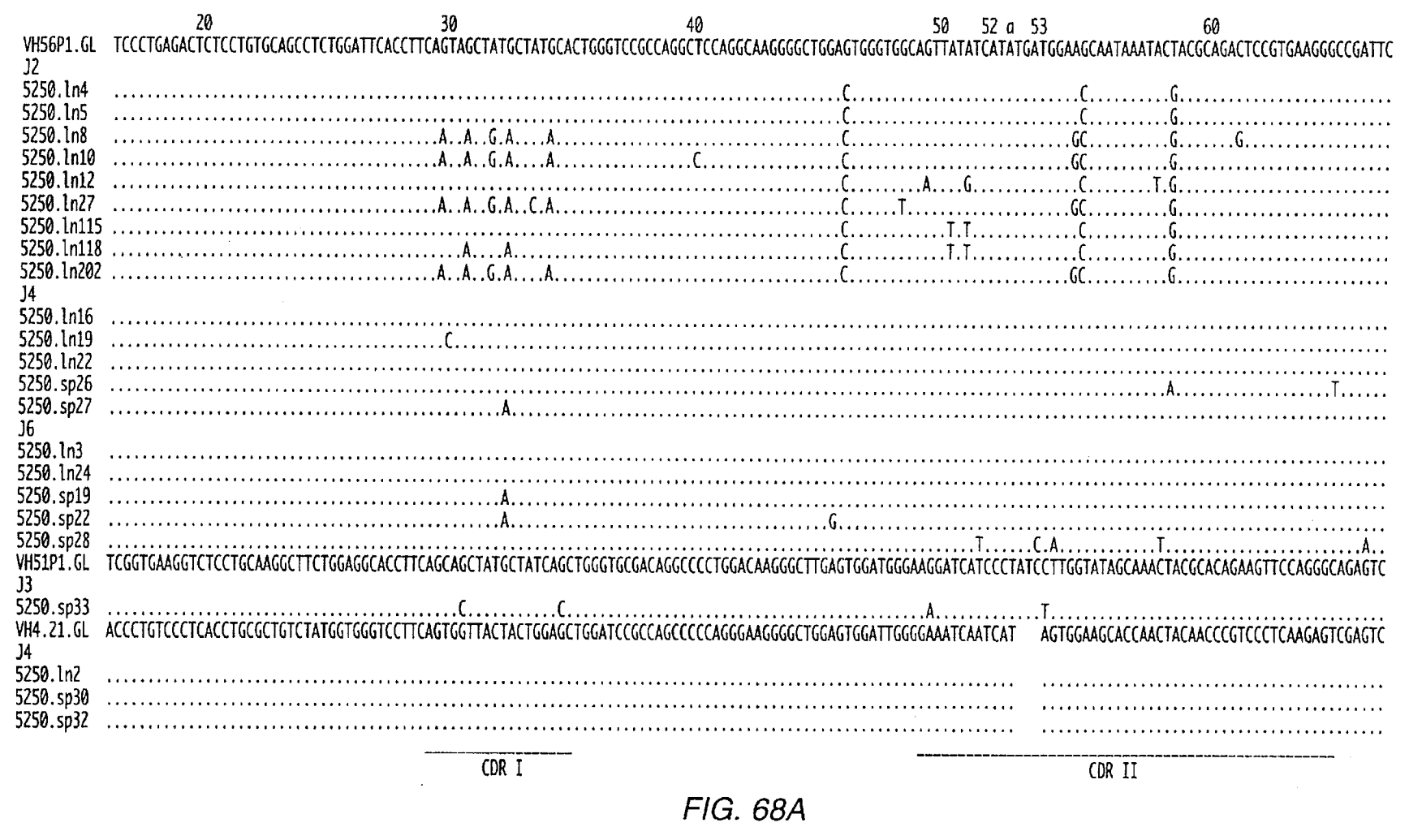
Figure 68B:
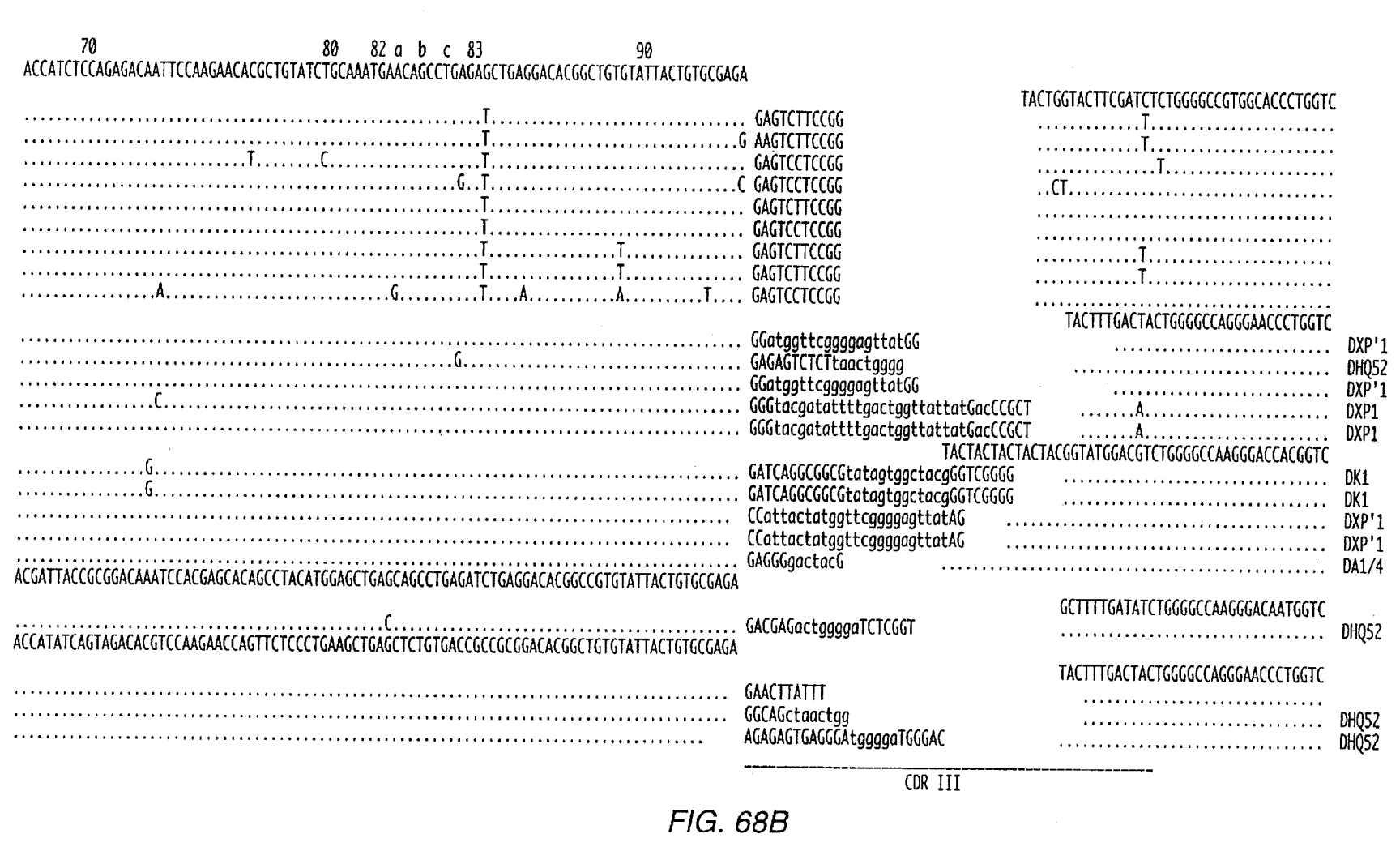

FIG. 68 indicates that VH51P1 and VH56P1 show extensive somatic mutation of in an unimmunized mouse. The partial nucleotide sequence of IgG heavy chain variable region cDNA clones from a 9 week old, unimmunized female HC2 line 2550 transgenic-JHD mouse (#5250). The overall frequency of somatic mutation with the 19 VH56p1 segments is 2.2% (101/4,674 bp). The overall frequency of somatic mutation within the single VH51p1 segment is 2.0% (5/246 bp). See legend to FIGS. 66A and 66B for explanation of symbols.

Figure 69:
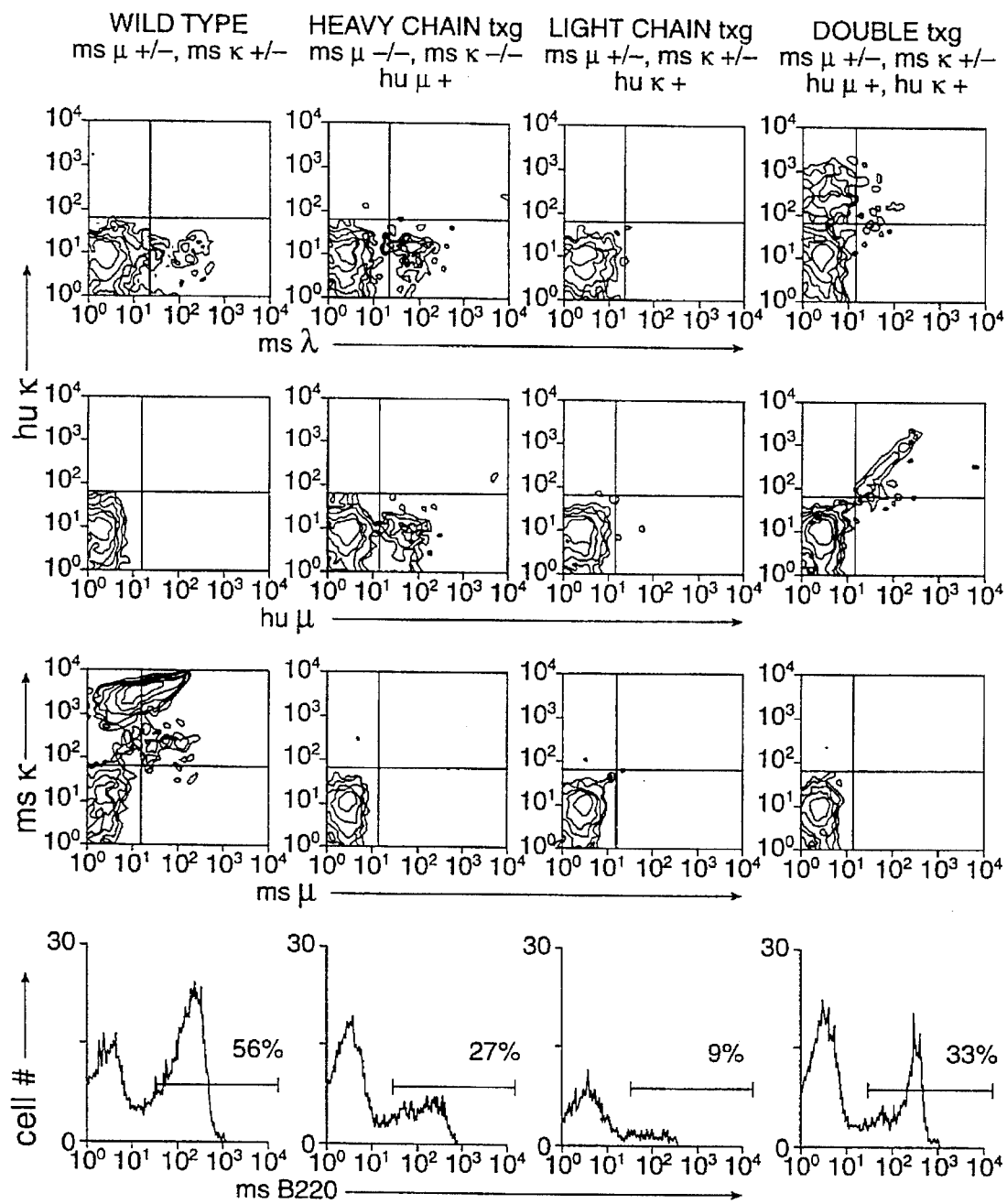

FIG. 69. Double transgenic mice with disrupted endogenous Ig loci contain human IgMκ positive B cells. FACS of cells isolated from spleens of 4 mice with different genotypes. Left column: control mouse (#9944, 6 wk old female JH+/−, JCκ+/−; heterozygous wild-type mouse heavy and κ-light chain loci, non-transgenic). Second column: human heavy chain transgenic (#9877, 6 wk old female JH−/−, JCκ−/−, HC2 line 2550 +; homozygous for disrupted mouse heavy and κ-light chain loci, hemizygous for HC2 transgene). Third column: human κ-light chain transgenic (#9878, 6 wk old female JH−/−, JCκ−/−, KCo4 line 4437 +; homozygous for disrupted mouse heavy and κ-light chain loci, hemizygous for KCo4 transgene). Right column: double transgenic (#9879, 6 wk old female JH−/−m JCκ−/−, HC2 line 2550 +, KCo4 line 4437 +; homozygous for disrupted mouse heavy and κk-light chain loci, hemizygous for HC2 and KCo4 transgenes). Top row: spleen cells stained for expression of mouse λ light chain (x-axis) and human κ light chain (y-axis). Second row: spleen cells stained for expression of human μ heavy chain (x-axis) and human κ light chain (y-axis). Third row: spleen cells stained for expression of mouse μ heavy chain (x-axis) and mouse κ light chain (y-axis). Bottom row: histogram of spleen cells stained for expression of mouse B220 antigen (log fluorescence: x-axis; cell number: y-axis). For each of the two color panels, the relative number of cells in each of the displayed quadrants is given as percent of a e-parameter gate based on propidium iodide staining and light scatter. The fraction of B220+ cells in each of the samples displayed in the bottom row is given as a percent of the lymphocyte light scatter gate.

Figure 70:
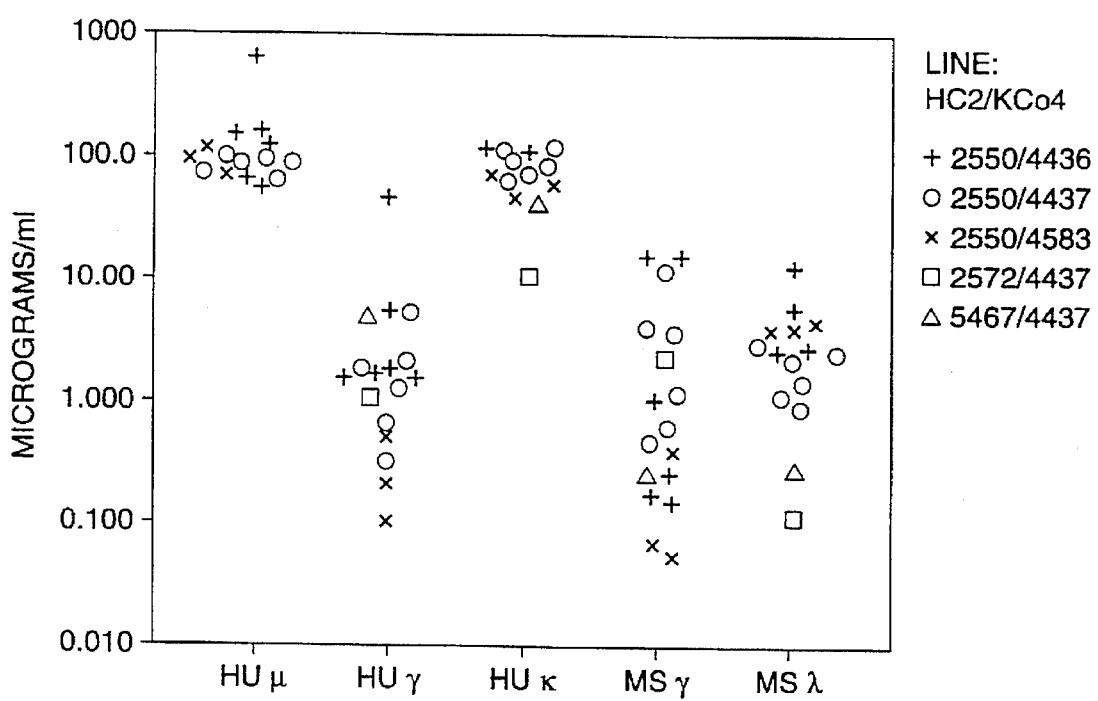

FIG. 70. Secreted immunoglobulin levels in the serum of double transgenic mice. Human μ, γ, and κ, and mouse γ and λ from 18 individual HC2/KCo4 double transgenic mice homozygous for endogenous heavy and κ-light chain locus disruption. Mice: (+) HC2 line 2550 (~5 copies of HC2 per integration), KCo4 line 4436 (1–2 copies of KCo4 per integration); (O) HC2 line 2550, KCo4 line 4437 (~10 copies of KCo4 per integration); (x) HC2 line 2550, KCo4 line 4583 (~5 copies of KCo4 per integration); (□) HC2 line 2572 (30–50 copies of HC2 per integration, KCo4 line 4437; (Δ) HC2 line 5467 (20–30 copies of HC2 per integration, KCo4 line 4437.

Figure 71A:
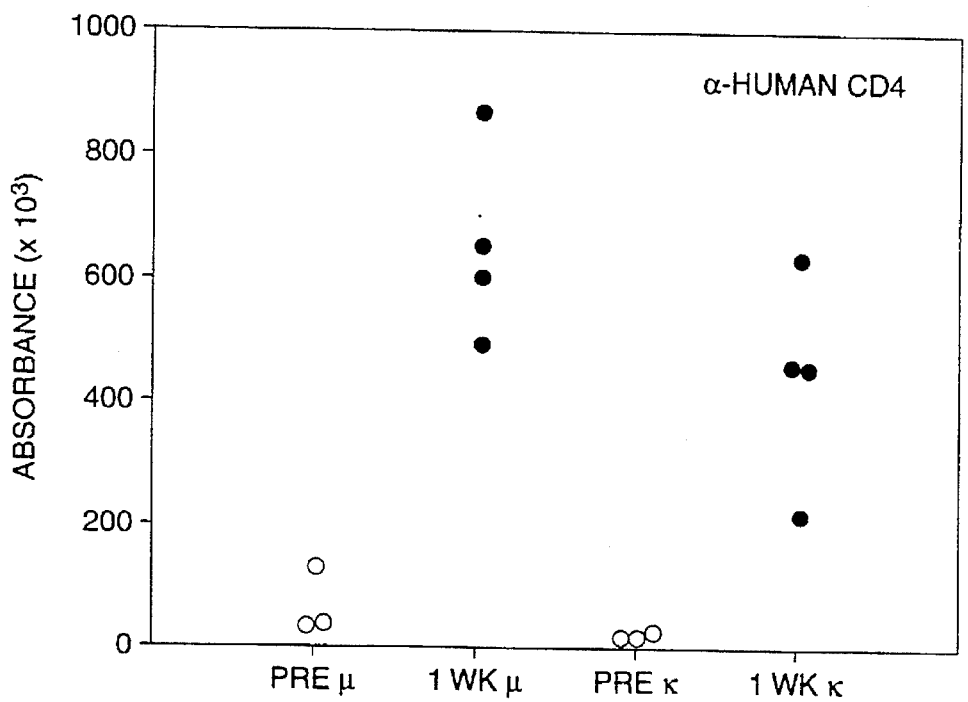
Figure 71B:
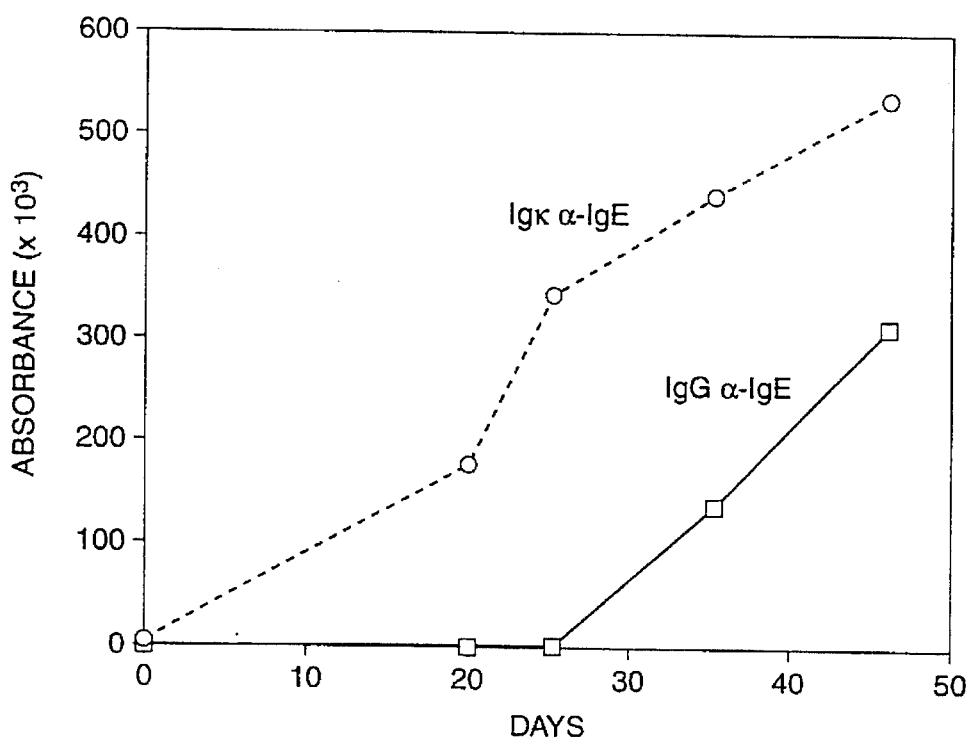

FIGS. 71A and 71B show human antibody responses to human antigens. FIG. 71A: Primary response to recombinant human soluble CD4. Levels of human IgM and human κ light chain are reported for prebleed (O) and post-immunization (•) serum from four double transgenic mice. FIG. 71B: Switching to human IgG occurs in vivo. Human IgG (circles) was detected with peroxidase conjugated polyclonal anti-human IgG used in the presence of 1.5 μ/ml excess IgE, κ and 1% normal mouse serum to inhibit non-specific cross-reactivity. Human κ light chain (squares) was detected using a peroxidase conjugated polyclonal anti-human κ reagent in the presence of 1% normal mouse serum. A representative result from one mouse (#9344; HC2 line 2550, KCo4 line 4436) is shown. Each point represents an average of duplicate wells minus background absorbance.

Figure 72:
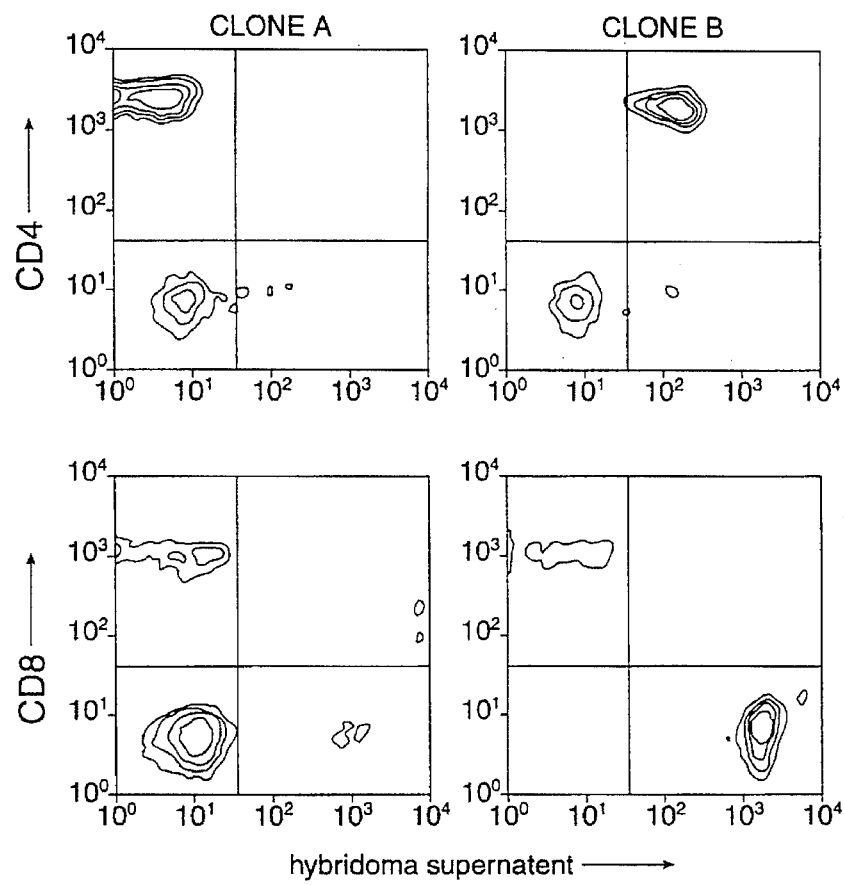

FIG. 72 shows FACS analysis of human PBL with a hybridoma supernatant that discriminates human CD4+ lymphocytes from human CD8+ lymphocytes.

Figure 73:
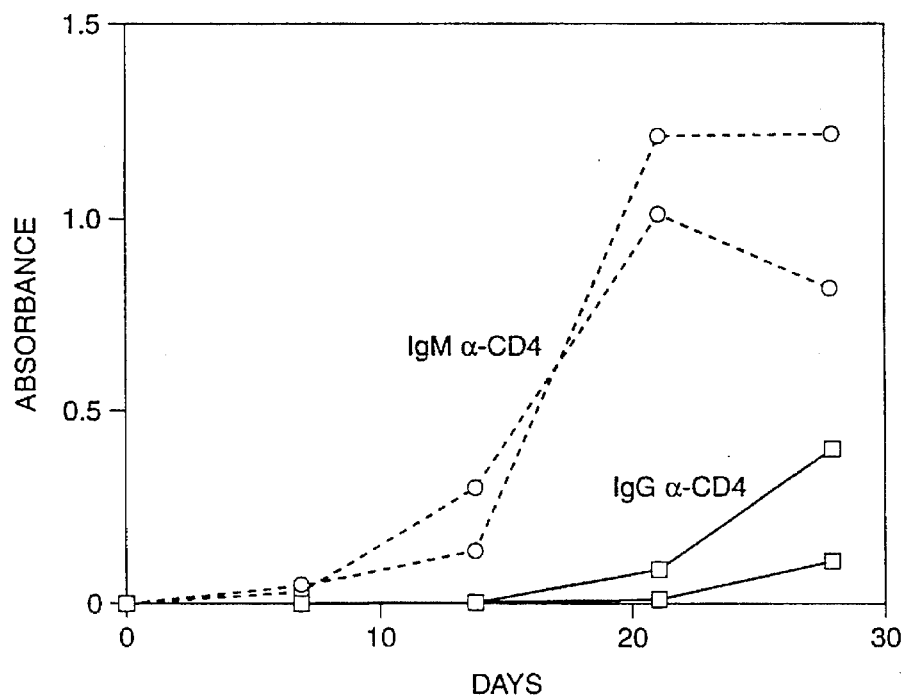

FIG. 73 shows human α-CD4 IgM anf IgG in transgenic mouse serum.

Figure 74:
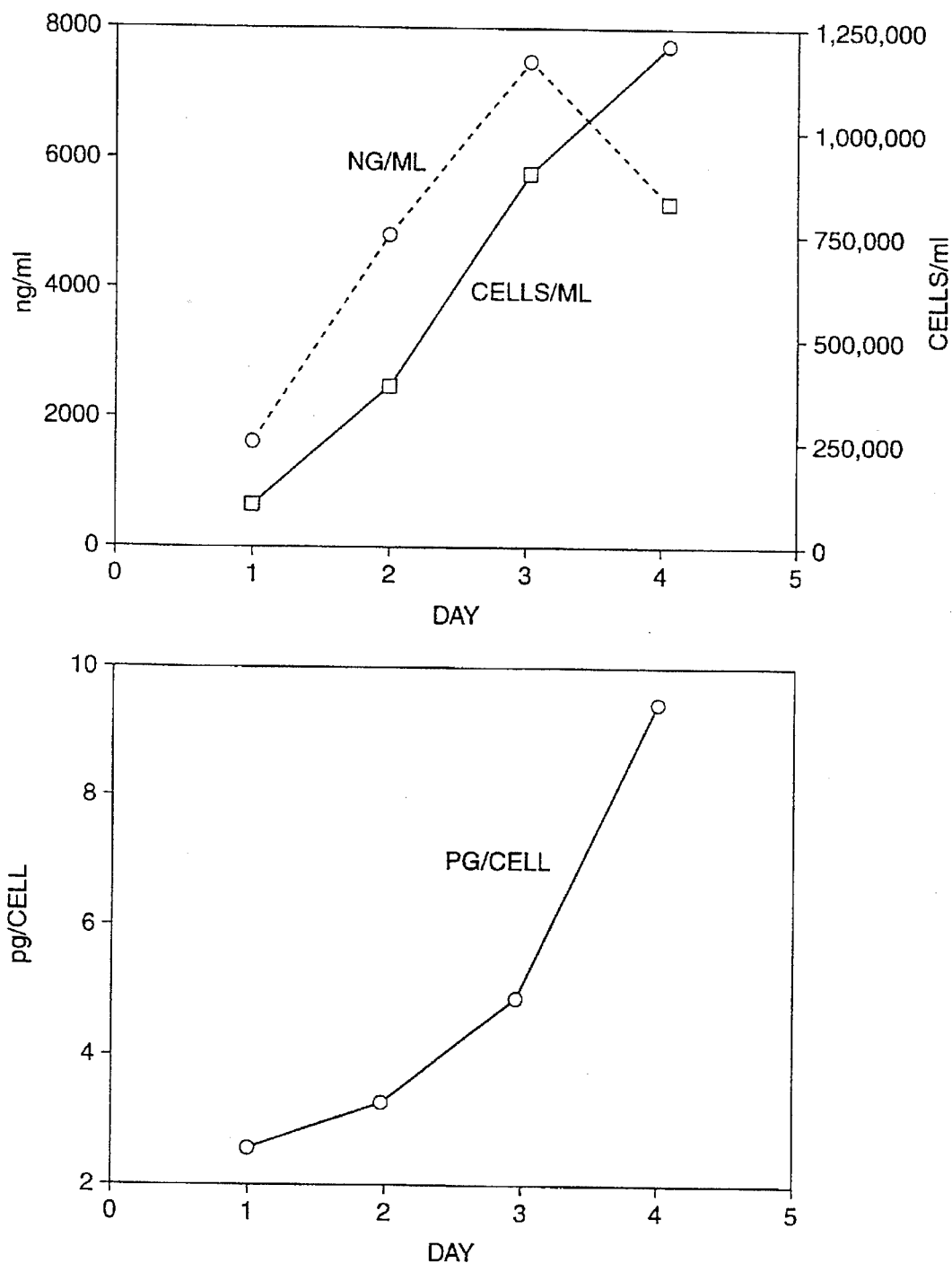

FIG. 74 shows competition binding experiments comparing a transgenic mouse α-human CD4 hybridoma monoclonal, 2C11-8, to the RPA-TA and Leu-3A monoclonals.

FIG. 75 shows production data for Ig expression of cultured 2C11-8 hybridoma.

Figure 76:
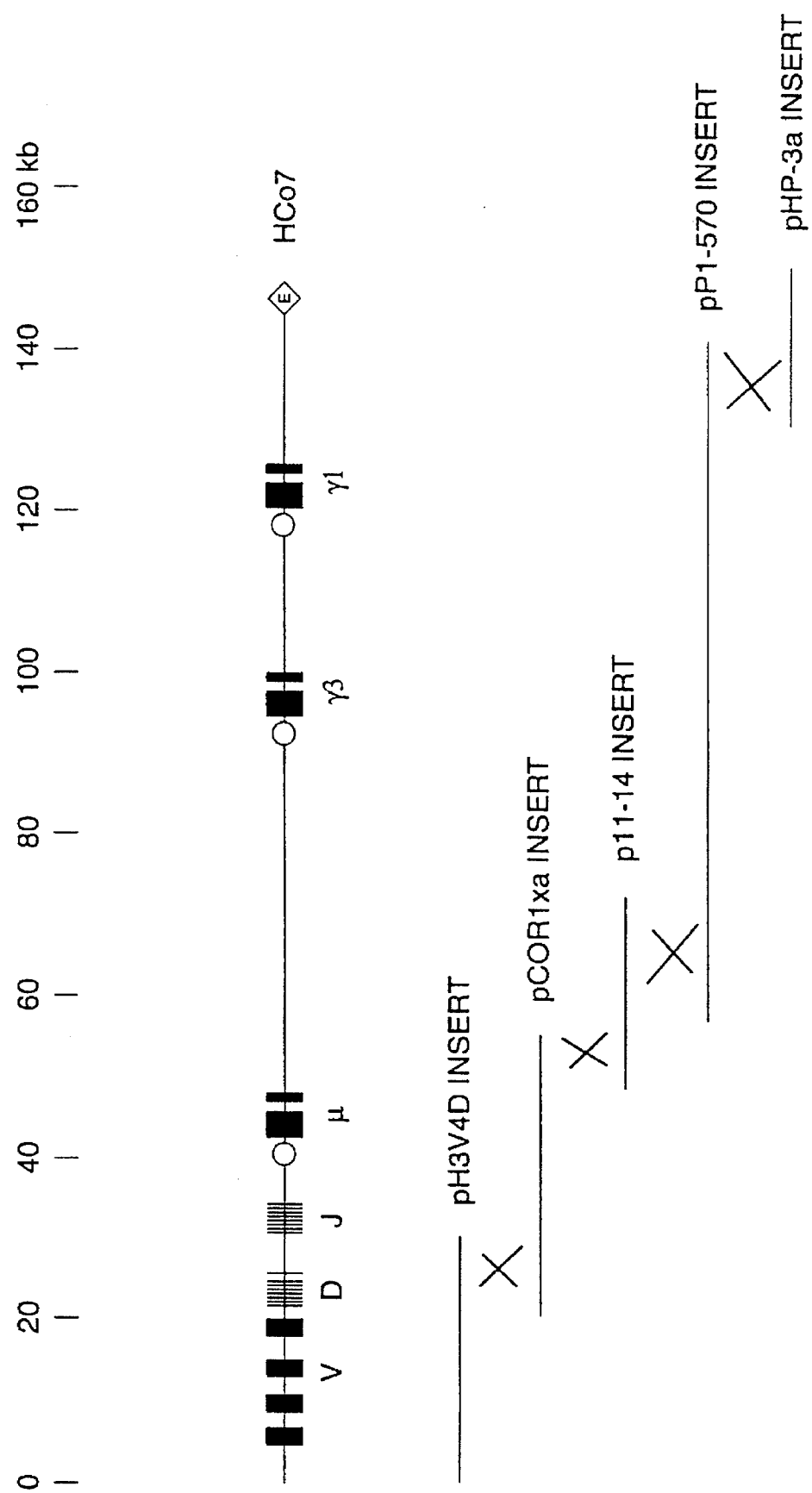

FIG. 76 shows an overlapping set of plasmid inserts constituting the HCo7 transgene.

FIG. 77A depicts the nucleotide sequence and restriction map of pGP2b plasmid vector.

Figure 77B:
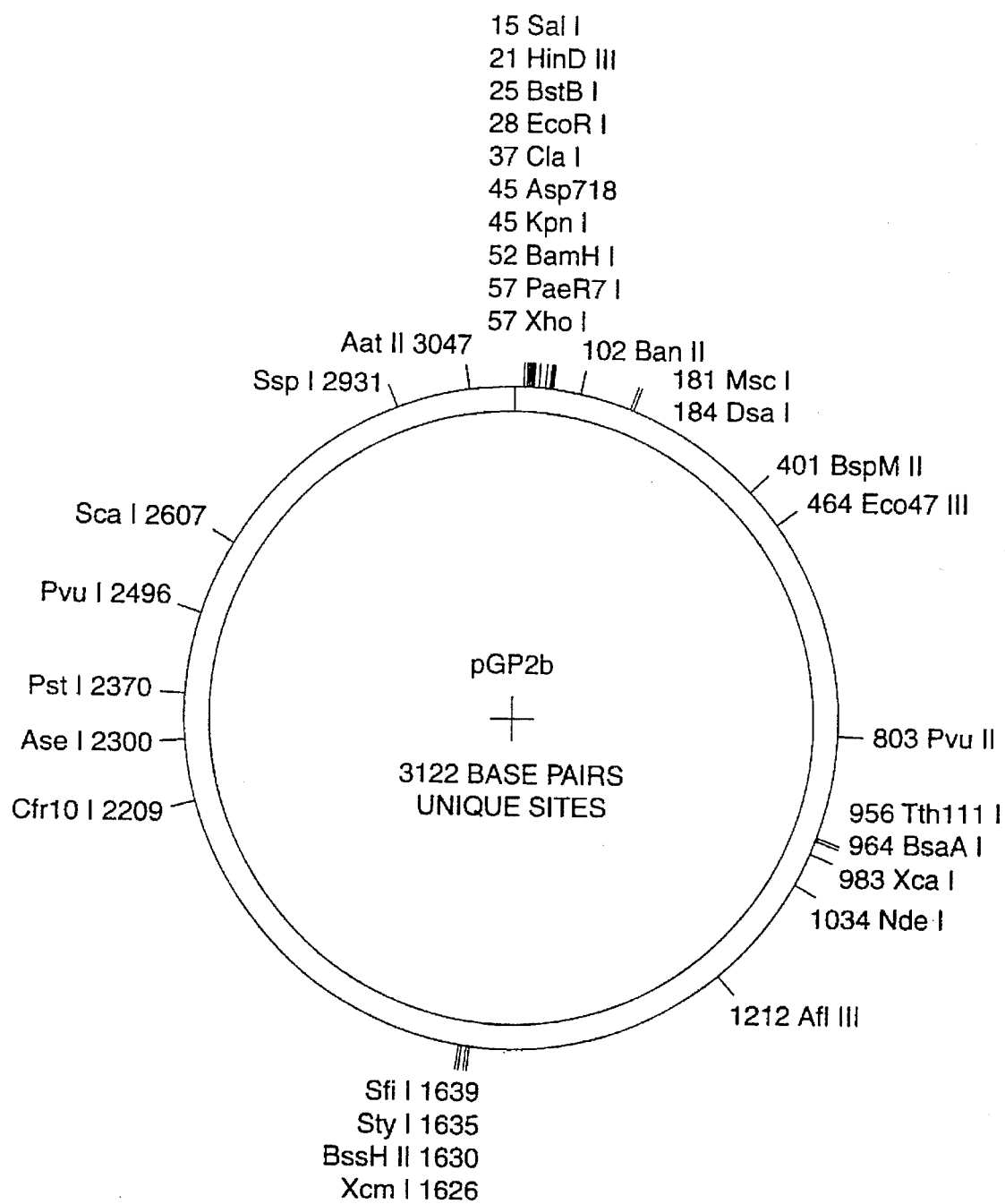

FIG. 77B depicts the restriction map of pGP2b plasmid vector.

Figure 78:
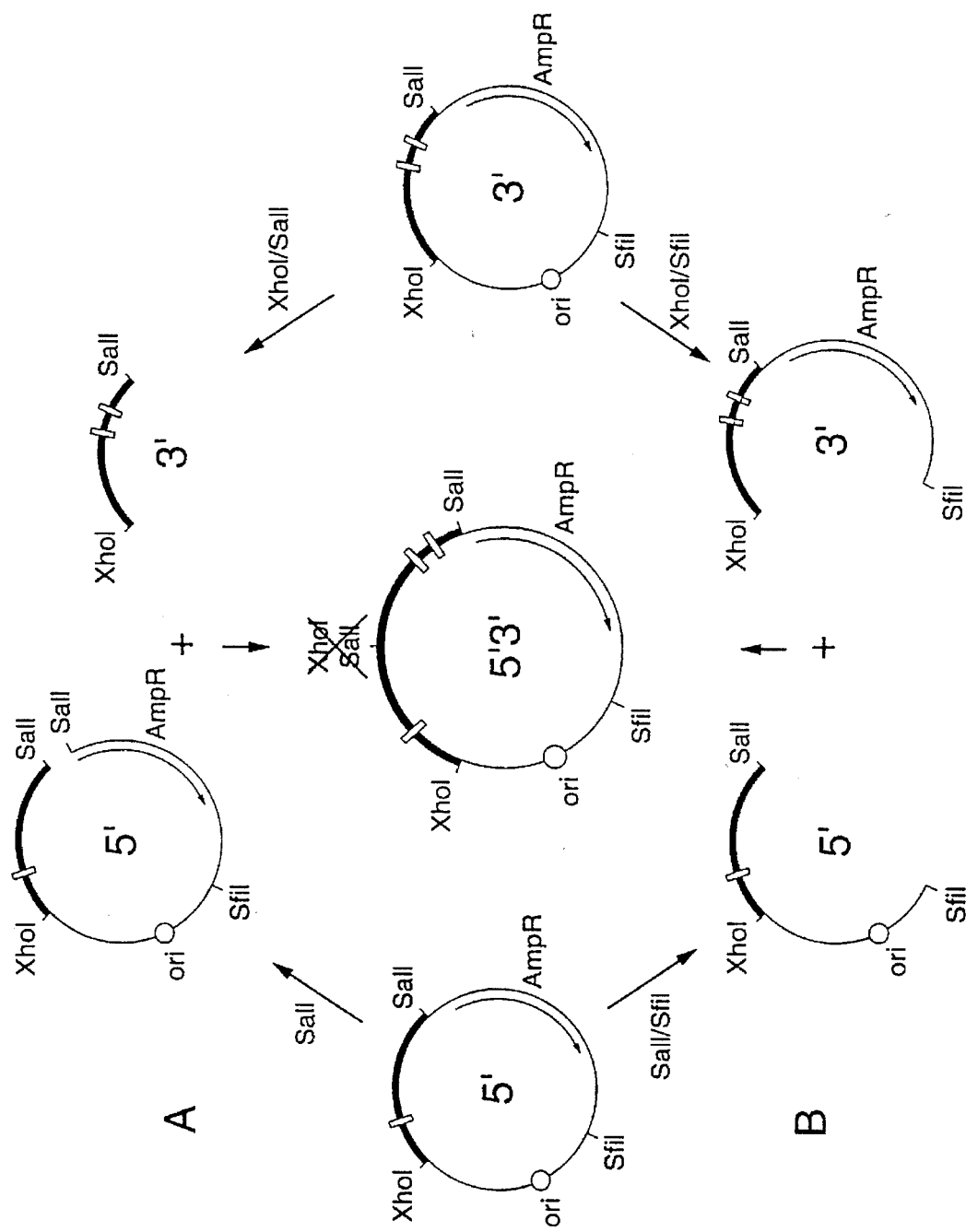

FIG. 78 (parts A and B) depicts cloning strategy for assembling large transgenes.

Figure 79:
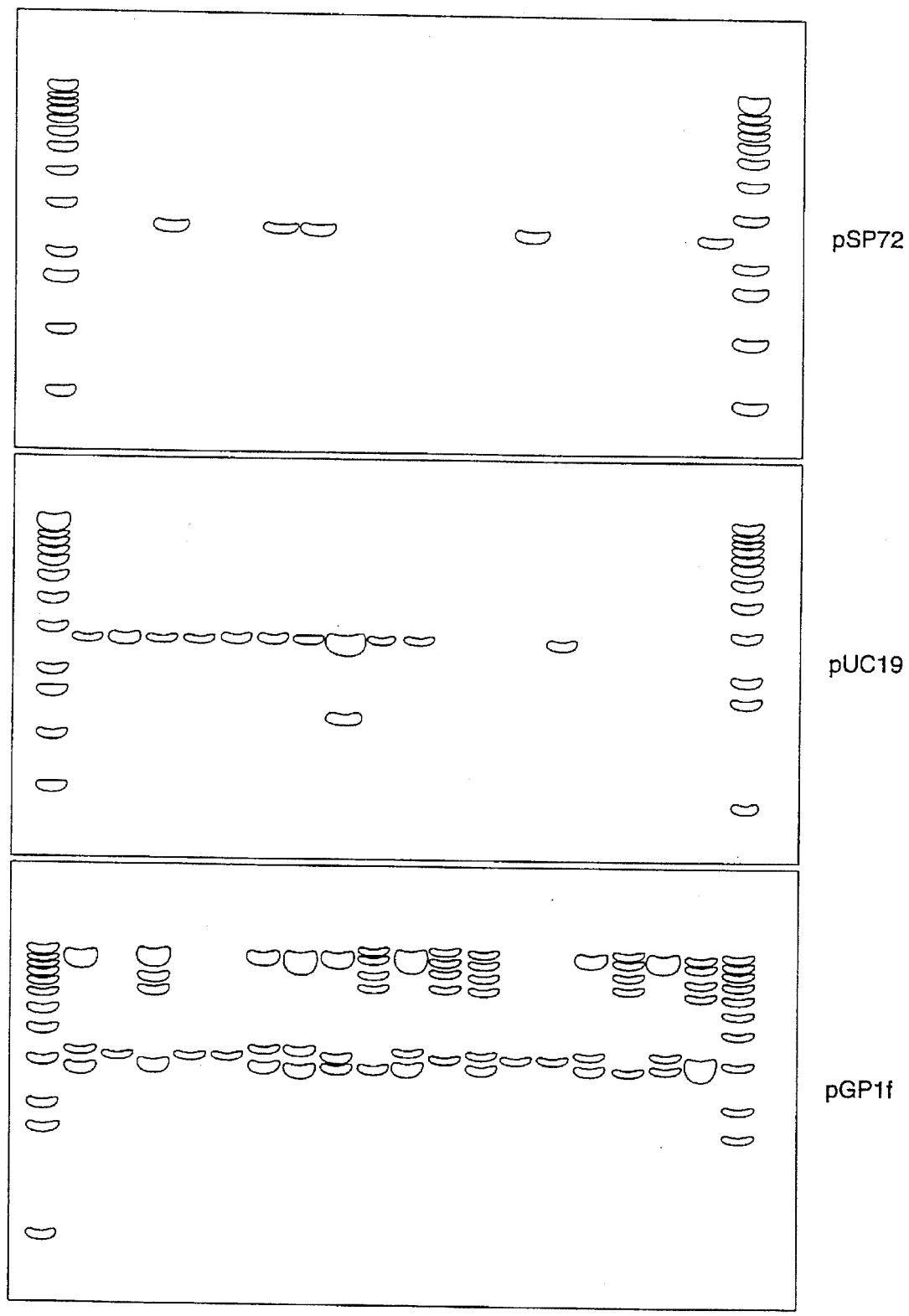

FIG. 79 shows that large inserts are unstable in high-copy pUC derived plasmids.

Figure 80:
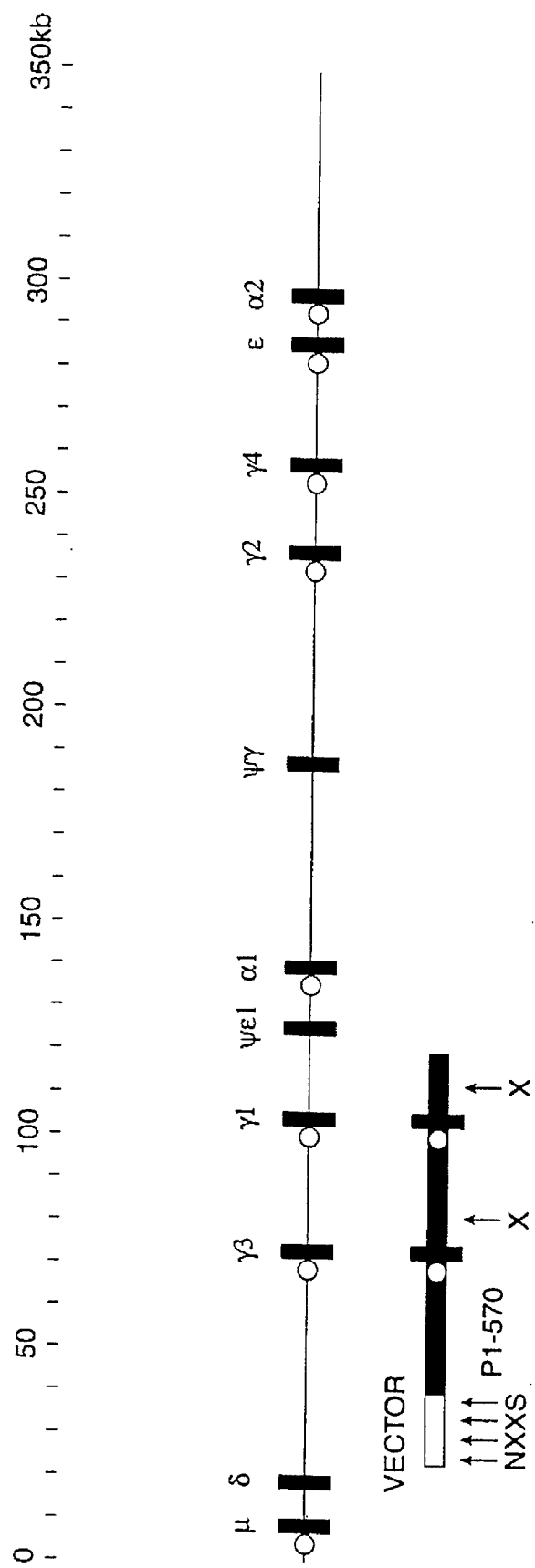

FIG. 80 shows phage P1 clone P1-570. Insert spans portion of human heavy chain constant region covering γ3 and γ1, together with switch elements. N, NotI; S, SalI, X, XhoI.

Figure 81:
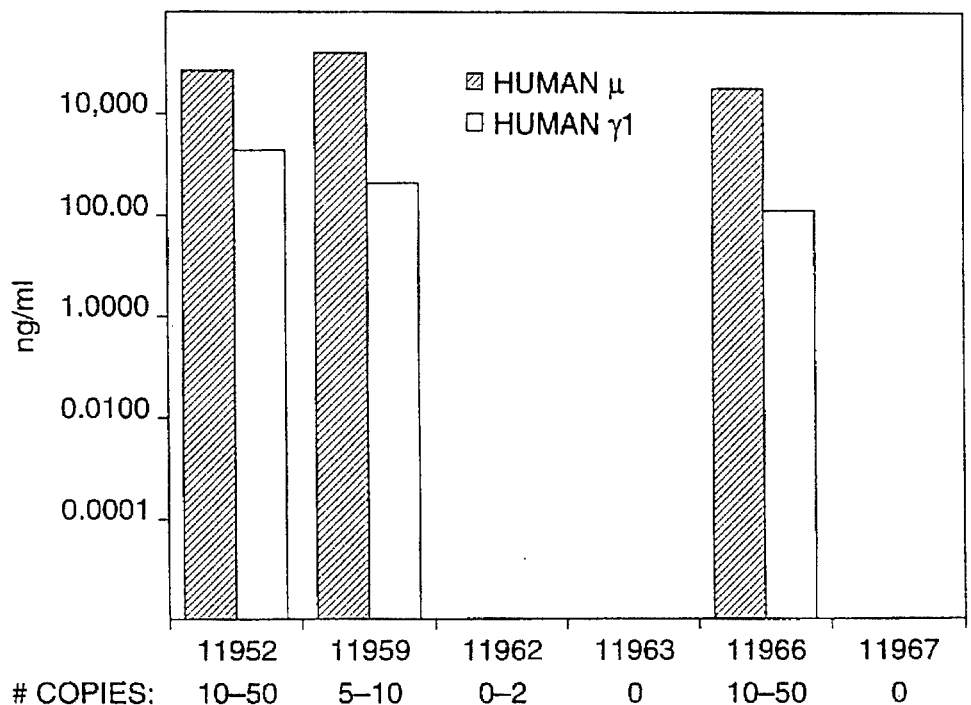

FIG. 81 shows serum expression of human μ and γ1 in HCo7 transgenic founder animals.

Figure 82:
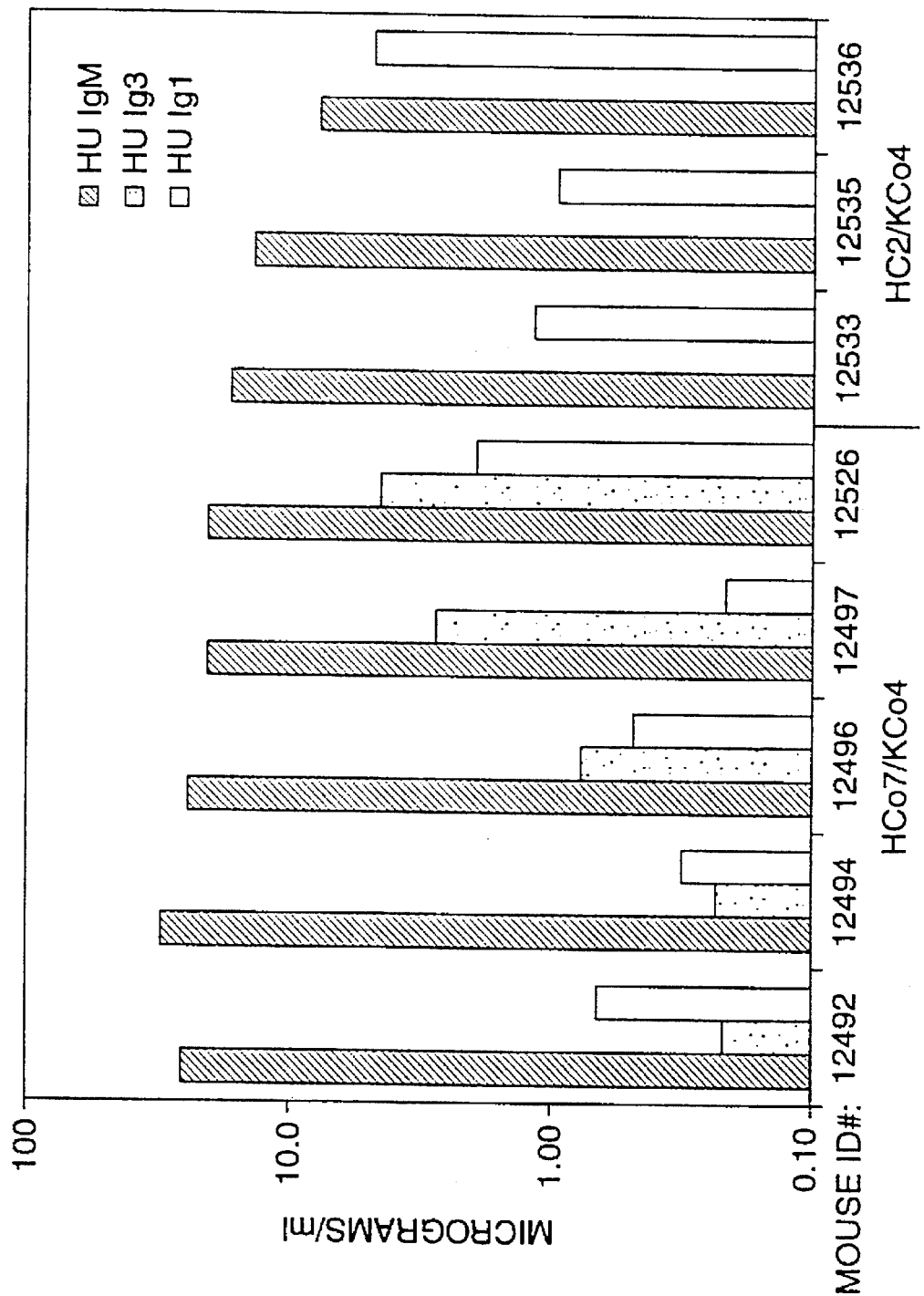

FIG. 82 shows serum expression of human immunoglobulins in HCo7/KCo4 double transgenic/double deletion mice.

Figure 83:
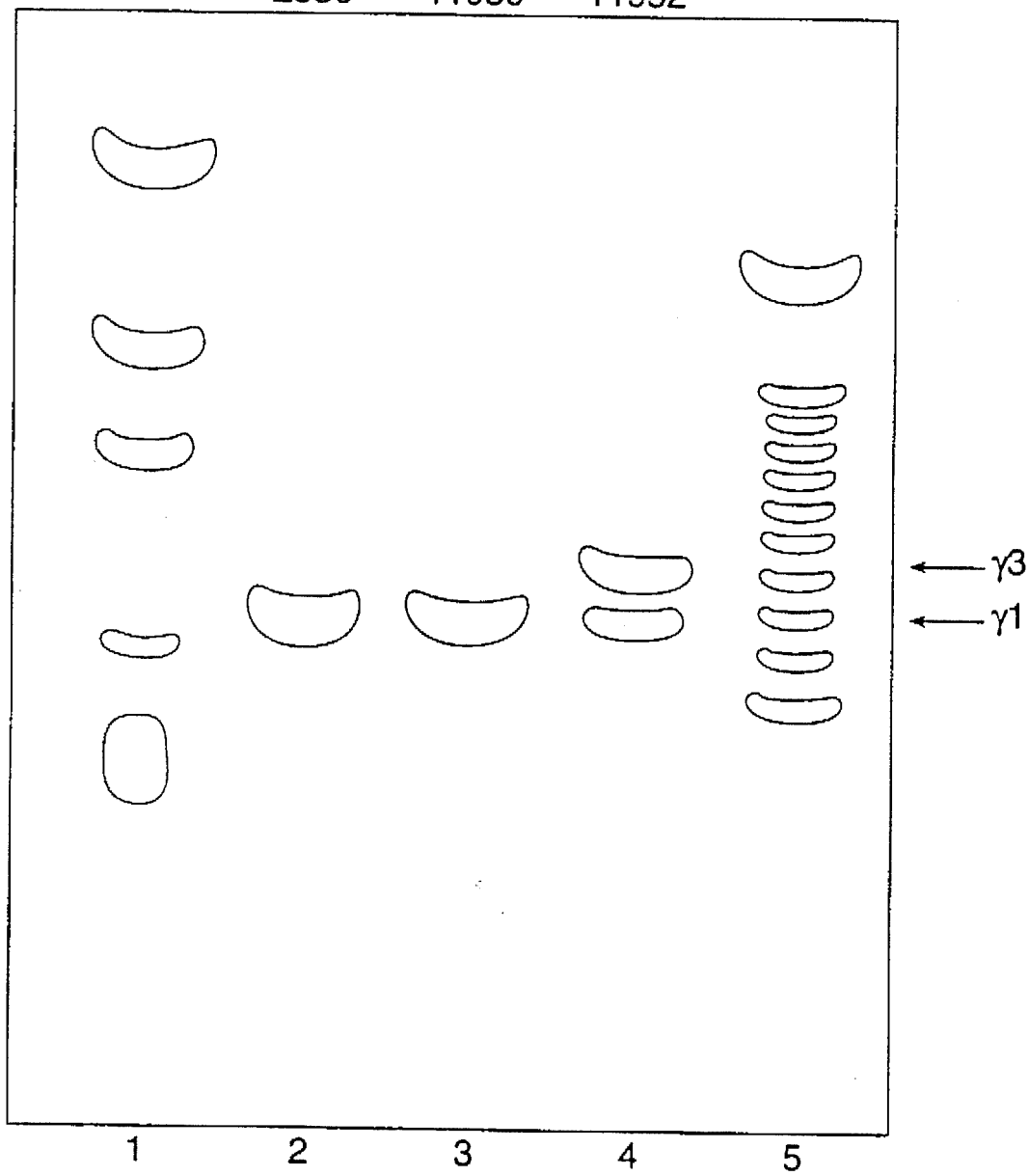

FIG. 83 shows RT PCR detection of human γ1 and γ3 transcripts in HCo7 transgenic mouse spleen RNA.

Figure 84:
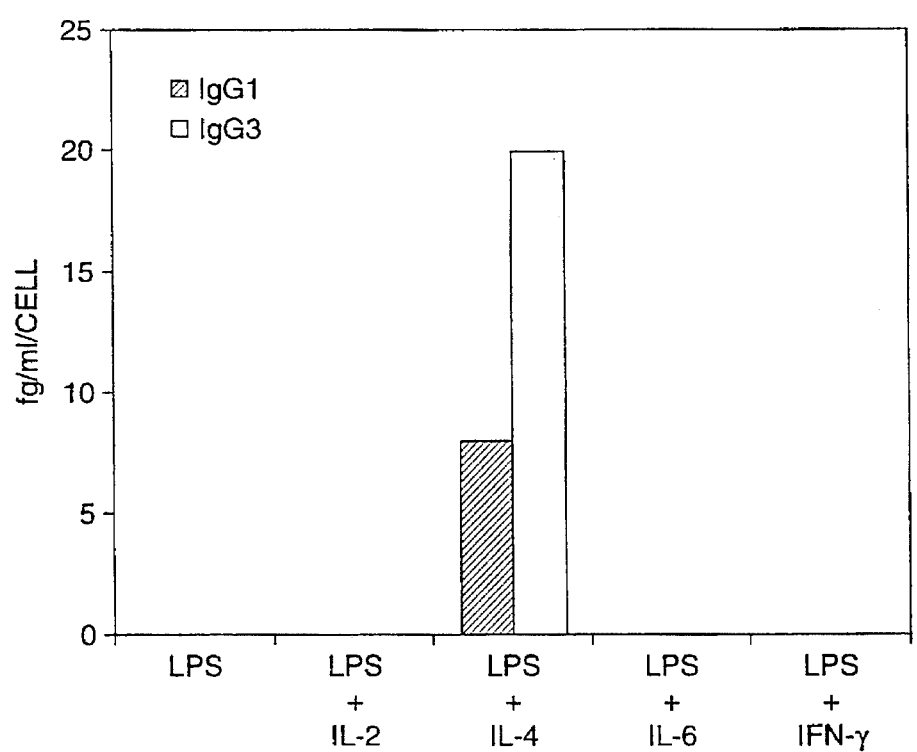

FIG. 84 shows induction of human IgG1 and IgG3 by LPS and IL-4 in vitro.

Table 1 depicts the sequence of vector pGPe.

Table 2 depicts the sequence of gene $V_H49.8$.

Table 3 depicts the detection of human IgM and IgG in the serum of transgenic mice of this invention.

Table 4 depicts sequences of VDJ joints.

Table 5 depicts the distribution of J segments incorporated into pHC1 transgene encoded transcripts to J segments found in adult human peripheral blood lymphocytes (PBL).

Table 6 depicts the distribution of D segments incorporated into pHC1 transgene encoded transcripts to D segments found in adult human peripheral blood lymphocytes (PBL).

Table 7 depicts the length of the CDR3 peptides from transcripts with in-frame VDJ joints in the pHC1 transgenic mouse and in human PBL.

Table 8 depicts the predicted amino acid sequences of the VDJ regions from 30 clones analyzed from a pHC1 transgenic.

Table 9 shows transgenic mice of line 112 that were used in the indicated experiments; (+) indicates the presence of the respective transgene, (++) indicates that the animal is homozygous for the $J_HD$ knockout transgene.

Table 10 shows the genotypes of several 0011 mice.

Table 11 shows transgene V and J segment usage.

Table 12 shows the occurrence of somatic mutation in the HC2 heavy chain transgene in transgenic mice.

DETAILED DESCRIPTION

As has been discussed supra, it is desirable to produce human immunoglobulins that are reactive with specific human antigens that are promising therapeutic and/or diagnostic targets. However, producing human immunoglobulins that bind specifically with human antigens is problematic.

First, the immunized animal that serves as the source of B cells must make an immune response against the presented antigen. In order for an animal to make an immune response, the antigen presented must be foreign and the animal must not be tolerant to the antigen. Thus, for example, if it is desired to produce a human monoclonal antibody with an idiotype that binds to a human protein, self-tolerance will prevent an immunized human from making a substantial immune response to the human protein, since the only epitopes of the antigen that may be immunogenic will be those that result from polymorphism of the protein within the human population (allogeneic epitopes).

Second, if the animal that serves as the source of B-cells for forming a hybridoma (a human in the illustrative given example) does make an immune response against an authentic self antigen, a severe autoimmune disease may result in the animal. Where humans would be used as a source of B-cells for a hybridoma, such autoimmunization would be considered unethical by contemporary standards. Thus, developing hybridomas secreting human immunoglobulin chainsspecifically reactive with predetermined human antigens is problematic, since a reliable source of human antibody-secreting B cells that can evoke an antibody response against predetermined human antigens is needed.

One methodology that can be used to obtain human antibodies that are specifically reactive with human antigens is the production of a transgenic mouse harboring the human immunoglobulin transgene constructs of this invention. Briefly, transgenes containing all or portions of the human immunoglobulin heavy and light chain loci, or transgenes containing synthetic "miniloci" (described infra, and in copending applications U.S. Ser. No. 07/990,860, filed 16 Dec. 1992, U.S. Ser. No. 07/810,279 filed 17 Dec. 1991, U.S. Ser. No. 07/904,068 filed 23 June 1992; U.S. Ser. No. 07/853,408, filed 18 March 1992, U.S. Ser. No. 07/574,748 filed Aug. 29, 1990, U.S. Ser. No. 07/575,962 filed Aug. 31, 1990, and PCT/US91/06185 filed Aug. 28, 1991, each incorporated herein by reference) which comprise essential functional elements of the human heavy and light chain loci, are employed to produce a transgenic nonhuman animal. Such a transgenic nonhuman animal will have the capacity to produce immunoglobulin chains that are encoded by human immunoglobulin genes, and additionally will be capable of making an immune response against human antigens. Thus, such transgenic animals can serve as a source of immune sera reactive with specified human antigens, and B-cells from such transgenic animals can be fused with myeloma cells to produce hybridomas that secrete monoclonal antibodies that are encoded by human immunoglobulin genes and which are specifically reactive with human antigens.

The production of transgenic mice containing various forms of immunoglobulin genes has been reported previously. Rearranged mouse immunoglobulin heavy or light chain genes have been used to produce transgenic mice. In addition, functionally rearranged human Ig genes including the μ or γ1 constant region have been expressed in transgenic mice. However, experiments in which the transgene comprises unrearranged (V-D-J or V-J not rearranged) immunoglobulin genes have been variable, in some cases, producing incomplete or minimal rearrangement of the transgene. However, there are no published examples of either rearranged or unrearranged immunoglobulin transgenes which undergo successful isotype switching between $C_H$ genes within a transgene.

The invention also provides a method for identifying candidate hybridomas which secrete a monoclonal antibody comprising a human immunoglobulin chain consisting essentially of a human VDJ sequence in polypeptide linkage to a human constant region sequence. Such candidate hybridomas are identified from a pool of hybridoma clones comprising: (1) hybridoma clones that express immunoglobulin chains consisting essentially of a human VDJ region and a human constant region, and (2) trans-switched hybridomas that express heterohybrid immunoglobulin chains consisting essentially of a human VDJ region and a murine constant region. The supernatant(s) of individual or pooled hybridoma clones is contacted with a predetermined antigen, typically an antigen which is immobilized by adsoption onto a solid substrate (e.g., a microtiter well), under binding conditions to select antibodies having the predetermined antigen binding specificity. An antibody that specifically binds to human constant regions is also contacted with the hybridoma supernatant and predetermined antigen under binding conditions so that the antibody selectively binds to at least one human constant region epitope but substantially does not bind to murine constant region epitopes; thus forming complexes consisting essentially of hybridoma supernatant (transgenic monoclonal antibody) bound to a predetermined antigen and to an antibody that specifically binds human constant regions (and which may be labeled with a detectable label or reporter). Detection of the formation of such complexes indicates hybridoma clones or pools which express a human immunoglobulin chain.

Definitions

As used herein, the term "antibody" refers to a glycoprotein comprising at least two light polypeptide chains and two heavy polypeptide chains. Each of the heavy and light polypeptide chains contains a variable region (generally the amino terminal portion of the polypeptide chain) which contains a binding domain which interacts with antigen. Each of the heavy and light polypeptide chains also comprises a constant region of the polypeptide chains (generally the carboxyl terminal portion) which may mediate the binding of the immunoglobulin to host tissues or factors including various cells of the immune system, some phagocytic cells and the first component (C1q) of the classical complement system.

As used herein, a "heterologous antibody" is defined in relation to the transgenic non-human organism producing such an antibody. It is defined as an antibody having an amino acid sequence or an encoding DNA sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody.

As used herein, "isotype" refers to the antibody class (e.g., IgM or IgG$_1$) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the $C_H$ gene encoding the nonswitched isotype is typically the first $C_H$ gene immediately downstream from the functionally rearranged VDJ gene.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the $C_H$ genes of the transgene were derived.

As used herein, "specific binding" refers to the property of the antibody: (1) to bind to a predetermined antigen with an affinity of at least $1 \times 10^7$ M$^{-1}$, and (2) to preferentially bind to the predetermined antigen with an affinity that is at least two-fold greater than its affinity for binding to a non-specific antigen (e.g., BSA, casein) other than the predetermined antigen or a closely-related antigen.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98 to 99.5% of the nucleotides. Alternatively, substantial homology exists when the segments will hybridize under selective hybridization conditions, to the complement of the strand. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley-Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

Transgenic Nonhuman Animals Capable of Producing Heterologous Antibodies

The design of a transgenic non-human animal that responds to foreign antigen stimulation with a heterologous antibody repertoire, requires that the heterologous immunoglobulin transgenes contained within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

As will be apparent from the following disclosure, not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y., which is incorporated herein by reference.

In one aspect of the invention, transgenic non-human animals are provided that contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences made be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 18:7305–7316 (1991); Sideras et al., *Intl. Immunol.* 1:631–642 (1989), which are incorporated herein by reference).

For each of the foregoing transgenic animals, functionally rearranged heterologous heavy and light chain immunoglobulin transgenes are found in a significant fraction of the B-cells of the transgenic animal (at least 10 percent).

The transgenes of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment.

The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

The invention also includes transgenic animals containing germ line cells having a heavy and light transgene wherein one of the said transgenes contains rearranged gene segments with the other containing unrearranged gene segments. In the preferred embodiments, the rearranged transgene is a light chain immunoglobulin transgene and the unrearranged transgene is a heavy chain immunoglobulin transgene.

The Structure and Generation of Antibodies

The basic structure of all immunoglobulins is based upon a unit consisting of two light polypeptide chains and two heavy polypeptide chains. Each light chain comprises two regions known as the variable light chain region and the constant light chain region. Similarly, the immunoglobulin heavy chain comprises two regions designated the variable heavy chain region and the constant heavy chain region.

The constant region for the heavy or light chain is encoded by genomic sequences referred to as heavy or light constant region gene ($C_H$) segments. The use of a particular heavy chain gene segment defines the class of immunoglobulin. For example, in humans, the μ constant region gene segments define the IgM class of antibody whereas the use of a γ, γ2, γ3 or γ4 constant region gene segment defines the IgG class of antibodies as well as the IgG subclasses IgG1 through IgG4. Similarly, the use of a $\alpha_1$ or $\alpha_2$ constant region gene segment defines the IgA class of antibodies as well as the subclasses IgA1 and IgA2. The δ and ε constant region gene segments define the IgD and IgE antibody classes, respectively.

The variable regions of the heavy and light immunoglobulin chains together contain the antigen binding domain of the antibody. Because of the need for diversity in this region of the antibody to permit binding to a wide range of antigens, the DNA encoding the initial or primary repertoire variable region comprises a number of different DNA segments derived from families of specific variable region gene segments. In the case of the light chain variable region, such families comprise variable (V) gene segments and joining (J) gene segments. Thus, the initial variable region of the light chain is encoded by one V gene segment and one J gene segment each selected from the family of V and J gene segments contained in the genomic DNA of the organism. In the case of the heavy chain variable region, the DNA encoding the initial or primary repertoire variable region of the heavy chain comprises one heavy chain V gene segment, one heavy chain diversity (D) gene segment and one J gene segment, each selected from the appropriate V, D and J families of immunoglobulin gene segments in genomic DNA.

In order to increase the diversity of sequences that contribute to forming antibody binding sites, it is preferable that a heavy chain transgene include cis-acting sequences that support functional V-D-J rearrangement that can incorporate all or part of a D region gene sequence in a rearranged V-D-J gene sequence. Typically, at least about 1 percent of expressed transgene-encoded heavy chains (or mRNAs) include recognizable D region sequences in the V region. Preferably, at least about 10 percent of transgene-encoded V regions include recognizable D region sequences, more preferably at least about 30 percent, and most preferably more than 50 percent include recognizable D region sequences.

A recognizable D region sequence is generally at least about eight consecutive nucleotides corresponding to a sequence present in a D region gene segment of a heavy chain transgene and/or the amino acid sequence encoded by such D region nucleotide sequence. For example, if a transgene includes the D region gene DHQ52, a transgene-encoded mRNA containing the sequence 5'-TAACTGGG-3' located in the V region between a V gene segment sequence and a J gene segment sequence is recognizable as containing a D region sequence, specifically a DHQ52 sequence. Similarly, for example, if a transgene includes the D region gene DHQ52, a transgene-encoded heavy chain polypeptide containing the amino acid sequence -DAF- located in the V region between a V gene segment amino acid sequence and a J gene segment amino acid sequence may be recognizable as containing a D region sequence, specifically a DHQ52 sequence. However, since D region segments may be incorporated in VDJ joining to various extents and in various reading frames, a comparison of the D region area of a heavy chain variable region to the D region segments present in the transgene is necessary to determine the incorporation of particular D segments. Moreover, potential exonuclease digestion during recombination may lead to imprecise V-D and D-J joints during V-D-J recombination.

However, because of somatic mutation and N-region addition, some D region sequences may be recognizable but may not correspond identically to a consecutive D region sequence in the transgene. For example, a nucleotide sequence 5'-CTAAXTGGGG-3', where X is A, T, or G, and which is located in a heavy chain V region and flanked by a V region gene sequence and a J region gene sequence, can be recognized as corresponding to the DHQ52 sequence 5'-CTAACTGGG-3'. Similarly, for example, the polypeptide sequences -DAFDI-, -DYFDY-, or -GAFDI- located in a V region and flanked on the amino-terminal side by an amino acid sequence encoded by a transgene V gene sequence and flanked on the carboxyterminal side by an amino acid sequence encoded by a transgene J gene sequence is recognizable as a D region sequence.

Therefore, because somatic mutation and N-region addition can produce mutations in sequences derived from a transgene D region, the following definition is provided as a guide for determining the presence of a recognizable D region sequence. An amino acid sequence or nucleotide sequence is recognizable as a D region sequence if: (1) the sequence is located in a V region and is flanked on one side by a V gene sequence (nucleotide sequence or deduced amino acid sequence) and on the other side by a J gene sequence (nucleotide sequence or deduced amino acid sequence) and (2) the sequence is substantially identical or substantially similar to a known D gene sequence (nucleotide sequence or encoded amino acid sequence).

The term "substantial identity" as used herein denotes a characteristic of a polypeptide sequence or nucleic acid sequence, wherein the polypeptide sequence has at least 50 percent sequence identity compared to a reference sequence, and the nucleic acid sequence has at least 70 percent sequence identity compared to a reference sequence. The percentage of sequence identity is calculated excluding small deletions or additions which total less than 35 percent of the reference sequence. The reference sequence may be a subset of a larger sequence, such as an entire D gene; however, the reference sequence is at least 8 nucleotides long in the case of polynucleotides, and at least 3 amino residues long in the case of a polypeptide. Typically, the reference sequence is at least 8 to 12 nucleotides or at least 3 to 4 amino acids, and preferably the reference sequence is 12 to 15 nucleotides or more, or at least 5 amino acids.

The term "substantial similarity" denotes a characteristic of an polypeptide sequence, wherein the polypeptide sequence has at least 80 percent similarity to a reference sequence. The percentage of sequence similarity is calculated by scoring identical amino acids or positional conservative amino acid substitutions as similar. A positional conservative amino acid substitution is one that can result from a single nucleotide substitution; a first amino acid is replaced by a second amino acid where a codon for the first amino acid and a codon for the second amino acid can differ by a single nucleotide substitution. Thus, for example, the sequence -Lys-Glu-Arg-Val- is substantially similar to the sequence -Asn-Asp-Ser-Val-, since the codon sequence -AAA-GAA-AGA-GUU- can be mutated to -AAC-GAC-AGC-GUU- by introducing only 3 substitution mutations, single nucleotide substitutions in three of the four original codons. The reference sequence may be a subset of a larger sequence, such as an entire D gene; however, the reference sequence is at least 4 amino residues long. Typically, the reference sequence is at least 5 amino acids, and preferably the reference sequence is 6 amino acids or more.

The Primary Repertoire

The process for generating DNA encoding the heavy and light chain immunoglobulin genes occurs primarily in developing B-cells. Prior to the joining of various immunoglobulin gene segments, the V, D, J and constant (C) gene segments are found, for the most part, in clusters of V, D, J and C gene segments in the precursors of primary repertoire B-cells. Generally, all of the gene segments for a heavy or light chain are located in relatively close proximity on a single chromosome. Such genomic DNA prior to recombination of the various immunoglobulin gene segments is referred to herein as "unrearranged" genomic DNA. During B-cell differentiation, one of each of the appropriate family members of the V, D, J (or only V and J in the case of light chain genes) gene segments are recombined to form functionally rearranged heavy and light immunoglobulin genes. Such functional rearrangement is of the variable region segments to form DNA encoding a functional variable region. This gene segment rearrangement process appears to be sequential. First, heavy chain D-to-J joints are made, followed by heavy chain V-to-DJ joints and light chain V-to-J joints. The DNA encoding this initial form of a functional variable region in a light and/or heavy chain is referred to as "functionally rearranged DNA" or "rearranged DNA". In the case of the heavy chain, such DNA is referred to as "rearranged heavy chain DNA" and in the case of the light chain, such DNA is referred to as "rearranged light chain DNA". Similar language is used to describe the functional rearrangement of the transgenes of the invention.

The recombination of variable region gene segments to form functional heavy and light chain variable regions is mediated by recombination signal sequences (RSS's) that flank recombinationally competent V, D and J segments. RSS's necessary and sufficient to direct recombination, comprise a dyad-symmetric heptamer, an AT-rich nonamer and an intervening spacer region of either 12 or 23 base pairs. These signals are conserved among the different loci and species that carry out D-J (or V-J) recombination and are functionally interchangeable. See Oettinger, et al. (1990), *Science*, 248, 1517–1523 and references cited therein. The heptamer comprises the sequence CACAGTG or its analogue followed by a spacer of unconserved sequence and then a nonamer having the sequence ACAAAAACC or its analogue. These sequences are found on the J, or downstream side, of each V and D gene segment. Immediately preceding the germline D and J segments are again two recombination signal sequences, first the nonamer and then the heptamer again separated by an unconserved sequence. The heptameric and nonameric sequences following a $V_L$, $V_H$ or D segment are complementary to those preceding the $J_L$, D or $J_H$ segments with which they recombine. The spacers between the heptameric and nonameric sequences are either 12 base pairs long or between 22 and 24 base pairs long.

In addition to the rearrangement of V, D and J segments, further diversity is generated in the primary repertoire of immunoglobulin heavy and light chain by way of variable recombination between the V and J segments in the light chain and between the D and J segments of the heavy chain. Such variable recombination is generated by variation in the exact place at which such segments are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity.

After VJ and/or VDJ rearrangement, transcription of the rearranged variable region and one or more constant region gene segments located downstream from the rearranged variable region produces a primary RNA transcript which upon appropriate RNA splicing results in an mRNA which encodes a full length heavy or light immunoglobulin chain. Such heavy and light chains include a leader signal sequence to effect secretion through and/or insertion of the immunoglobulin into the transmembrane region of the B-cell. The DNA encoding this signal sequence is contained within the first exon of the V segment used to form the variable region of the heavy or light immunoglobulin chain. Appropriate regulatory sequences are also present in the mRNA to control translation of the mRNA to produce the encoded heavy and light immunoglobulin polypeptides which upon proper association with each other form an antibody molecule.

The net effect of such rearrangements in the variable region gene segments and the variable recombination which may occur during such joining, is the production of a primary antibody repertoire. Generally, each B-cell which has differentiated to this stage, produces a single primary repertoire antibody. During this differentiation process, cellular events occur which suppress the functional rearrangement of gene segments other than those contained within the functionally rearranged Ig gene. The process by which diploid B-cells maintain such mono-specificity is termed allelic exclusion.

The Secondary Repertoire

B-cell clones expressing immunoglobulins from within the set of sequences comprising the primary repertoire are immediately available to respond to foreign antigens. Because of the limited diversity generated by simple VJ and VDJ joining, the antibodies produced by the so-called primary response are of relatively low affinity. Two different types of B-cells make up this initial response: precursors of primary antibody-forming cells and precursors of secondary repertoire B-cells (Linton et al., *Cell* 59:1049-1059 (1989)). The first type of B-cell matures into IgM-secreting plasma cells in response to certain antigens. The other B-cells respond to initial exposure to antigen by entering a T-cell dependent maturation pathway.

During the T-cell dependent maturation of antigen stimulated B-cell clones, the structure of the antibody molecule on the cell surface changes in two ways: the constant region switches to a non-IgM subtype and the sequence of the variable region can be modified by multiple single amino acid substitutions to produce a higher affinity antibody molecule.

Figure 1:
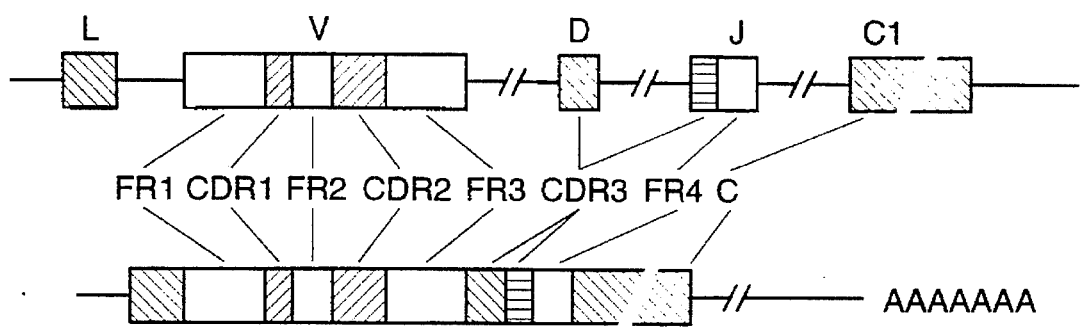
FIG. 1 depicts the complementarity determining regions CDR1, CDR2 and CDR3 and framework regions FR1, FR2, FR3 and FR4 in unrearranged genomic DNA and mRNA expressed from a rearranged immunoglobulin heavy chain gene.
Figure 2:
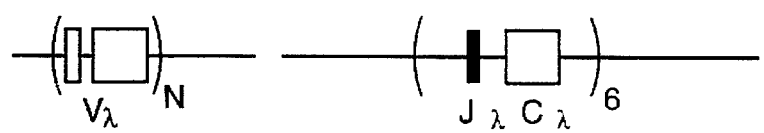
FIG. 2 depicts the human λ chain locus.
Figure 3:
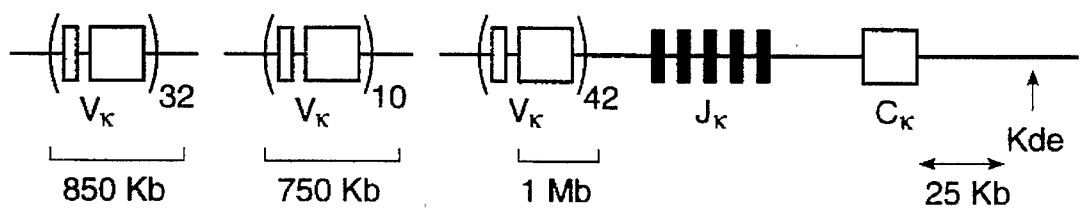
FIG. 3 depicts the human κ chain locus.

As previously indicated, each variable region of a heavy or light Ig chain contains an antigen binding domain. It has been determined by amino acid and nucleic acid sequencing that somatic mutation during the secondary response occurs throughout the V region including the three complementary determining regions (CDR1, CDR2 and CDR3) also referred to as hypervariable regions 1, 2 and 3 (Kabat et al. *Sequences of Proteins of Immunological Interest* (1991) U.S. Department of Health and Human Services, Washington, D.C., incorporated herein by reference. The CDR1 and CDR2 are located within the variable gene segment whereas the CDR3 is largely the result of recombination between V and J gene segments or V, D and J gene segments. Those portions of the variable region which do not consist of CDR1, 2 or 3 are commonly referred to as framework regions designated FR1, FR2, FR3 and FR4. See FIG. 1. During hypermutation, the rearranged DNA is mutated to give rise to new clones with altered Ig molecules. Those clones with higher affinities for the foreign antigen are selectively expanded by helper T-cells, giving rise to affinity maturation of the expressed antibody. Clonal selection typically results in expression of clones containing new mutation within the CDR1, 2 and/or 3 regions. However, mutations outside these regions also occur which influence the specificity and affinity of the antigen binding domain.

Transgenic Non-Human Animals Capable of Producing Heterologous Antibody

Transgenic non-human animals in one aspect of the invention are produced by introducing at least one of the immunoglobulin transgenes of the invention (discussed hereinafter) into a zygote or early embryo of a non-human animal. The non-human animals which are used in the invention generally comprise any mammal which is capable of rearranging immunoglobulin gene segments to produce a primary antibody response. Such nonhuman transgenic animals may include, for example, transgenic pigs, transgenic rats, transgenic rabbits, transgenic cattle, and other transgenic animal species, particularly mammalian species, known in the art. A particularly preferred non-human animal is the mouse or other members of the rodent family.

However, the invention is not limited to the use of mice. Rather, any non-human mammal which is capable of mounting a primary and secondary antibody response may be used. Such animals include non-human primates, such as chimpanzee, bovine, ovine, and porcine species, other members of the rodent family, e.g. rat, as well as rabbit and guinea pig. Particular preferred animals are mouse, rat, rabbit and guinea pig, most preferably mouse.

In one embodiment of the invention, various gene segments from the human genome are used in heavy and light chain transgenes in an unrearranged form. In this embodiment, such transgenes are introduced into mice. The unrearranged gene segments of the light and/or heavy chain transgene have DNA sequences unique to the human species which are distinguishable from the endogenous immunoglobulin gene segments in the mouse genome. They may be readily detected in unrearranged form in the germ line and somatic cells not consisting of B-cells and in rearranged form in B-cells.

In an alternate embodiment of the invention, the transgenes comprise rearranged heavy and/or light immunoglobulin transgenes. Specific segments of such transgenes corresponding to functionally rearranged VDJ or VJ segments, contain immunoglobulin DNA sequences which are also clearly distinguishable from the endogenous immunoglobulin gene segments in the mouse.

Such differences in DNA sequence are also reflected in the amino acid sequence encoded by such human immunoglobulin transgenes as compared to those encoded by mouse B-cells. Thus, human immunoglobulin amino acid sequences may be detected in the transgenic non-human animals of the invention with antibodies specific for immunoglobulin epitopes encoded by human immunoglobulin gene segments.

Transgenic B-cells containing unrearranged transgenes from human or other species functionally recombine the appropriate gene segments to form functionally rearranged light and heavy chain variable regions. It will be readily apparent that the antibody encoded by such rearranged transgenes has a DNA and/or amino acid sequence which is heterologous to that normally encountered in the nonhuman animal used to practice the invention.

Unrearranged Transgenes

As used herein, an "unrearranged immunoglobulin heavy chain transgene" comprises DNA encoding at least one variable gene segment, one diversity gene segment, one joining gene segment and one constant region gene segment. Each of the gene segments of said heavy chain transgene are derived from, or has a sequence corresponding to, DNA encoding immunoglobulin heavy chain gene segments from a species not consisting of the non-human animal into which said transgene is introduced. Similarly, as used herein, an "unrearranged immunoglobulin light chain transgene" comprises DNA encoding at least one variable gene segment, one joining gene segment and at least one constant region gene segment wherein each gene segment of said light chain transgene is derived from, or has a sequence corresponding to, DNA encoding immunoglobulin light chain gene segments from a species not consisting of the non-human animal into which said light chain transgene is introduced.

Such heavy and light chain transgenes in this aspect of the invention contain the above-identified gene segments in an unrearranged form. Thus, interposed between the V, D and J segments in the heavy chain transgene and between the V and J segments on the light chain transgene are appropriate recombination signal sequences (RSS's). In addition, such transgenes also include appropriate RNA splicing signals to join a constant region gene segment with the VJ or VDJ rearranged variable region.

In order to facilitate isotype switching within a heavy chain transgene containing more than one C region gene segment, e.g. Cμ and Cγ1 from the human genome, as explained below "switch regions" are incorporated upstream from each of the constant region gene segments and downstream from the variable region gene segments to permit recombination between such constant regions to allow for immunoglobulin class switching, e.g. from IgM to IgG. Such heavy and light immunoglobulin transgenes also contain transcription control sequences including promoter regions situated upstream from the variable region gene segments which typically contain TATA motifs. A promoter region can be defined approximately as a DNA sequence that, when operably linked to a downstream sequence, can produce transcription of the downstream sequence. Promoters may require the presence of additional linked cis-acting sequences in order to produce efficient transcription. In addition, other sequences that participate in the transcription of sterile transcripts are preferably included. Examples of sequences that participate in expression of sterile transcripts can be found in the published literature, including Rothman et al., *Intl. Immunol.* 2:621–627 (1990); Reid et al., *Proc. Natl. Acad. Sci. USA* 86:840–844 (1989); Stavnezer et al., *Proc. Natl. Acad. Sci. USA* 85:7704–7708 (1988); and Mills et al., *Nucl. Acids Res.* 18:7305–7316 (1991), each of which is incorporated herein by reference. These sequences typically include about at least 50 bp immediately upstream of a switch region, preferably about at least 200 bp upstream of a switch region; and more preferably about at least 200–1000 bp or more upstream of a switch region. Suitable sequences occur immediately upstream of the human $S_{\gamma 1}$, $S_{\gamma 2}$, $S_{\gamma 3}$, $S_{\gamma 4}$, $S_{\alpha 1}$, $S_{\alpha 2}$, and $S_\epsilon$ switch regions; the sequences immediately upstream of the human $S_{\gamma 1}$, and $S_{\gamma 3}$ switch regions can be used to advantage, with $S_{\gamma 1}$ generally preferred. Alternatively, or in combination, murine Ig switch sequences may be used; it may frequently be advantageous to employ Ig switch sequences of the same species as the transgenic non-human animal. Furthermore, interferon (IFN) inducible transcriptional regulatory elements, such as IFN-inducible enhancers, are preferably included immediately upstream of transgene switch sequences.

In addition to promoters, other regulatory sequences which function primarily in B-lineage cells are used. Thus, for example, a light chain enhancer sequence situated preferably between the J and constant region gene segments on the light chain transgene is used to enhance transgene expression, thereby facilitating allelic exclusion. In the case of the heavy chain transgene, regulatory enhancers and also employed. Such regulatory sequences are used to maximize the transcription and translation of the transgene so as to induce allelic exclusion and to provide relatively high levels of transgene expression.

Although the foregoing promoter and enhancer regulatory control sequences have been generically described, such regulatory sequences may be heterologous to the nonhuman animal being derived from the genomic DNA from which the heterologous transgene immunoglobulin gene segments are obtained. Alternately, such regulatory gene segments are derived from the corresponding regulatory sequences in the genome of the non-human animal, or closely related species, which contains the heavy and light transgene.

In the preferred embodiments, gene segments are derived from human beings. The transgenic non-human animals harboring such heavy and light transgenes are capable of mounting an Ig-mediated immune response to a specific antigen administered to such an animal. B-cells are produced within such an animal which are capable of producing heterologous human antibody. After immortalization, and the selection for an appropriate monoclonal antibody (Mab), e.g. a hybridoma, a source of therapeutic human monoclonal antibody is provided. Such human Mabs have significantly reduced immunogenicity when therapeutically administered to humans.

Although the preferred embodiments disclose the construction of heavy and light transgenes containing human gene segments, the invention is not so limited. In this regard, it is to be understood that the teachings described herein may be readily adapted to utilize immunoglobulin gene segments from a species other than human beings. For example, in addition to the therapeutic treatment of humans with the antibodies of the invention, therapeutic antibodies encoded by appropriate gene segments may be utilized to generate monoclonal antibodies for use in the veterinary sciences.

Rearranged Transgenes

In an alternative embodiment, transgenic nonhuman animals contain functionally at least one rearranged heterologous heavy chain immunoglobulin transgene in the germline of the transgenic animal. Such animals contain primary repertoire B-cells that express such rearranged heavy transgenes. Such B-cells preferably are capable of undergoing somatic mutation when contacted with an antigen to form a heterologous antibody having high affinity and specificity for the antigen. Said rearranged transgenes will contain at least two $C_H$ genes and the associated sequences required for isotype switching.

The invention also includes transgenic animals containing germ line cells having heavy and light transgenes wherein one of the said transgenes contains rearranged gene segments with the other containing unrearranged gene segments. In such animals, the heavy chain transgenes shall have at least two $C_H$ genes and the associated sequences required for isotype switching.

The invention further includes methods for generating a synthetic variable region gene segment repertoire to be used in the transgenes of the invention. The method comprises generating a population of immunoglobulin V segment DNAs wherein each of the V segment DNAs encodes an immunoglobulin V segment and contains at each end a cleavage recognition site of a restriction endonuclease. The population of immunoglobulin V segment DNAs is thereafter concatenated to form the synthetic immunoglobulin V segment repertoire. Such synthetic variable region heavy chain transgenes shall have at least two $C_H$ genes and the associated sequences required for isotype switching.

Isotype Switching

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain.

The use of µ or δ constant regions is largely determined by alternate splicing, permitting IgM and IgD to be coexpressed in a single cell. The other heavy chain isotypes (γ, α, and ε) are only expressed natively after a gene rearrangement event deletes the Cµ and Cδ exons. This gene rearrangement process, termed isotype switching, typically occurs by recombination between so called switch segments located immediately upstream of each heavy chain gene (except δ). The individual switch segments are between 2 and 10 kb in length, and consist primarily of short repeated sequences. The exact point of recombination differs for individual class switching events. Investigations which have used solution hybridization kinetics or Southern blotting with cDNA-derived $C_H$ probes have confirmed that switching can be associated with loss of $C_H$ sequences from the cell.

The switch (S) region of the µ gene, $S_\mu$, is located about 1 to 2 kb 5' to the coding sequence and is composed of numerous tandem repeats of sequences of the form $(GAGCT)_n(GGGGT)$, where n is usually 2 to 5 but can range as high as 17. (See T. Nikaido et al. *Nature* 292:845–848 (1981))

Similar internally repetitive switch sequences spanning several kilobases have been found 5' of the other $C_H$ genes. The $S_\alpha$ region has been sequenced and found to consist of tandemly repeated 80-bp homology units, whereas murine $S_{\gamma 2a}$, $S_{\gamma 2b}$, and $S_{\gamma 3}$ all contain repeated 49-bp homology units very similar to each other. (See, P. Szurek et al., *J. Immunol* 135:620–626 (1985) and T. Nikaido et al., *J. Biol. Chem.* 257:7322–7329 (1982), which are incorporated herein by reference.) All the sequenced S regions include numerous occurrences of the pentamers GAGCT and GGGGT that are the basic repeated elements of the $S_\mu$ gene (T. Nikaido et al., *J. Biol. Chem.* 257:7322–7329 (1982) which is incorporated herein by reference); in the other S regions these pentamers are not precisely tandemly repeated as in $S_\mu$, but instead are embedded in larger repeat units. The $S_{\gamma 1}$ region has an additional higher-order structure: two direct repeat sequences flank each of two clusters of 49-bp tandem repeats. (See M. R. Mowatt et al., *J. Immunol.* 136:2674–2683. (1986), which is incorporated herein by reference).

Switch regions of human H chain genes have been found to be very similar to their mouse homologs. Indeed, similarity between pairs of human and mouse clones 5' to the $C_H$ genes has been found to be confined to the S regions, a fact that confirms the biological significance of these regions.

A switch recombination between µ and α genes produces a composite $S_\mu$–$S_\alpha$ sequence. Typically, there is no specific site, either in $S_\mu$ or in any other S region, where the recombination always occurs.

Generally, unlike the enzymatic machinery of V-J recombination, the switch machinery can apparently accommodate different alignments of the repeated homologous regions of germline S precursors and then join the sequences at different positions within the alignment. (See, T. H. Rabbits et al., *Nucleic Acids Res.* 9:4509–4524 (1981) and J. Ravetch et al., *Proc. Natl. Acad. Sci. USA* 77:6734–6738 (1980), which are incorporated herein by reference.)

The exact details of the mechanism(s) of selective activation of switching to a particular isotype are unknown. Although exogenous influences such as lymphokines and cytokines might upregulate isotype-specific recombinases, it is also possible that the same enzymatic machinery catalyzes switches to all isotypes and that specificity lies in targeting this machinery to specific switch regions.

The T-cell-derived lymphokines IL-4 and $IFN_\gamma$ have been shown to specifically promote the expression of certain isotypes: in the mouse, IL-4 decreases IgM, IgG2a, IgG2b, and IgG3 expression and increases IgE and IgG1 expression; while $IFN_\gamma$ selectively stimulates IgG2a expression and antagonizes the IL-4-induced increase in IgE and IgG1 expression (Coffman et al., *J. Immunol.* 136: 949 (1986) and Snapper et al., *Science* 236: 944 (1987), which are incorporated herein by reference). A combination of IL-4 and IL-5 promotes IgA expression (Coffman et al., *J. Immunol.* 139: 3685 (1987), which is incorporated herein by reference).

Most of the experiments implicating T-cell effects on switching have not ruled out the possibility that the observed increase in cells with particular switch recombinations might reflect selection of preswitched or precommitted cells; but the most likely explanation is that the lymphokines actually promote switch recombination.

Induction of class switching appears to be associated with sterile transcripts that initiate upstream of the switch segments (Lutzker et al., *Mol. Cell. Biol.* 8:1849 (1988); Stavnezer et al., *Proc. Natl. Acad. Sci. USA* 85:7704 (1988); Esser and Radbruch, *EMBO J.* 8:483 (1989); Berton et al., *Proc. Natl. Acad. Sci. USA* 86:2829 (1989); Rothman et al., *Int. Immunol.* 2:621 (1990), each of which is incorporated by reference). For example, the observed induction of the γ1 sterile transcript by IL-4 and inhibition by IFN-γ correlates with the observation that IL-4 promotes class switching to γ1 in B-cells in culture, while IFN-γ inhibits γ1 expression. Therefore, the inclusion of regulatory sequences that affect the transcription of sterile transcripts may also affect the rate of isotype switching. For example, increasing the transcription of a particular sterile transcript typically can be expected to enhance the frequency of isotype switch recombination involving adjacent switch sequences.

For these reasons, it is preferable that transgenes incorporate transcriptional regulatory sequences within about 1–2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. This 5' flanking region is typically about at least 50 nucleotides in length, preferably about at least 200 nucleotides in length, and more preferably at least 500–1000 nucleotides.

Although a 5' flanking sequence from one switch region can be operably linked to a different switch region for transgene construction (e.g., a 5' flanking sequence from the human $S_{\gamma 1}$ switch can be grafted immediately upstream of the $S_{\alpha 1}$ switch; a murine $S_{\gamma 1}$ flanking region can be grafted adjacent to a human γ1 switch sequence; or the murine $S_{\gamma 1}$ switch can be grafted onto the human γ1 coding region), in some embodiments it is preferred that each switch region incorporated in the transgene construct have the 5' flanking region that occurs immediately upstream in the naturally occurring germline configuration.

Monoclonal Antibodies

Monoclonal antibodies can be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.*, 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Various techniques useful in these arts are discussed, for example, in Harlow and Lane, *Antibodies: A Laboratory Manual*, Cold Spring Harbor, N.Y. (1988) including: immunization of animals to produce immunoglobulins; production of monoclonal antibodies; labeling immunoglobulins for use as probes; immunoaffinity purification; and immunoassays.

The Transgenic Primary Repertoire

A. The Human Immunoglobulin Loci

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus is estimated to consist of approximately 200 V gene segments (current data supports the existence of about 50–100 V gene segments) spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14.

B. Gene Fragment Transgenes

1. Heavy Chain Transgene

In a preferred embodiment, immunoglobulin heavy and light chain transgenes comprise unrearranged genomic DNA from humans. In the case of the heavy chain, a preferred transgene comprises a NotI fragment having a length between 670 to 830 kb. The length of this fragment is ambiguous because the 3' restriction site has not been accurately mapped. It is known, however, to reside between the α1 and ψα gene segments. This fragment contains members of all six of the known $V_H$ families, the D and J gene segments, as well as the μ, δ, γ3, γ1 and α1 constant regions (Berman et al., *EMBO J.* 7:727–738 (1988), which is incorporated herein by reference). A transgenic mouse line containing this transgene correctly expresses a heavy chain class required for B-cell development (IgM) and at least one switched heavy chain class ($IgG_1$), in conjunction with a sufficiently large repertoire of variable regions to trigger a secondary response for most antigens.

2. Light Chain Transgene

A genomic fragment containing all of the necessary gene segments and regulatory sequences from a human light chain locus may be similarly constructed. Such transgenes are constructed as described in the Examples and in copending application, entitled "Transgenic Non-Human Animals Capable of Producing Heterologous Antibodies," filed Aug. 29, 1990, under U.S. Ser. No. 07/574,748.

C. Transgenes Generated Intracellularly by In Vivo Recombination

It is not necessary to isolate the all or part of the heavy chain locus on a single DNA fragment. Thus, for example, the 670–830 kb NotI fragment from the human immunoglobulin heavy chain locus may be formed in vivo in the non-human animal during transgenesis. Such in vivo transgene construction is produced by introducing two or more overlapping DNA fragments into an embryonic nucleus of the non-human animal. The overlapping portions of the DNA fragments have DNA sequences which are substantially homologous. Upon exposure to the recombinases contained within the embryonic nucleus, the overlapping DNA fragments homologously recombined in proper orientation to form the 670–830 kb NotI heavy chain fragment.

In vivo transgene construction can be used to form any number of immunoglobulin transgenes which because of their size are otherwise difficult, or impossible, to make or manipulate by present technology. Thus, in vivo transgene construction is useful to generate immunoglobulin transgenes which are larger than DNA fragments which may be manipulated by YAC vectors (Murray and Szostak, *Nature* 305:189–193 (1983)). Such in vivo transgene construction may be used to introduce into a non-human animal substantially the entire immunoglobulin loci from a species not consisting of the transgenic non-human animal.

In addition to forming genomic immunoglobulin transgenes, in vivo homologous recombination may also be utilized to form "mini-locus" transgenes as described in the Examples.

In the preferred embodiments utilizing in vivo transgene construction, each overlapping DNA fragment preferably has an overlapping substantially homologous DNA sequence between the end portion of one DNA fragment and the end portion of a second DNA fragment. Such overlapping portions of the DNA fragments preferably comprise about 500 bp to about 2000 bp, most preferably 1.0 kb to 2.0 kb. Homologous recombination of overlapping DNA fragments to form transgenes in vivo is further described in commonly assigned U.S. patent application entitled "Intracellular Generation of DNA by Homologous Recombination of DNA Fragments" filed Aug. 29, 1990, under U.S. Ser. No. 07/574,747.

D. Minilocus Transgenes

As used herein, the term "immunoglobulin minilocus" refers to a DNA sequence (which may be within a longer sequence), usually of less than about 150 kb, typically between about 25 and 100 kb, containing at least one each of the following: a functional variable (V) gene segment, a functional joining (J) region segment, at least one functional constant (C) region gene segment, and—if it is a heavy chain minilocus—a functional diversity (D) region segment, such that said DNA sequence contains at least one substantial discontinuity (e.g., a deletion, usually of at least about 2 to 5 kb, preferably 10–25 kb or more, relative to the homologous genomic DNA sequence). A light chain minilocus transgene will be at least 25 kb in length, typically 50 to 60 kb. A heavy chain transgene will typically be about 70 to 80 kb in length, preferably at least about 60 kb with two constant regions operably linked to switch regions. Furthermore, the individual elements of the minilocus are preferably in the germline configuration and capable of undergoing gene rearrangement in the pre-B cell of a transgenic animal so as to express functional antibody molecules with diverse antigen specificities encoded entirely by the elements of the minilocus. Further, a heavy chain minilocus comprising at least two $C_H$ genes and the requisite switching sequences is typically capable of undergoing isotype switching, so that functional antibody molecules of different immunoglobulin classes will be generated. Such isotype switching may occur in vivo in B-cells residing within the transgenic nonhuman animal, or may occur in cultured cells of the B-cell lineage which have been explanted from the transgenic nonhuman animal.

In an alternate preferred embodiment, immunoglobulin heavy chain transgenes comprise one or more of each of the $V_H$, D, and $J_H$ gene segments and two or more of the $C_H$ genes. At least one of each appropriate type gene segment is incorporated into the minilocus transgene. With regard to the $C_H$ segments for the heavy chain transgene, it is preferred that the transgene contain at least one μ gene segment and at least one other constant region gene segment, more preferably a γ gene segment, and most preferably γ3 or γ1. This preference is to allow for class switching between IgM and IgG forms of the encoded immunoglobulin and the production of a secretable form of high affinity non-IgM immunoglobulin. Other constant region gene segments may also be used such as those which encode for the production of IgD, IgA and IgE.

Those skilled in the art will also construct transgenes wherein the order of occurrence of heavy chain $C_H$ genes will be different from the naturally-occurring spatial order found in the germline of the species serving as the donor of the $C_H$ genes.

Additionally, those skilled in the art can select $C_H$ genes from more than one individual of a species (e.g., allogeneic $C_H$ genes) and incorporate said genes in the transgene as supernumerary $C_H$ genes capable of undergoing isotype switching; the resultant transgenic nonhuman animal may then, in some embodiments, make antibodies of various classes including all of the allotypes represented in the species from which the transgene $C_H$ genes were obtained.

Still further, those skilled in the art can select $C_H$ genes from different species to incorporate into the transgene. Functional switch sequences are included with each $C_H$ gene, although the switch sequences used are not necessarily those which occur naturally adjacent to the $C_H$ gene. Interspecies $C_H$ gene combinations will produce a transgenic nonhuman animal which may produce antibodies of various classes corresponding to $C_H$ genes from various species. Transgenic nonhuman animals containing interspecies $C_H$ transgenes may serve as the source of B-cells for constructing hybridomas to produce monoclonals for veterinary uses.

The heavy chain J region segments in the human comprise six functional J segments and three pseudo genes clustered in a 3 kb stretch of DNA. Given its relatively compact size and the ability to isolate these segments together with the μ gene and the 5' portion of the δ gene on a single 23 kb SFiI/SpeI fragment (Sado et al., Biochem. Biophys. Res. Comm. 154:264271 (1988), which is incorporated herein by reference), it is preferred that all of the J region gene segments be used in the mini-locus construct. Since this fragment spans the region between the μ and δ genes, it is likely to contain all of the 3' cis-linked regulatory elements required for μ expression. Furthermore, because this fragment includes the entire J region, it contains the heavy chain enhancer and the μ switch region (Mills et al., Nature 306:809 (1983); Yancopoulos and Alt, Ann. Rev. Immunol. 4:339–368 (1986), which are incorporated herein by reference). It also contains the transcription start sites which trigger VDJ joining to form primary repertoire B-cells (Yancopoulos and Alt, Cell 40:271–281 (1985), which is incorporated herein by reference). Alternatively, a 36 kb BssHII/SpeI1 fragment, which includes part on the D region, may be used in place of the 23 kb SfiI/SpeI1 fragment. The use of such a fragment increases the amount of 5' flanking sequence to facilitate efficient D-to-J joining.

Figure 4:
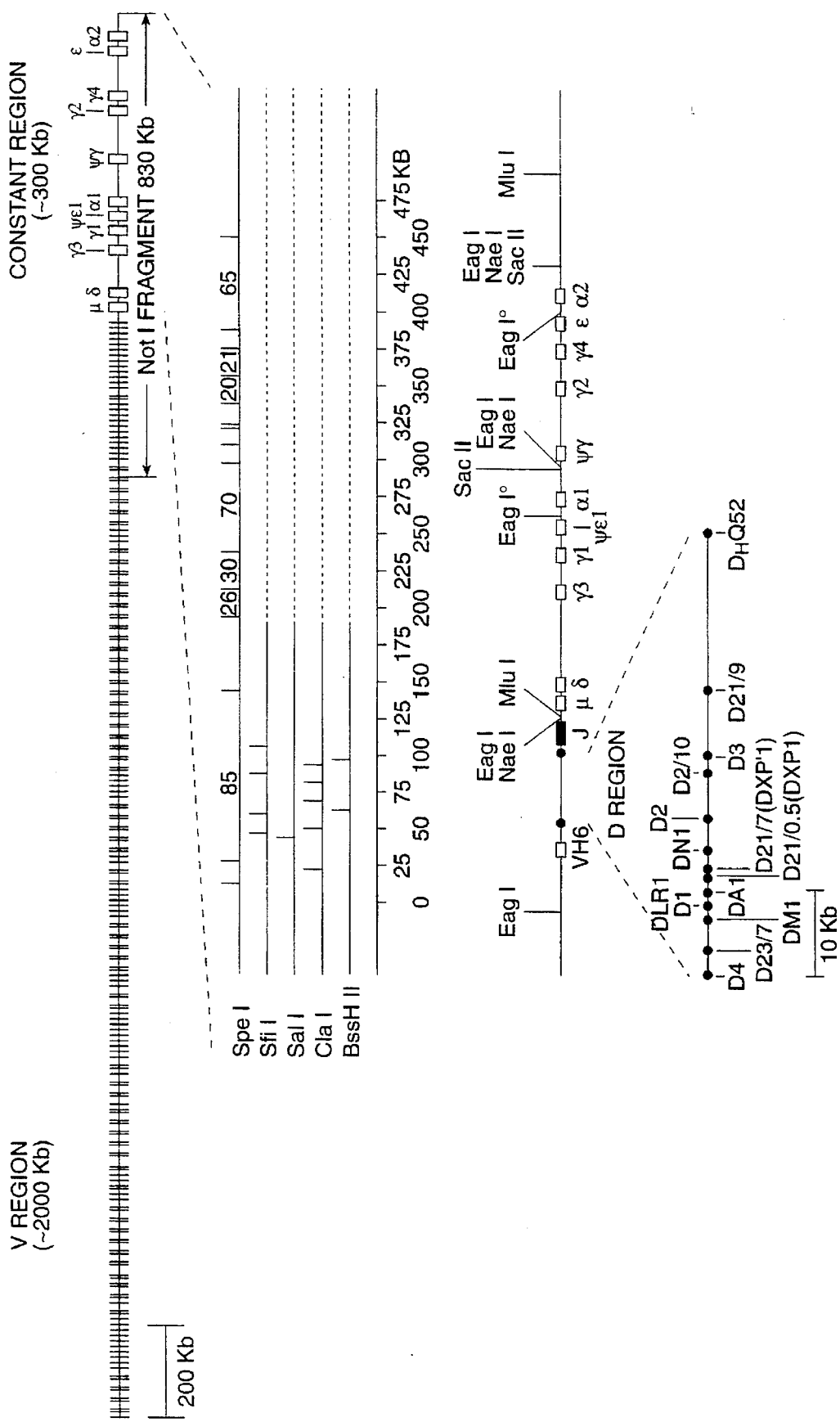
FIG. 4 depicts the human heavy chain locus.
Figure 5:
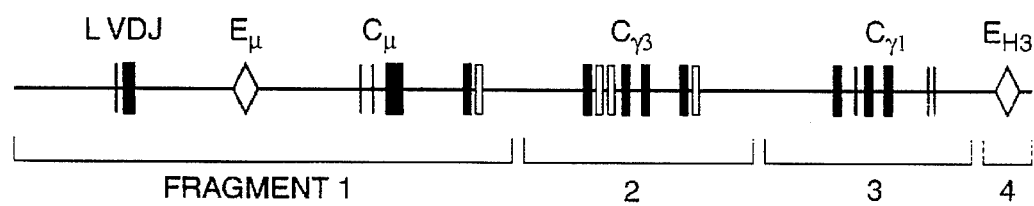
FIG. 5 depicts a transgene construct containing a rearranged IgM gene ligated to a 25 kb fragment that contains human γ3 and γ1 constant regions followed by a 700 bp fragment containing the rat chain 3' enhancer sequence.
Figure 6:
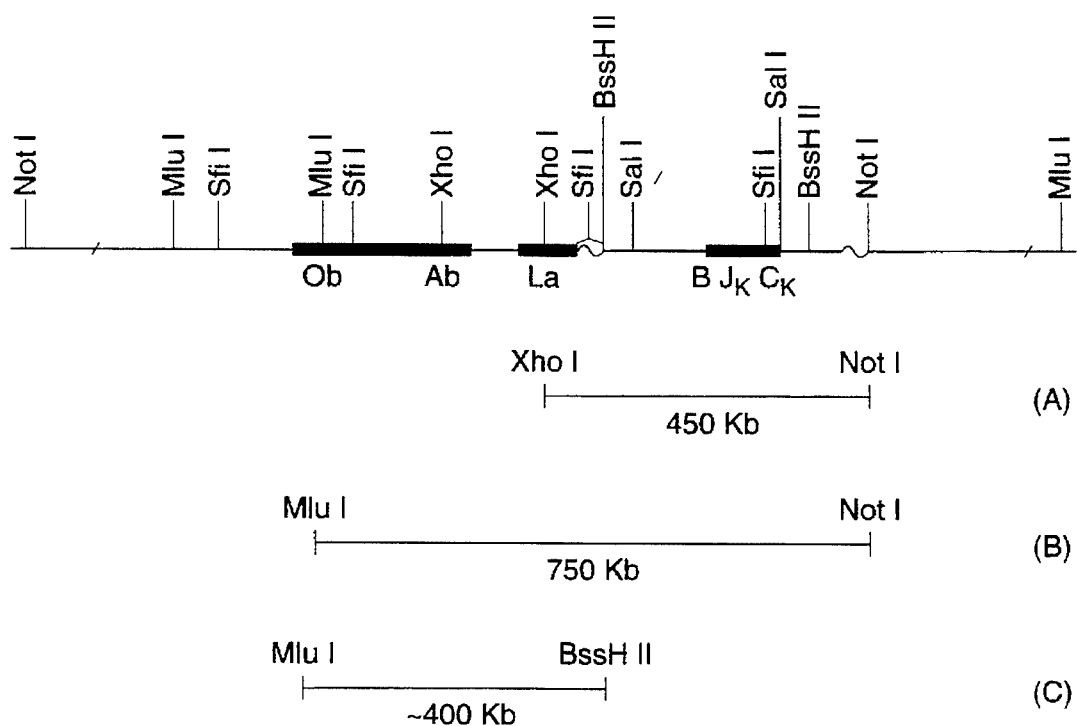
FIG. 6 is a restriction map of the human κ chain locus depicting the fragments to be used to form a light chain transgene by way of in vivo homologous recombination.

The human D region consists of 4 homologous 9 kb subregions, linked in tandem (Siebenlist, et al. (1981), Nature, 294, 631–635). Each subregion contains up to 10 individual D segments. Some of these segments have been mapped and are shown in FIG. 4. Two different strategies are used to generate a mini-locus D region. The first strategy involves using only those D segments located in a short contiguous stretch of DNA that includes one or two of the repeated D subregions. A candidate is a single 15 kb fragment that contains 12 individual D segments. This piece of DNA consists of 2 contiguous EcoRI fragments and has been completely sequenced (Ichihara, et al. (1988), EMBO J., 7, 4141–4150). Twelve D segments should be sufficient for a primary repertoire. However, given the dispersed nature of the D region, an alternative strategy is to ligate together several non-contiguous D-segment containing fragments, to produce a smaller piece of DNA with a greater number of segments. Additional D-segment genes can be identified, for example, by the presence of characteristic flanking nonamer and heptamer sequences, supra, and by reference to the literature.

At least one, and preferably more than one V gene segment is used to construct the heavy chain minilocus transgene. Rearranged or unrearranged V segments with or without flanking sequences can be isolated as described in copending applications, U.S. Ser. No. 07/574,748 filed Aug. 29, 1990, PCT/US91/06185 filed Aug. 28, 1991, and U.S. Ser. No. 07/810,279 filed Dec. 17, 1991, each of which is incorporated herein by reference.

Rearranged or unrearranged V segments, D segments, J segments, and C genes, with or without flanking sequences, can be isolated as described in copending applications U.S. Ser. No. 07/574,748 filed Aug. 29, 1990 and PCT/US91/06185 filed Aug. 28, 1991.

A minilocus light chain transgene may be similarly constructed from the human λ or κ immunoglobulin locus. Thus, for example, an immunoglobulin heavy chain minilocus transgene construct, e.g., of about 75 kb, encoding V, D, J and constant region sequences can be formed from a plurality of DNA fragments, with each sequence being substantially homologous to human gene sequences. Preferably, the sequences are operably linked to transcription regulatory sequences and are capable of undergoing rearrangement. With two or more appropriately placed constant region sequences (e.g., μ and γ) and switch regions, switch recombination also occurs. An exemplary light chain transgene construct can be formed similarly from a plurality of DNA fragments, substantially homologous to human DNA and capable of undergoing rearrangement, as described in copending application, U.S. Ser. No. 07/574, 748 filed Aug. 29, 1990.

E. Transgene Constructs Capable of Isotype Switching

Ideally, transgene constructs that are intended to undergo class switching should include all of the cis-acting sequences necessary to regulate sterile transcripts. Naturally occurring switch regions and upstream promoters and regulatory sequences (e.g., IFN-inducible elements) are preferred cis-acting sequences that are included in transgene constructs capable of isotype switching. About at least 50 basepairs, preferably about at least 200 basepairs, and more preferably at least 500 to 1000 basepairs or more of sequence immediately upstream of a switch region, preferably a human γ1 switch region, should be operably linked to a switch sequence, preferably a human γ1 switch sequence.

Further, switch regions can be linked upstream of (and adjacent to) $C_H$ genes that do not naturally occur next to the particular switch region. For example, but not for limitation, a human $\gamma_1$ switch region may be linked upstream from a human $\alpha_2$ $C_H$ gene, or a murine $\gamma_1$ switch may be linked to a human $C_H$ gene.

An alternative method for obtaining non-classical isotype switching (e.g., δ-associated deletion) in transgenic mice involves the inclusion of the 400 bp direct repeat sequences (σμ and εμ) that flank the human μ gene (Yasui et al., *Eur. J. Immunol.* 19:1399 (1989)). Homologous recombination between these two sequences deletes the μ gene in IgD-only B-cells. Heavy chain transgenes can be represented by the following formulaic description:

$$(V_H)_x\text{-}(D)_y\text{-}(J_H)_z\text{-}(S_D)_m\text{-}(C_1)_n\text{-}[(T)\text{-}(S_A)_p\text{-}(C_2)]_q$$

where:

$V_H$ is a heavy chain variable region gene segment,

D is a heavy chain D (diversity) region gene segment, $J_H$ is a heavy chain J (joining) region gene segment, $S_D$ is a donor region segment capable of participating in a recombination event with the $S_a$ acceptor region segments such that isotype switching occurs, $C_1$ is a heavy chain constant region gene segment encoding an isotype utilized in for B cell development (e.g., μ or δ), T is a cis-acting transcriptional regulatory region segment containing at least a promoter, $S_A$ is an acceptor region segment capable of participating in a recombination event with selected $S_D$ donor region segments, such that isotype switching occurs, $C_2$ is a heavy chain constant region gene segment encoding an isotype other than μ (e.g., $\gamma_1$, $\gamma_2$, $\gamma_3$, $\gamma_4$, $\alpha_1$, $\alpha_2$, ε).

x, y, z, m, n, p, and q are integers. x is 1–100, n is 0–10, y is 1–50, p is 1–10, z is 1–50, q is 0–50, m is 0–10. Typically, when the transgene is capable of isotype switching, q must be at least 1, m is at least 1, n is at least 1, and m is greater than or equal to n.

$V_H$, D, $J_H$, $S_D$, $C_1$, T, $S_A$, and $C_Z$ segments may be selected from various species, preferably mammalian species, and more preferably from human and murine germline DNA.

$V_H$ segments may be selected from various species, but are preferably selected from $V_H$ segments that occur naturally in the human germline, such as $V_{H251}$. Typically about 2 $V_H$ gene segments are included, preferably about 4 $V_H$ segments are included, and most preferably at least about 10 $V_H$ segments are included.

At least one D segment is typically included, although at least 10 D segments are preferably included, and some embodiments include more than ten D segments. Some preferred embodiments include human D segments.

Typically at least one $J_H$ segment is incorporated in the transgene, although it is preferable to include about six $J_H$ segments, and some preferred embodiments include more than about six $J_H$ segments. Some preferred embodiments include human $J_H$ segments, and further preferred embodiments include six human $J_H$ segments and no nonhuman $J_H$ segments.

$S_D$ segments are donor regions capable of participating in recombination events with the $S_A$ segment of the transgene. For classical isotype switching, $S_D$ and $S_A$ are switch regions such as $S_\mu$, $S_{\gamma1}$, $S_{\gamma2}$, $S_{\gamma3}$, $S_{\gamma4}$, $S_\alpha$, $S_{\alpha2}$, and $S_\epsilon$. Preferably the switch regions are murine or human, more preferably $S_D$ is a human or murine $S_\mu$ and $S_A$ is a human or murine $S_{\gamma1}$. For nonclassical isotype switching (δ-associated deletion), $S_D$ and $S_A$ are preferably the 400 basepair direct repeat sequences that flank the human μ gene.

$C_1$ segments are typically μ or δ genes, preferably a μ gene, and more preferably a human or murine μ gene.

T segments typically include 5' flanking sequences that are adjacent to naturally occurring (i.e., germline) switch regions. T segments typically at least about at least 50 nucleotides in length, preferably about at least 200 nucleotides in length, and more preferably at least 500–1000 nucleotides in length. Preferably T segments are 5' flanking sequences that occur immediately upstream of human or murine switch regions in a germline configuration. It is also evident to those of skill in the art that T segments may comprise cis-acting transcriptional regulatory sequences that do not occur naturally in an animal germline (e.g., viral enhancers and promoters such as those found in SV40, adenovirus, and other viruses that infect eukaryotic cells).

$C_2$ segments are typically a $\gamma_1$, $\gamma_2$, $\gamma_3$, $\gamma_4$, $\alpha_1$, $\alpha_2$, or ε $C_H$ gene, preferably a human $C_H$ gene of these isotypes, and more preferably a human $\gamma_1$ or $\gamma_3$ gene. Murine $\gamma_{2a}$ and $\gamma_{2b}$ may also be used, as may downstream (i.e., switched) isotype genes form various species. Where the heavy chain transgene contains an immunoglobulin heavy chain minilocus, the total length of the transgene will be typically 150 kilo basepairs or less.

In general, the transgene will be other than a native heavy chain Ig locus. Thus, for example, deletion of unnecessary regions or substitutions with corresponding regions from other species will be present.

F. Methods for Determining Functional Isotype Switching in Ig Transgenes

The occurrence of isotype switching in a transgenic nonhuman animal may be identified by any method known to those in the art. Preferred embodiments include the following, employed either singly or in combination:

1. detection of mRNA transcripts that contain a sequence homologous to at least one transgene downstream $C_H$ gene other than δ and an adjacent sequence homologous to a transgene $V_H$-$D_H$-$J_H$ rearranged gene; such detection may be by Northern hybridization, $S_1$ nuclease protection assays, PCR amplification, cDNA cloning, or other methods;

2. detection in the serum of the transgenic animal, or in supernatants of cultures of hybridoma cells made from B-cells of the transgenic animal, of immunoglobulin proteins encoded by downstream $C_H$ genes, where such proteins can also be shown by immunochemical methods to comprise a functional variable region;

3. detection, in DNA from B-cells of the transgenic animal or in genomic DNA from hybridoma cells, of DNA rearrangements consistent with the occurrence of isotype switching in the transgene, such detection may be accomplished by Southern blot hybridization, PCR amplification, genomic cloning, or other method; or 4. identification of other indicia of isotype switching, such as production of sterile transcripts, production of characteristic enzymes involved in switching (e.g., "switch recombinase"), or other manifestations that may be detected, measured, or observed by contemporary techniques.

Because each transgenic line may represent a different site of integration of the transgene, and a potentially different tandem array of transgene inserts, and because each different configuration of transgene and flanking DNA sequences can affect gene expression, it is preferable to identify and use lines of mice that express high levels of human immunoglobulins, particularly of the IgG isotype, and contain the least number of copies of the transgene. Single copy transgenics minimize the potential problem of incomplete allelic expression. Transgenes are typically integrated into host chromosomal DNA, most usually into germline DNA and propagated by subsequent breeding of germline transgenic breeding stock animals. However, other vectors and transgenic methods known in the present art or subsequently developed may be substituted as appropriate and as desired by a practitioner.

Trans-switching to endogenous nonhuman heavy chain constant region genes can occur and produce chimeric heavy chains and antibodies comprising such chimeric human/mouse heavy chains. Such chimeric antibodies may be desired for certain uses described herein or may be undesirable.

G. Functional Disruption of Endogenous Immunoglobulin Loci

The expression of successfully rearranged immunoglobulin heavy and light transgenes is expected to have a dominant effect by suppressing the rearrangement of the endogenous immunoglobulin genes in the transgenic nonhuman animal. However, another way to generate a nonhuman that is devoid of endogenous antibodies is by mutating the endogenous immunoglobulin loci. Using embryonic stem cell technology and homologous recombination, the endogenous immunoglobulin repertoire can be readily eliminated. The following describes the functional description of the mouse immunoglobulin loci. The vectors and methods disclosed, however, can be readily adapted for use in other non-human animals.

Briefly, this technology involves the inactivation of a gene, by homologous recombination, in a pluripotent cell line that is capable of differentiating into germ cell tissue. A DNA construct that contains an altered, copy of a mouse immunoglobulin gene is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells entirely derived from the mutant cell line. Therefore, by breeding the chimeric mice it is possible to obtain a new line of mice containing the introduced genetic lesion (reviewed by Capecchi (1989), Science, 244, 1288–1292).

Because the mouse λ locus contributes to only 5% of the immunoglobulins, inactivation of the heavy chain and/or κ-light chain loci is sufficient. There are three ways to disrupt each of these loci, deletion of the J region, deletion of the J-C intron enhancer, and disruption of constant region coding sequences by the introduction of a stop codon. The last option is the most straightforward, in terms of DNA construct design. Elimination of the μ gene disrupts B-cell maturation thereby preventing class switching to any of the functional heavy chain segments. The strategy for knocking out these loci is outlined below.

To disrupt the mouse μ and κ genes, targeting vectors are used based on the design employed by Jaenisch and co-workers (Zijlstra, et al. (1989), Nature, 342,435–438) for the successful disruption of the mouse β2-microglobulin gene. The neomycin resistance gene (neo), from the plasmid pMCIneo is inserted into the coding region of the target gene. The pMCIneo insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zijlstra, et al., supra.).

A preferred strategy for disrupting the heavy chain locus is the elimination of the J region. This region is fairly compact in the mouse, spanning only 1.3 kb. To construct a gene targeting vector, a 15 kb KpnI fragment containing all of the secreted A constant region exons from mouse genomic library is isolated. The 1.3 kb J region is replaced with the 1.1 kb insert from pMCIneo. The HSV tk gene is then added to the 5' end of the KpnI fragment. Correct integration of this construct, via homologous recombination, will result in the replacement of the mouse $J_H$ region with the neogene. Recombinants are screened by PCR, using a primer based on the neogene and a primer homologous to mouse sequences 5' of the KpnI site in the D region.

Alternatively, the heavy-chain locus is knocked out by disrupting the coding region of the μ gene. This approach involves the same 15 kb KpnI fragment used in the previous approach. The 1.1 kb insert from pMCIneo is inserted at a unique BamHI site in exon II, and the HSV tk gene added to the 3' KpnI end. Double crossover events on either side of the neo insert, that eliminate the tk gene, are then selected for. These are detected from pools of selected clones by PCR amplification. One of the PCR primers is derived from neo sequences and the other from mouse sequences outside of the targeting vector. The functional disruption of the mouse immunoglobulin loci is presented in the Examples.

G. Suppressing Expression of Endogenous Immunoglobulin Loci

In addition to functional disruption of endogenous Ig loci, an alternative method for preventing the expression of an endogenous Ig locus is suppression. Suppression of endogenous Ig genes may be accomplished with antisense RNA produced from one or more integrated transgenes, by antisense oligonucleotides, and/or by administration of antisera specific for one or more endogenous Ig chains.

Antisense Polynucleotides

Antisense RNA transgenes can be employed to partially or totally knock-out expression of specific genes (Pepin et al. (1991) Nature 355: 725; Helene., C. and Toulme, J. (1990) Biochimica Biophys. Acta 1049: 99; Stout, J. and Caskey, T. (1990) Somat. Cell Mol. Genet. 16: 369; Munir et al. (1990) Somat. Cell Mol. Genet. 16: 383, each of which is incorporated herein by reference).

"Antisense polynucleotides" are polynucleotides that: (1) are complementary to all or part of a reference sequence, such as a sequence of an endogenous Ig $C_H$ or $C_L$ region, and (2) which specifically hybridize to a complementary target sequence, such as a chromosomal gene locus or a Ig mRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include soluble antisense RNA or DNA oligonucleotides which can hybridize specifically to individual mRNA species and prevent transcription and/or RNA processing of the mRNA species and/or translation of the encoded polypeptide (Ching et al., Proc. Natl. Acad. Sci. U.S.A. 86:10006–10010 (1989); Broder et al., Ann. Int. Med. 113:604–618 (1990); Loreau et al., FEBS Letters 274:53–56 (1990); Holcenberg et al., WO91/11535; U.S. Ser. No. 07/530,165 ("New human CRIPTO gene"); WO91/09865; WO91/04753; WO90/13641; and EP 386563, each of which is incorporated herein by reference). An antisense sequence is a polynucleotide sequence that is complementary to at least one immunoglobulin gene sequence of at least about 15 contiguous nucleotides in length, typically at least 20 to 30 nucleotides in length, and preferably more than about 30 nucleotides in length. However, in some embodiments, antisense sequences may have substitutions, additions, or deletions as compared to the complementary immunoglobulin gene sequence, so long as specific hybridization is retained as a property of the antisense polynucleotide. Generally, an antisense sequence is complementary to an endogenous immunoglobulin gene sequence that encodes, or has the potential to encode after DNA rearrangement, an immunoglobulin chain. In some cases, sense sequences corresponding to an immunoglobulin gene sequence may function to suppress expression, particularly by interfering with transcription.

The antisense polynucleotides therefore inhibit production of the encoded polypeptide(s). In this regard, antisense polynucleotides that inhibit transcription and/or translation of one or more endogenous Ig loci can alter the capacity and/or specificity of a non-human animal to produce immunoglobulin chains encoded by endogenous Ig loci.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual, or a transgenic non-human animal. Alternatively, the antisense polynucleotides may comprise soluble oligonucleotides that are administered to the external milieu, either in culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties, alternatively phosphorothiolates or O-methylribonucleotides may be used, and chimeric oligonucleotides may also be used (Dagle et al. (1990) *Nucleic Acids Res.* 18: 4751). For some applications, antisense oligonucleotides may comprise polyamide nucleic acids (Nielsen et al. (1991) *Science* 254: 1497). For general methods relating to antisense polynucleotides, see *Antisense RNA and DNA*, (1988), D. A. Melton, Ed., Cold Spring Harbor Laboratory, Cold Spring Harbor, N.Y.).

Antisense polynucleotides complementary to one or more sequences are employed to inhibit transcription, RNA processing, and/or translation of the cognate mRNA species and thereby effect a reduction in the amount of the respective encoded polypeptide. Such antisense polynucleotides can provide a therapeutic function by inhibiting the formation of one or more endogenous Ig chains in vivo.

Whether as soluble antisense oligonucleotides or as antisense RNA transcribed from an antisense transgene, the antisense polynucleotides of this invention are selected so as to hybridize preferentially to endogenous Ig sequences at physiological conditions in vivo. Most typically, the selected antisense polynucleotides will not appreciably hybridize to heterologous Ig sequences encoded by a heavy or light chain transgene of the invention (i.e., the antisense oligonucleotides will not inhibit transgene Ig expression by more than about 25 to 35 percent).

Antiserum Suppression

Partial or complete suppression of endogenous Ig chain expression can be produced by injecting mice with antisera against one or more endogenous Ig chains (Weiss et al. (1984) *Proc. Natl. Acad. Sci. (U.S.A.)* 81 211, which is incorporated herein by reference). Antisera are selected so as to react specifically with one or more endogenous (e.g., murine) Ig chains but to have minimal or no cross-reactivity with heterologous Ig chains encoded by an Ig transgene of the invention. Thus, administration of selected antisera according to a schedule as typified by that of Weiss et al. op.cit. will suppress endogenous Ig chain expression but permits expression of heterologous Ig chain(s) encoded by a transgene of the present invention. Suitable antibody sources for antibody comprise:

(1) monoclonal antibodies, such as a monoclonal antibody that specifically binds to a murine $\mu$, $\gamma$, $\kappa$, or $\lambda$ chains but does not react with the human immunoglobulin chain(s) encoded by a human Ig transgene of the invention;

(2) mixtures of such monoclonal antibodies, so that the mixture binds with multiple epitopes on a single species of endogenous Ig chain, with multiple endogenous Ig chains (e.g., murine $\mu$ and murine $\gamma$, or with multiple epitopes and multiple chains or endogenous immunoglobulins;

(3) polyclonal antiserum or mixtures thereof, typically such antiserum/antisera is monospecific for binding to a single species of endogenous Ig chain (e.g., murine $\mu$, murine $\gamma$, murine $\kappa$, murine $\lambda$) or to multiple species of endogenous Ig chain, and most preferably such antisera possesses negligible binding to human immunoglobulin chains encoded by a transgene of the invention; and/or (4) a mixture of polyclonal antiserum and monoclonal antibodies binding to a single or multiple species of endogenous Ig chain, and most preferably possessing negligible binding to human immunoglobulin chains encoded by a transgene of the invention. Generally, polyclonal antibodies are preferred, and such substantially monospecific polyclonal antibodies can be advantageously produced from an antiserum raised against human immunoglobulin(s) by preadsorption with antibodies derived from the nonhuman animal species (e.g., murine) and/or, for example, by affinity chromatography of the antiserum or purified fraction thereof on an affinity resin containing immobilized human Ig (wherein the bound fraction is enriched for the desired anti-human Ig in the antiserum; the bound fraction is typically eluted with conditions of low pH or a chaotropic salt solution).

Cell separation and/or complement fixation can be employed to provide the enhancement of antibody-directed cell depletion of lymphocytes expressing endogenous (e.g., murine) immunoglobulin chains. In one embodiment, for example, antibodies are employed for ex vivo depletion of murine Ig-expressing explanted hematopoietic cells and/or B-lineage lymphocytes obtained from a transgenic mouse harboring a human Ig transgene. Thus, hematopoietic cells and/or B-lineage lymphocytes are explanted from a transgenic nonhuman animal harboring a human Ig transgene (preferably harboring both a human heavy chain transgene and a human light chain transgene) and the explanted cells are incubated with an antibody (or antibodies) which (1) binds to an endogenous immunoglobulin (e.g., murine $\mu$ and/or $\kappa$) and (2) lacks substantial binding to human immunoglobulin chains encoded by the transgene(s). Such antibodies are referred to as "suppression antibodies" for clarity. The explanted cell population is selectively depleted of cells which bind to the suppression antibody(ies); such depletion can be accomplished by various methods, such as (1) physical separation to remove suppression antibody-bound cells from unbound cells (e.g., the suppression antibodies may be bound to a solid support or magnetic bead to immobilize and remove cells binding to the suppression antibody), (2) antibody-dependent cell killing of cells bound by the suppression antibody (e.g., by ADCC, by complement fixation, or by a toxin linked to the suppression antibody), and (3) clonal anergy induced by the suppression antibody, and the like.

Frequently, antibodies used for antibody suppression of endogenous Ig chain production will be capable of fixing complement. It is frequently preferable that such antibodies may be selected so as to react well with a convenient complement source for ex vivo/in vitro depletion, such as rabbit or guinea pig complement. For in vivo depletion, it is generally preferred that the suppressor antibodies possess effector functions in the nonhuman transgenic animal species; thus, a suppression antibody comprising murine effector functions (e.g., ADCC and complement fixation) generally would be preferred for use in transgenic mice.

In one variation, a suppression antibody that specifically binds to a predetermined endogenous immunoglobulin chain is used for ex vivo/in vitro depletion of lymphocytes expressing an endogenous immunoglobulin. A cellular explant (e.g., lymphocyte sample) from a transgenic nonhuman animal harboring a human immunoglobulin transgene is contacted with a suppression antibody and cells specifically binding to the suppression antibody are depleted (e.g., by immobilization, complement fixation, and the like), thus generating a cell subpopulation depleted in cells expressing endogenous (nonhuman) immunoglobulins (e.g., lymphocytes expressing murine Ig). The resultant depleted lymphocyte population (T cells, human Ig-positive B-cells, etc.) can be transferred into a immunocompatible (i.e., MHC-compatible) nonhuman animal of the same species and which is substantially incapable of producing endogenous antibody (e.g., SCID mice, RAG-1 or RAG-2 knockout mice). The reconstituted animal (mouse) can then be immunized with an antigen (or reimmunized with an antigen used to immunize the donor animal from which the explant was obtained) to obtain high-affinity (affinity matured) antibodies and B-cells producing such antibodies. Such B-cells may be used to generate hybridomas by conventional cell fusion and screened. Antibody suppression can be used in combination with other endogenous Ig inactivation/suppression methods (e.g., $J_H$ knockout, $C_H$ knockout, D-region ablation, antisense suppression, compensated frameshift inactivation).

Complete Endogenous Ig Locus Inactivation

In certain embodiments, it is desirable to effect complete inactivation of the endogenous Ig loci so that hybrid immunoglobulin chains comprising a human variable region and a non-human (e.g., murine) constant region cannot be formed (e.g., by trans-switching between the transgene and endogenous Ig sequences). Knockout mice bearing endogenous heavy chain alleles with are functionally disrupted in the $J_H$ region only frequently exhibit trans-switching, typically wherein a rearranged human variable region (VDJ) encoded by a transgene is expressed as a fusion protein linked to an endogenous murine constant region, although other trans-switched junctions are possible. To overcome this potential problem, it is generally desirable to completely inactivate the endogenous heavy chain locus by any of various methods, including but not limited to the following: (1) functionally disrupting and/or deleting by homologous recombination at least one and preferably all of the endogenous heavy chain constant region genes, (2) mutating at least one and preferably all of the endogenous heavy chain constant region genes to encode a termination codon (or frameshift) to produce a truncated or frameshifted product (if trans-switched), and other methods and strategies apparent to those of skill in the art. Deletion of a substantial portion or all of the heavy chain constant region genes and/or D-region genes may be accomplished by various methods, including sequential deletion by homologous recombination targeting vectors, especially of the "hit-and-run" type and the like. Similarly, functional disruption and/or deletion of at least one endogenous light chain locus (e.g., κ) to ablate endogenous light chain constant region genes is often preferable.

Frequently, it is desirable to employ a frameshifted transgene wherein the heterologous transgene comprises a frameshift in the J segment(s) and a compensating frameshift (i.e., to regenerate the original reading frame) in the initial region (i.e., amino-terminal coding portion) of one or more (preferably all) of the transgene constant region genes. Trans-switching to an endogenous IgH locus constant gene (which does not comprise a compensating frameshift) will result in a truncated or missense product that results in the trans-switched B cell being deleted or non-selected, thus suppressing the trans-switched phenotype.

Antisense suppression and antibody suppression may also be used to effect a substantially complete functional inactivation of endogenous Ig gene product expression (e.g., murine heavy and light chain sequences) and/or trans-switched antibodies (e.g., human variable/murine constant chimeric antibodies).

Various combinations of the inactivation and suppression strategies may be used to effect essentially total suppression of endogenous (e.g., murine) Ig chain expression.

Trans-Switching

In some variations, it may be desirable to produce a trans-switched immunoglobulin. For example, such trans-switched heavy chains can be chimeric (i.e., a non-murine (human) variable region and a murine constant region). Antibodies comprising such chimeric trans-switched immunoglobulins can be used for a variety of applications where it is desirable to have a non-human (e.g., murine) constant region (e.g., for retention of effector functions in the host, for the presence of murine immunological determinants such as for binding of a secondary antibody which does not bind human constant regions). For one example, a human variable region repertoire may possess advantages as compared to the murine variable region repertoire with respect to certain antigens. Presumably the human $V_H$, D, $J_H$, $V_L$, and $J_L$ genes have been selected for during evolution for their ability to encode immunoglobulins that bind certain evolutionarily important antigens; antigens which provided evolutionary selective pressure for the murine repertoire can be distinct from those antigens which provided evolutionary pressure to shape the human repertoire. Other repertoire adavantages may exist, making the human variable region repertoire advantageous when combined with a murine constant region (e.g., a trans-switched murine) isotype. The presence of a murine constant region can afford advantages over a human constant region. For example, a murine γ constant region linked to a human variable region by trans-switching may provide an antibody which possesses murine effector functions (e.g., ADCC, murine complement fixation) so that such a chimeric antibody (preferably monoclonal) which is reactive with a predetermined antigen (e.g., human IL-2 receptor) may be tested in a mouse disease model, such as a mouse model of graft-versus-host disease wherein the T lymphocytes in the mouse express a functional human IL-2 receptor. Subsequently, the human variable region encoding sequence may be isolated (e.g., by PCR amplification or cDNA cloning from the source (hybridoma clone)) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation. For some applications, the chimeric antibodies may be used directly without replacing the murine constant region with a human constant region. Other variations and uses of trans-switched chimeric antibodies will be evident to those of skill in the art.

The present invention provides transgenic nonhuman animals containing B lymphocytes which express chimeric antibodies, generally resulting from trans-switching between a human heavy chain transgene and an endogenous murine heavy chain constant region gene. Such chimeric antibodies comprise a human sequence variable region and a murine constant region, generally a murine switched (i.e., non-μ, non-δ) isotype. The transgenic nonhuman animals capable of making chimeric antibodies to a predetermined antigen are usually also competent to make fully human sequence antibodies if both human heavy chain and human light chain transgenes encoding human variable and human constant region genes are integrated. Most typically, the animal is homozygous for a functionally disrupted heavy chain locus and/or light chain locus but retains one or more endogenous heavy chain constant region gene(s) capable of trans-switching (e.g., γ, α, ε) and frequently retains a cis-linked enhancer. Such a mouse is immunized with a predetermined antigen, usually in combination with an adjuvant, and an immune response comprising a detectable amount of chimeric antibodies comprising heavy chains composed of human sequence variable regions linked to murine constant region sequences is produced. Typically, the serum of such an immunized animal can comprise such chimeric antibodies at concentrations of about at least 1 μg/ml, often about at least 10 μg/ml, frequently at least 30 μg/ml, and up to 50 to 100 μg/ml or more. The antiserum containing antibodies comprising chimeric human variable/mouse constant region heavy chains typically also comprises antibodies which comprise human variable/human constant region (complete human sequence) heavy chains. Chimetic trans-switched antibodies usually comprise (1) a chimeric heavy chain composed of a human variable region and a murine constant region (typically a murine gamma) and (2) a human transgene-encoded light chain (typically kappa) or a murine light chain (typically lambda in a kappa knockout background). Such chimeric trans-switched antibodies generally bind to a predetermined antigen (e.g., the immunogen) with an affinity of about at least $1\times10^7$ $M^{-1}$, preferably with an affinity of about at least $5\times10^7$ $M^{-1}$, more preferably with an affinity of at least $1\times10^8$ $M^{-1}$ to $1\times10^9$ $M^{-1}$ or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

The invention provides transgenic nonhuman animals comprising a genome comprising: (1) a homozygous functionally disrupted endogenous heavy chain locus comprising at least one murine constant region gene capable of trans-switching (e.g., in cis linkage to a functional switch recombination sequence and typically to a functional enhancer), (2) a human heavy chain transgene capable of rearranging to encode end express a functional human heavy chain variable region and capable of trans-switching (e.g., having a cis-linked RSS); optionally further comprising (3) a human light chain (e.g., kappa) transgene capable of rearranging to encode a functional human light chain variable region and expressing a human sequence light chain; optionally further comprising (4) a homozygous functionally disrupted endogenous light chain locus (κ, preferably κ and λ); and optionally further comprising (5) a serum comprising an antibody comprising a chimeric heavy chain composed of a human sequence variable region encoded by a human transgene and a murine constant region sequence encoded by an endogenous murine heavy chain constant region gene (e.g., γ1, γ2a, γ2b, γ3).

Such transgenic mice may further comprise a serum comprising chimeric antibodies which bind a predetermined human antigen (e.g., CD4, CD8, CEA) with an affinity of about at least $1\times10^4$ $M^{-1}$, preferably with an affinity of about at least $5\times10^4$ $M^{-1}$, more preferably with an affinity of at least $1\times10^7$ $M^{-1}$ to $1\times10^9$ $M^{-1}$ or more. Frequently, hybridomas can be made wherein the monoclonal antibodies produced thereby have an affinity of at least $8\times10^7$ $M^{-1}$. Chimeric antibodies comprising a heavy chain composed of a murine constant region and a human variable region, often capable of binding to a nonhuman antigen, may also be present in the serum or as an antibody secreted from a hybridoma.

In some variations, it is desirable to generate transgenic mice which have inactivated endogenous mouse heavy chain loci which retain intact heavy chain constant region genes, and which have a human heavy chain transgene capable of trans-switching, and optionally also have a human light chain transgene, optionally with one or more inactivated endogenous mouse light chain loci. Such mice may advantageously produce B cells capable of alternatively expressing antibodies comprising fully human heavy chains and antibodies comprising chimeric (human variable/mouse constant) heavy chains, by trans-switching. The serum of said mice would contain antibodies comprising fully human heavy chains and antibodies comprising chimeric (human variable/mouse constant) heavy chains, preferably in combination with fully human light chains. Hybridomas can be generated from the B cells of said mice.

Generally, such chimeric antibodies can be generated by trans-switching, wherein a human transgene encoding a human variable region (encoded by productive V-D-J rearrangement in vivo) and a human constant region, typically human μ, undergoes switch recombination with a non-transgene immunoglobulin constant gene switch sequence (RSS) thereby operably linking the transgene-encoded human variable region with a heavy chain constant region which is not encoded by said transgene, typically an endogenous murine immunoglobulin heavy chain constant region or a heterologous (e.g., human) heavy chain constant region encoded on a second transgene. Whereas cis-switching refers to isotype-switching by recombination of RSS elements within a transgene, trans-switching involves recombination between a transgene RSS and an RSS element outside the transgene, often on a different chromosome than the chromosome which harbors the transgene.

Trans-switching generally occurs between an RSS of an expressed transgene heavy chain constant region gene and either an RSS of an endogenous murine constant region gene (of a non-μ isotype, typically γ) or an RSS of a human constant region gene contained on a second transgene, often integrated on a separate chromosome.

When trans-switching occurs between an RSS of a first, expressed transgene heavy chain constant region gene (e.g., μ) and an RSS of a human heavy chain constant region gene contained on a second transgene, a non-chimeric antibody having a substantially fully human sequence is produced. For example and not limitation, a polynucleotide encoding a human heavy chain constant region (e.g., γ1) and an operably linked RSS (e.g., a γ1 RSS) can be introduced (e.g., transfected) into a population of hybridoma cells generated from a transgenic mouse B-cell (or B cell population) expressing an antibody comprising a transgene-encoded human μ chain. The resultant hybridoma cells can be selected for the presence of the introduced polynucleotide and/or for the expression of trans-switched antibody comprising a heavy chain having the variable region (idiotype/ antigen reactivity) of the human μ chain and having the constant region encoded by the introduced polynucleotide sequence (e.g., human γ1). Trans-switch recombination between the RSS of the transgene-encoded human μ chain and the RSS of the introduced polynucleotide encoding a downstream isotype (e.g., γ1) thereby can generate a trans-switched antibody.

The invention also provides a method for producing such chimeric trans-switched antibodies comprising the step of immunizing with a predetermined antigen a transgenic mouse comprising a genome comprising: (1) a homozygous functionally disrupted endogenous heavy chain locus comprising at least one murine constant region gene capable of trans-switching (e.g., γ2a, γ2b, γ1, γ3), (2) a human heavy chain transgene capable of rearranging to encode a functional human heavy chain variable region and expressing a human sequence heavy chain and capable of undergoing isotype switching (and/or trans-switching), and optionally further comprising (3) a human light chain (e.g., kappa) transgene capable of rearranging to encode a functional human light (e.g., kappa) chain variable region and expressing a human sequence light chain, and optionally further comprising (4) a homozygous functionally disrupted endogenous light chain locus (typically κ, preferably both κ and λ), and optionally further comprising (5) a serum comprising an antibody comprising a chimeric heavy chain composed of a human sequence variable region encoded by a human transgene and a murine constant region sequence encoded by an endogenous murine heavy chain constant region gene (e.g., γ1, γ2a, γ2b, γ3).

Affinity Tagging: Selecting for Switched Isotypes

Advantageously, trans-switching (and cis-switching) is associated with the process of somatic mutation. Somatic mutation expands the range of antibody affinities encoded by clonal progeny of a B-cell. For example, antibodies produced by hybridoma cells which have undergone switching (trans- or cis-) represent a broader range of antigen-binding affinities than is present in hybridoma cells which have not undergone switching. Thus, a hybridoma cell population (typically clonal) which expresses a first antibody comprising a heavy chain comprising a first human heavy chain variable region in polypeptide linkage to a first human heavy chain constant region (e.g., μ) can be screened for hybridoma cell clonal variants which express an antibody comprising a heavy chain containing said first human heavy chain variable region in polypeptide linkage to a second heavy chain constant region (e.g., a human γ, α, or ε constant region). Such clonal variants can be produced by natural clonal variation producing cis-switching in vitro, by induction of class switching (trans- or cis-) as through the administration of agents that promote isotype switching, such as T-cell-derived lymphokines (e.g., IL-4 and IFN$_\gamma$), by introduction of a polynucleotide comprising a functional RSS and a heterologous (e.g. human) heavy chain constant region gene to serve as a substrate for trans-switching, or by a combination of the above, and the like. Often, polynucleotides containing a human downstream isotype constant region (e.g., γ1, γ3, and the like) with an operably linked RSS will also be introduced into hybridoma cells to promote isotype switching via the trans-switch mechanism.

Class switching and affinity maturation take place within the same population of B cells derived from transgenic animals of the present invention. Therefore, identification of class-switched B cells (or hybridomas derived therefrom) can be used as a screening step for obtaining high affinity monoclonal antibodies. A variety of approaches can be employed to facilitate class switching events such as cis-switching (intratransgene switching), trans-switching, or both. For example, a single continuous human genomic fragment comprising both μ and γ constant region genes with the associated RSS elements and switch regulatory elements (e.g., sterile transcript promoter) can be used as a transgene. However, some portions of the desired single contiguous human genomic fragment can be difficult to clone efficiently, such as due to instability problems when replicated in a cloning host or the like; in particular, the region between δ and γ3 can prove difficult to clone efficiently, especially as a contiguous fragment comprising the μ gene, γ3 gene, a V gene, D gene segments, and J gene segments.

Also for example, a discontinuous human transgene (minigene) composed of a human μ gene, human γ3 gene, a human V gene(s), human D gene segments, and human J gene segments, with one or more deletions of an intervening (intronic) or otherwise nonessential sequence (e.g., one or more V, D, and/or J segment and/or one or more non-μ constant region gene(s)). Such minigenes have several advantages as compared to isolating a single contiguous segment of genomic DNA spanning all of the essential elements for efficient immunoglobulin expression and switching. For example, such a minigene avoids the necessity of isolating large pieces of DNA which may contain sequences which are difficult to clone (e.g., unstable sequences, poison sequences, and the like). Moreover, miniloci comprising elements necessary for isotype switching (e.g., human γ sterile transcript promoter) for producing cis- or trans-switching, can advantageously undergo somatic mutation and class switching in vivo. As many eukaryotic DNA sequences can prove difficult to clone, omitting nonessential sequences can prove advantageous.

In a variation, hybridoma clones producing antibodies having high binding affinity (e.g., at least $1 \times 10^7$ M$^{-1}$, preferably at least $1 \times 10^8$ M$^{-1}$, more preferably at least $1 \times 10^9$ M$^{-1}$ or greater) are obtained by selecting, from a pool of hybridoma cells derived from B cells of transgenic mice harboring a human heavy chain transgene capable of isotype switching (see, supra) and substantially lacking endogenous murine heavy chain loci capable of undergoing productive (in-frame) V-D-J rearrangement, hybridomas which express an antibody comprising a heavy chain comprising a human sequence heavy chain variable region in polypeptide linkage to a human (or mouse) non-μ heavy chain constant region; said antibodys are termed "switched antibodies" as they comprise a "switched heavy chain" which is produced as a consequence of cis-switching and/or trans-switching in vivo or in cell culture. Hybridomas producing switched antibodies generally have undergone the process of somatic mutation, and a pool of said hybridomas will generally have a broader range of antigen binding affinities from which hybridoma clones secreting high affinity antibodies can be selected. Typically, hybridomas secreting a human sequence antibody having substantial binding affinity (greater than $1\times10^7$ M$^{-1}$ to $1\times10^8$ M$^{-1}$) for a predetermined antigen and wherein said human sequence antibody comprises human immunoglobulin variable region(s) can be selected by a method comprising a two-step process. One step is to identify and isolate hybridoma cells which secrete immunoglobulins which comprise a switched heavy chain (e.g., by binding hybridoma cells to an immobilized immunoglobulin which specifically binds a switched heavy chain and does not substantially bind to an unswitched isotype, e.g., µ). The other step is to identify hybridoma cells which bind to the predetermined antigen with substantial binding affinity (e.g., by ELISA of hybridoma clone supernatants, FACS analysis using labeled antigen, and the like). Typically, selection of hybridomas which secrete switched antibodies is performed prior to identifying hybridoma cells which bind predetermined antigen. Hybridoma cells which express switched antibodies that have substantial binding affinity for the predetermined antigen are isolated and cultured under suitable growth conditions known in the art, typically as individual selected clones. Optionally, the method comprises the step of culturing said selected clones under conditions suitable for expression of monocloanl antibodies; said monoclonal antibodies are collected and can be administered for therapeutic, prophylactic, and/or diagnostic purposes.

Often, the selected hybridoma clones can serve as a source of DNA or RNA for isolating immunoglobulin sequences which encode immunoglobulins (e.g. a variable region) that bind to (or confer binding to) the predetermined antigen. Subsequently, the human variable region encoding sequence may be isolated (e.g., by PCR amplification or cDNA cloning from the source (hybridoma clone)) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

Xenoenhancers

A heterologous transgene capable of encoding a human immunoglobulin (e.g., a heavy chain) advantageously comprises a cis-linked enhancer which is not derived from the mouse genome, and/or which is not naturally associated in cis with the exons of the heterologous transgene. For example, a human κ transgene (e.g., a K minilocus) can advantageously comprise a human Vκ gene, a human Jκ gene, a human Cκ gene, and a xenoenhancer, typically said xenoenhancer comprises a human heavy chain intronic enhancer and/or a murine heavy chain intronic enhancer, typically located between a Jκ gene and the Cκ gene, or located downstream of the Cκ gene. For example, the mouse heavy chain J-µ intronic enhancer (Banerji et al. (1983) *Cell* 33: 729) can be isolated on a 0.9 kb XbaI fragment of the plasmid pKVe2 (see, infra). The human heavy chain J-µ intronic enhancer (Hayday et al. (1984) *Nature* 307: 334) can be isolated as a 1.4 kb MluI/HindIII fragment (see, infra). Addition of a transcriptionally active xenoenhancer to a transgene, such as a combined xenoenhancer consisting essentially of a human J-µ intronic enhancer linked in cis to a mouse J-µ intronic enhancer, can confer high levels of expression of the transgene, especially where said transgene encodes a light chain, such as human κ. Similarly, a rat 3' enhancer can be advantageously included in a minilocus construct capable of encoding a human heavy chain.

Specific Preferred Embodiments

A preferred embodiment of the invention is an animal containing at least one, typically 2–10, and sometimes 25–50 or more copies of the transgene described in Example 12 (e.g., pHC1 or pHC2) bred with an animal containing a single copy of a light chain transgene described in Examples 5, 6, 8, or 14, and the offspring bred with the $J_H$ deleted animal described in Example 10. Animals are bred to homozygosity for each of these three traits. Such animals have the following genotype: a single copy (per haploid set of chromosomes) of a human heavy chain unrearranged mini-locus (described in Example 12), a single copy (per haploid set of chromosomes) of a rearranged human κ light chain construct (described in Example 14), and a deletion at each endogenous mouse heavy chain locus that removes all of the functional $J_H$ segments (described in Example 10). Such animals are bred with mice that are homozygous for the deletion of the $J_H$ segments (Examples 10) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and λ chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. Of course, the IgG to IgM ratio will be much lower in the immature mouse. In general, greater than about 10%, preferably 40 to 80% of the spleen and lymph node B cells express exclusively human IgG protein.

The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, including, but not limited to: pigeon cytochrome C, chicken lysozyme, pokeweed mitogen, bovine serum albumin, keyhole limpit hemocyanin, influenza hemagglutinin, staphylococcus protein A, sperm whale myoglobin, influenza neuraminidase, and lambda repressor protein. Some of the immunoglobulins will exhibit an affinity for preselected antigens of at least about $10^7 \underline{M}^{-1}$, preferably $10^8 \underline{M}^{-1}$ to $10^9 \underline{M}^{-1}$ or greater.

In some embodiments, it may be preferable to generate mice with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans).

Thus, prior to rearrangement of a transgene containing various heavy or light chain gene segments, such gene segments may be readily identified, e.g. by hybridization or DNA sequencing, as being from a species of organism other than the transgenic animal.

Although the foregoing describes a preferred embodiment of the transgenic animal of the invention, other embodiments are defined by the disclosure herein and more particularly by the transgenes described in the Examples. Four categories of transgenic animal may be defined:

I. Transgenic animals containing an unrearranged heavy and rearranged light immunoglobulin transgene.

II. Transgenic animals containing an unrearranged heavy and unrearranged light immunoglobulin transgene III. Transgenic animal containing rearranged heavy and an unrearranged light immunoglobulin transgene, and IV. Transgenic animals containing rearranged heavy and rearranged light immunoglobulin transgenes.

Of these categories of transgenic animal, the preferred order of preference is as follows II>I>III>IV where the endogenous light chain genes (or at least the κ gene) have been knocked out by homologous recombination (or other method) and I>II>III>IV where the endogenous light chain genes have not been knocked out and must be dominated by allelic exclusion.

EXPERIMENTAL EXAMPLES

Methods and Materials

Transgenic mice are derived according to Hogan, et al., "Manipulating the Mouse Embryo: A Laboratory Manual", Cold Spring Harbor Laboratory, which is incorporated herein by reference.

Embryonic stem cells are manipulated according to published procedures (Teratocarcinomas and embryonic stem cells: a practical approach, E. J. Robertson, ed., IRL Press, Washington, D.C., 1987; Zjilstra et al., *Nature* 342:435-438 (1989); and Schwartzberg et al., *Science* 246:799-803 (1989), each of which is incorporated herein by reference).

DNA cloning procedures are carried out according to J. Sambrook, et al. in Molecular Cloning: A Laboratory Manual, 2d ed., 1989, Cold Spring Harbor Laboratory Press, Cold Spring Harbor, N.Y., which is incorporated herein by reference.

Oligonucleotides are synthesized on an Applied Bio Systems oligonucleotide synthesizer according to specifications provided by the manufacturer.

Hybridoma cells and antibodies are manipulated according to "Antibodies: A Laboratory Manual", Ed Harlow and David Lane, Cold Spring Harbor Laboratory (1988), which is incorporated herein by reference.

Example 1

Genomic Heavy Chain Human Ig Transgene

This Example describes the cloning and microinjection of a human genomic heavy chain immunoglobulin transgene which is microinjected into a murine zygote.

Nuclei are isolated from fresh human placental tissue as described by Marzluff et al., "Transcription and Translation: A Practical Approach", B. D. Hammes and S. J. Higgins, eds., pp. 89-129, IRL Press, Oxford (1985)). The isolated nuclei (or PBS washed human spermatocytes) are embedded in a low melting point agarose matrix and lysed with EDTA and proteinase κ to expose high molecular weight DNA, which is then digested in the agarose with the restriction enzyme NotI as described by M. Finney in Current Protocols in Molecular Biology (F. Ausubel, et al., eds. John Wiley & Sons, Supp. 4, 1988, Section 2.5.1).

The NotI digested DNA is then fractionated by pulsed field gel electrophoresis as described by Anand et al., *Nucl. Acids Res.* 17:3425-3433 (1989). Fractions enriched for the NotI fragment are assayed by Southern hybridization to detect one or more of the sequences encoded by this fragment. Such sequences include the heavy chain D segments, J segments, μ and γ1 constant regions together with representatives of all 6 VH families (although this fragment is identified as 670 kb fragment from HeLa cells by Berman et al. (1988), supra., we have found it to be as 830 kb fragment from human placental an sperm DNA). Those fractions containing this NotI fragment (see FIG. 4) are pooled and cloned into the NotI site of the vector pYACNN in Yeast cells. Plasmid pYACNN is prepared by digestion of pYAC-4 Neo (Cook et al., *Nucleic Acids Res.* 16: 11817 (1988)) with EcoRI and ligation in the presence of the oligonucleotide 5' - AAT TGC GGC CGC - 3'.

YAC clones containing the heavy chain NotI fragment are isolated as described by Brownstein et al., *Science* 244:1348-1351 (1989), and Green et al., *Proc. Natl. Acad. Sci. USA* 87:1213-1217 (1990), which are incorporated herein by reference. The cloned NotI insert is isolated from high molecular weight yeast DNA by pulse field gel electrophoresis as described by M. Finney, op cit. The DNA is condensed by the addition of 1 mM spermine and microinjected directly into the nucleus of single cell embryos previously described.

Example 2

Genomic κ Light Chain Human Ig Transgene Formed by In Vivo Homologous Recombination A map of the human μ light chain has been described in Lorenz et al., *Nucl. Acids Res.* 15:9667-9677 (1987), which is incorporated herein by reference.

A 450 kb XhoI to NotI fragment that includes all of $C_\kappa$, the 3' enhancer, all J segments, and at least five different V segments is isolated and microinjected into the nucleus of single cell embryos as described in Example 1.

Example 3

Genomic κ Light Chain Human Ig Transgene Formed by In Vivo Homologous Recombination A 750 kb MluI to NotI fragment that includes all of the above plus at least 20 more V segments is isolated as described in Example 1 and digested with BssHII to produce a fragment of about 400 kb.

The 450 kb XhoI to NotI fragment plus the approximately 400 kb MluI to BssHII fragment have sequence overlap defined by the BssHII and XhoI restriction sites. Homologous recombination of these two fragments upon microinjection of a mouse zygote results in a transgene containing at least an additional 15–20 V segments over that found in the 450 kb XhoI/NotI fragment (Example 2).

B. Construction of pRE3 (rat enhancer 3')

An enhancer sequence located downstream of the rat constant region is included in the heavy chain constructs.

The heavy chain region 3' enhancer described by Petterson et al., *Nature* 344:165–168 (1990), which is incorporated herein by reference) is isolated and cloned. The rat IGH 3' enhancer sequence is PCR amplified by using the following oligonucleotides:

```
5' CAG GAT CCA GAT ATC AGT ACC TGA AAC AGG GCT TGC 3'
5' GAG CAT GCA CAG GAC CTG GAG CAC ACA CAG CCT TCC 3'
```

Example 4

Construction of Heavy Chain Mini-Locus

Figure 8:
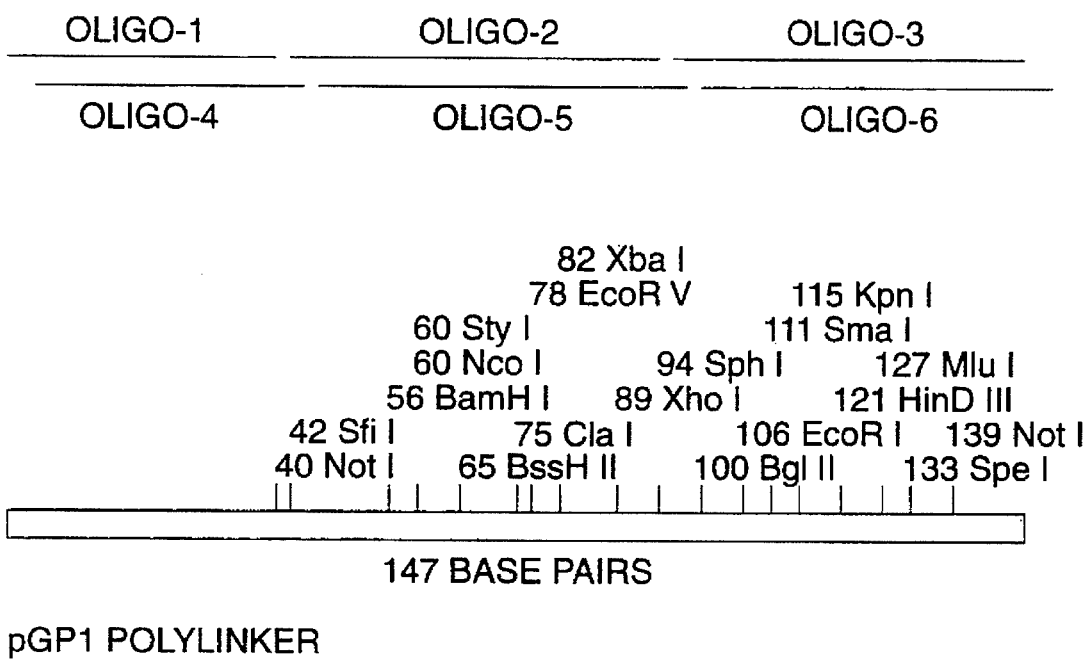
FIG. 8 depicts the construction of the polylinker contained in pGP1.
Figure 9:
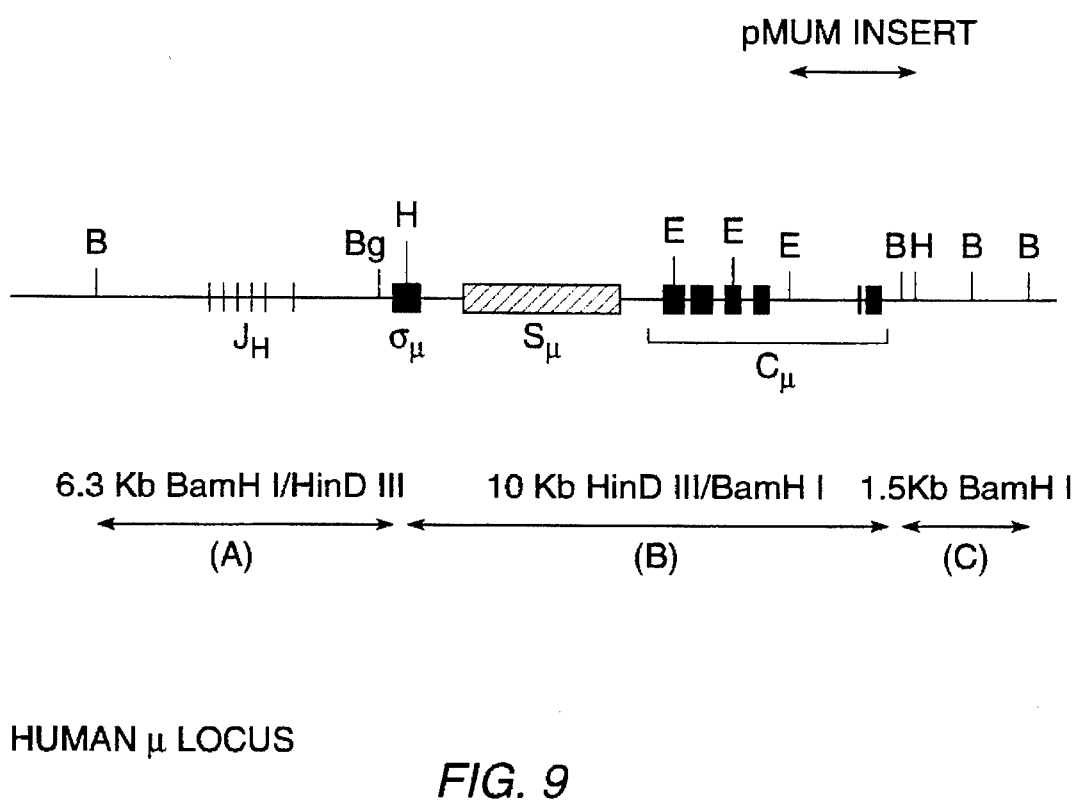
FIG. 9 depicts the fragments used to construct a human heavy chain transgene of the invention.

A. Construction of pGP1 and pGP2 pBR322 is digested with EcoRI and StyI and ligated with the following oligonucleotides to generate pGP1 which contains a 147 base pair insert containing the restriction sites shown in FIG. 8. The general overlapping of these oligos is also shown in FIG. 9.

The oligonucleotides are:

```
oligo-1 5'- CTT GAG CCC GCC TAA TGA GCG GGC TTT
           TTT TTG CAT ACT GCG GCC -3' oligo-2 5'- GCA ATG GCC TGG ATC CAT GGC GCG CTA
           GCA TCG ATA TCT AGA GCT CGA GCA -3' oligo-3 5'- TGC AGA TCT GAA TTC CCG GGT ACC AAG
           CTT ACG CGT ACT AGT GCG GCC GCT -3' oligo-4 5'- AAT TAG CGG CCG CAC TAG TAC GCG TAA
           GCT TGG TAC CCG GGA ATT -3' oligo-5 5'- CAG ATC TGC ATG CTC GAG CTC TAG ATA
           TCG ATG CTA GCG CGC CAT GGA TCC -3' oligo-6 5'- AGG CCA TTG CGG CCG CAG TAT GCA AAA
           AAA AGC CCG CTC ATT AGG CGG GCT -3'
```

This plasmid contains a large polylinker flanked by rare cutting NotI sites for building large inserts that can be isolated from vector sequences for microinjection. The plasmid is based on pBR322 which is relatively low copy compared to the pUC based plasmids (pGP1 retains the pBR322 copy number control region near the origin of replication). Low copy number reduces the potential toxicity of insert sequences. In addition, pGP1 contains a strong transcription terminator sequence derived from trpA (Christie et al., *Proc. Natl. Acad. Sci. USA* 78:4180 (1981)) inserted between the ampicillin resistance gene and the polylinker. This further reduces the toxicity associated with certain inserts by preventing readthrough transcription coming from the ampicillin promoters.

Plasmid pGP2 is derived from pGP1 to introduce an additional restriction site (SfiI) in the polylinker. pGP1 is digested with MluI and SpeI to cut the recognition sequences in the polylinker portion of the plasmid.

The following adapter oligonucleotides are ligated to the thus digested pGP1 to form pGP2.

```
5' CGC GTG GCC GCA ATG GCC A 3'
5' CTA GTG GCC ATT GCG GCC A 3'
``` pGP2 is identical to pGP1 except that it contains an additional Sfi I site located between the MluI and SpeI sites. This allows inserts to be completely excised with SfiI as well as with NotI.

The thus formed double stranded DNA encoding the 3' enhancer is cut with BamHI and SphI and clone into BamHI/SphI cut pGP2 to yield pRE3 (rat enhancer 3').

C. Cloning of Human J-μ Region

A substantial portion of this region is cloned by combining two or more fragments isolated from phage lambda inserts. See FIG. 9.

A 6.3 kb BamHI/HindIII fragment that includes all human J segments (Matsuda et al., *EMBO J.*, 7:1047–1051 (1988); Ravetech et al.m *Cell*, 27:583–591 (1981), which are incorporated herein by reference) is isolated from human genomic DNA library using the oligonucleotide GGA CTG TGT CCC TGT GTG ATG CTT TTG ATG TCT GGG GCC AAG.

An adjacent 10 kb HindIII/BamII fragment that contains enhancer, switch and constant region coding exons (Yasui et al., *Eur. J. Immunol.* 19:1399–1403 (1989)) is similarly isolated using the oligonucleotide:

```
CAC CAA GTT GAC CTG CCT GGT CAC AGA CCT GAC
CAC CTA TGA
```

An adjacent 3' 1.5 kb BamHI fragment is similarly isolated using clone pMUM insert as probe (pMUM is 4 kb EcoRI/HindIII fragment isolated from human genomic DNA library with oligonucleotide:

```
CCT GTG GAC CAC CGC CTC CAC CTT CAT
CGT CCT CTT CCT CCT
``` mu membrane exon 1) and cloned into pUC19.

pGP1 is digested with BamHI and BglII followed by treatment with calf intestinal alkaline phosphatase.

Fragments (a) and (b) from FIG. 9 are cloned in the digested pGP1. A clone is then isolated which is oriented such that 5' BamHI site is destroyed by BamHI/Bgl fusion. It is identified as pMU (see FIG. 10). pMU is digested with BamHI and fragment (c) from FIG. 9 is inserted. The orientation is checked with HindIII digest. The resultant plasmid pHIG1 (FIG. 10) contains an 18 kb insert encoding J and Cμ segments.

Figure 14:
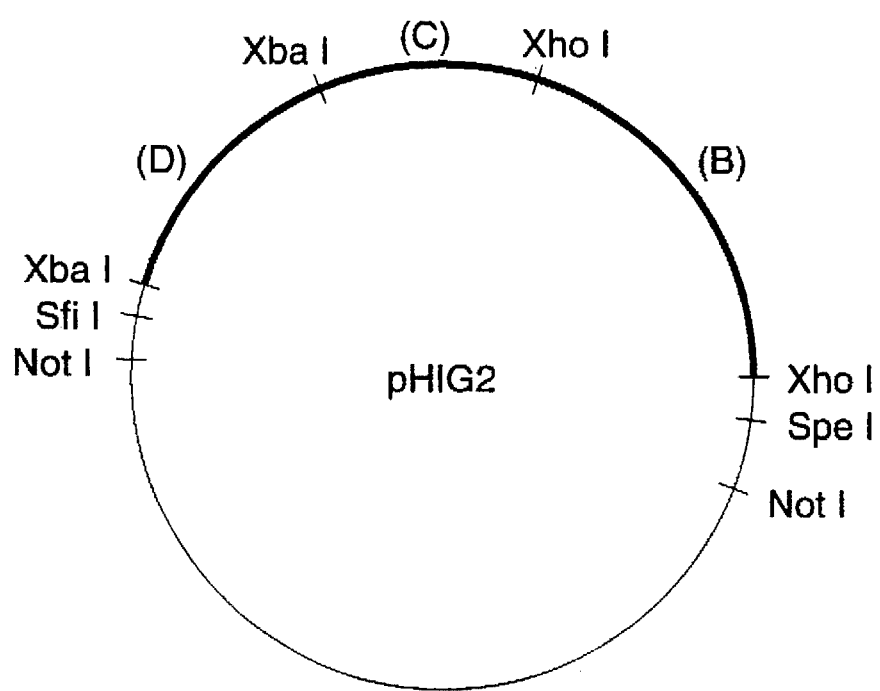
FIG. 14 depicts the construction of pHIG2 (D segment containing plasmid).
Figure 15:
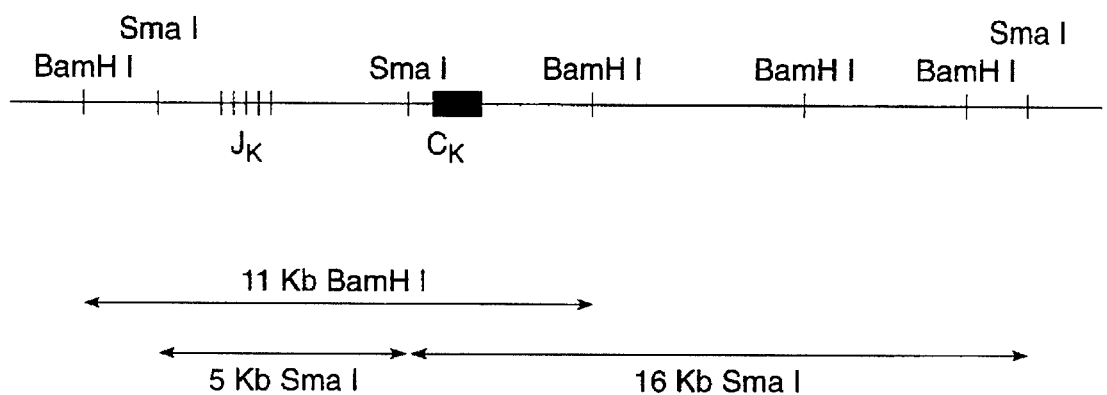
FIG. 15 depicts the fragments covering the human Jκ and human Cκ gene segments used in constructing a transgene of the invention.

D. Cloning of Cμ Region pGP1 is digested with BamHI and HindIII is followed by treatment with calf intestinal alkaline phosphatase (FIG. 14). The so treated fragment (b) of FIG. 14 and fragment (c) of FIG. 14 are cloned into the BamHI/HindIII cut pGP1. Proper orientation of fragment (c) is checked by HindIII digestion to form pCON1 containing a 12 kb insert encoding the Cμ region.

Whereas pHIG1 contains J segments, switch and μ sequences in its 18 kb insert with an SfiI 3' site and a SpeI 5' site in a polylinker flanked by NotI sites, will be used for rearranged VDJ segments. pCON1 is identical except that it lacks the J region and contains only a 12 kb insert. The use of pCON1 in the construction of fragment containing rearranged VDJ segments will be described hereinafter.

E. Cloning of γ-1 Constant Region (pREG2)

Figure 16:
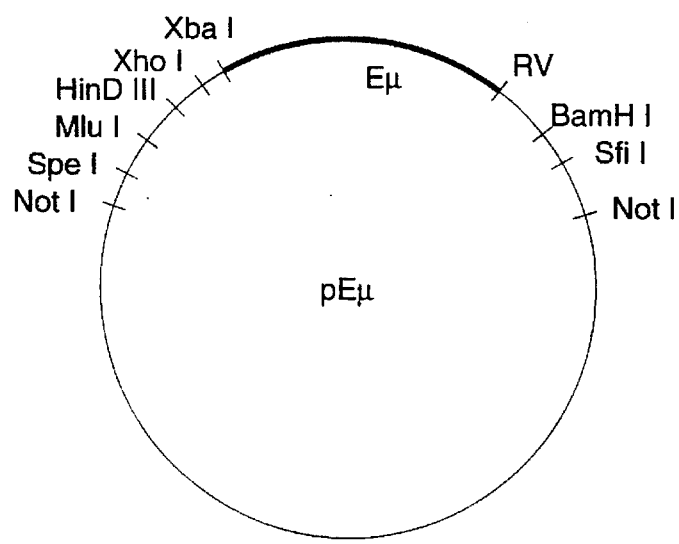
FIG. 16 depicts the structure of pEμ.
Figure 18A:
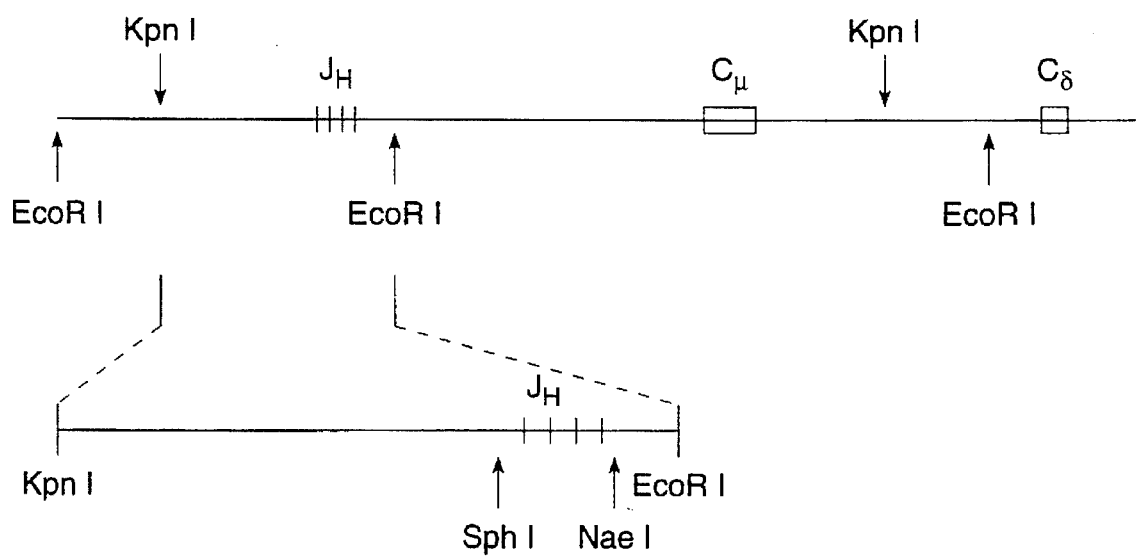
Figure 18C:
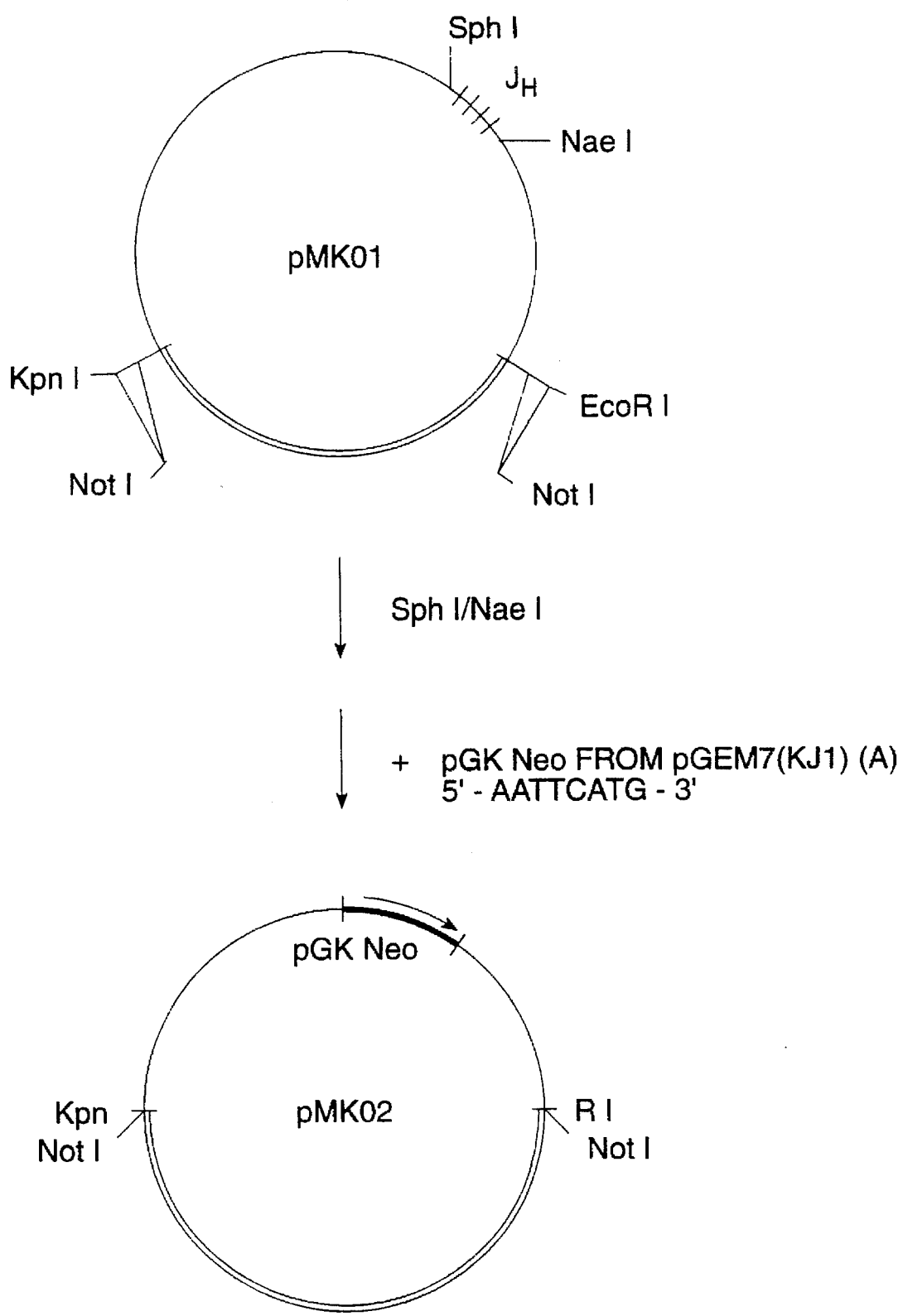
Figure 18D:
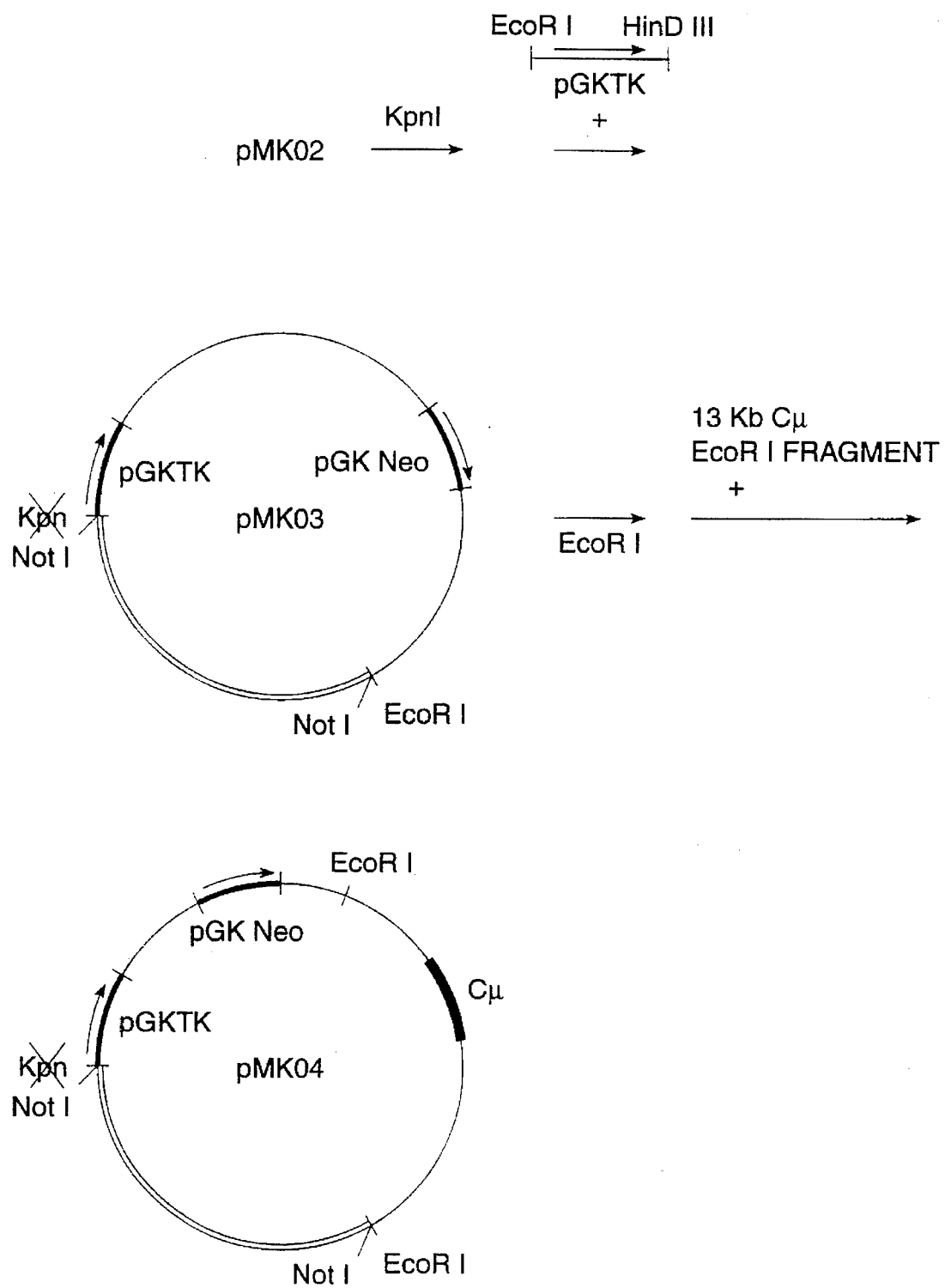
Figure 19A:
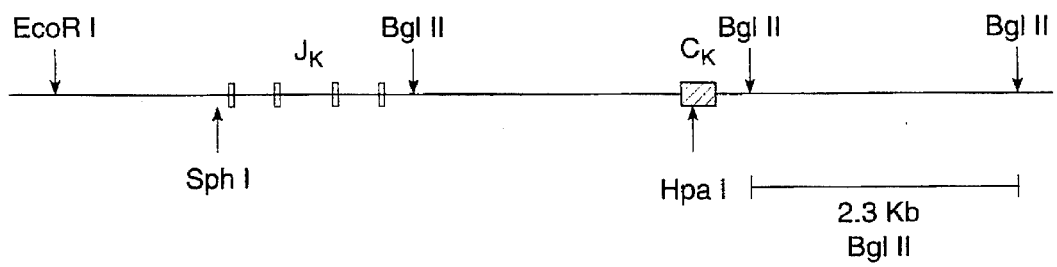
Figure 19B:
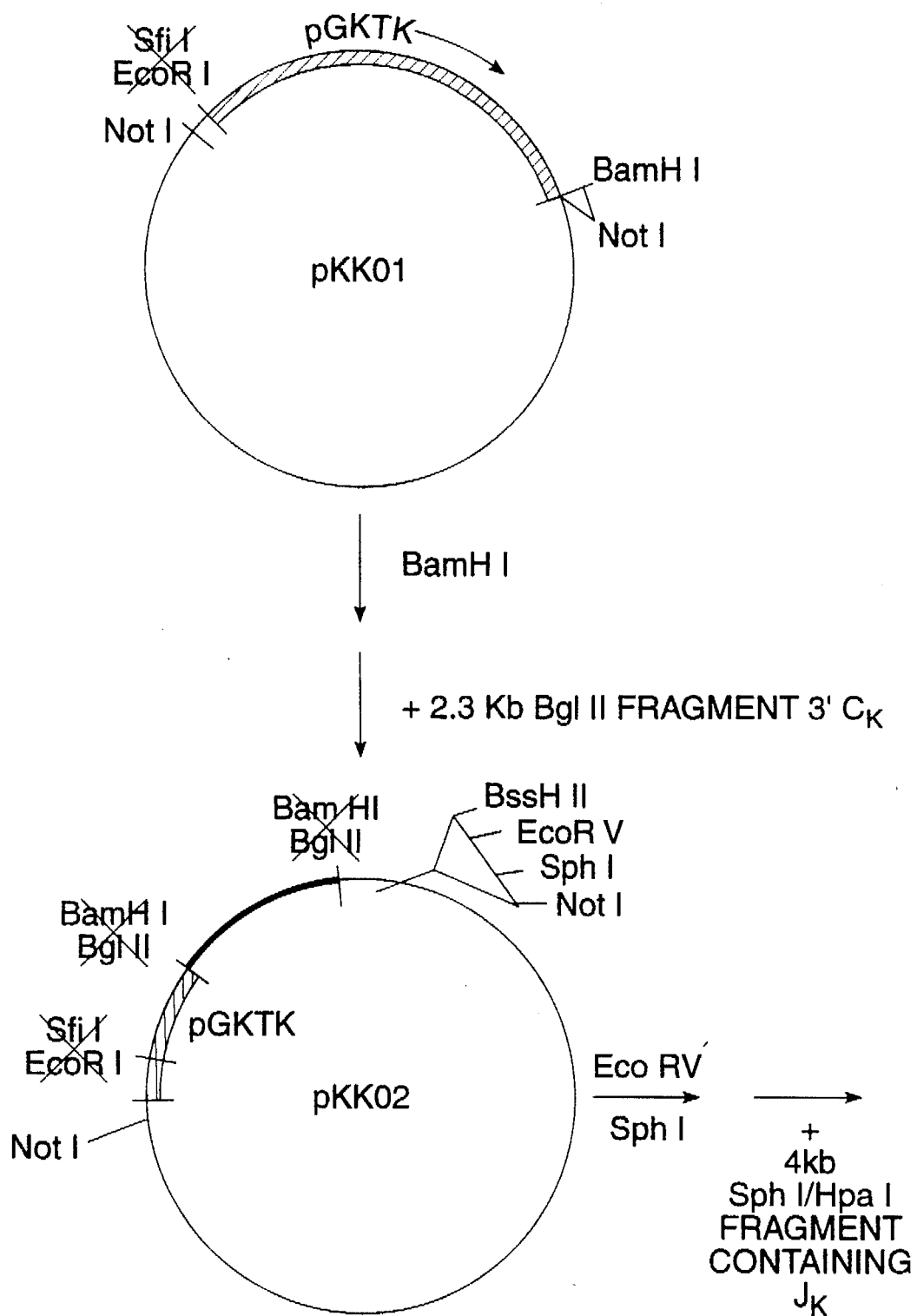

The cloning of the human γ-1 region is depicted in FIG. 16.

Yamamura et al., *Proc. Natl. Acad. Sci. USA* 83:2152–2156 (1986) reported the expression of membrane bound human γ-1 from a transgene construct that had been partially deleted on integration. Their results indicate that the 3' BamHI site delineates a sequence that includes the transmembrane rearranged and switched copy of the gamma gene with a V-C intron of less than 5 kb. Therefore, in the unrearranged, unswitched gene, the entire switch region is included in a sequence beginning less than 5 kb from the 5' end of the first γ-1 constant exon. Therefore it is included in the 5' 5.3 kb HindIII fragment (Ellison et al., *Nucleic Acids Res.* 10:4071–4079 (1982), which is incorporated herein by reference). Takahashi et al., *Cell* 29: 671–679 (1982), which is incorporated herein by reference, also reports that this fragment contains the switch sequence, and this fragment together with the 7.7 kb HindIII to BamHI fragment must include all of the sequences we need for the transgene construct. An intronic sequence is a nucleotide sequence of at least 15 contiguous nucleotides that occurs in an intron of a specified gene.

Phage clones containing the γ-1 region are identified and isolated using the following oligonucleotide which is specific for the third exon of γ-I (CH3).

```
5' TGA GCC ACG AAG ACC CTG AGG
   TCA AGT TCA ACT GGT ACG TGG 3'
```

Figure 11:
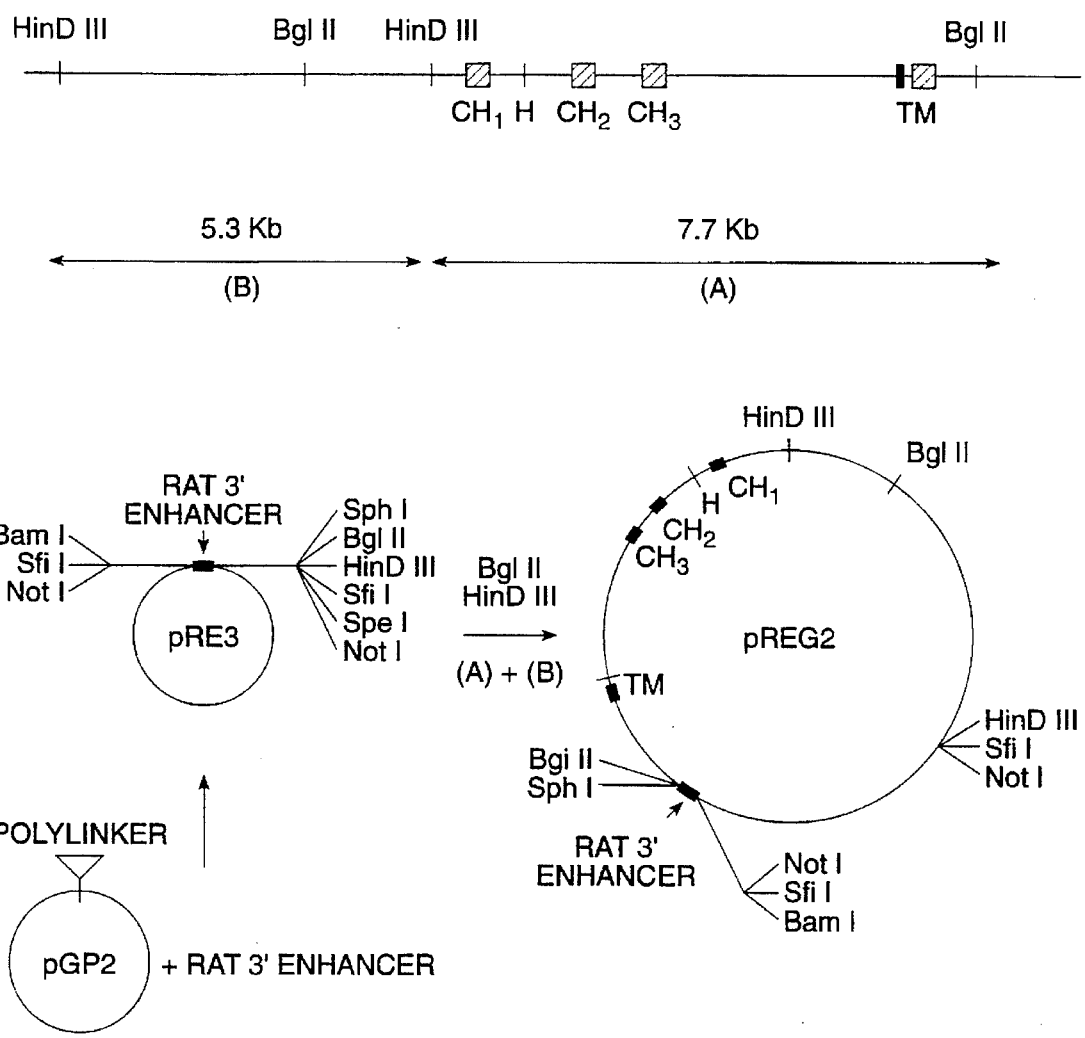
FIG. 11 depicts the human Cγ1 fragments which are inserted into pRE3 (rat enhancer 3') to form pREG2.

A 7.7 kb HindIII to BglII fragment (fragment (a) in FIG. 11) is cloned into HindIII/BglII cut pRE3 to form pREG1. The upstream 5.3 kb HindIII fragment (fragment (b) in FIG. 11) is cloned into HindIII digested pREG1 to form pREG2. Correct orientation is confirmed by BamHI/SpeI digestion.

F. Combining Cγ and Cμ

Figure 10:
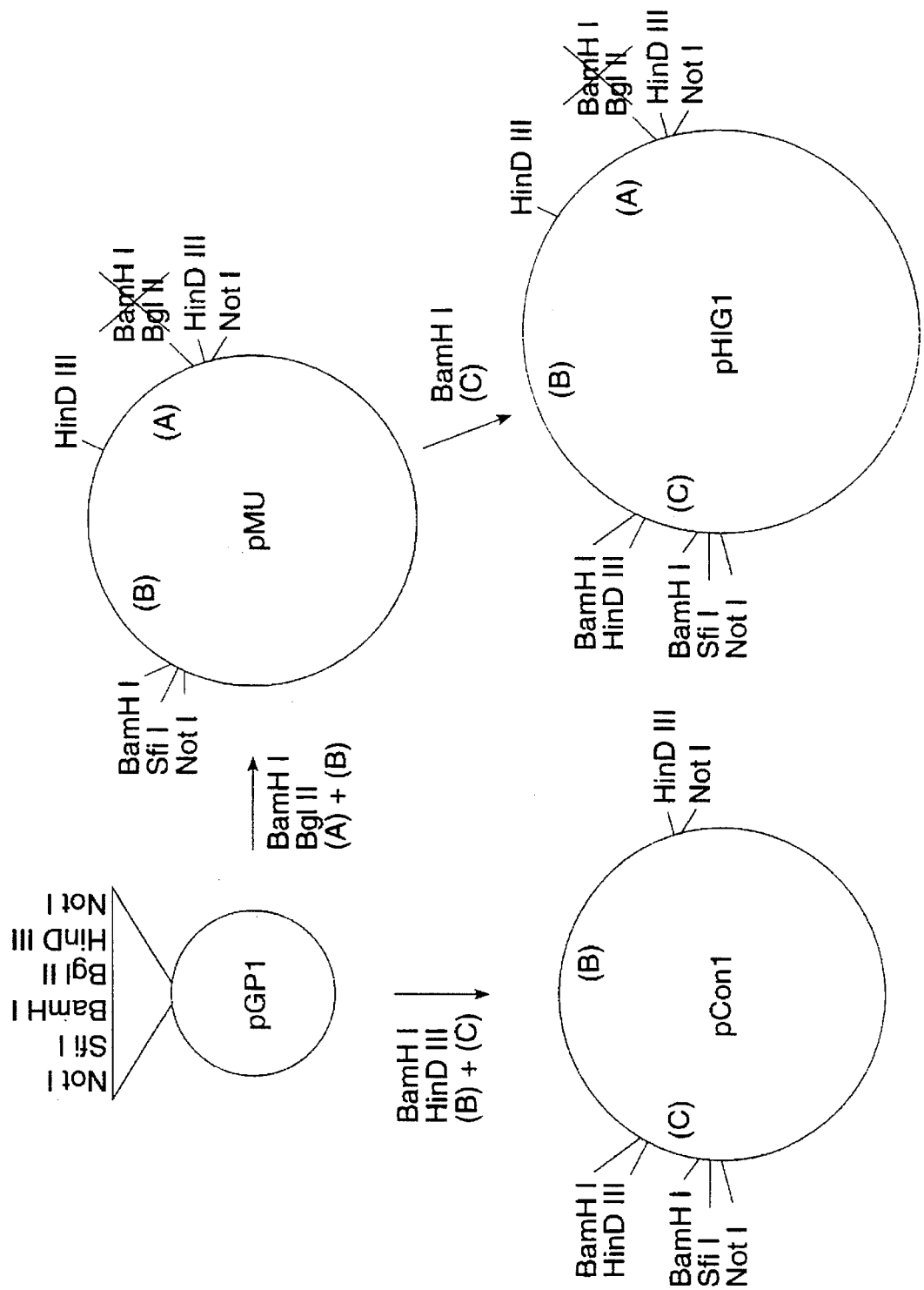
FIG. 10 depicts the construction of pHIG1 and pCON1.

The previously described plasmid pHIG1 contains human J segments and the Cμ constant region exons. To provide a transgene containing the Cμ constant region gene segments, pHIG1 was digested with SfiI (FIG. 10). The plasmid pREG2 was also digested with SfiI to produce a 13.5 kb insert containing human Cγ exons and the rat 3' enhancer sequence. These sequences were combined to produce the plasmid pHIG3' (FIG. 12) containing the human J segments, the human Cμ constant region, the human Cγ1 constant region and the rat 3' enhancer contained on a 31.5 kb insert.

A second plasmid encoding human Cμ and human Cγ1 without J segments is constructed by digesting pCON1 with SfiI and combining that with the SfiI fragment containing the human Cγ region and the rat 3' enhancer by digesting pREG2 with SfiI. The resultant plasmid, pCON (FIG. 12) contains a 26 kb NotI/SpeI insert containing human Cμ, human γ1 and the rat 3' enhancer sequence.

G. Cloning of D Segment

Figure 13:
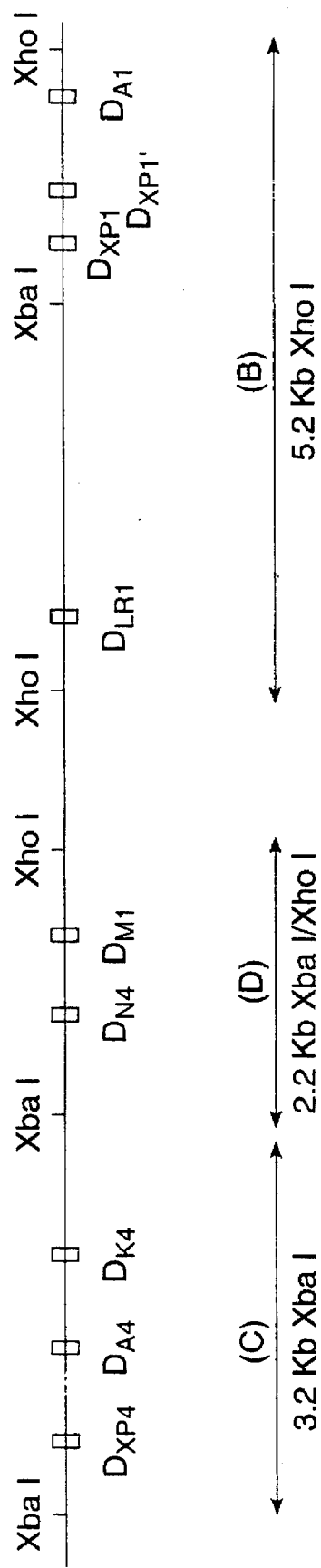
FIG. 13 depicts the fragment containing human D region segments used in construction of the transgenes of the invention.

The strategy for cloning the human D segments is depicted in FIG. 13. Phage clones from the human genomic library containing D segments are identified and isolated using probes specific for diversity region sequences (Ichihara et al., *EMBO J.* 7:4141–4150 (1988)). The following oligonucleotides are used:

```
DXP1:  5'- TGG TAT TAC TAT GGT TCG GGG AGT TAT TAT
           AAC CAC AGT GTC -3'

DXP4:  5'- GCC TGA AAT GGA GCC TCA GGG CAC AGT GGG
           CAC GGA CAC TGT -3'

DNA:   5'- GCA GGG AGG ACA TGT TTA GGA TCT GAG GCC
           GCA CCT GAC ACC -3'
```

A 5.2 kb XhoI fragment (fragment (b) in FIG. 13) containing DLR1, DXP1, DXP'1, and DA1 is isolated from a phage clone identified with oligo DXP1.

A 3.2 kb XbaI fragment (fragment (c) in FIG. 13) containing DXP4, DA4 and DK4 is isolated from a phage clone identified with oligo DXP4.

Fragments (b), (c) and (d) from FIG. 13 are combined and cloned into the XbaI/XhoI site of pGP1 to form pHIG2 which contains a 10.6 kb insert.

This cloning is performed sequentially. First, the 5.2 kb fragment (b) in FIG. 13 and the 2.2 kb fragment (d) of FIG. 13 are treated with calf intestinal alkaline phosphatase and cloned into pGP1 digested with XhoI and XbaI. The resultant clones are screened with the 5.2 and 2.2 kb insert. Half of those clones testing positive with the 5.2 and 2.2 kb inserts have the 5.2 kb insert in the proper orientation as determined by BamHI digestion. The 3.2 kb XbaI fragment from FIG. 13 is then cloned into this intermediate plasmid containing fragments (b) and (d) to form pHIG2. This plasmid contains diversity segments cloned into the polylinker with a unique 5' SfiI site and unique 3' SpeI site. The entire polylinker is flanked by NotI sites.

H. Construction of Heavy Chain Minilocus

The following describes the construction of a human heavy chain mini-locus which contain one or more V segments.

An unrearranged V segment corresponding to that identified as the V segment contained in the hybridoma of Newkirk et al., *J. Clin. Invest.* 81:1511–1518 (1988), which is incorporated herein by reference, is isolated using the following oligonucleotide:

```
5'- GAT CCT GGT TTA GTT AAA GAG GAT TTT
    ATT CAC CCC TGT GTC -3'
```

A restriction map of the unrearranged V segment is determined to identify unique restriction sites which provide upon digestion a DNA fragment having a length approximately 2 kb containing the unrearranged V segment together with 5' and 3' flanking sequences. The 5' prime sequences will include promoter and other regulatory sequences whereas the 3' flanking sequence provides recombination sequences necessary for V-DJ joining. This approximately 3.0 kb V segment insert is cloned into the polylinker of pGB2 to form pVH1.

pVH1 is digested with SfiI and the resultant fragment is cloned into the SfiI site of pHIG2 to form a pHIG5'. Since pHIG2 contains D segments only, the resultant pHIG5' plasmid contains a single V segment together with D segments. The size of the insert contained in pHIG5 is 10.6 kb plus the size of the V segment insert.

The insert from pHIG5 is excised by digestion with NotI and SpeI and isolated. pHIG3' which contains J, Cμ and cγ1 segments is digested with SpeI and NotI and the 3' kb fragment containing such sequences and the rat 3' enhancer sequence is isolated. These two fragments are combined and ligated into NotI digested pGP1 to produce pHIG which contains insert encoding a V segment, nine D segments, six functional J segments, Cμ, Cγ and the rat 3' enhancer. The size of this insert is approximately 43 kb plus the size of the V segment insert.

I. Construction of Heavy Chain Minilocus by Homologous Recombination

As indicated in the previous section, the insert of pHIG is approximately 43 to 45 kb when a single V segment is employed. This insert size is at or near the limit of that which may be readily cloned into plasmid vectors. In order to provide for the use of a greater number of V segments, the following describes in vivo homologous recombination of overlapping DNA fragments which upon homologous recombination within a zygote or ES cell form a transgene containing the rat 3' enhancer sequence, the human Cμ, the human Cγ1, human J segments, human D segments and a multiplicity of human V segments.

A 6.3 kb BamHI/HindIII fragment containing human J segments (see fragment (a) in FIG. 9) is cloned into MluI/SpeI digested pHIG5' using the following adapters:

```
5' GAT CCA AGC AGT 3'
5' CTA GAC TGC TTG 3'
5' CGC GTC GAA CTA 3'
5' AGC TTA GTT CGA 3'
```

The resultant is plasmid designated pHIG5'O (overlap). The insert contained in this plasmid contains human V, D and J segments. When the single V segment from pVH1 is used, the size of this insert is approximately 17 kb plus 2 kb. This insert is isolated and combined with the insert from pHIG3' which contains the human J, Cμ, γ1 and rat 3' enhancer sequences. Both inserts contain human J segments which provide for approximately 6.3 kb of overlap between the two DNA fragments. When coinjected into the mouse zygote, in vivo homologous recombination occurs generating a transgene equivalent to the insert contained in pHIG.

This approach provides for the addition of a multiplicity of V segments into the transgene formed in vivo. For example, instead of incorporating a single V segment into pHIG5', a multiplicity of V segments contained on (1) isolated genomic DNA, (2) ligated DNA derived from genomic DNA, or (3) DNA encoding a synthetic V segment repertoire is cloned into pHIG2 at the SfiI site to generate pHIG5' $V_N$. The J segments fragment (a) of FIG. 9 is then cloned into pHIG5' $V_N$ and the insert isolated. This insert now contains a multiplicity of V segments and J segments which overlap with the J segments contained on the insert isolated from pHIG3'. When cointroduced into the nucleus of a mouse zygote, homologous recombination occurs to generate in vivo the transgene encoding multiple V segments and multiple J segments, multiple D segments, the Cμ region, the Cγ1 region (all from human) and the rat 3' enhancer sequence.

Example 5

Construction of Light Chain Minilocus

A. Construction of pEμ1

The construction of pEμ1 is depicted in FIG. 16. The mouse heavy chain enhancer is isolated on the XbaI to EcoRI 678 bp fragment (Banerji et al., Cell 33:729–740 (1983)) from phage clones using oligo:

```
5' GAA TGG GAG TGA GGC TCT CTC ATA CCC
   TAT TCA GAA CTG ACT 3'
```

This Eμ fragment is cloned into EcoRV/XbaI digested pGP1 by blunt end filling in EcoRI site. The resultant plasmid is designated pEμ1.

B. Construction of κ Light chain Minilocus

The κ construct contains at least one human $V_κ$ segment, all five human $J_κ$ segments, the human $J-C_κ$ enhancer, human κ constant region exon, and, ideally, the human 3' κ enhancer (Meyer et al., EMBO J. 8:1959–1964 (1989)). The κ enhancer in mouse is 9 kb downstream from $C_κ$. However, it is as yet unidentified in the human. In addition, the construct contains a copy of the mouse heavy chain J-Cμ enhancers.

The minilocus is constructed from four component fragments:

(a) A 16 kb SmaI fragment that contains the human $C_κ$ exon and the 3' human enhancer by analogy with the mouse locus;

(b) A 5' adjacent 5 kb SmaI fragment, which contains all five J segments;

(c) The mouse heavy chain intronic enhancer isolated from pEμ1 (this sequence is included to induce expression of the light chain construct as early as possible in B-cell development. Because the heavy chain genes are transcribed earlier than the light chain genes, this heavy chain enhancer is presumably active at an earlier stage than the intronic κ enhancer); and (d) A fragment containing one or more V segments.

The preparation of this construct is as follows. Human placental DNA is digested with SmaI and fractionated on agarose gel by electrophoresis. Similarly, human placental DNA is digested with BamHI and fractionated by electrophoresis. The 16 kb fraction is isolated from the SmaI digested gel and the 11 kb region is similarly isolated from the gel containing DNA digested with BamHI.

The 16 kb SmaI fraction is cloned into Lambda FIX II (Stratagene, La Jolla, Calif.) which has been digested with XhoI, treated with klenow fragment DNA polymerase to fill in the XhoI restriction digest product. Ligation of the 16 kb SmaI fraction destroys the SmaI sites and lases XhoI sites intact.

The 11 kb BamHI fraction is cloned into λ EMBL3 (Strategene, La Jolla, Calif.) which is digested with BamHI prior to cloning.

Clones from each library were probed with the Cκ specific oligo:

```
5' GAA CTG TGG CTG CAC CAT CTG TCT
   TCA TCT TCC CGC CAT CTG 3'
```

A 16 kb XhoI insert that was subcloned into the XhoI cut pEμ1 so that Cκ is adjacent to the SmaI site. The resultant plasmid was designated pKap1.

The above Cκ specific oligonucleotide is used to probe the λ EMBL3/BamHI library to identify an 11 kb clone. A 5 kb SmaI fragment (fragment (b) in FIG. 20) is subcloned and subsequently inserted into pKap1 digested with SmaI. Those plasmids containing the correct orientation of J segments, Cκ and the Eμ enhancer are designated pKap2.

One or more Vκ segments are thereafter subcloned into the MluI site of pKap2 to yield the plasmid pKapH which encodes the human Vκ segments, the human Jκ segments, the human Cκ segments and the human Eμ enhancer. This insert is excised by digesting pKapH with NotI and purified by agarose gel electrophoresis. The thus purified insert is microinjected into the pronucleus of a mouse zygote as previously described.

C. Construction of κ Light Chain Minilocus by In Vivo Homologous Recombination

The 11 kb BamHI fragment is cloned into BamHI digested pGP1 such that the 3' end is toward the SfiI site. The resultant plasmid is designated pKAPint. One or more Vκ segments is inserted into the polylinker between the BamHI and SpeI sites in pKAPint to form pKapHV. The insert of pKapHV is excised by digestion with NotI and purified. The insert from pKap2 is excised by digestion with NotI and purified. Each of these fragments contain regions of homology in that the fragment from pKapHV contains a 5 kb sequence of DNA that include the $J_κ$ segments which is substantially homologous to the 5 kb SmaI fragment contained in the insert obtained from pKap2. As such, these inserts are capable of homologously recombining when microinjected into a mouse zygote to form a transgene encoding $V_κ$, $J_κ$ and $C_κ$.

Example 6

Isolation of Genomic Clones Corresponding to Rearranged and Expressed Copies of Immunoglobulin κ Light Chain Genes This example describes the cloning of immunoglobulin κ light chain genes from cultured cells that express an immunoglobulin of interest. Such cells may contain multiple alleles of a given immunoglobulin gene. For example, a hybridoma might contain four copies of the κ light chain gene, two copies from the fusion partner cell line and two copies from the original B-cell expressing the immunoglobulin of interest. Of these four copies, only one encodes the immunoglobulin of interest, despite the fact that several of them may be rearranged. The procedure described in this example allows for the selective cloning of the expressed copy of the κ light chain.

A. Double Stranded cDNA

Cells from human hybridoma, or lymphoma, or other cell line that synthesizes either cell surface or secreted or both forms of IgM with a κ light chain are used for the isolation of polyA+ RNA. The RNA is then used for the synthesis of oligo dT primed cDNA using the enzyme reverse transcriptase (for general methods see, Goodspeed et al. (1989) Gene 76: 1; Dunn et al. (1989) J. Biol. Chem. 264: 13057). The single stranded cDNA is then isolated and G residues are added to the 3' end using the enzyme polynucleotide terminal transferase. The G-tailed single-stranded cDNA is then purified and used as template for second strand synthesis (catalyzed by the enzyme DNA polymerase) using the following oligonucleotide as a primer:

5'- GAG GTA CAC TGA CAT ACT GGC ATG CCC CCC CCC CCC -3'

The double stranded cDNA is isolated and used for determining the nucleotide sequence of the 5' end of the mRNAs encoding the heavy and light chains of the expressed immunoglobulin molecule. Genomic clones of these expressed genes are then isolated. The procedure for cloning the expressed light chain gene is outlined in part B below.

B. Light Chain

The double stranded cDNA described in part A is denatured and used as a template for a third round of DNA synthesis using the following oligonucleotide primer:

5'- GTA CGC CAT ATC AGC TGG ATG AAG TCA TCA GAT GGC GGG AAG ATG AAG ACA GAT GGT GCA -3'

This primer contains sequences specific for the constant portion of the κ light chain message (TCA TCA GAT GGC GGG AAG ATG AAG ACA GAT GGT GCA) as well as unique sequences that can be used as a primer for the PCR amplification of the newly synthesized DNA strand (GTA CGC CAT ATC AGC TGG ATG AAG). The sequence is amplified by PCR using the following two oligonucleotide primers:

5'- GAG GTA CAC TGA CAT ACT GGC ATG -3'
5'- GTA CGC CAT ATC AGC TGG ATG AAG -3'

The PCR amplified sequence is then purified by gel electrophoresis and used as template for dideoxy sequencing reactions using the following oligonucleotide as a primer:

5' - GAG GTA CAC TGA CAT ACT GGC ATG - 3'

The first 42 nucleotides of sequence will then be used to synthesize a unique probe for isolating the gene from which immunoglobulin message was transcribed. This synthetic 42 nucleotide segment of DNA will be referred to below as o-kappa.

A Southern blot of DNA, isolated from the Ig expressing cell line and digested individually and in pairwise combinations with several different restriction endonucleases including SmaI, is then probed with the 32-P labelled unique oligonucleotide o-kappa. A unique restriction endonuclease site is identified upstream of the rearranged V segment.

DNA from the Ig expressing cell line is then cut with SmaI and second enzyme (or BamHI or KpnI if there is SmaI site inside V segment). Any resulting non-blunted ends are treated with the enzyme T4 DNA polymerase to give blunt ended DNA molecules. Then add restriction site encoding linkers (BamHI, EcoRI or XhoI depending on what site does not exist in fragment) and cut with the corresponding linker enzyme to give DNA fragments with BamHI, EcoRI or XhoI ends. The DNA is then size fractionated by agarose gel electrophoresis, and the fraction including the DNA fragment covering the expressed V segment is cloned into lambda EMBL3 or Lambda FIX (Stratagene, La Jolla, Calif.). V segment containing clones are isolated using the unique probe o-kappa. DNA is isolated from positive clones and subcloned into the polylinker of pKap1. The resulting clone is called pRKL.

Example 7

Isolation of Genomic Clones Corresponding to Rearranged Expressed Copies of Immunoglobulin Heavy Chain μ Genes This example describes the cloning of immunoglobulin heavy chain μ genes from cultured cells of expressed and immunoglobulin of interest. The procedure described in this example allows for the selective cloning of the expressed copy of a μ heavy chain gene.

Double-stranded cDNA is prepared and isolated as described herein before. The double-stranded cDNA is denatured and used as a template for a third round of DNA synthesis using the following oligonucleotide primer:

5'- GTA CGC CAT ATC AGC TGG ATG AAG ACA GGA GAC
GAG GGG GAA AAG GGT TGG GGC GGA TGC -3'

This primer contains sequences specific for the constant portion of the μ heavy chain message (ACA GGA GAC GAG GGG GAA AAG GGT TGG GGC GGA TGC) as well as unique sequences that can be used as a primer for the PCR amplification of the newly synthesized DNA strand (GTA CGC CAT ATC AGC TGG ATG AAG). The sequence is amplified by PCR using the following two oligonucleotide primers:

5'- GAG GTA CAC TGA CAT ACT GGC ATG -3'
5'- GTA CTC CAT ATC AGC TGG ATG AAG -3'

The PCR amplified sequence is then purified by gel electrophoresis and used as template for dideoxy sequencing reactions using the following oligonucleotide as a primer:

5' - GAG GTA CAC TGA CAT ACT GGC ATG - 3'

The first 42 nucleotides of sequence are then used to synthesize a unique probe for isolating the gene from which immunoglobulin message was transcribed. This synthetic 42 nucleotide segment of DNA will be referred to below as o-mR.

A Southern blot of DNA, isolated from the Ig expressing cell line and digested individually and in pairwise combinations with several different restriction endonucleases including MluI (MluI is a rare cutting enzyme that cleaves between the J segment and mu CH1), is then probed with the 32-P labelled unique oligonucleotide o-mu. A unique restriction endonuclease site is identified upstream of the rearranged V segment.

DNA from the Ig expressing cell line is then cut with MluI and second enzyme. MluI or SpeI adapter linkers are then ligated onto the ends and cut to convert the upstream site to MluI or SpeI. The DNA is then size fractionated by agarose gel electrophoresis, and the fraction including the DNA fragment covering the expressed V segment is cloned directly into the plasmid pGPI. V segment containing clones are isolated using the unique probe o-mu, and the insert is subcloned into MluI or MluI/SpeI cut plasmid pCON2. The resulting plasmid is called pRMGH.

Example 8

Construction of Human κ Miniloci Transgenes
Light Chain Minilocus

A human genomic DNA phage library was screened with kappa light chain specific oligonucleotide probes and isolated clones spanning the $J_\kappa$-C region. A 5.7 kb ClaI/XhoI fragment containing $J_\kappa 1$ together with a 13 kb XhoI fragment containing $J_\kappa 2$-5 and $C_\kappa$ into pGP1d was cloned and used to create the plasmid pKcor. This plasmid contains $J_\kappa 1$-5, the kappa intronic enhancer and $C_\kappa$ together with 4.5 kb of 5' and 9 kb of 3' flanking sequences. It also has a unique 5' XhoI site for cloning $V_\kappa$ segments and a unique 3' SalI site for inserting additional cis-acting regulatory sequences.

V Kappa Genes

A human genomic DNA phage library was screened with $V_\kappa$ light chain specific oligonucleotide probes and isolated clones containing human $V_\kappa$ segments. Functional V segments were identified by DNA sequence analysis. These clones contain TATA boxes, open reading frames encoding leader and variable peptides (including 2 cysteine residues), splice sequences, and recombination heptamer-12 bp spacer-nonamer sequences. Three of the clones were mapped and sequenced. Two of the clones, 65.5 and 65.8 appear to be functional, they contain TATA boxes, open reading frames encoding leader and variable peptides (including 2 cysteine residues), splice sequences, and recombination heptamer-12 bp spacer-nonamer sequences. The third clone, 65.4, appears to encode a $V_\kappa I$ pseudogene as it contains a non-canonical recombination heptamer.

One of the functional clones, Vk 65-8, which encodes a VkIII family gene, was used to build a light chain minilocus construct.

pKC1

Figure 32:
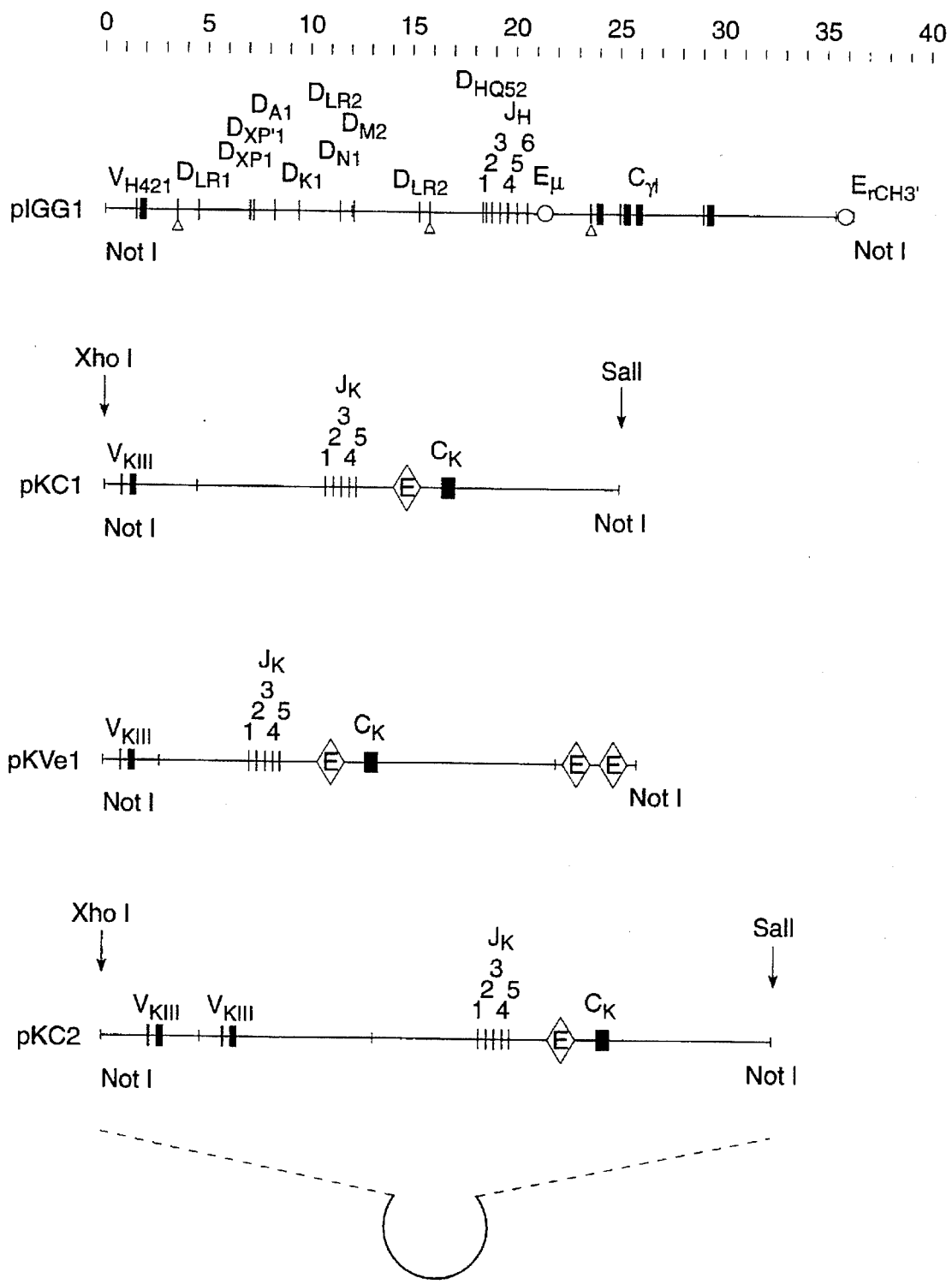
FIG. 32 is a schematic representation of the heavy chain minilocus construct pIGG1 and the κ light chain minilocus construct pKC1, pKVe1, and pKC2.

The kappa light chain minilocus transgene pKC1 (FIG. 32) was generated by inserting a 7.5 kb XhoI/SalI fragment containing $V_\kappa$ 65.8 into the 5' XhoI site of pKcor. The transgene insert was isolated by digestion with NotI prior to injection.

The purified insert was microinjected into the pronuclei of fertilized (C57BL/6×CBA)F2 mouse embryos and transferred the surviving embryos into pseudopregnant females as described by Hogan et al. (in Methods of Manipulating the Mouse Embryo, 1986, Cold Spring Harbor Laboratory, N.Y.). Mice that developed from injected embryos were analyzed for the presence of transgene sequences by Southern blot analysis of tail DNA. Transgene copy number was estimated by band intensity relative to control standards containing known quantities of cloned DNA. Serum was isolated from these animals and assayed for the presence of transgene encoded human Ig kappa protein by ELISA as described by Harlow and Lane (in Antibodies: A Laboratory Manual, 1988, Cold Spring Harbor Laboratory, New York). Microtiter plate wells were coated with mouse monoclonal antibodies specific for human Ig kappa (clone 6E1, #0173, AMAC, Inc., Westbrook, Me.), human IgM (Clone AF6, #0285, AMAC, Inc., Westbrook, Me.) and human IgG1 (clone JL512, #0280, AMAC, Inc., Westbrook, Me.). Serum samples were serially diluted into the wells and the presence of specific immunoglobulins detected with affinity isolated alkaline phosphatase conjugated goat anti-human Ig (polyvalent) that had been pre-adsorbed to minimize cross-reactivity with mouse immunoglobulins.

Figure 35:
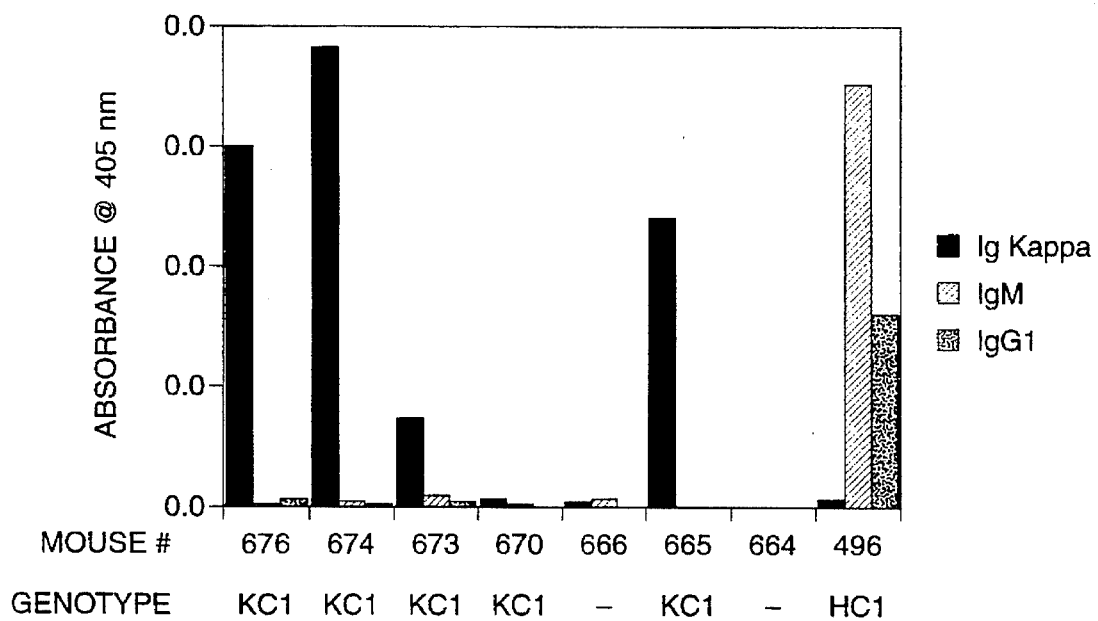
FIG. 35 depicts the results of an ELISA assay of serum from 8 transgenic mice.

FIG. 35 shows the results of an ELISA assay of serum from 8 mice (I.D. #676, 674, 673, 670, 666, 665, 664, and 496). The first seven of these mice developed from embryos that were injected with the pKC1 transgene insert and the eighth mouse is derived from a mouse generated by microinjection of the pHC1 transgene (described previously). Two of the seven mice from KC1 injected embryos (I.D.#'s 666 and 664) did not contain the transgene insert as assayed by DAN Southern blot analysis, and five of the mice (I.D.#'s 676, 674, 673, 670, and 665) contained the transgene. All but one of the KC1 transgene positive animals express detectable levels of human Ig kappa protein, and the single non-expressing animal appears to be a genetic mosaic on the basis of DNA Southern blot analysis. The pHC1 positive transgenic mouse expresses human IgM and IgG1 but not Ig kappa, demonstrating the specificity of the reagents used in the assay.

pKC2

The kappa light chain minilocus transgene pKC2 was generated by inserting an 8 kb XhoI/SalI fragment containing $V_\kappa$ 65.5 into the 5' XhoI site of pKC1. The resulting transgene insert, which contains two $V_\kappa$ segments, was isolated prior to microinjection by digestion with NotI.

pKVe2

This construct is identical to pKC1 except that it includes 1.2 kb of additional sequence 5' of $J_\kappa$ and is missing 4.5 kb of sequence 3' of $V_\kappa$ 65.8. In additional it contains a 0.9 kb XbaI fragment containing the mouse heavy chain J-μ intronic enhancer (Banerji et al., Cell 33:729–740 (1983)) together with a 1.4 kb MluI/HindIII fragment containing the human heavy chain J-μ intronic enhancer (Hayday et al., Nature 307:334–340 (1984)) inserted downstream. This construct tests the feasibility of initiating early rearrangement of the light chain minilocus to effect allelic and isotypic exclusion. Analogous constructs can be generated with different enhancers, i.e., the mouse or rat 3' kappa or heavy chain enhancer (Meyer and Neuberger, EMBO J. 8:1959–1964 (1989); Petterson et al. Nature 344:165–168 (1990), which are incorporated herein by reference).

Rearranged Light Chain Transgenes

Figure 33:
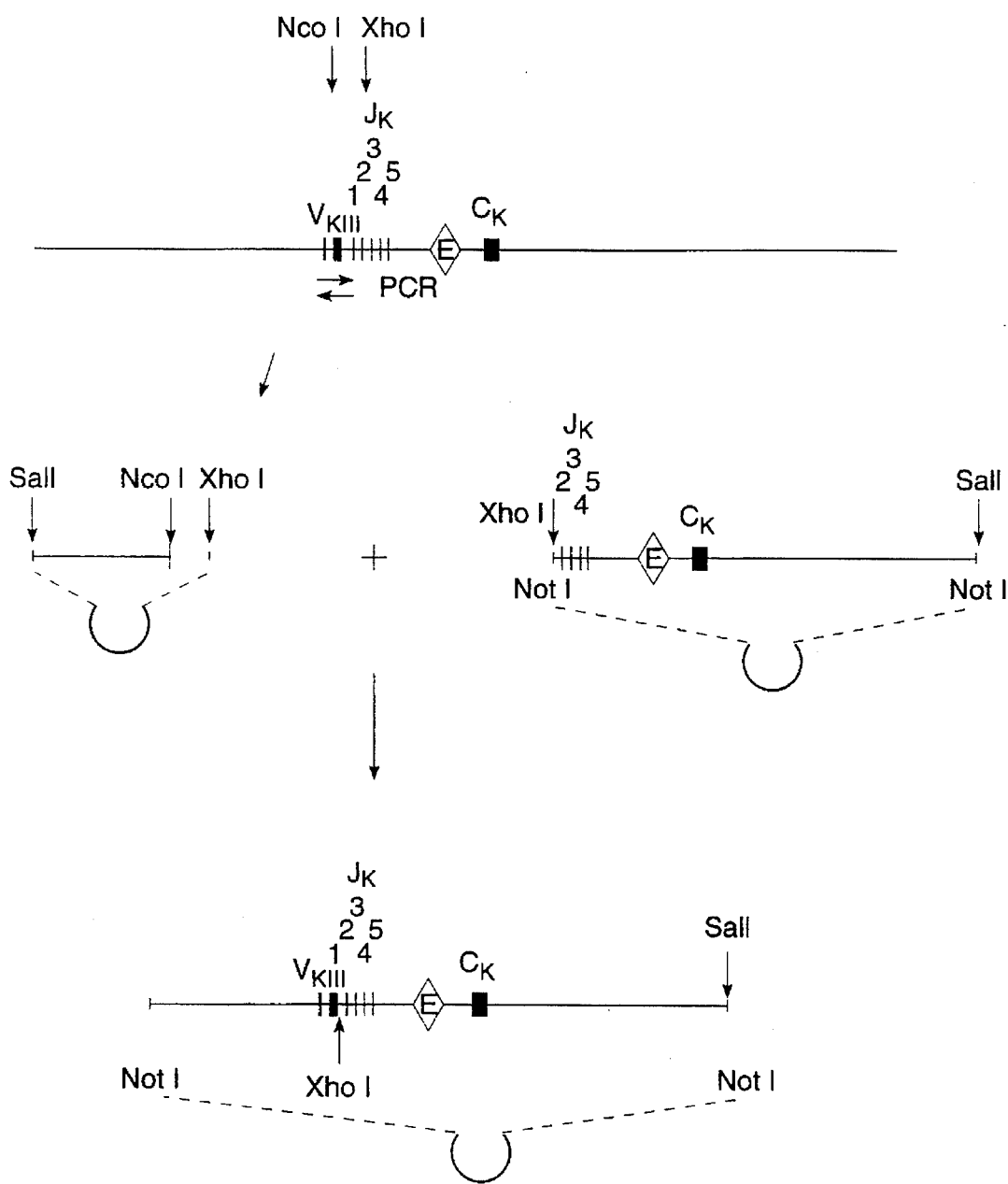
FIG. 33 depicts a scheme to reconstruct functionally rearranged light chain genes.

A kappa light chain expression cassette was designed to reconstruct functionally rearranged light chain genes that have been amplified by PCR from human B-cell DNA. The scheme is outlined in FIG. 33. PCR amplified light chain genes are cloned into the vector pK5nx that includes 3.7 kb of 5' flanking sequences isolated from the kappa light chain gene 65.5. The VJ segment fused to the 5' transcriptional sequences are then cloned into the unique XhoI site of the vector pK31s that includes $J_\kappa$2-4, the $J_\kappa$ intronic enhancer, $C_\kappa$, and 9 kb of downstream sequences. The resulting plasmid contains a reconstructed functionally rearranged kappa light chain transgene that can be excised with NotI for microinjection into embryos. The plasmids also contain unique SalI sites at the 3' end for the insertion of additional cis-acting regulatory sequences.

Two synthetic oligonucleotides (o-130, o-131) were used to amplify rearranged kappa light chain genes from human spleen genomic DNA. Oligonucleotide o-131 (gga ccc aga (g,c)gg aac cat gga a(g,a)(g,a,t,c)) is complementary to the 5' region of $V_\kappa$III family light chain genes and overlaps the first ATC of the leader sequence. Oligonucleotide o-130 (gtg caa tca att ctc gag ttt gac tac aga c) is complementary to a sequence approximately 150 bp 3' of $J_\kappa$1 and includes an XhoI site. These two oligonucleotides amplify a 0.7 kb DNA fragment from human spleen DNA corresponding to rearranged $V_\kappa$III genes joined to $J_\kappa$1 segments. The PCR amplified DNA was digested with NcoI and XhoI and cloned individual PCR products into the plasmid pNN03. The DNA sequence of 5 clones was determined and identified two with functional VJ joints (open reading frames). Additional functionally rearranged light chain clones are collected. The functionally rearranged clones can be individually cloned into light chain expression cassette described above (FIG. 33). Transgenic mice generated with the rearranged light chain constructs can be bred with heavy chain minilocus transgenics to produce a strain of mice that express a spectrum of fully human antibodies in which all of the diversity of the primary repertoire is contributed by the heavy chain. One source of light chain diversity can be from somatic mutation. Because not all light chains will be equivalent with respect to their ability to combine with a variety of different heavy chains, different strains of mice, each containing different light chain constructs can be generated and tested. The advantage of this scheme, as opposed to the use of unrearranged light chain miniloci, is the increased light chain allelic and isotypic exclusion that comes from having the light chain ready to pair with a heavy chain as soon as heavy chain VDJ joining occurs. This combination can result in an increased frequency of B-cells expressing fully human antibodies, and thus it can facilitate the isolation of human Ig expressing hybridomas.

NotI inserts of plasmids pIGM1, pHC1, pIGG1, pKC1, and pKC2 were isolated away from vector sequences by agarose gel electrophoresis. The purified inserts were microinjected into the pronuclei of fertilized (C57BL/6×CBA)F2 mouse embryos and transferred the surviving embryos into pseudopregnant females as described by Hogan et al. (Hogan et al., Methods of Manipulating the Mouse Embryo, Cold Spring Harbor Laboratory, New York (1986)).

Example 9

Inactivation of the Mouse Kappa Light Chain Gene by Homologous Recombination This example describes the inactivation of the mouse endogenous kappa locus by homologous recombination in embryonic stem (ES) cells followed by introduction of the mutated gene into the mouse germ line by injection of targeted ES cells bearing an inactivated kappa allele into early mouse embryos (blastocysts).

The strategy is to delete $J_K$ and $C_K$ by homologous recombination with a vector containing DNA sequences homologous to the mouse kappa locus in which a 4.5 kb segment of the locus, spanning the $J_K$ gene and $C_K$ segments, is deleted and replaced by the selectable marker neo.

Construction of the Kappa Targeting Vector

The plasmid pGEM7 (KJ1) contains the neomycin resistance gene (neo), used for drug selection of transfected ES cells, under the transcriptional control of the mouse phosphoglycerate kinase (pgk) promoter (XbaI/TaqI fragment; Adra et al. (1987) Gene 60: 65) in the cloning vector pGEM-7Zf(+). The plasmid also includes a heterologous polyadenylation site for the neogene, derived from the 3' region of the mouse pgk gene (PvuII/HindIII fragment; Boer et al., Biochemical Genetics, 28:299–308 (1990)). This plasmid was used as the starting point for construction of the kappa targeting vector. The first step was to insert sequences homologous to the kappa locus 3' of the neo expression cassette.

Mouse kappa chain sequences (FIG. 20a) were isolated from a genomic phage library derived from liver DNA using oligonucleotide probes specific for the Cκ locus:

5'- GGC TGA TGC TGC ACC AAC TGT ATC CAT CTT CCC ACC ATC CAG -3' and for the J$\kappa$5 gene segment:

5'- CTC ACG TTC GGT GCT GGG ACC AAG CTG GAG CTG AAA CGT AAG -3'.

An 8 kb BglII/SacI fragment extending 3' of the mouse C$_\kappa$ segment was isolated from a positive phage clone in two pieces, as a 1.2 kb BglII/SacI fragment and a 6.8 kb SacI fragment, and subcloned into BglII/SacI digested pGEM7 (KJ1) to generate the plasmid pNEO-K3' (FIG. 20b).

A 1.2 kb EcoRI/SphI fragment extending 5' of the J$_\kappa$ region was also isolated from a positive phage clone. An SphI/XbaI/BglII/EcoRI adaptor was ligated to the SphI site of this fragment, and the resulting EcoRI fragment was ligated into EcoRI digested pNEO-K3', in the same 5' to 3' orientation as the neogene and the downstream 3' kappa sequences, to generate pNEO-K5'3' (FIG. 20c).

The Herpes Simplex Virus (HSV) thymidine kinase (TK) gene was then included in the construct in order to allow for enrichment of ES clones bearing homologous recombinants, as described by Mansour et al., Nature 236:348–352 (1988), which is incorporated herein by reference. The HSV TK cassette was obtained from the plasmid pGEM7 (TK), which contains the structural sequences for the HSV TK gene bracketed by the mouse pgk promoter and polyadenylation sequences as described above for pGEM7 (KJ1). The EcoRI site of pGEM7 (TK) was modified to a BamHI site and the TK cassette was then excised as a BamHI/HindIII fragment and subcloned into pGP1b to generate pGP1b-TK. This plasmid was linearized at the XhoI site and the XhoI fragment from pNEO-K5'3', containing the neo gene flanked by genomic sequences from 5' of J$\kappa$ and 3' of C$\kappa$, was inserted into pGP1b-TK to generate the targeting vector J/C K1 (FIG. 20d). The putative structure of the genomic kappa locus following homologous recombination with J/C K1 is shown in FIG. 20e.

Generation and Analysis of ES Cells with Targeted Inactivation of a Kappa Allele The ES cells used were the AB-1 line grown on mitotically inactive SNL76/7 cell feeder layers (McMahon and Bradley, Cell 62:1073–1085 (1990)) essentially as described (Robertson, E. J. (1987) in Teratocarcinomas and Embryonic Stem Cells: A Practical Approach. E. J. Robertson, ed. (Oxford: IRL Press), p. 71–112). Other suitable ES lines include, but are not limited to, the E14 line (Hooper et al. (1987) Nature 326: 292–295), the D3 line (Doetschman et al. (1985) J. Embryol. Exp. Morph. 87: 27–45), and the CCE line (Robertson et al. (1986) Nature 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57Bl/6J blastocysts to ascertain whether the cells are capable of generating chimeric mice with extensive ES cell contribution and whether the majority of these chimeras can transmit the ES genome to progeny.

The kappa chain inactivation vector J/C K1 was digested with NotI and electroporated into AB-1 cells by the methods described (Hasty et al., Nature, 350:243–246 (1991)). Electroporated cells were plated onto 100 mm dishes at a density of 1–2×10$^6$ cells/dish. After 24 hours, G418 (200 µg/ml of active component) and FIAU (0.5 µM) were added to the medium, and drug-resistant clones were allowed to develop over 10–11 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described (Laird et al., Nucl. Acids Res. 19:4293 (1991)) digested with XbaI and probed with the 800 bp EcoRI/XbaI fragment indicated in FIG. 20e as probe A. This probe detects a 3.7 kb XbaI fragment in the wild type locus, and a diagnostic 1.8 kb band in a locus which has homologously recombined with the targeting vector (see FIG. 20a and e). Of 901 G418 and FIAU resistant clones screened by Southern blot analysis, 7 displayed the 1.8 kb XbaI band indicative of a homologous recombination into one of the kappa genes. These 7 clones were further digested with the enzymes BglII, SacI, and PstI to verify that the vector integrated homologously into one of the kappa genes. When probed with the diagnostic 800 bp EcoRI/XbaI fragment (probe A), BglII, SacI, and PstI digests of wild type DNA produce fragments of 4.1, 5.4, and 7 kb, respectively, whereas the presence of a targeted kappa allele would be indicated by fragments of 2.4, 7.5, and 5.7 kb, respectively (see FIG. 20a and e). All 7 positive clones detected by the XbaI digest showed the expected BglII, SacI, and PstI restriction fragments diagnostic of a homologous recombination at the kappa light chain. In addition, Southern blot analysis of an NsiI digest of the targeted clones using a neo specific probe (probe B, FIG. 20e) generated only the predicted fragment of 4.2 kb, demonstrating that the clones each contained only a single copy of the targeting vector.

Generation of Mice Bearing the Inactivated Kappa Chain

Five of the targeted ES clones described in the previous section were thawed and injected into C57Bl/6J blastocysts as described (Bradley, A. (1987) in Teratocarcinomas and Embryonic Stem Cells: A Practical Approach. E. J. Robertson, ed. (Oxford: IRL Press), p. 113–151) and transferred into the uteri of pseudopregnant females to generate chimeric mice resulting from a mixture of cells derived from the input ES cells and the host blastocyst. The extent of ES cell contribution to the chimeras can be visually estimated by the amount of agouti coat coloration, derived from the ES cell line, on the black C57Bl/6J background. Approximately half of the offspring resulting from blastocyst injection of the targeted clones were chimeric (i.e., showed agouti as well as black pigmentation) and of these, the majority showed extensive (70 percent or greater) ES cell contribution to coat pigmentation. The AB1 ES cells are an XY cell line and a majority of these high percentage chimeras were male due to sex conversion of female embryos colonized by male ES cells. Male chimeras derived from 4 of the 5 targeted clones were bred with C57BL/6J females and the offspring monitored for the presence of the dominant agouti coat color indicative of germline transmission of the ES genome. Chimeras from two of these clones consistently generated agouti offspring. Since only one copy of the kappa locus was targeted in the injected ES clones, each agouti pup had a 50 percent chance of inheriting the mutated locus. Screening for the targeted gene was carried out by Southern blot analysis of Bgl II-digested DNA from tail biopsies, using the probe utilized in identifying targeted ES clones (probe A, FIG. 20e). As expected, approximately 50 percent of the agouti offspring showed a hybridizing Bgl II band of 2.4 kb in addition to the wild-type band of 4.1 kb, demonstrating the germline transmission of the targeted kappa locus.

In order to generate mice homozygous for the mutation, heterozygotes were bred together and the kappa genotype of the offspring determined as described above. As expected, three genotypes were derived from the heterozygote matings: wild-type mice bearing two copies of a normal kappa locus, heterozygotes carrying one targeted copy of the kappa gene and one NT kappa gene, and mice homozygous for the kappa mutation. The deletion of kappa sequences from these latter mice was verified by hybridization of the Southern blots with a probe specific for $J_K$ (probe C, FIG. 20a). Whereas hybridization of the $J_K$ probe was observed to DNA samples from heterozygous and wild-type siblings, no hybridizing signal was present in the homozygotes, attesting to the generation of a novel mouse strain in which both copies of the kappa locus have been inactivated by deletion as a result of targeted mutation.

Example 10

Inactivation of the Mouse Heavy Chain Gene by Homologous Recombination

This example describes the inactivation of the endogenous murine immunoglobulin heavy chain locus by homologous recombination in embryonic stem (ES) cells. The strategy is to delete the endogenous heavy chain J segments by homologous recombination with a vector containing heavy chain sequences from which the $J_H$ region has been deleted and replaced by the gene for the selectable marker neo.

Construction of a Heavy Chain Targeting Vector

Mouse heavy chain sequences containing the $J_H$ region (FIG. 21a) were isolated from a genomic phage library derived from the D3 ES cell line (Gossler et al., *Proc. Natl. Acad. Sci. U.S.A.* 83:9065–9069 (1986)) using a $J_H4$ specific oligonucleotide probe:

5'- ACT ATG CTA TGG ACT ACT GGG GTC AAG GAA CCT CAG TCA CCG -3'

A 3.5 kb genomic SacI/StuI fragment, spanning the $J_H$ region, was isolated from a positive phage clone and subcloned into SacI/SmaI digested pUC18. The resulting plasmid was designated pUC18 $J_H$. The neomycin resistance gene (neo), used for drug selection of transfected ES cells, was derived from a repaired version of the plasmid pGEM7 (KJ1). A report in the literature (Yenofsky et al. (1990) *Proc. Natl. Acad. Sci.* (*U.S.A.*) 87: 3435–3439) documents a point mutation the neo coding sequences of several commonly used expression vectors, including the construct pMC1neo (Thomas and Cappechi (1987) *Cell* 51: 503–512) which served as the source of the neo gene used in pGEM7 (KJ1). This mutation reduces the activity of the neo gene product and was repaired by replacing a restriction fragment encompassing the mutation with the corresponding sequence from a wild-type neo clone. The HindIII site in the prepared pGEM7 (KJ1) was converted to a SalI site by addition of a synthetic adaptor, and the neo expression cassette excised by digestion with XbaI/SalI. The ends of the neo fragment were then blunted by treatment with the Klenow-form of DNA polI, and the neo fragment was subcloned into the NaeI site of pUC18 $J_H$, generating the plasmid pUC18 $J_H$-neo (FIG. 21b).

Further construction of the targeting vector was carried out in a derivative of the plasmid pGP1b. pGP1b was digested with the restriction enzyme NotI and ligated with the following oligonucleotide as an adaptor:

5'- GGC CGC TCG ACG ATA GCC TCG AGG CTA TAA ATC TAG AAG AAT
TCC AGC AAA GCT TTG GC -3'

The resulting plasmid, called pGMT, was used to build the mouse immunoglobulin heavy chain targeting construct.

The Herpes Simplex Virus (HSV) thymidine kinase (TK) gene was included in the construct in order to allow for enrichment of ES clones bearing homologous recombinants, as described by Mansour et al. (*Nature* 336, 348–352 (1988)). The HSV TK gene was obtained from the plasmid pGEM7 (TK) by digestion with EcoRI and HindIII. The TK DNA fragment was subcloned between the EcoRI and HindIII sites of pGMT, creating the plasmid pGMT-TK (FIG. 21c).

To provide an extensive region of homology to the target sequence, a 5.9 kb genomic XbaI/XhoI fragment, situated 5' of the $J_H$ region, was derived from a positive genomic phage clone by limit digestion of the DNA with XhoI, and partial digestion with XbaI. As noted in FIG. 21a, this XbaI site is not present in genomic DNA, but is rather derived from phage sequences immediately flanking the cloned genomic heavy chain insert in the positive phage clone. The fragment was subcloned into XbaI/XhoI digested pGMT-TK, to generate the plasmid pGMT-TK-$J_H5$' (FIG. 21d).

The final step in the construction involved the excision from pUC18 $J_H$-neo of the 2.8 kb EcoRI fragment which contained the neogene and flanking genomic sequences 3' of $J_H$. This fragment was blunted by Klenow polymerase and subcloned into the similarly blunted XhoI site of pGMT-TK-$J_H$5'. The resulting construct, $J_H$KO1 (FIG. 21e), contains 6.9 kb of genomic sequences flanking the $J_H$ locus, with a 2.3 kb deletion spanning the $J_H$ region into which has been inserted the neogene. FIG. 21f shows the structure of an endogenous heavy chain gene after homologous recombination with the targeting construct.

Example 11

Generation and Analysis of Targeted ES Cells

AB-1 ES cells (McMahon and Bradley, *Cell* 62:1073–1085 (1990)) were grown on mitotically inactive SNL76/7 cell feeder layers essentially as described (Robertson, E. J. (1987) *Teratocarcinomas and Embryonic Stem Cells: A Practical Approach*. E. J. Robertson, ed. (Oxford: IRL Press), pp. 71–112). As described in the previous example, prior to electropotation of ES cells with the targeting construct $J_H$KO1, the pluripotency of the ES cells was determined by generation of AB-1 derived chimeras which were shown capable of germline transmission of the ES genome.

The heavy chain inactivation vector $J_H$KO1 was digested with NotI and electroporated into AB-1 cells by the methods described (Hasty et al., *Nature* 350:243–246 (1991)). Electroporated cells were plated into 100 mm dishes at a density of 1–2×10⁶ cells/dish. After 24 hours, G418 (200 mg/ml of active component) and FIAU (0.5 mM) were added to the medium, and drug-resistant clones were allowed to develop over 8–10 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described (Laird et al. (1991) *Nucleic Acids Res.* 19: 4293), digested with StuI and probed with the 500 bp EcoRI/StuI fragment designated as probe A in FIG. 21f. This probe detects a StuI fragment of 4.7 kb in the wild-type locus, whereas a 3 kb band is diagnostic of homologous recombination of endogenous sequences with the targeting vector (see FIG. 21a and f). Of 525 G418 and FIAU doubly-resistant clones screened by Southern blot hybridization, 12 were found to contain the 3 kb fragment diagnostic of recombination with the targeting vector. That these clones represent the expected targeted events at the $J_H$ locus (as shown in FIG. 21f) was confirmed by further digestion with HindIII, SpeI and HpaI. Hybridization of probe A (see FIG. 21f) to Southern blots of HindIII, SpeI, and HpaI digested DNA produces bands of 2.3 kb, >10 kb, and >10 kb, respectively, for the wild-type locus (see FIG. 21a), whereas bands of 5.3 kb, 3.8 kb, and 1.9 kb, respectively, are expected for the targeted heavy chain locus (see FIG. 21f). All 12 positive clones detected by the StuI digest showed the predicted HindIII, SpeI, and HpaI bands diagnostic of a targeted $J_H$ gene. In addition, Southern blot analysis of a StuI digest of all 12 clones using a neo-specific probe (probe B, FIG. 21f) generated only the predicted fragment of 3 kb, demonstrating that the clones each contained only a single copy of the targeting vector.

Generation of Mice Carrying the $J_H$ Deletion

Three of the targeted ES clones described in the previous section were thawed and injected into C57BL/6J blastocysts as described (Bradley, A. (1987) in *Teratocarcinomas and Embryonic Stem Cells: A Practical Approach*, E. J. Robertson, ed. (Oxford: IRL Press), p.113–151) and transferred into the uteri of pseudopregnant females. The extent of ES cell contribution to the chimera was visually estimated from the amount of agouti coat coloration, derived from the ES cell line, on the black C57BL/6J background. Half of the offspring resulting from blastocyst injection of two of the targeted clones were chimeric (i.e., showed agouti as well as black pigmentation); the third targeted clone did not generate any chimeric animals. The majority of the chimeras showed significant (approximately 50 percent or greater) ES cell contribution to coat pigmentation. Since the AB-1 ES cells are an XY cell line, most of the chimeras were male, due to sex conversion of female embryos colonized by male ES cells. Males chimeras were bred with C57BL/6J females and the offspring monitored for the presence of the dominant agouti coat color indicative of germline transmission of the ES genome. Chimeras from both of the clones consistently generated agouti offspring. Since only one copy of the heavy chain locus was targeted in the injected ES clones, each agouti pup had a 50 percent chance of inheriting the mutated locus. Screening for the targeted gene was carried out by Southern blot analysis of StuI-digested DNA from tail biopsies, using the probe utilized in identifying targeted ES clones (probe A, FIG. 21f). As expected, approximately 50 percent of the agouti offspring showed a hybridizing StuI band of approximately 3 kb in addition to the wild-type band of 4.7 kb, demonstrating germline transmission of the targeted $J_H$ gene segment.

In order to generate mice homozygous for the mutation, heterozygotes were bred together and the heavy chain genotype of the offspring determined as described above. As expected, three genotypes were derived from the heterozygote matings: wild-type mice bearing two copies of the normal $J_H$ locus, heterozygotes carrying one targeted copy of the gene and one normal copy, and mice homozygous for the $J_H$ mutation. The absence of $J_H$ sequences from these latter mice was verified by hybridization of the Southern blots of StuI-digested DNA with a probe specific for $J_H$ (probe C, FIG. 21a). Whereas hybridization of the $J_H$ probe to a 4.7 kb fragment in DNA samples from heterozygous and wild-type siblings was observed, no signal was present in samples from the $J_H$-mutant homozygotes, attesting to the generation of a novel mouse strain in which both copies of the heavy chain gene have been mutated by deletion of the $J_H$ sequences.

Example 12

Heavy Chain Minilocus Transgene

A. Construction of Plasmid Vectors for Cloning Large DNA Sequences 1. pGP1a

The plasmid pBR322 was digested with EcoRI and StyI and ligated with the following oligonucleotides:

```
oligo-42 5'- caa gag ccc gcc taa tga gcg ggc ttt ttt ttg cat
             act gcg gcc gct -3' oligo-43 5'- aat tag cgg ccg cag tat gca aaa aaa agc ccg ctc
             att agg cgg gct -3'
```

The resulting plasmid, pGP1a, is designed for cloning very large DNA constructs that can be excised by the rare cutting restriction enzyme NotI. It contains a NotI restriction site downstream (relative to the ampicillin resistance gene, AmpR) of a strong transcription termination signal derived from the trpA gene (Christie et al., *Proc. Natl. Acad. Sci. USA* 78:4180 (1981)). This termination signal reduces the potential toxicity of coding sequences inserted into the NotI site by eliminating readthrough transcription from the AmpR gene. In addition, this plasmid is low copy relative to the pUC plasmids because it retains the pBR322 copy number control region. The low copy number further reduces the potential toxicity of insert sequences and reduces the selection against large inserts due to DNA replication. The vectors pGP1b, pGP1c, pGP1d, and pGP1f are derived from pGP1a and contain different polylinker cloning sites. The polylinker sequences are given below pGP1a

```
       NotI
     GCGGCCGC
``` pGP1b

```
  NotI XhoI    ClaI     BamHI   HindIII  NotI
GCggccgcctcgagatcactatcgattaattaaggatccagcagtaagcttgcGGCCGC
``` pGI1c

```
  NotI   SmaI  XhoI SalI  HindIII BamHI SacII   NotI
GCggccgcatcccgggtctcgaggtcgacaagctttcgagg a t c c gcGGCCGC
``` pGP1d

```
  NotI  SalI HindIII ClaI BamHI XhoI   NotI
GCggccgctgtcgacaagcttatcgatgg at c c tcgagtgcGGCCGC
``` pGP1f

```
  NotI  SalI HindIII EcoRI ClaI   KpnI BamHI XhoI  NotI
GCggccgctgtcgacaagcttcga a t t cagatcgatgtggt acctg g a t c ct c gagtgcGGCCGC
```

Each of these plasmids can be used for the construction of large transgene inserts that are excisable with NotI so that the transgene DNA can be purified away from vector sequences prior to microinjection.

2. pGP1b pGP1a was digested with NotI and ligated with the following oligonucleotides:

oligo-47 5'- ggc cgc aag ctt act gct gga tcc tta att aat cga tag tga tct cga ggc -3' oligo-48 5'- ggc cgc ctc gag atc act atc gat taa tta agg atc cag cag taa gct tgc -3'

The resulting plasmid, pGP1b, contains a short polylinker region flanked by NotI sites. This facilitates the construction of large inserts that can be excised by NotI digestion.

3. pGPe

The following oligonucleotides:

oligo-44 5'- ctc cag gat cca gat atc agt acc tga aac agg gct tgc -3' oligo-45 5'- ctc gag cat gca cag gac ctg gag cac aca cag cct tcc -3' were used to amplify the immunoglobulin heavy chain 3' enhancer (S. Petterson, et al., Nature 344:165–168 (1990)) from rat liver DNA by the polymerase chain reaction technique.

Figure 22:
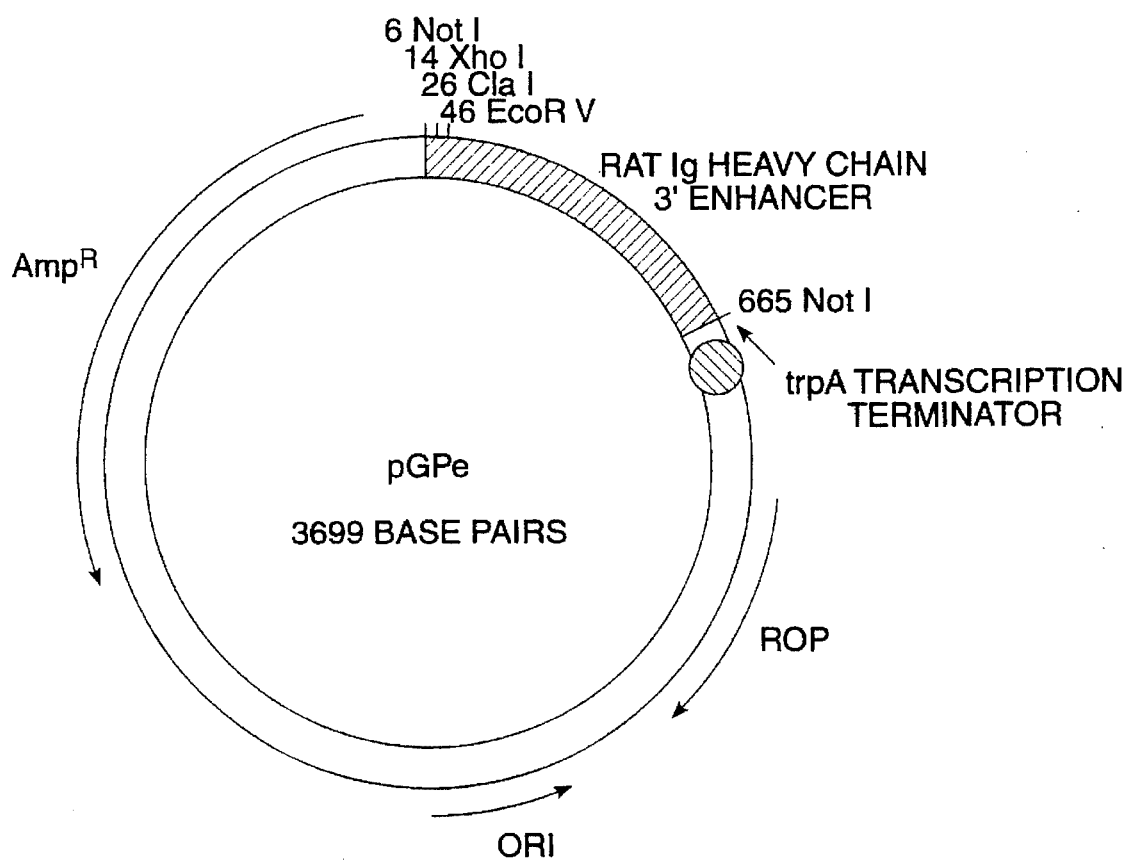
FIG. 22 depicts the map of vector pGPe.

The amplified product was digested with BamHI and SphI and cloned into BamHI/SphI digested pNNO3 (pNNO3 is a pUC derived plasmid that contains a polylinker with the following restriction sites, listed in order: NotI, BamHI, NcoI, ClaI, EcoRV, XbaI, SacI, XhoI, SphI, PstI, BglII, EcoRI, SmaI, KpnI, HindIII, and NotI). The resulting plasmid, pRE3, was digested with BamHI and HindIII, and the insert containing the rat Ig heavy chain 3' enhancer cloned into BamHI/HindIII digested pGP1b. The resulting plasmid, pGPe (FIG. 22 and Table 1), contains several unique restriction sites into which sequences can be cloned and subsequently excised together with the 3' enhancer by NotI digestion.

TABLE 1

Sequence of vector pGPe.

AATTAGCggccgcctcgagatcactatcgattaattaaggatccagatatcagtacctgaaacagggcttgctcacaaca
tctctctctctgtctctctgtctctgtgtgtgtctctctctgtctctgtctctctctgtctctgtctctctgtgtgtg
tctctctctgtctctctctctgtctctctgtctctctgtctgtctctgtctctgtctctgtctctctctctctctctc
tctctctctctctctcacacacacacacacacacacacacacacacctgccgagtgactcactctgtgcagggttggccc
tcggggcacatgcaaatggatgtttgttccatgcagaaaaacatgtttctcattctctgagccaaaaatagcatcaatga
ttcccccaccctgcagctgcaggttcaccccacctggccaggttgaccagcttttggggatggggctggggggttccatgac
ccctaacggtgacattgaattcagtgttttcccatttatcgacactgctggaatctgaccctaggagggaatgacaggag
ataggcaaggtccaaacacccccagggaagtgggagagacaggaaggctgtgtgtgctccaggtcctgtgcatgctgcaga
tctgaattcccgggtaccaagcttgcGGCCGCAGTATGCAAAAAAAAGCCCGCTCATTAGGCGGGCTCTTGGCAGAACAT
ATCCATCGCGTCCGCCATCTCCAGCAGCCGCACGCGGCGCATCTCGGGCAGCGTTGGGTCCTGGCCACGGGTGCGCATGA
TCGTGCTCCTGTCGTTGAGGACCCGGCTAGGCTGGCGGGGTTGCCTTACTGGTTAGCAGAATGAATCACCGATACGCGAG
CGAACGTGAAGCGACTGCTGCTGCAAAACGTCTGCGACCTGAGCAACAACATGAATGGTCTTCGGTTTCCGTGTTTCGTA
AAGTCTGGAAACGCGGAAGTCAGCGCCCTGCACCATTATGTTCCGGATCTGCATCGCAGGATGCTGCTGGCTACCCTGTG
GAACACCTACATCTGTATTAACGAAGCGCTGGCATTGACCCTGAGTGATTTTTCTCTGGTCCCGCCGCATCCATACCGCC
AGTTGTTTACCCTCACAACGTTCCAGTAACCGGGCATGTTCATCATCAGTAACCCGTATCGTGCGCATCCTCTCTCGTTT TABLE 1-continued Sequence of vector pGPe.

CATCGGTATCATTACCCCCATGAACAGAAATTCCCCCTTACACGGAGGCATCAAGTGACCAAACAGGAAAAAACCGCCCT
TAACATGGCCCGCTTTATCAGAAGCCAGACATTAACGCTTCTGGAGAAACTCAACGAGCTGGACGCGGATGAACAGGCAG
ACATCTGTGAATCGCTTCACGACCACGCTGATGAGCTTTACCGCAGCTGCCTCGCGCGTTTCGGTGATGACGGTGAAAAC
CTCTGACACATGCAGCTCCCGGAGACGGTCACGCTTGTCTGTAAGCGGATGCCGGGAGCAGACAAGCCCGTCAGGGCGC
GTCAGCGGGTGTTGGCGGGTGTCGGGGCGCAGCCATGACCCAGTCACGTAGCGATAGCGGAGTGTATACTGGCTTAACTA
TGCGGCATCAGCGCAGATTGTACTGAGAGTGCACCATATGCGGTGTGAAATACCGCACAGATGCGTAAGGAGAAAATACC
GCATCAGGCGCTCTTCCGCTTCCTCGCTCACTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCACTGGCAGCAGCCACTGGTAACAGG
ATTAGCAGCGCGAGGTATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGTCGTGTAGATA
ACTACGATACGGGAGGGCTTACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTGCAGGCATCGTG
GTGTCACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTCTTATCACTCATGGTTA
TGGCAGCACTGCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAACACGGGATAATACCGCGCCACATAGCAGAAC
TTTAAAAGTGCTCATCATTGGAAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCTGGGTGAGCAAAAACAGGAAGG
CAAAATGCCGCAAAAAAGGGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAACAAATAGGGGTTCCGCGCA
CATTTCCCCGAAAAGTGCCACCTGACGTCTAAGAAACCATTATTATCATGACATTAACCTATAAAAATAGGCGRARCACG
AGGCCCTTTCGTCTTCAAG

B. Construction of IgM Expressing Minilocus Transgene, pIGM1

1. Isolation of J-μ Constant Region Clones and Construction of pJM1

A human placental genomic DNA library cloned into the phage vector λEMBL3/SP6/T7 (Clonetech Laboratories, Inc., Palo Alto, Calif.) was screened with the human heavy chain J region specific oligonucleotide:

oligo-1  5'- gga ctg tgt ccc tgt gtg atg ctt ttg atg tct ggg gcc aag -3' and the phage clone λ1.3 isolated. A 6 kb HindIII/KpnI fragment from this clone, containing all six J segments as well as D segment DHQ52 and the heavy chain J-μ intronic enhancer, was isolated. The same library was screened with the human μ specific oligonucleotide:

oligo-2  5'- cac caa gtt gac ctg cct ggt cac aga cct gac cac cta tga -3' and the phage clone λ2.1 isolated. A 10.5 kb HindIII/XhoI fragment, containing the μ switch region and all of the μ constant region exons, was isolated from this clone. These two fragments were ligated together with KpnI/XhoI digested pNNO3 to obtain the plasmid pJM1.

2. pJM2

Figure 23:
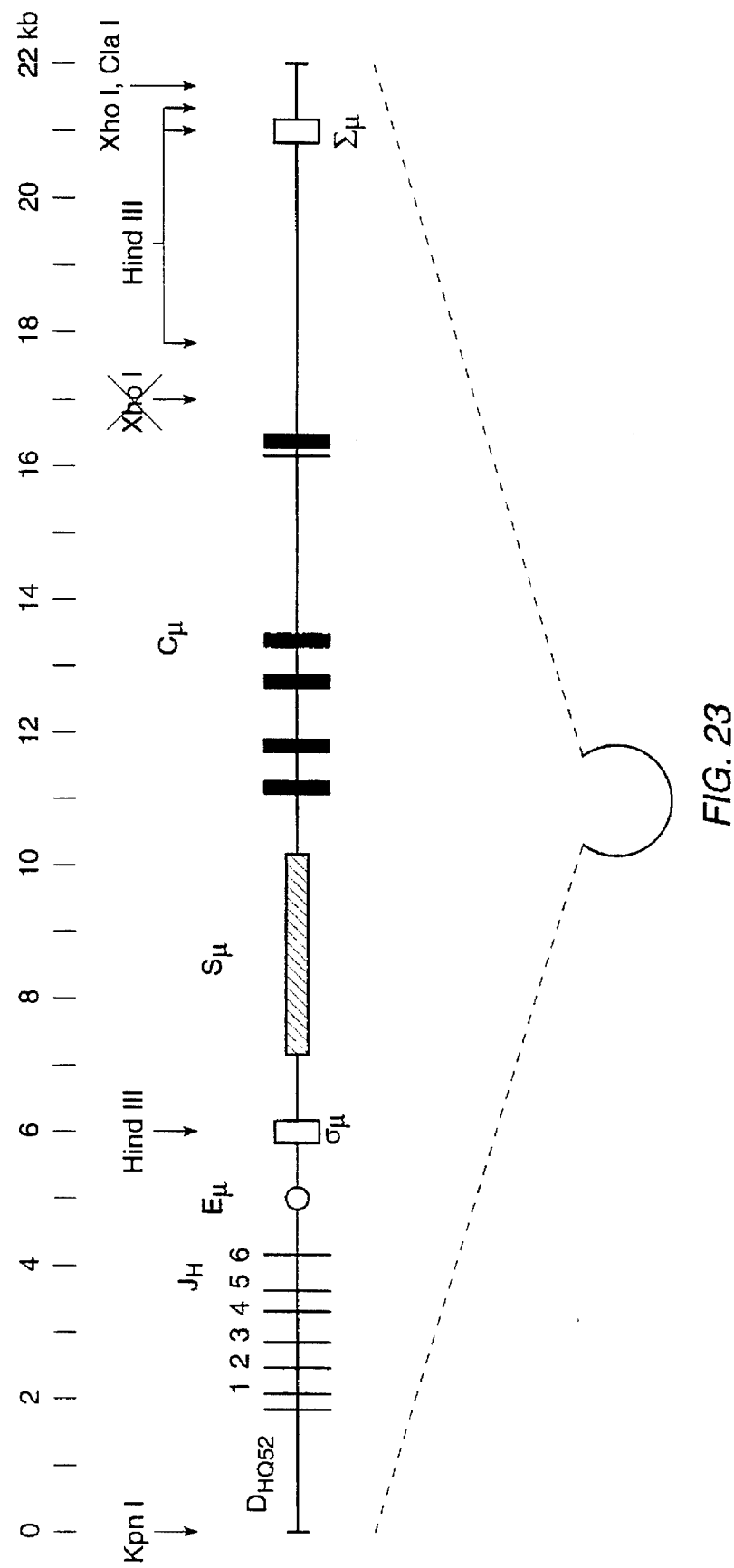
FIG. 23 depicts the structure of vector pJM2.

A 4 kb XhoI fragment was isolated from phage clone λ2.1 that contains sequences immediately downstream of the sequences in pJM1, including the so called Σμ element involved in δ-associated deleteon of the μ in certain IgD expressing B-cells (Yasui et al., *Eur. J. Immunol.* 19:1399 (1989), which is incorporated herein by reference). This fragment was treated with the Klenow fragment of DNA polymerase I and ligated to XhoI cut, Klenow treated, pJM1. The resulting plasmid, pJM2 (FIG. 23), had lost the internal XhoI site but retained the 3' XhoI site due to incomplete reaction by the Klenow enzyme. pJM2 contains the entire human J region, the heavy chain J-μ intronic enhancer, the μ switch region and all of the μ constant region exons, as well as the two 0.4 kb direct repeats, σμ and Σμ, involved in δ-associated deletion of the μ gene.

3. Isolation of D Region Clones and Construction of pDH1

The following human D region specific oligonucleotide:

oligo-4  5'- tgg tat tac tat ggt tcg ggg agt tat tat aac cac agt gtc -3' was used to screen the human placenta genomic library for D region clones. Phage clones λ4.1 and λ4.3 were isolated. A 5.5 kb XhoI fragment, that includes the D elements $D_{K1}$, $D_{N1}$, and $D_{M2}$ (Ichihara et al., *EMBO J.* 7:4141 (1988)), was isolated from phage clone λ4.1. An adjacent upstream 5.2 kb XhoI fragment, that includes the D elements $D_{LR1}$, $D_{XP1}$, $D_{XP'1}$, and $D_{A1}$, was isolated from phage clone λ4.3. Each of these D region XhoI fragments were cloned into the SalI site of the plasmid vector pSP72 (Promega, Madison, Wis.) so as to destroy the XhoI site linking the two sequences. The upstream fragment was then excised with XhoI and SmaI, and the downstream fragment with EcoRV and XhoI. The resulting isolated fragments were ligated together with SalI digested pSP72 to give the plasmid pDH1. pDH1 contains a 10.6 kb insert that includes at least 7 D segments and can be excised with XhoI (5') and EcoRV (3').

4. pCOR1

Figure 24:
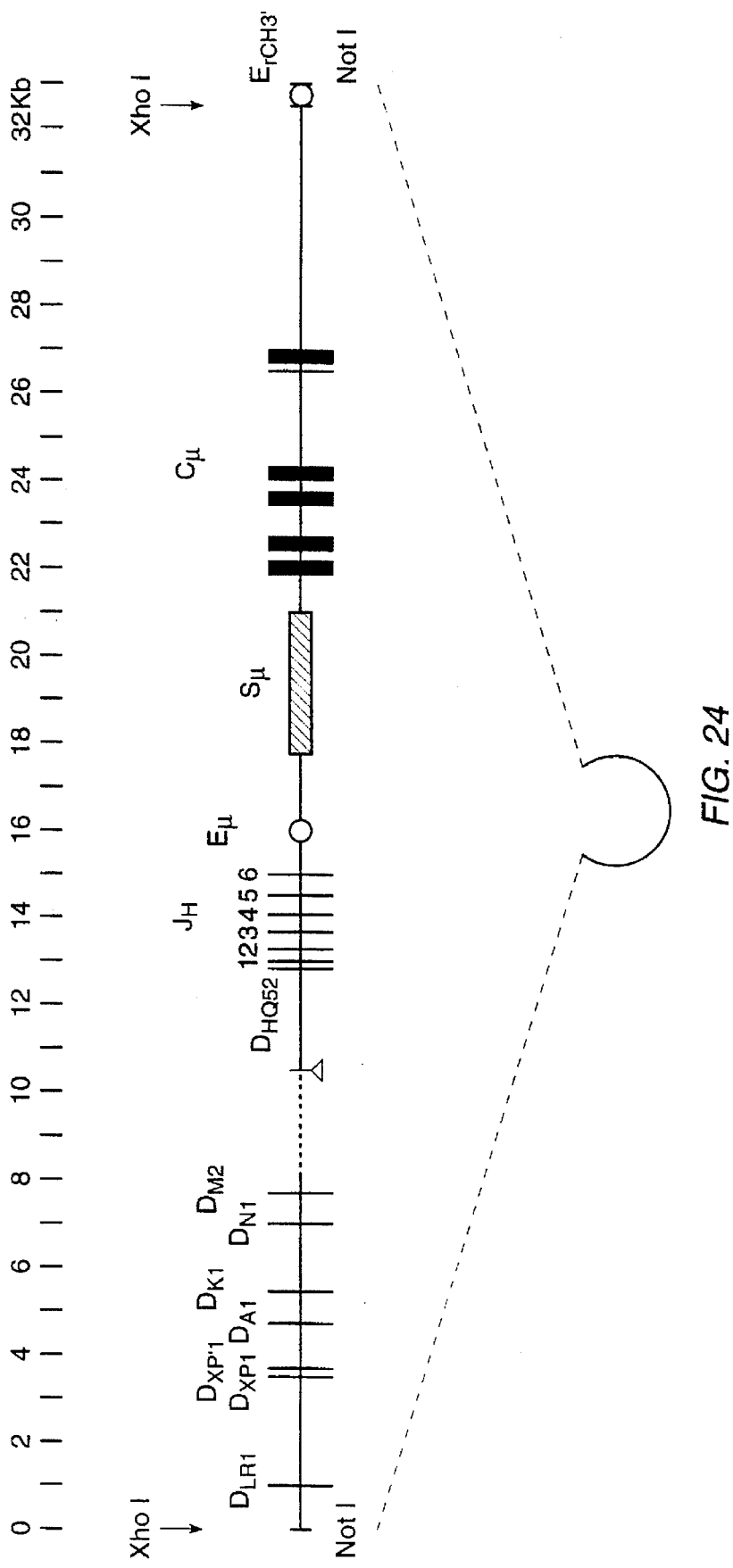
FIG. 24 depicts the structure of vector pCOR1.

The plasmid pJM2 was digested with Asp718 (an isoschizomer of KpnI) and the overhang filled in with the Klenow fragment of DNA polymerase I. The resulting DNA was then digested with ClaI and the insert isolated. This insert was ligated to the XhoI/EcoRV insert of pDH1 and XhoI/ClaI digested pGPe to generate pCOR1 (FIG. 24).

5. pVH251

A 10.3 kb genomic HindIII fragment containing the two human heavy chain variable region segments $V_H251$ and $V_H105$ (Humphries et al., *Nature* 331:446 (1988), which is incorporated herein by reference) was subcloned into pSP72 to give the plasmid pVH251.

6. pIGM1

Figure 25:
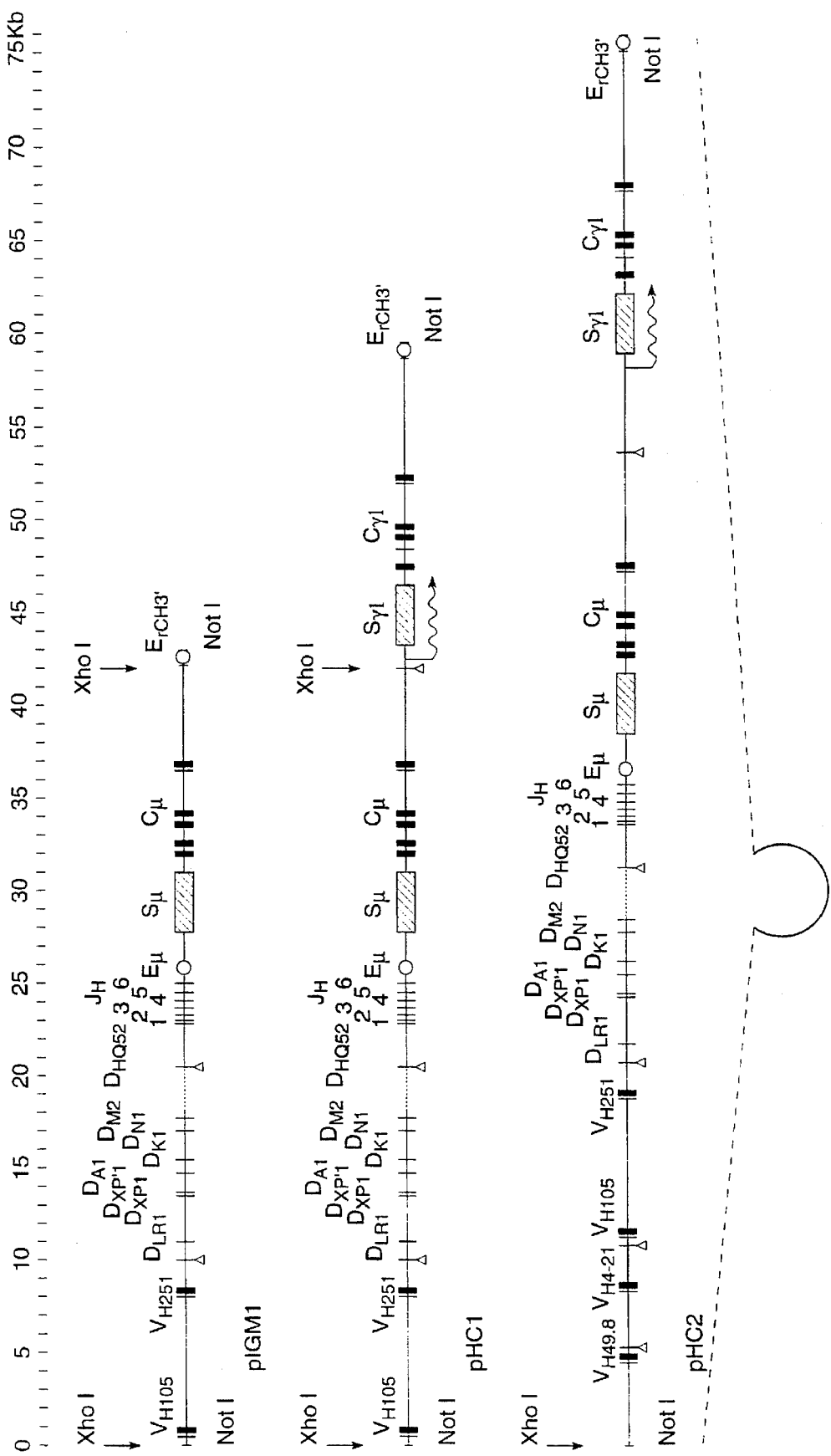
FIG. 25 depicts the transgene constructs for pIGM1, pHC1 and pHC2.

The plasmid pCOR1 was partially digested with XhoI and the isolated XhoI/SalI insert of pVH251 cloned into the upstream XhoI site to generate the plasmid pIGM1 (FIG. 25). pIGM1 contains 2 functional human variable region segments, at least 8 human D segments all 6 human $J_H$ segments, the human J-μ enhancer, the human σμ element, the human μ switch region, all of the human μ coding exons, and the human Σμ element, together with the rat heavy chain 3' enhancer, such that all of these sequence elements can be isolated on a single fragment, away from vector sequences, by digestion with NotI and microinjected into mouse embryo pronuclei to generate transgenic animals.

C. Construction of IgM and IgG Expressing Minilocus Transgene, pHC1

1. Isolation of γ Constant Region Clones

The following oligonucleotide, specific for human Ig g constant region genes:

Phage clones λ29.5 and λSγ1.13 were both determined to be of the γ1 subclass.

2. pγe1

A 7.8 kb HindIII fragment of phage clone λ29.5, containing the γ1 coding region was cloned into pUC18. The resulting plasmid, pLT1, was digested with XhoI, Klenow treated, and religated to destroy the internal XhoI site. The resulting clone, pLT1xk, was digested with HindIII and the insert isolated and cloned into pSP72 to generate the plasmid clone pLT1xks. Digestion of pLT1xks at a polylinker XhoI site and a human sequence derived BamHI site generates a 7.6 kb fragment containing the γ1 constant region coding exons. This 7.6 kb XhoI/BamHI fragment was cloned together with an adjacent downstream 4.5 kb BamHI fragment from phage clone λ29.5 into XhoI/BamHI digested pGPe to generate the plasmid clone pγe1. pγe1 contains all of the γ1 constant region coding exons, together with 5 kb of downstream sequences, linked to the rat heavy chain 3' enhancer.

3. pγe2

Figure 26:
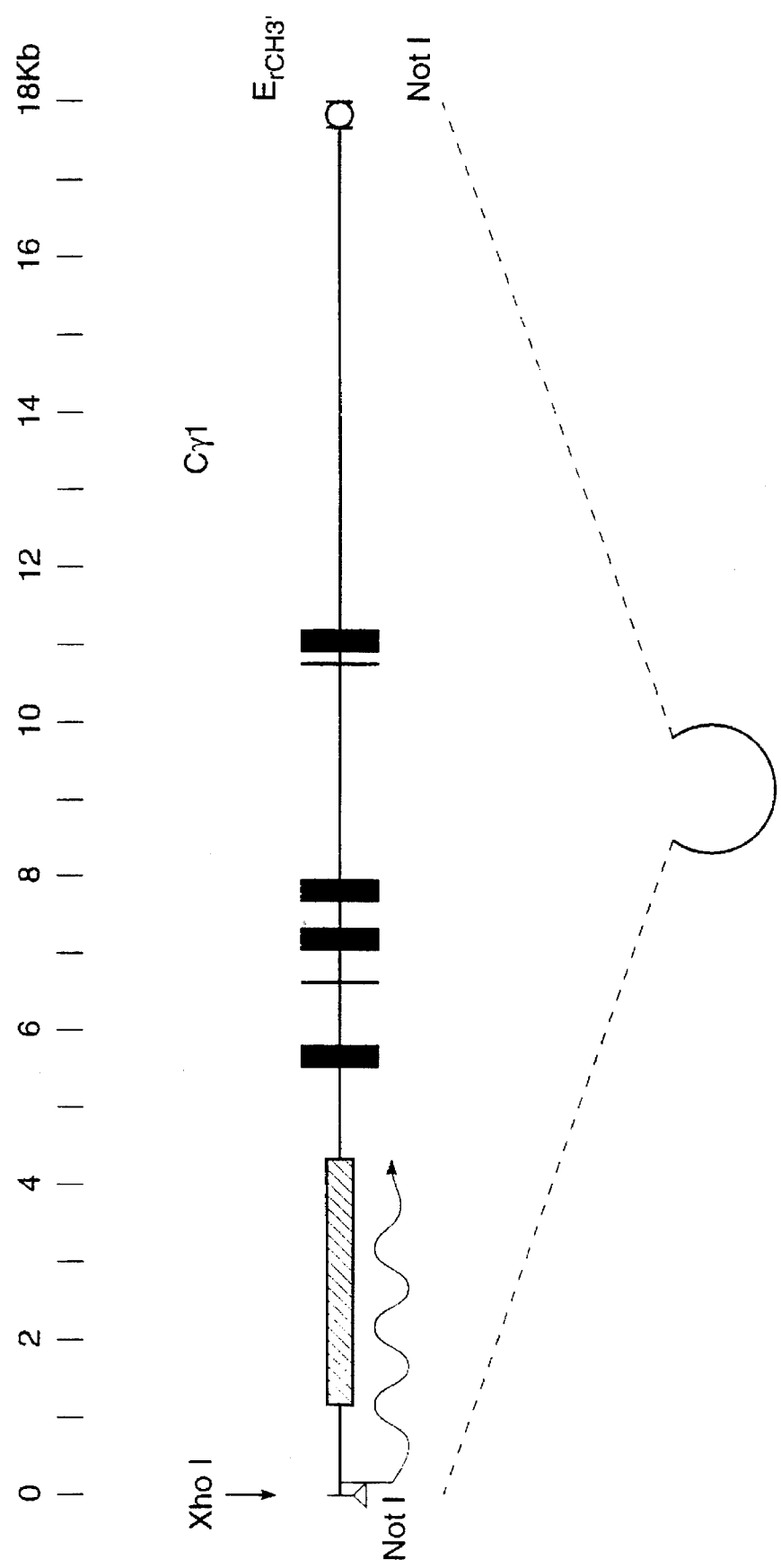
FIG. 26 depicts the structure of pγe2.

A 5.3 kb HindIII fragment containing the γ1 switch region and the first exon of the pre-switch sterile transcript (P. Sideras et al. (1989) *International Immunol.* 1, 631) was isolated from phage clone λSγ1.13 and cloned into pSP72 with the polylinker XhoI site adjacent to the 5' end of the insert, to generate the plasmid clone pSγ1s. The XhoI/SalI insert of pSγ1s was cloned into XhoI digested pγe1 to generate the plasmid clone pγe2 (FIG. 26). pγe2 contains all of the γ1 constant region coding exons, and the upstream switch region and sterile transcript exons, together with 5 kb of downstream sequences, linked to the rat heavy chain 3' enhancer. This clone contains a unique XhoI site at the 5' end of the insert. The entire insert, together with the XhoI site and the 3' rat enhancer can be excised from vector sequences by digestion with NotI.

4. pHC1

The plasmid pIGM1 was digested with XhoI and the 43 kb insert isolated and cloned into XhoI digested pge2 to generate the plasmid pHC1 (FIG. 25). pHC1 contains 2 functional human variable region segments, at least 8 human D segments all 6 human $J_H$ segments, the human J-μ enhancer, the human σμ element, the human μ switch region, all of the human μ coding exons, the human Σμ element, and the human γ1 constant region, including the associated switch region and sterile transcript associated exons, together with the rat heavy chain 3' enhancer, such that all of these sequence elements can be isolated on a single oligo-29   5'- cag cag gtg cac acc caa tgc cca tga gcc cag aca ctg gac -3' was used to screen the human genomic library. Phage clones 129.4 and λ29.5 were isolated. A 4 kb HindIII fragment of phage clone λ29.4, containing a γ switch region, was used to probe a human placenta genomic DNA library cloned into the phage vector lambda FIX™ II (Stratagene, La Jolla, Calif.). Phage clone λSg1.13 was isolated. To determine the subclass of the different γ clones, dideoxy sequencing reactions were carried out using subclones of each of the three phage clones as templates and the following oligonucleotide as a primer:

oligo-67   5'- tga gcc cag aca ctg gac -3' fragment, away from vector sequences, by digestion with NotI and microinjected into mouse embryo pronuclei to generate transgenic animals.

D. Construction of IgM and IgG Expressing Minilocus Transgene, pHC2

1. Isolation of Human Heavy Chain V Region Gene VH49.8

The human placental genomic DNA library lambda, FIX™ II, Stratagene, La Jolla, Calif.) was screened with the following human VH1 family specific oligonucleotide:

oligo-49  5'- gtt  aaa  gag  gat  ttt  att  cac  ccc  tgt  gtc  ctc  tcc  aca  ggt  gtc -3'

Phage clone λ49.8 was isolated and a 6.1 kb XbaI fragment containing the variable segment VH49.8 subcloned into pNN03 (such that the polylinker ClaI site is downstream of VH49.8 and the polylinker XhoI site is upstream) to generate the plasmid pVH49.8. An 800 bp region of this insert was sequenced, and VH49.8 found to have an open reading frame and intact splicing and recombination signals, thus indicating that the gene is functional (Table 2).

orientation, with a unique SalI site at the 3' end of the insert and a unique XhoI site at the 5' end.

3. pSγ1-5'

A 0.7 kb XbaI/HindIII fragment (representing sequences immediately upstream of, and adjacent to, the 5.3 kb γ1 switch region containing fragment in the plasmid pγe2) together with the neighboring upstream 3.1 kb XbaI fragment were isolated from the phage clone λSg1.13 and cloned into HindIII/XbaI digested pUC18 vector. The result-

TABLE 2

Sequence of human $V_HI$ family gene $V_H$ 49.8

| | | | | | | |
|---|---|---|---|---|---|---|
| TTCCTCAGGC | AGGATTTAGG | GCTTGGTCTC | TCAGCATCCC | ACACTTGTAC | | 50 |
| AGCTGATGTG | GCATCTGTGT | TTTCTTTCTC | ATCCTAGATC | AAGCTTTGAG | | 100 |
| CTGTGAAATA | CCCTGCCTCA | TGAATATGCA | AATAATCTGA | GGTCTTCTGA | | 150 |
| GATAAATATA | GATATATTGG | TGCCCTGAGA | GCATCACATA | ACAACCAGAT | | 200 |
| TCCTCCTCTA | AAGAAGCCCC | TGGGAGCACA | GCTCATCACC | ATGGACTGGA MetAspTrpT | | 250 |
| CCTGGAGGTT hrTrpArgPh | CCTCTTTGTG eLeuPheVal | GTGGCAGCAG ValAlaAlaA | CTACAGgtaa laThr | ggggcttcct | | 300 |
| agtcctaagg | ctgaggaagg | gatcctggtt | tagttaaaga | ggattttatt | | 350 |
| cacccctgtg | tcctctccac | agGTGTCCAG GlyValGln | TCCCAGGTCC SerGlnValG | AGCTGGTGCA lnLeuValGl | | 400 |
| GTCTGGGGCT nSerGlyAla | GAGGTGAAGA GluValLysL | AGCCTGGGTC ysProGlySe | CTCGGTGAAG rSerValLys | GTCTCCTGCA ValSerCysL | | 450 |
| AGGCTTCTGG ysAlaSerGl | AGGCACCTTC yGlyThrPhe | AGCAGCTATG SerSerTyrA | CTATCAGCTG laIleSerTr | GGTGCGACAG pValArgGln | | 500 |
| GCCCCTGGAC AlaProGlyG | AAGGGCTTGA lnGlyLeuGl | GTGGATGGA uTrpMetGly | AGGATCATCC ArgIleIleP | CTATCCTTGG roIleLeuGl | | 550 |
| TATAGCAAAC yIleAlaAsn | TACGCACAGA TyrAlaGlnL | AGTTCCAGGG ysPheGlnGl | CAGAGTCACG yArgValThr | ATTACCGCGG IleThrAlaA | | 600 |
| ACAAATCCAC spLysSerTh | GAGCACAGCC rSerThrAla | TACATGGAGC TyrMetGluL | TGAGCAGCCT euSerSerLe | GAGATCTGAG uArgSerGlu | | 650 |
| GACACGGCCG AspThrAlaV | TGTATTACTG alTyrTyrCy | TGCGAGAGAC ACAGTGTGAA sAlaArg | | AACCCACATC | | 700 |
| CTGAGAGTGT CAGAAACC CT | | GAGGGAGAAG | GCAGCTGTGC | CGGGCTGAGG | | 750 |
| AGAT GACAGG | GTTTATTAGG | TTTAAGGCTG | TTTACAAAAT | GGGTTATATA | | 800 |
| TTTGAGAAAA | AA | | | | | 812 |

2. pV2

A 4 kb XbaI genomic fragment containing the human $V_HIV$ family gene $V_H$4-21 (Sanz et al., *EMBO J.*, 8:3741 (1989)), subcloned into the plasmid pUC12, was excised with SmaI and HindIII, and treated with the Klenow fragment of polymerase I. The blunt ended fragment was then cloned into ClaI digested, Klenow treated, pVH49.8. The resulting plasmid, pV2, contains the human heavy chain gene VH49.8 linked upstream of VH4-21 in the same ing plasmid, pSγ1-5', contains a 3.8 kb insert representing sequences upstream of the initiation site of the sterile transcript found in B-cells prior to switching to the γ1 isotype (P. Sideras et al., *International Immunol.* 1:631 (1989)). Because the transcript is implicated in the initiation of isotype switching, and upstream cis-acting sequences are often important for transcription regulation, these sequences are included in transgene constructs to promote correct expression of the sterile transcript and the associated switch recombination.

4. pVGE1

The pSγ1-5' insert was excised with SmaI and HindIII, treated with Klenow enzyme, and ligated with the following oligonucleotide linker:

5'- ccg gtc gac cgg -3'

Figure 27:
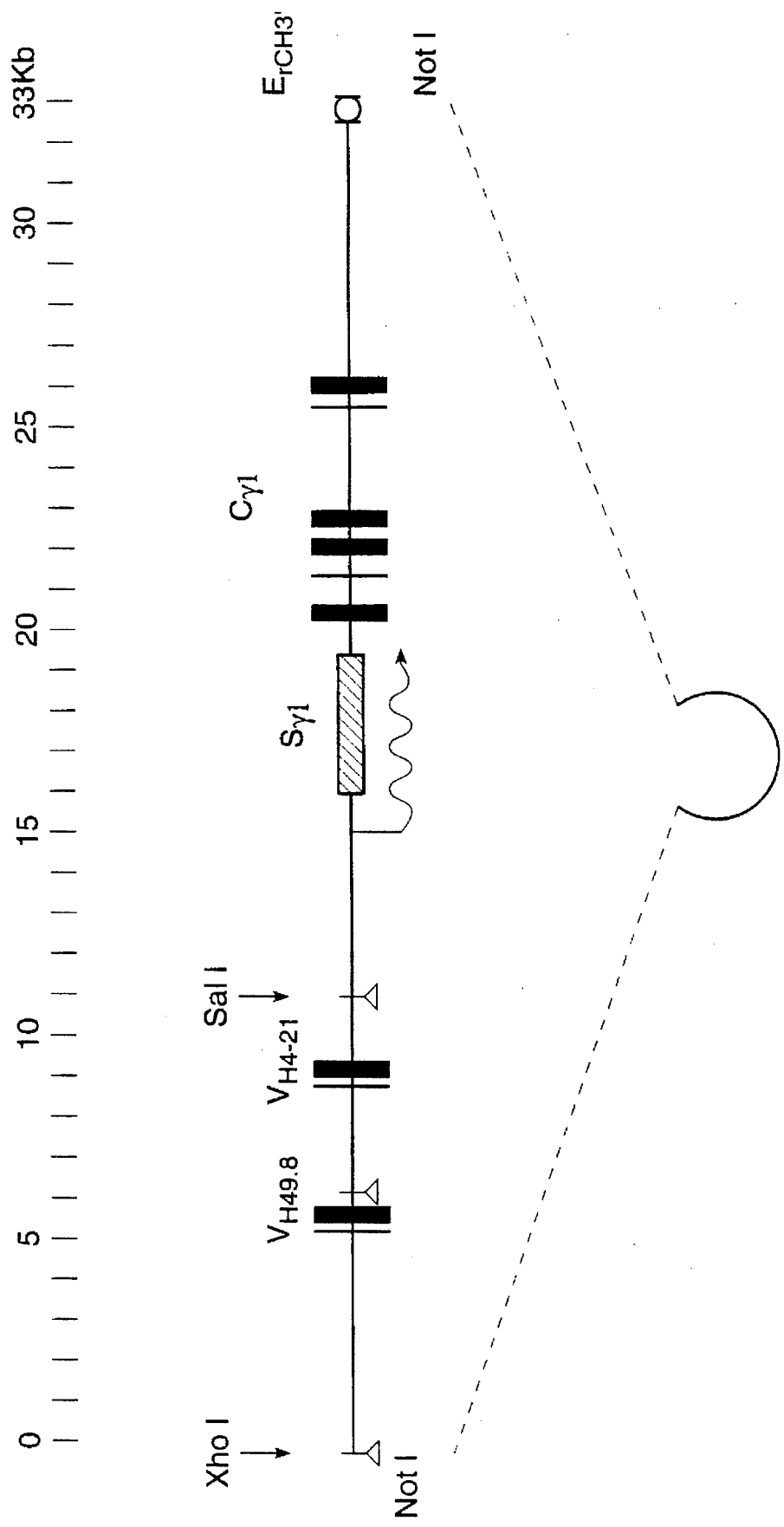
FIG. 27 depicts the structure of pVGE1.

The ligation product was digested with SalI and ligated to SalI digested pV2. The resulting plasmid, pVP, contains 3.8 kb of γ1 switch 5' flanking sequences linked downstream of the two human variable gene segments VH49.8 and VH4-21 (see Table 2). The pVP insert is isolated by partial digestion with SalI and complete digestion with XhoI, followed by purification of the 15 kb fragment on an agarose gel. The insert is then cloned into the XhoI site of pγe2 to generate the plasmid clone pVGE1 (FIG. 27). pVGE1 contains two human heavy chain variable gene segments upstream of the human γ1 constant gene and associated switch region. A unique SalI site between the variable and constant regions can be used to clone in D, J, and μ gene segments. The rat heavy chain 3' enhancer is linked to the 3' end of the γ1 gene and the entire insert is flanked by NotI sites.

5. pHC2

The plasmid clone pVGE1 is digested with SalI and the XhoI insert of pIGM1 is cloned into it. The resulting clone, pHC2 (FIG. 25), contains 4 functional human variable region segments, at least 8 human D segments all 6 human $J_H$ segments, the human J-m enhancer, the human σμ element, the human μ switch region, all of the human μ coding exons, the human Σμ element, and the human γ1 constant region, including the associated switch region and sterile transcript associated exons, together with 4 kb flanking sequences upstream of the sterile transcript initiation site. These human sequences are linked to the rat heavy chain 3' enhancer, such that all of the sequence elements can be isolated on a single fragment, away from vector sequences, by digestion with NotI and microinjected into mouse embryo pronuclei to generate transgenic animals. A unique XhoI site at the 5' end of the insert can be used to clone in additional human variable gene segments to further expand the recombinational diversity of this heavy chain minilocus.

E. Transgenic Mice

Figure 28:
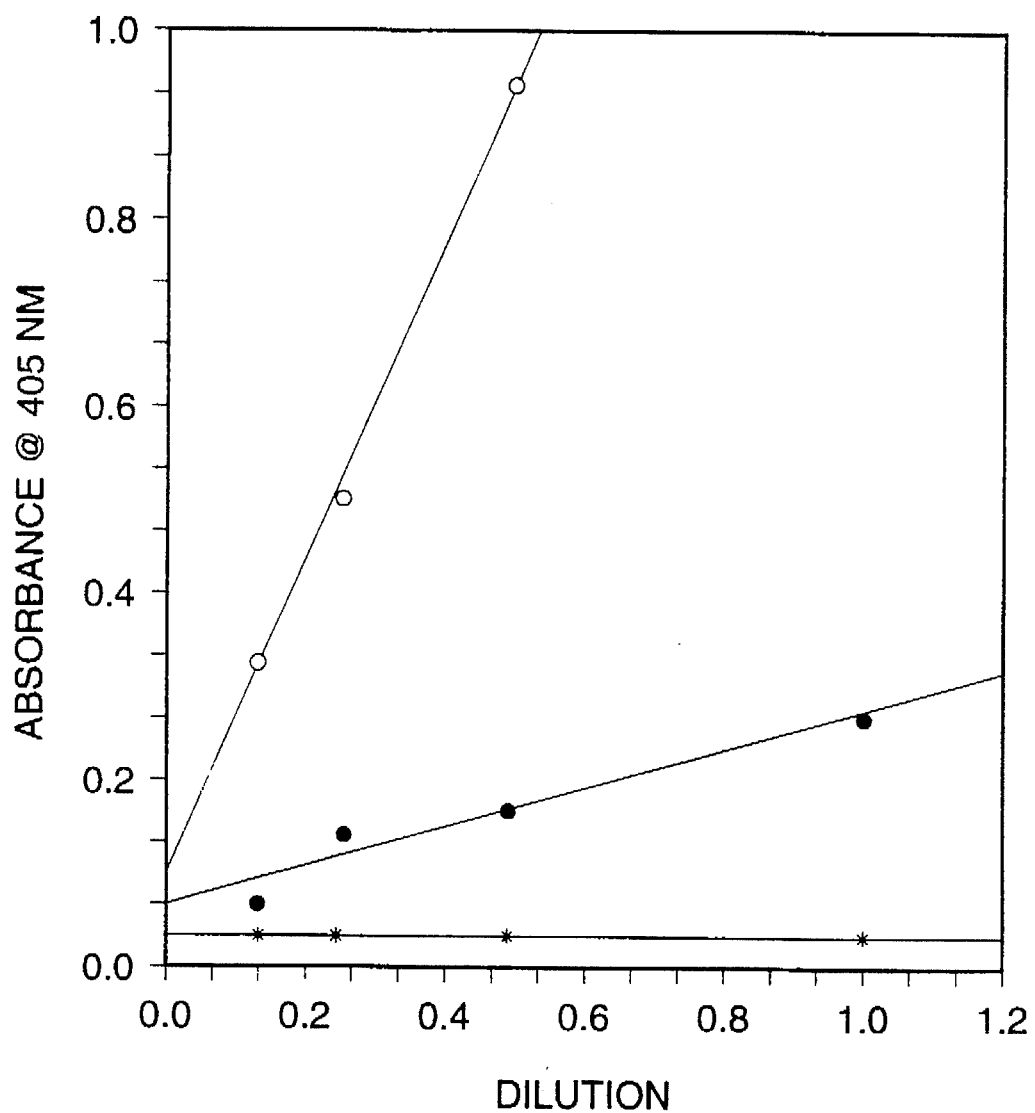
FIG. 28 depicts the assay results of human Ig expression in a pHC1 transgenic mouse.
Figure 29:
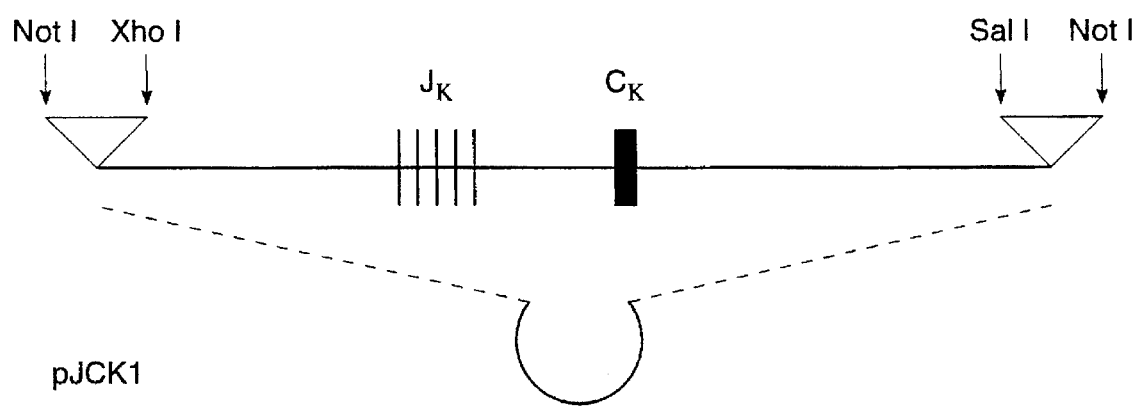
FIG. 29 depicts the structure of pJCK1.
Figure 30:
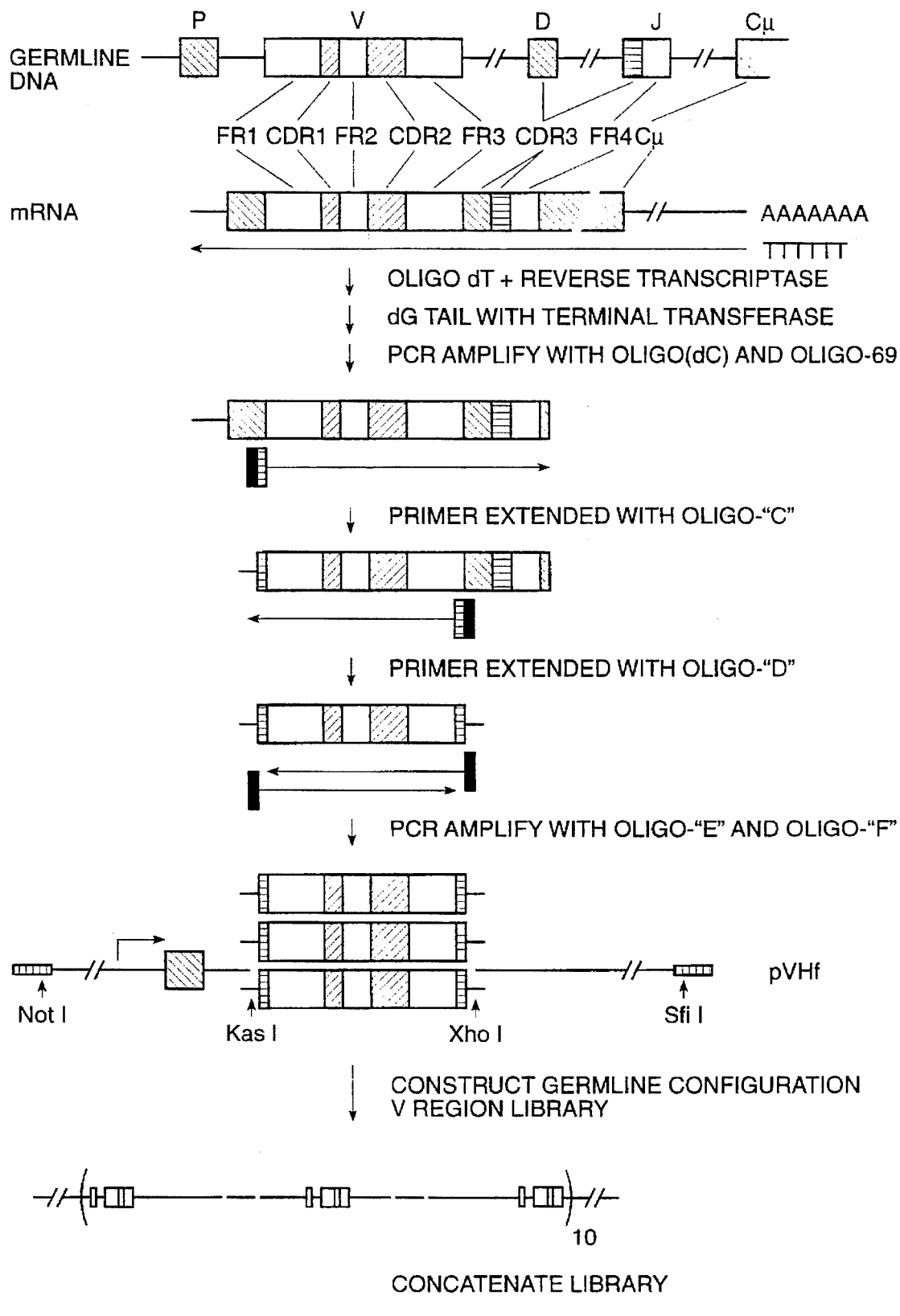
FIG. 30 depicts the construction of a synthetic heavy chain variable region.
Figure 31:
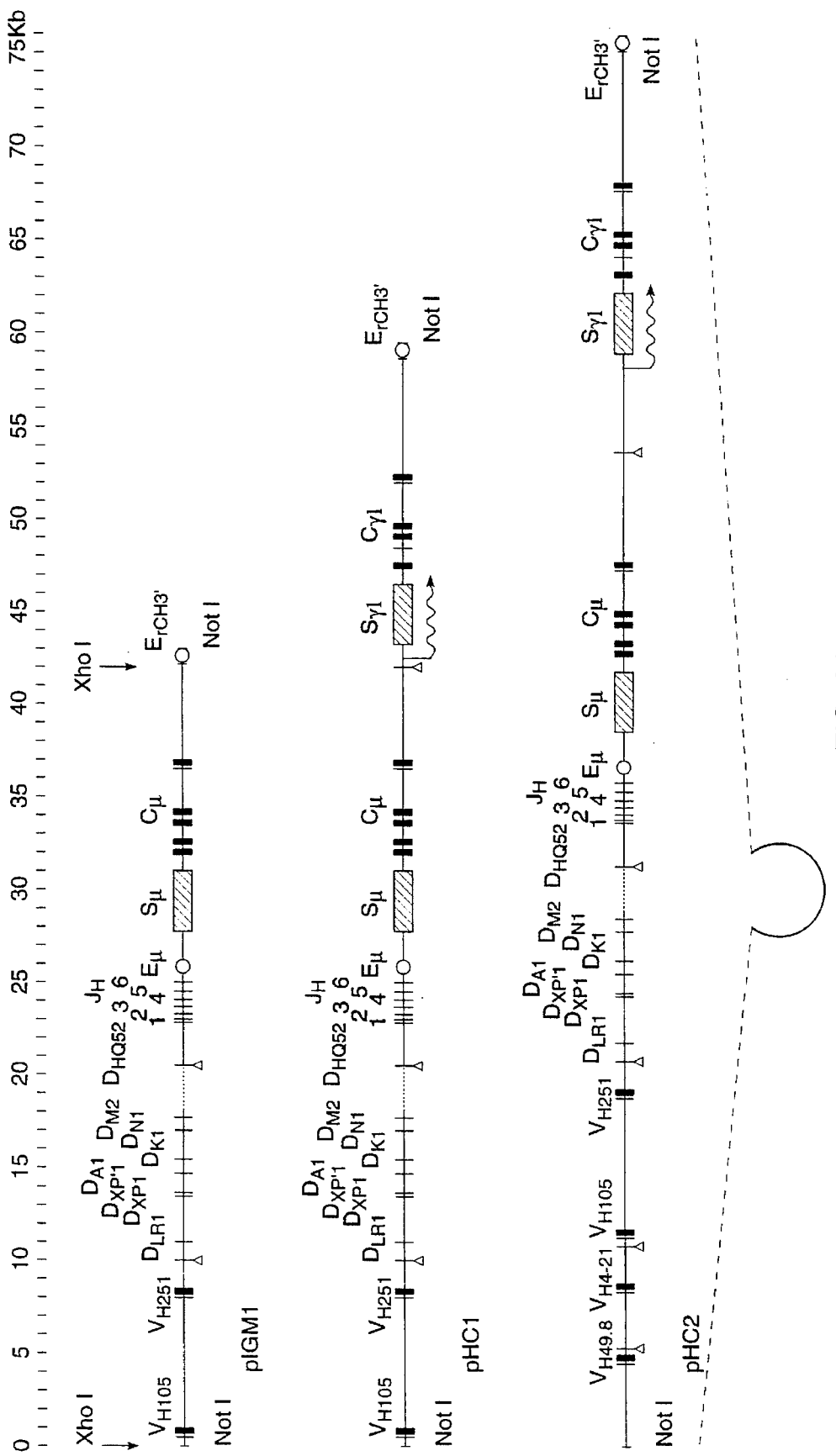
FIG. 31 is a schematic representation of the heavy chain minilocus constructs pIGM$_1$, pHC1, and pHC2.

The NotI inserts of plasmids pIGM1 and pHC1 were isolated from vector sequences by agarose gel electrophoresis. The purified inserts were microinjected into the pronuclei of fertilized (C57BL/6×CBA)F2 mouse embryos and transferred the surviving embryos into pseudopregnant females as described by Hogan et al. (B. Hogan, F. Costantini, and E. Lacy, Methods of Manipulating the Mouse Embryo, 1986, Cold Spring Harbor Laboratory, New York). Mice that developed from injected embryos were analyzed for the presence of transgene sequences by Southern blot analysis of tail DNA. Transgene copy number was estimated by band intensity relative to control standards containing known quantities of cloned DNA. At 3 to 8 weeks of age, serum was isolated from these animals and assayed for the presence of transgene encoded human IgM and IgG1 by ELISA as described by Harlow and Lane (E. Harlow and D. Lane. Antibodies: A Laboratory Manual, 1988, Cold Spring Harbor Laboratory, New York). Microtiter plate wells were coated with mouse monoclonal antibodies specific for human IgM (clone AF6, #0285, AMAC, Inc. Westbrook, Me.) and human IgG1 (clone JL512, #0280, AMAC, Inc. Westbrook, Me.). Serum samples were serially diluted into the wells and the presence of specific immunoglobulins detected with affinity isolated alkaline phosphatase conjugated goat anti-human Ig (polyvalent) that had been pre-adsorbed to minimize cross-reactivity with mouse immunoglobulins. Table 3 and FIG. 28 show the results of an ELISA assay for the presence of human IgM and IgG1 in the serum of two animals that developed from embryos injected with the transgene insert of plasmid pHC1. All of the control non-transgenic mice tested negative for expression of human IgM and IgG1 by this assay. Mice from two lines containing the pIGM1 NotI insert (lines #6 and 15) express human IgM but not human IgG1. We tested mice from 6 lines that contain the pHC1 insert and found that 4 of the lines (lines #26, 38, 57 and 122) express both human IgM and human IgG1, while mice from two of the lines (lines #19 and 21) do not express detectable levels of human immunoglobulins. The pHC1 transgenic mice that did not express human immunoglobulins were so-called $G_o$ mice that developed directly from microinjected embryos and may have been mosaic for the presence of the transgene. Southern blot analysis indicates that many of these mice contain one or fewer copies of the transgene per cell. The detection of human IgM in the serum of pIGM1 transgenics, and human IgM and IgG1 in pHC1 transgenics, provides evidence that the transgene sequences function correctly in directing VDJ joining, transcription, and isotype switching. One of the animals (#18) was negative for the transgene by Southern blot analysis, and showed no detectable levels of human IgM or IgG1. The second animal (#38) contained approximately 5 copies of the transgene, as assayed by Southern blotting, and showed detectable levels of both human IgM and IgG1. The results of ELISA assays for 11 animals that developed from transgene injected embryos is summarized in the table below (Table 3).

TABLE 3

Detection of human IgM and IgG1 in the serum of transgenic animals by ELISA assay

| animal # | injected transgene | approximate transgene copies per cell | human IgM | human IgG1 |
|---|---|---|---|---|
| 6 | pIGM1 | 1 | ++ | − |
| 7 | pIGM1 | 0 | − | − |
| 9 | pIGM1 | 0 | − | − |
| 10 | pIGM1 | 0 | − | − |
| 12 | pIGM1 | 0 | − | − |
| 15 | pIGM1 | 10 | ++ | − |
| 18 | pHC1 | 0 | − | − |
| 19 | pHC1 | 1 | − | − |
| 21 | pHC1 | <1 | − | − |
| 26 | pHC1 | 2 | ++ | + |
| 38 | pHC1 | 5 | ++ | + |

Table 3 shows a correlation between the presence of integrated transgene DNA and the presence of transgene encoded immunoglobulins in the serum. Two of the animals that were found to contain the pHC1 transgene did not express detectable levels of human immunoglobulins. These were both low copy animals and may not have contained complete copies of the transgenes, or the animals may have been genetic mosaics (indicated by the <1 copy per cell estimated for animal #21), and the transgene containing cells may not have populated the hematopoietic lineage. Alternatively, the transgenes may have integrated into genomic locations that are not conducive to their expression. The detection of human IgM in the serum of pIGM1 transgenics, and human IgM and IgG1 in pHC1 transgenics, indicates that the transgene sequences function correctly in directing VDJ joining, transcription, and isotype switching.

F. cDNA Clones

To assess the functionality of the pHC1 transgene in VDJ joining and class switching, as well the participation of the transgene encoded human B-cell receptor in B-cell development and allelic exclusion, the structure of immunoglobulin cDNA clones derived from transgenic mouse spleen mRNA were examined. The overall diversity of the transgene encoded heavy chains, focusing on D and J segment usage, N region addition, CDR3 length distribution, and the frequency of joints resulting in functional mRNA molecules was examined. Transcripts encoding IgM and IgG incorporating VH105 and VH251 were examined.

Figure 34:
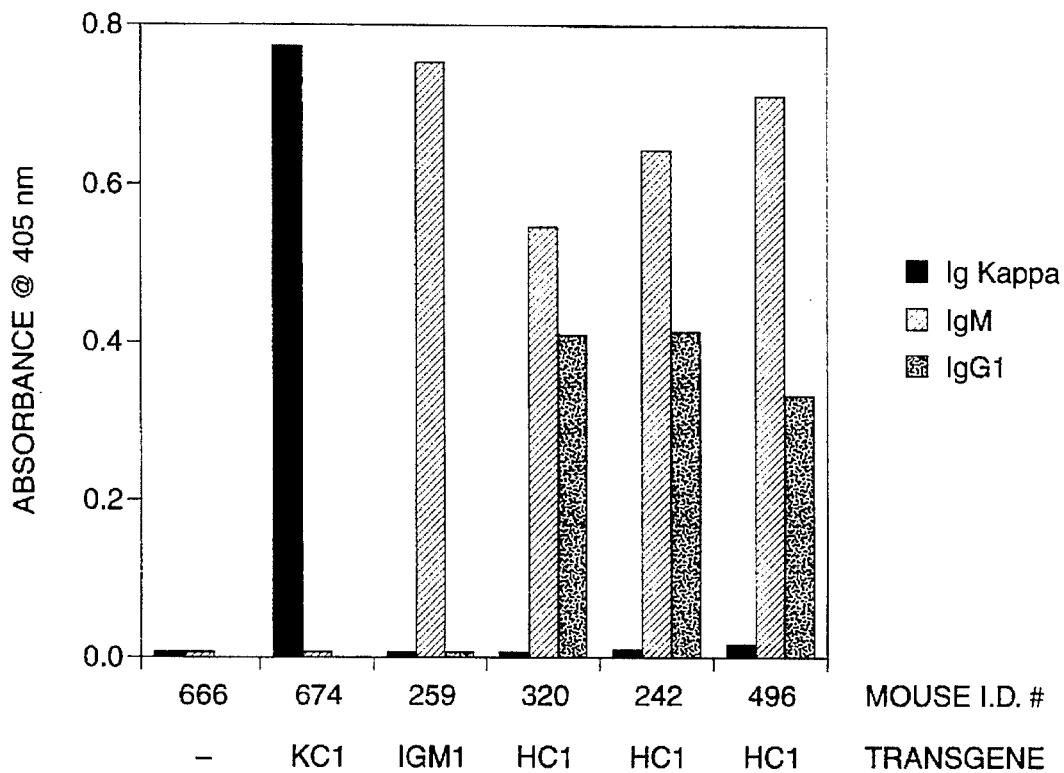
FIG. 34 depicts serum ELISA results

Polyadenylated RNA was isolated from an eleven week old male second generation line-57 pHC1 transgenic mouse. This RNA was used to synthesize oligo-dT primed single stranded cDNA. The resulting cDNA was then used as template for four individual PCR amplifications using the following four synthetic oligonucleotides as primers: VH251 specific oligo-149, cta gct cga gtc caa gga gtc tgt gcc gag gtg cag ctg (g,a,t,c); VH105 specific o-150, gtt gct cga gtg aaa ggt gtc cag tgt gag gtg cag ctg (g,a,t,c); human gamma1 specific oligo-151, ggc gct cga gtt cca cga cac cgt cac cgg ttc; and human mu specific oligo-152, cct gct cga ggc agc caa cgg cca cgc tgc tcg. Reaction 1 used primers o-149 and o-151 to amplify VH251-gammal transcripts, reaction 2 used o-149 and o-152 to amplify VH251-mu transcripts, reaction 3 used o-150 and o-151 to amplify VH105-gammal transcripts, and reaction 4 used o-150 and o-152 to amplify VH105-mu transcripts. The resulting 0.5 kb PCR products were isolated from an agarose gel; the μ transcript products were more abundant than the γ transcript products, consistent with the corresponding ELISA data (FIG. 34). The PCR products were digested with XhoI and cloned into the plasmid pNN03. Double-stranded plasmid DNA was isolated from minipreps of nine clones from each of the four PCR amplifications and dideoxy sequencing reactions were performed. Two of the clones turned out to be deletions containing no D or J segments. These could not have been derived from normal RNA splicing products and are likely to have originated from deletions introduced during PCR amplification. One of the DNA samples turned out to be a mixture of two individual clones, and three additional clones did not produce readable DNA sequence (presumably because the DNA samples were not clean enough). The DNA sequences of the VDJ joints from the remaining 30 clones are compiled in Table 4. Each of the sequences are unique, indicating that no single pathway of gene rearrangement, or single clone of transgene expressing B-cells is dominant. The fact that no two sequences are alike is also an indication of the large diversity of immunoglobulins that can be expressed from a compact minilocus containing only 2 V segments, 10 D segments, and 6 J segments. Both of the V segments, all six of the J segments, and 7 of the 10 D segments that are included in the transgene are used in VDJ joints. In addition, both constant region genes (mu and gammal) are incorporated into transcripts. The VH105 primer turned out not to be specific for VH105 in the reactions performed. Therefore many of the clones from reactions 3 and 4 contained VH251 transcripts. Additionally, clones isolated from ligated reaction 3 PCR product turned out to encode IgM rather than IgG; however this may reflect contamination with PCR product from reaction 4 as the DNA was isolated on the same gel. An analogous experiment, in which immunoglobulin heavy chain sequences were amplified from adult human peripheral blood lymphocytes (PBL), and the DNA sequence of the VDJ joints determined, was recently reported by Yamada et al. (*J. Exp. Med.* 173:395–407 (1991), which is incorporated herein by reference). We compared the data from human PBL with our data from the pHC1 transgenic mouse.

TABLE 4

|    |       |       |    |    | V            | n-D-n |
|----|-------|-------|----|----|--------------|-------|
| 1  | VH251 | DHQ52 | J3 | γ1 | TACTGTGCGAGA | CGGCTAACTGGGGTTGAT |
| 2  | VH251 | DN1   | J4 | γ1 | TACTGTGCGAGA | CACCGTATAGCAGCAGCTGG |
| 3  | VH251 | D?    | J6 | γ1 | TACTGTGCGAGA | T |
| 4  | VH251 | DXP'1 | J6 | γ1 | TACTGTGCGAGA | CATTACGATATTTTGACTGGTC |
| 5  | VH251 | DXP'1 | J4 | γ1 | TACTGTGCGAGA | CGGAGGTACTATGGTTCGGGGAGTTATTATAACGT |
| 6  | VH251 | D?    | J3 | γ1 | TACTGTGCGAGA | CGGGGGGTGTCTGAT |
| 7  | VH251 | DHQ52 | J3 | μ  | TACTGTGCGAGA | GCAACTGGC |
| 8  | VH251 | DHQ52 | J6 | μ  | TACTGTGCGAGA | TCGGCTAACTGGGGATC |
| 9  | VH251 | —     | J1 | μ  | TACTGTGCGAGA | |
| 10 | VH251 | DLR2  | J4 | μ  | TACTGTGCGAGA | CACGTAGCTAACTCT |
| 11 | VH251 | DXP'1 | J4 | μ  | TACTGTGCGAGA | CAAATTACTATGGTTCGGGGAGTTCC |
| 12 | VH251 | D?    | J1 | μ  | TACTGTGCGAGA | C |
| 13 | VH251 | DHQ52 | J6 | μ  | TACTGTGCGAGA | CAAACTGGGG |
| 14 | VH251 | DXP'1 | J6 | μ  | TACTGTGCGAGA | CATTACTATGGTTCGGGGAGTTATG |
| 15 | VH251 | DXP'1 | J4 | γ1 | TACTGTGCGAGA | CAGGGAG |
| 16 | VH105 | DXP'1 | J5 | μ  | TACTGTGTGAGA | TTCTGGGAG |
| 17 | VH251 | DXP'1 | J4 | γ1 | TACTGTGCGAGA | CGGAGGTACTATGGTTCGGGGAGTTATTATAACGT |
| 18 | VH251 | DHQ52 | J4 | γ1 | TACTGTGCGAGA | CAAACCTGGGGAGGA |
| 19 | VH251 | DK1   | J6 | γ1 | TACTGTGCGAGA | GGATATAGTGGCTACGATA |
| 20 | VH251 | DHQ52 | J4 | μ  | TACTGTGCGAGA | CAAACTGGGGAGG |
| 21 | VH251 | DK1   | J2 | γ1 | TACTGTGCGAGA | TATAGTGGCTACGATTAC |
| 22 | VH251 | DIR2  | J6 | γ1 | TACTGTGCGAGA | GCATCCCTCCCCTCCTTTG |
| 23 | VH251 | DIR2  | J4 | μ  | TACTCTGCGAGA | CGGGGTGGGGG |
| 24 | VH105 | D?    | J6 | μ  | TACTGTGTG    | CCGGTCGAAACT |
| 25 | VH105 | DXP1  | J4 | μ  | TACTGTGTGAGA | GATATTTTGACTGGTTAACG |
| 26 | VH251 | DN1   | J3 | μ  | TACTGTGCGAGA | CATGGTATAGCAGCAGCTGGTAC |
| 27 | VH105 | DHQ52 | J3 | μ  | TACTGTGTGAGA | TCAACTGGGGTTG |
| 28 | VH251 | DN1   | J4 | μ  | TACTGTGCG    | GAAATAGCAGCAGCTGCC |
| 29 | VH105 | DN1   | J4 | μ  | TACTGTGTG    | TGTATAGCAGCAGCTGGTAAAGGAAACGG |
| 30 | VH251 | DHQ52 | J4 | μ  | TACTGTGCGAGA | CAAACTGGGG |

TABLE 4-continued

|  | J | C |
|---|---|---|
| 1 | GCTTTTGATATCTGGGGCCAAGGGACAATGGTCACCGTCTCTTCAG | CCTCCACCAAG |
| 2 | CTTTGACTACTGGGGCCAGGGAACCCTGGTCACCGTCTCCTCAG | CCTCCACCAAG |
| 3 | ATTACTACTACTACTACGGTATGGACGTCTGGGGCCAAGGGACCACGGTCACCGTCTCCTCAG | CCTCCACCAAG |
| 4 | CTACTACTACTACGGTATGGACGTCTGGGGCCAAGGGACCACGGTCACCGTCTCCTCAG | CCTCCACCAAG |
| 5 | CTTTGACTACTGGGGCCAGGGAACCCTGGTCACCGTCTCCTCAG | CCTCCACCAAG |
| 6 | GCTTTTGATATCTGGGGCCAAGGGACAATGGTCACCGTCTCTTCAG | CCTCCACCAAG |
| 7 | GCTTTTGATATCTGGGGCCAAGGGACAATCCTCACCGTCTCTTCAG | GGAGTGCATCC |
| 8 | CTACTACTACTACGGTATGGACGTCTGGGGCCAAGGGACCACGGTCACCGTCTCCTCAG | GGAGTGCATCC |
| 9 | TACTTCCAGCACTGGGGCCAGGGCACCCTGGTCACCGTCTCCTCAG | GGAGTGCGTCC |
| 10 | TTTGACTACTGGGGCCAGGGAACCCTGGTCACCGTCTCCTCAG | GGAGTGCATCC |
| 11 | CTTGACTACTGGGGCCAGGGAACCCTGGTCACCGTCTCCTCAG | GGAGTGCATCC |
| 12 | AATACTTCCAGCACTGGGGCCAGGGCACCCTGGTCACCGTCTCTCAG | GGAGTGCATCC |
| 13 | ACTACTACTACTACGGTATGGACGTCTGGGGCCAAGGGACCACGGTCACCGTCTCCTCAG | GGAGTGCATCC |
| 14 | ACTACTACTACTACGGTATGGACGTCTGGGGCCAAGGGACCACGGTCACCGTCTCCTCAG | GGAGTGCATCC |
| 15 | TGGGGCCAGGGAACCCTGGTCACCGTCTCCTCAG | CCTCCACCAAG |
| 16 | ACTGGTTCGACCCCTGGGGCCAGGGAACCCTGGTCACCGTCTCCTCAG | GGAGTGCATCC |
| 17 | CTTTGACTACTGGGGCCAGGGAACCCTGGTCACCGTCTCCTCAG | CCTCCACCAAG |
| 18 | GACTACTGGGGCCAGGGAACCCTGGTCACCGTCTCCTCAG | CCTCCACCAAG |
| 19 | ACTACTACTACGGTATGGACGTCTGGGGCCAAGGGACCACGGTCACCGTCTCCTCAG | CCTCCACCAAG |
| 20 | ACTACTTTGACTACTGGGGCCAGGGAACCCTGGTCACCGTCTCCTCAG | GGAGTGCATCC |
| 21 | CTACTGGTACTTCGATCTCTGGGGCCGTGGCACCCTGGTCACTGTCTCCTCAG | CCTCCACCGAG |
| 22 | ACTACTACGGTATGGACGTCTGGGGCCAAGGGACCACGGTCACCGTCTCCTCAG | CCTCCACCAAG |
| 23 | TTTGACTACTGGGGCCAGGGAACCCTGGTCACCGTCTCCTCAG | GGAGTGCATCC |
| 24 | TTACTACTACTACTACGGTATGGACGTCTGGGGCCAAGGGACCACGGTCACCGTCTCCTCAG | GGAGTGCATCC |
| 25 | TGACTACTGGGGCCAGGGAACCCTGGTCACCGTCTCCTCAG | GGAGTGCATCC |
| 26 | TGCTTTTGATATCTGGGGCCAAGGGACAATGGTCACCGTCTCTTCAG | GGAGTGCATCC |
| 27 | ATGCTTTTGATATCTGGGGCCAAGGGACAATGGTCACCGTCTCTTCAG | GGAGTGCATCC |
| 28 | CTACTTTGACTACTGGGGCCAGGGAACCTGGTCACCGTCTCCTCAG | GGAGTGCATCC |
| 29 | CTACTGGGGCCAGGGAACCCTGGTCACCGTCTCCTCAG | GGAGTGCATCC |
| 30 | TGACTACTGGGGCCAGGGAACCCTGGTCACCGTCTCCTCAG | GGAGTGCATCC |

G. J Segment Choice

Table 5 compared the distribution of J segments incorporated into pHC1 transgene encoded transcripts to J segments found in adult human PBL immunoglobulin transcripts. The distribution profiles are very similar, J4 is the dominant segment in both systems, followed by J6. J2 is the least common segment in human PBL and the transgenic animal.

TABLE 5

J. Segment Choice

| | Percent Usage (±3%) | |
|---|---|---|
| J. Segment | HC1 transgenic | Human PBL |
| J1 | 7 | 1 |
| J2 | 3 | <1 |
| J3 | 17 | 9 |
| J4 | 44 | 53 |
| J5 | 3 | 15 |
| J6 | 26 | 22 |
| | 100% | 100% |

H. D Segment Choice

49% (40 of 82) of the clones analyzed by Yamada et al. incorporated D segments that are included in the pHC1 transgene. An additional 11 clones contained sequences that were not assigned by the authors to any of the known D segments. Two of these 11 unassigned clones appear to be derived from an inversion of the DIR2 segments which is included in the pHC1 construct. This mechanism, which was predicted by Ichihara et al. (*EMBO J.* 7:4141 (1988)) and observed by Sanz (*J. Immunol.* 147:1720–1729 (1991)), was not considered by Yamada et al. (*J. Exp. Med.* 173:395–407 (1991)). Table 5 is a comparison of the D segment distribution for the pHC1 transgenic mouse and that observed for human PBL transcripts by Yamada et al. The data of Yamada et al. was recompiled to include DIR2 use, and to exclude D segments that are not in the pHC1 transgene. Table 6 demonstrates that the distribution of D segment incorporation is very similar in the transgenic mouse and in human PBL. The two dominant human D segments, DXP'1 and DN1, are also found with high frequency in the transgenic mouse. The most dramatic dissimilarity between the two distributions is the high frequency of DHQ52 in the transgenic mouse as compared to the human. The high frequency of DHQ52 is reminiscent of the D segment distribution in the human fetal liver. Sanz has observed that 14% of the heavy chain transcripts contained DHQ52 sequences. If D segments not found in pHC1 are excluded from the analysis, 31% of the fetal transcripts analyzed by Sanz contain DHQ52. This is comparable to the 27% that we observe in the pHC1 transgenic mouse.

TABLE 6

D Segment Choice

| | Percent Usage (±3%) | |
|---|---|---|
| D. Segment | HC1 transgenic | Human PBL |
| DLR1 | <1 | <1 |
| DXP1 | 3 | 6 |
| DXP'1 | 25 | 19 |
| DA1 | <1 | 12 |
| DK1 | 7 | 12 |
| DN1 | 12 | 22 |
| DIR2 | 7 | 4 |
| DM2 | <1 | 2 |
| DLR2 | 3 | 4 |
| DHQ52 | 26 | 2 |
| ? | 17 | 17 |
| | 100% | 100% |

I. Functionality of VDJ Joints

Table 7 shows the predicted amino acid sequences of the VDJ regions from 30 clones that were analyzed from the pHC1 transgenic. The translated sequences indicate that 23 of the 30 VDJ joints (77%) are in-frame with respect to the variable and J segments.

TABLE 7

Functionality of V—D—J Joints

|    |       |       |    |     | FR3  | CDR3                        | FR4              |
|----|-------|-------|----|-----|------|-----------------------------|------------------|
| 1  | VH251 | DHQ52 | J3 | γ1  | YCAR | RLTGVDAFDI                  | WGQGTMVTVSSASTK  |
| 2  | VH251 | DN1   | J4 | γ1  | YCAR | HRIAAAGFDY                  | WGQGTLVTVSSASTK  |
| 3  | VH251 | D?    | J6 | γ1  | YCAR | YYYYYYGMDV                  | WGQGTTVTVSSASTK  |
| 4  | VH251 | DXP'1 | J6 | γ1  | YCAR | HYDILTGPTTTTVWTSGAKGPRSPSPQPPP |                  |
| 5  | VH251 | DXP'1 | J4 | γ1  | YCAR | RRYYGSGSYYNVFDY             | WGQGTLVTVSSASTK  |
| 6  | VH251 | D?    | J3 | γ1  | YCAR | RGVSDAFDI                   | WGQGTMVTVSSASTK  |
| 7  | VH251 | DHQ52 | J3 | μ   | YCAR | ATGAFDI                     | WGQGTMVTVSSGSAS  |
| 8  | VH251 | DHQ52 | J6 | μ   | YCAR | SANWGSYYYYGMDV              | WGQGTTVTVSSGSAS  |
| 9  | VH251 | —     | J1 | μ   | YCAR | YFQH                        | WGQGTLVTVSSGSAS  |
| 10 | VH251 | DLR2  | J4 | μ   | YCAR | HVANSFDY                    | WGQGTLVTVSSGSAS  |
| 11 | VH251 | DXP'1 | J4 | μ   | YCAR | QITMVRGVPFDY                | WGQGTLVTVSSGSAS  |
| 12 | VH251 | D?    | J1 | μ   | YCAR | QYFQH                       | WGQGTLVTVSSGSAS  |
| 13 | VH251 | DHQ52 | J6 | μ   | YCAR | QTGDYYYYGMDV                | WGQGTTVTVSSGSAS  |
| 14 | VH251 | DXP'1 | J6 | μ   | YCAR | HYYGSGSYDYYYYGMDV           | WGQGTTVTVSSGSAS  |
| 15 | VH251 | DXP'1 | J4 | γ1  | YCVR | QGVGPGNPGHRLLSLHQ           |                  |
| 16 | VH105 | DXP'1 | J5 | μ   | YCAR | FWETGSTPGAREPWSPSPQGVH      |                  |
| 17 | VH251 | DXP'1 | J4 | γ1  | YCAR | RRYYGSGSYYNVFDY             | WGQGTLVTVSSASTK  |
| 18 | VH251 | DHQ52 | J4 | γ1  | YCAR | QTWGGDY                     | WGQGTLVTVSSASTK  |
| 19 | VH251 | DK1   | J6 | γ1  | YCAR | GYSGYDNYYYGIHV              | WGQGTTVTVSSASTK  |
| 20 | VH251 | DHQ52 | J4 | μ   | YCAR | QTGEDYFDY                   | WGQGTLVTVSSGSAS  |
| 21 | VH251 | DK1   | J2 | γ1  | YCAR | YSGYDYLLVLRSLGPWHPGHCLLSLHR |                  |
| 22 | VH251 | DIR2  | J6 | γ1  | YCAR | ASLPSFDYYGMDV               | WGQGTTVTVSSASTK  |
| 23 | VH251 | DIR2  | J4 | μ   | YCAR | RGGGLTTGAREPWSPSPQGVH       |                  |
| 24 | VH105 | D?    | J6 | μ   | YCVP | VETLLLLLRYGRLGPRDHGHRLLRECI |                  |
| 25 | VH105 | DXP1  | J4 | μ   | YCVR | DILTGXRDY                   | WGQGTLVTVSSGSAS  |
| 26 | VH251 | DN1   | J3 | μ   | YCAR | HGIAAAGTAFDI                | WGQGTMVTVSSGSAS  |
| 27 | VH105 | DHQ52 | J3 | μ   | YCVR | STGVDAFDI                   | WGQGTMVTVSSGSAS  |
| 28 | VH251 | DN1   | J4 | μ   | YCAE | IAAAALLXLLGPGNPGHRLLRECI    |                  |
| 29 | VH105 | DN1   | J4 | μ   | YCVC | IAAAGKGNGY                  | WGQGTLVTVSSGSAS  |
| 30 | VH251 | DHQ52 | J4 | μ   | YCAR | QNWGDY                      | WGQGTLVTVSSGSAS  |

J. CDR3 Length Distribution

Table 8 compared the length of the CDR3 peptides from transcripts with in-frame VDJ joints in the pHC1 transgenic mouse to those in human PBL. Again the human PBL data comes from Yamada et al. The profiles are similar with the transgenic profile skewed slightly toward smaller CDR3 peptides than observed from human PBL. The average length of CDR3 in the transgenic mouse is 10.3 amino acids. This is substantially the same as the average size reported for authentic human CDR3 peptides by Sanz (*J. Immunol.* 147:1720–1729 (1991)).

TABLE 8

CDR3 Length Distribution

|                     | Percent Occurrence (±3%) |           |
|---------------------|--------------------------|-----------|
| # amino acids in CDR3 | HC1 transgenic         | Human PBL |
| 3–8                 | 26                       | 14        |
| 9–12                | 48                       | 41        |
| 13–18               | 26                       | 37        |
| 19–23               | <1                       | 7         |
| >23                 | <1                       | 1         |
|                     | 100%                     | 100%      |

Example 13

Rearranged Heavy Chain Transgenes

A. Isolation of Rearranged Human Heavy Chain VDJ Segments

Two human leukocyte genomic DNA libraries cloned into the phage vector λEMBL3/SP6/T7 (Clonetech Laboratories, Inc., Palo Alto, Calif.) are screened with a 1 kb PacI/HindIII fragment of λ1.3 containing the human heavy chain J-μ intronic enhancer. Positive clones are tested for hybridization with a mixture of the following $V_H$ specific oligonucleotides:

```
oligo-7    5'-tca gtg aag gtt tcc tgc aag gca tct gga tac acc ttc acc-3' oligo-8    5'-tcc ctg aga ctc tcc tgt gca gcc tct gga ttc acc ttc agt-3'
```

Clones that hybridized with both V and J-μ probes are isolated and the DNA sequence of the rearranged VDJ segment determined.

B. Construction of Rearranged Human Heavy Chain Transgenes

Fragments containing functional VJ segments (open reading frame and splice signals) are subcloned into the plasmid vector pSP72 such that the plasmid derived XhoI site is adjacent to the 5' end of the insert sequence. A subclone containing a functional VDJ segment is digested with XhoI and PacI (PacI, a rare-cutting enzyme, recognizes a site near the J-m intronic enhancer), and the insert cloned into XhoI/PacI digested pHC2 to generate a transgene construct with a functional VDJ segment, the J-μ intronic enhancer, the μ switch element, the μ constant region coding exons, and the γ1 constant region, including the sterile transcript associated sequences, the γ1 switch, and the coding exons. This transgene construct is excised with NotI and microinjected into the pronuclei of mouse embryos to generate transgenic animals as described above.

```
oligo-87   5'-ggc cgc tgt cga caa gct tat cga tgg atc ctc gag tgc-3' oligo-88   5'-ggc cgc act cga gga tcc atc gat aag ctt gtc gac agc-3'
```

The resulting plasmid, pGP1d, contains a polylinker with SalI, HindIII, ClaI, BamHI, and XhoI restriction sites flanked by NotI sites.

Example 14

Light Chain Transgenes

A. Construction of Plasmid Vectors

1. Plasmid Vector pGP1c

Plasmid vector pGP1a is digested with NotI and the following oligonucleotides ligated in:

```
oligo-81   5'-ggc cgc atc ccg ggt ctc gag gtc gac aag ctt tcg agg atc cgc-3' oligo-82   5'-ggc cgc gga tcc tcg aaa gct tgt cga cct cga gac ccg gga tgc-3'
```

The resulting plasmid, pGP1c, contains a polylinker with XmaI, XhoI, SalI, HindIII, and BamHI restriction sites flanked by NotI sites.

2. Plasmid Vector pGP1d

Plasmid vector pGP1a is digested with NotI and the following oligonucleotides ligated in:

B. Isolation of Jκ and Cκ clones

A human placental genomic DNA library cloned into the phage vector λEMBL3/SP6/T7 (Clonetech Laboratories, Inc., Palo Alto, Calif.) was screened with the human kappa light chain J region specific oligonucleotide:

oligo-36  5'- cac ctt cgg cca agg gac acg act gga gat taa acg taa gca -3' and the phage clones 136.2 and 136.5 isolated. A 7.4 kb XhoI fragment that includes the Jκ1 segment was isolated from 136.2 and subcloned into the plasmid pNN03 to generate the plasmid clone p36.2. A neighboring 13 kb XhoI fragment that includes Jk segments 2 through 5 together with the Cκ gene segment was isolated from phage clone 136.5 and subcloned into the plasmid pNN03 to generate the plasmid clone p36.5. Together these two clones span the region beginning 7.2 kb upstream of Jκ1 and ending 9 kb downstream of Cκ.

C. Construction of Rearranged Light Chain Transgenes 1. pCK1, a Cκ Vector for Expressing Rearranged Variable Segments The 13 kb XhoI insert of plasmid clone p36.5 containing the Cκ gene, together with 9 kb of downstream sequences, is cloned into the SalI site of plasmid vector pGP1c with the 5' end of the insert adjacent to the plasmid XhoI site. The resulting clone, pCK1 can accept cloned fragments containing rearranged VJκ segments into the unique 5' XhoI site. The transgene can then be excised with NotI and purified from vector sequences by gel electrophoresis. The resulting transgene construct will contain the human J-Cκ intronic enhancer and may contain the human 3' κ enhancer.

2. pCK2, a Cκ Vector with Heavy Chain Enhancers for Expressing Rearranged Variable Segments A 0.9 kb XbaI fragment of mouse genomic DNA containing the mouse heavy chain J-μ intronic enhancer (J. Banerji et al., *Cell* 33:729-740 (1983)) was subcloned into pUC18 to generate the plasmid pJH22.1. This plasmid was linearized with SphI and the ends filled in with Klenow enzyme. The Klenow treated DNA was then digested with HindIII and a 1.4 kb MluI/HindIII fragment of phage clone λ1.3 (previous example), containing the human heavy chain J-μ intronic enhancer (Hayday et al., *Nature* 307:334-340 (1984)), to it. The resulting plasmid, pMHE1, consists of the mouse and human heavy chain J-μ intronic enhancers ligated together into pUC18 such that they are excised on a single BamHI/HindIII fragment. This 2.3 kb fragment is isolated and cloned into pGP1c to generate pMHE2. pMHE2 is digested with SalI and the 13 kb XhoI insert of p36.5 cloned in. The resulting plasmid, pCK2, is identical to pCK1, except that the mouse and human heavy chain J-μ intronic enhancers are fused to the 3' end of the transgene insert. To modulate expression of the final transgene, analogous constructs can be generated with different enhancers, i.e. the mouse or rat 3' kappa or heavy chain enhancer (Meyer and Neuberger, *EMBO J.*, 8:1959-1964 (1989); Petterson et al., *Nature*, 344:165-168 (1990)).

3. Isolation of Rearranged Kappa Light Chain Variable Segments

Two human leukocyte genomic DNA libraries cloned into the phage vector λEMBL3/SP6/T7 (Clonetech Laboratories, Inc., Palo Alto, Calif.) were screened with the human kappa light chain J region containing 3.5 kb XhoI/SmaI fragment of p36.5. Positive clones were tested for hybridization with the following Vκ specific oligonucleotide:

Clones that hybridized with both V and J probes are isolated and the DNA sequence of the rearranged VJκ segment determined.

4. Generation of Transgenic Mice Containing Rearranged Human Light Chain Constructs Fragments containing functional VJ segments (open reading frame and splice signals) are subcloned into the unique XhoI sites of vectors pCK1 and pCK2 to generate rearranged kappa light chain transgenes. The transgene constructs are isolated from vector sequences by digestion with NotI. Agarose gel purified insert is microinjected into mouse embryo pronuclei to generate transgenic animals. Animals expressing human kappa chain are bred with heavy chain minilocus containing transgenic animals to generate mice expressing fully human antibodies.

Because not all VJκ combinations may be capable of forming stable heavy-light chain complexes with a broad spectrum of different heavy chain VDJ combinations, several different light chain transgene constructs are generated, each using a different rearranged VJk clone, and transgenic mice that result from these constructs are bred with heavy chain minilocus transgene expressing mice. Peripheral blood, spleen, and lymph node lymphocytes are isolated from double transgenic (both heavy and light chain constructs) animals, stained with fluorescent antibodies specific for human and mouse heavy and light chain immunoglobulins (Pharmingen, San Diego, Calif.) and analyzed by flow cytometry using a FACScan analyzer (Becton Dickinson, San Jose, Calif.). Rearranged light chain transgenes constructs that result in the highest level of human heavy/light chain complexes on the surface of the highest number of B cells, and do not adversely affect the immune cell compartment (as assayed by flow cytometric analysis with B and T cell subset specific antibodies), are selected for the generation of human monoclonal antibodies.

D. Construction of Unrearranged Light Chain Minilocus Transgenes 1. pJCK1, a Jκ, Cκ Containing Vector for Constructing Minilocus Transgenes The 13 kb Cκ containing XhoI insert of p36.5 is treated with Klenow enzyme and cloned into HindIII digested, Klenow-treated, plasmid pGP1d. A plasmid clone is selected such that the 5' end of the insert is adjacent to the vector derived ClaI site. The resulting plasmid, p36.5-1d, is digested with ClaI and Klenow-treated. The Jκ1 containing 7.4 kb XhoI insert of p36.2 is then Klenow-treated and cloned into the ClaI, Klenow-treated p36.5-1d. A clone is selected in which the p36.2 insert is in the same orientation as the p36.5 insert. This clone, pJCK1 (FIG. 34), contains the entire human Jκ region and Cκ, together with 7.2 kb of upstream sequences and 9 kb of downstream sequences. The insert also contains the human J-Cκ intronic enhancer and may contain a human 3' κ enhancer. The insert is flanked by a unique 3' SalI site for the purpose of cloning additional 3' flanking sequences such as heavy chain or light chain enhancers. A unique XhoI site is located at the 5' end of the oligo-65  5'- agg ttc agt ggc agt ggg tct ggg aca gac ttc act ctc acc atc agc -3' insert for the purpose of cloning in unrearranged Vκ gene segments. The unique SalI and XhoI sites are in turn flanked by NotI sites that are used to isolate the completed transgene construct away from vector sequences.

2. Isolation of Unrearranged Vκ Gene Segments and Generation of Transgenic Animals Expressing Human Ig Light Chain Protein The Vκ specific oligonucleotide, oligo-65 (discussed above), is used to probe a human placental genomic DNA library cloned into the phage vector lEMBL3/SP6/T7 (Clonetech Laboratories, Inc., Palo Alto, Calif.). Variable gene segments from the resulting clones are sequenced, and clones that appear functional are selected. Criteria for judging functionality include: open reading frames, intact splice acceptor and donor sequences, and intact recombination sequence. DNA fragments containing selected variable gene segments are cloned into the unique XhoI site of plasmid pJCK1 to generate minilocus constructs. The resulting clones are digested with NotI and the inserts isolated and injected into mouse embryo pronuclei to generate transgenic animals. The transgenes of these animals will undergo V to J joining in developing B-cells. Animals expressing human kappa chain are bred with heavy chain minilocus containing transgenic animals to generate mice expressing fully human antibodies.

Example 15

Genomic Heavy Chain Human Ig Transgene

This Example describes the cloning of a human genomic heavy chain immunoglobulin transgene which is then introduced into the murine germline via microinjection into zygotes or integration in ES cells.

Nuclei are isolated from fresh human placental tissue as described by Marzluff, W. F., et al. (1985), *Transcription and Translation: A Practical Approach*, B. D. Hammes and S. J. Higgins, eds., pp. 89–129, IRL Press, Oxford). The isolated nuclei (or PBS washed human spermatocytes) are embedded in 0.5% low melting point agarose blocks and lysed with 1 mg/ml proteinase K in 500 mM EDTA, 1% SDS for nuclei, or with 1 mg/ml proteinase K in 500 mM EDTA, 1% SDS, 10 mM DTT for spermatocytes at 50° C. for 18 hours. The proteinase K is inactivated by incubating the blocks in 40 µg/ml PMSF in TE for 30 minutes at 50° C., and then washing extensively with TE. The DNA is then digested in the agarose with the restriction enzyme NotI as described by M. Finney in *Current Protocols in Molecular Biology* (F. Ausubel et al., eds. John Wiley & Sons, Supp. 4, 1988, e.g., Section 2.5.1).

The NotI digested DNA is then fractionated by pulsed field gel electrophoresis as described by Anand et al., *Nuc. Acids Res.* 17:3425–3433 (1989). Fractions enriched for the NotI fragment are assayed by Southern hybridization to detect one or more of the sequences encoded by this fragment. Such sequences include the heavy chain D segments, J segments, and γ1 constant regions together with representatives of all 6 $V_H$ families (although this fragment is identified as 670 kb fragment from HeLa cells by Berman et al. (1988), supra., we have found it to be an 830 kb fragment from human placental and sperm DNA). Those fractions containing this NotI fragment are ligated into the NotI cloning site of the vector pYACNN as described (McCormick et al., *Technique* 2:65–71 (1990)). Plasmid pYACNN is prepared by digestion of pYACneo (Clontech) with EcoRI and ligation in the presence of the oligonucleotide 5' - AAT TGC GGC CGC - 3'.

YAC clones containing the heavy chain NotI fragment are isolated as described by Traver et al., *Proc. Natl. Acad. Sci. USA*, 86:5898–5902 (1989). The cloned NotI insert is isolated from high molecular weight yeast DNA by pulse field gel electrophoresis as described by M. Finney, op. cit. The DNA is condensed by the addition of 1 mM spermine and microinjected directly into the nucleus of single cell embryos previously described. Alternatively, the DNA is isolated by pulsed field gel electrophoresis and introduced into ES cells by lipofection (Gnirke et al., *EMBO J.* 10:1629–1634 (1991)), or the YAC is introduced into ES cells by spheroplast fusion.

Example 16

Discontinuous Genomic Heavy Chain Ig Transgene

An 85 kb SpeI fragment of human genomic DNA, containing $V_H6$, D segments, J segments, the µ constant region and part of the γ constant region, has been isolated by YAC cloning essentially as described in Example 1. A YAC carrying a fragment from the germline variable region, such as a 570 kb NotI fragment upstream of the 670–830 kb NotI fragment described above containing multiple copies of $V_1$ through $V_5$, is isolated as described. (Berman et al. (1988), supra. detected two 570 kb NotI fragments, each containing multiple V segments.) The two fragments are coinjected into the nucleus of a mouse single cell embryo as described in Example 1.

Typically, coinjection of two different DNA fragments result in the integration of both fragments at the same insertion site within the chromosome. Therefore, approximately 50% of the resulting transgenic animals that contain at least one copy of each of the two fragments will have the V segment fragment inserted upstream of the constant region containing fragment. Of these animals, about 50% will carry out V to DJ joining by DNA inversion and about 50% by deletion, depending on the orientation of the 570 kb NotI fragment relative to the position of the 85 kb SpeI fragment. DNA is isolated from resultant transgenic animals and those animals found to be containing both transgenes by Southern blot hybridization (specifically, those animals containing both multiple human V segments and human constant region genes) are tested for their ability to express human immunoglobulin molecules in accordance with standard techniques.

Example 17

Identification of Functionally Rearranged Variable Region Sequences in Transgenic B Cells An antigen of interest is used to immunize (see Harlow and Lane, *Antibodies: A Laboratory Manual*, Cold Spring Harbor, N.Y. (1988)) a mouse with the following genetic traits: homozygosity at the endogenous having chain locus for a deletion of $J_H$ (Examples 10); hemizygous for a single copy of unrearranged human heavy chain minilocus transgene (examples 5 and 14); and hemizygous for a single copy of a rearranged human kappa light chain transgene (Examples 6 and 14).

Following the schedule of immunization, the spleen is removed, and spleen cells used to generate hybridomas. Cells from an individual hybridoma clone that secretes antibodies reactive with the antigen of interest are used to prepare genomic DNA. A sample of the genomic DNA is digested with several different restriction enzymes that recognize unique six base pair sequences, and fractionated on an agarose gel. Southern blot hybridization is used to identify two DNA fragments in the 2–10 kb range, one of which contains the single copy of the rearranged human heavy chain VDJ sequences and one of which contains the single copy of the rearranged human light chain VJ sequence. These two fragments are size fractionated on agarose gel and cloned directly into pUC18. The cloned inserts are then subcloned respectively into heavy and light chain expression cassettes that contain constant region sequences.

The plasmid clone pγe1 (Example 12) is used as a heavy chain expression cassette and rearranged VDJ sequences are cloned into the XhoI site. The plasmid clone pCK1 is used as a light chain expression cassette and rearranged VJ sequences are cloned into the XhoI site. The resulting clones are used together to transfect SP$_0$ cells to produce antibodies that react with the antigen of interest (Co. et al., *Proc. Natl. Acad. Sci. USA* 88:2869 (1991), which is incorporated herein by reference).

Alternatively, mRNA is isolated from the cloned hybridoma cells described above, and used to synthesize cDNA. The expressed human heavy and light chain VDJ and VJ sequence are then amplified by PCR and cloned (Larrick et al., *Biol. Technology*, 7:934–938 (1989)). After the nucleotide sequence of these clones has been determined, oligonucleotides are synthesized that encode the same polypeptides, and synthetic expression vectors generated as described by Queen et al., *Proc. Natl. Acad. Sci. USA*, 84:5454–5458 (1989).

Immunization of Transgenic Animals with Complex Antigens

The following experiment demonstrates that transgenic animals can be successfully immunized with complex antigens such as those on human red blood cells and respond with kinetics that are similar to the response kinetics observed in normal mice.

Blood cells generally are suitable immunogens and comprise many different types of antigens on the surface of red and white blood cells.

Immunization with Human Blood

Tubes of human blood from a single donor were collected and used to immunize transgenic mice having functionally disrupted endogenous heavy chain loci (J$_H$D) and harboring a human heavy chain minigene construct (HC1); these mice are designated as line 112. Blood was washed and resuspended in 50 mls Hanks' and diluted to 1×10$^8$ cells/ml 0.2 mls (2×10$^7$ cells) were then injected interperitoneally using a 28 gauge needle and 1 cc syringe. This immunization protocol was repeated approximately weekly for 6 weeks. Serum titers were monitored by taking blood from retro-orbital bleeds and collecting serum and later testing for specific antibody. A pre-immune bleed was also taken as a control. On the very last immunization, three days before these animals were sacrificed for serum and for hybridomas, a single immunization of 1×10$^7$ cells was given intravenously through the tail to enhance the production of hybridomas.

TABLE 9

| | Animals | | | | |
|---|---|---|---|---|---|
| | Mouse ID | Line | Sex | HC1-112 | JHD |
| 1 | 2343 | 112 | M | + | ++ |
| 2 | 2344 | 112 | M | − | + |
| 3 | 2345 | 112 | F | − | + |
| 4 | 2346 | 112 | F | − | ++ |
| 5 | 2347 | 112 | F | − | ++ |
| 6 | 2348 | 112 | F | + | ++ |
| 7 | 2349 | 112 | F | − | + |

Mice #2343 and 2348 have a desired phenotype: human heavy chain mini-gene transgenic on heavy chain knock-out background.

Generation of Hybridomas

Hybridomas were generated by fusing mouse spleen cells of approximately 16 week-old transgenic mice (Table 9) that had been immunized as described (supra) to a fusion partner consisting of the non-secreting HAT-sensitive myeloma cell line, X63 Ag8.653. Hybridoma clones were cultivated and hybridoma supernatants containing immunoglobulins having specific binding affinity for blood cell antigens were identified, for example, by flow cytometry.

Flow Cytometry

Serum and hybridoma supernatants were tested using flow cytometry. Red blood cells from the donor were washed 4× in Hanks' balanced salt solution and 50,000 cells were placed in 1.1 ml polypropylene microtubes. Cells were incubated with antisera or supernatant from the hybridomas for 30 minutes on ice in staining media (1× RPMI 1640 media without phenol red or biotin (Irvine Scientific) 3% newborn calf serum, 0.1% Na azide). Controls consisted of littermate mice with other genotypes. Cells were then washed by centrifugation at 4° C. in Sorvall RT600B for 5–10 minutes at 1000 rpm. Cells were washed two times and then antibody detected on the cell surface with a fluorescent developing reagent. Two monoclonal reagents were used to test. One was a FITC-labeled mouse anti-human μ heavy chain antibody (Pharmagen, San Diego, Calif.) and the other was a PE-labeled rat anti-mouse kappa light chain (Becton-Dickenson, San Jose, Calif.). Both of these reagents gave similar results. Whole blood (red blood cells and white blood cells) and white blood cells alone were used as target cells. Both sets gave positive results.

Serum of transgenic mice and littermate controls was incubated with either red blood cells from the donor, or white blood cells from another individual, washed and then developed with anti-human IgM FITC labeled antibody and analyzed in a flow cytometer. Results showed that serum from mice that are transgenic for the human mini-gene locus (mice 2343 and 2348) show human IgM reactivity whereas all littermate animals (2344, 2345, 2346, 2347) do not. Normal mouse serum (NS) and phosphate buffer saline (PBS) were used as negative controls. Red blood cells were ungated and white blood cells were gated to include only lymphocytes. Lines are drawn on the x and y axis to provide a reference. Flow cytometry was performed on 100 supernatants from fusion 2348. Four supernatants showed positive reactivity for blood cell antigens.

Example 18

Reduction of Endogenous Mouse Immunoglobulin Expression by Antisense RNA

A. Vector for Expression of Antisense Ig Sequences

1. Construction of the Cloning Vector pGP1h

The vector pGP1b (referred to in a previous example) is digested with XhoI and BamHI and ligated with the following oligonucleotides:

```
5'- gat cct cga gac cag gta cca gat ctt gtg aat tcg -3'

5'- tcg acg aat tca caa gat ctg gta cct ggt ctc gag -3'
``` to generate the plasmid pGP1h. This plasmid contains a polylinker that includes the following restriction sites: NotI, EcoRI, BglII, Asp718, XhoI, BamHI, HindIII, NotI.

Construction of pBCE1.

A 0.8 kb XbaI/BglII fragment of pVH251 (referred to in a previous example), that includes the promoter leader sequence exon, first intron, and part of the second exon of the human VH-V family immunoglobulin variable gene segment, was inserted into XbaI/BglII digested vector pNN03 to generate the plasmid pVH251.

The 2.2 kb BamHI/EcoRI DNA fragment that includes the coding exons of the human growth hormone gene (hGH; Seeburg, (1982) *DNA* 1:239–249) is cloned into BglII/EcoRI digested pGH1h. The resulting plasmid is digested with BamHI and the BamHI/BglII of pVH251N is inserted in the same orientation as the hGH gene to generate the plasmid pVhgh.

A 0.9 kb XbaI fragment of mouse genomic DNA containing the mouse heavy chain J-μ intronic enhancer (Banerji et al., (1983) *Cell* 33:729–740) was subcloned into pUC18 to generate the plasmid pJH22.1. This plasmid was linearized with SphI and the ends filled in with klenow enzyme. The klenow treated DNA was then digested with HindIII and a 1.4 kb MluI(klenow)/HindIII fragment of phage clone λ1.3 (previous example), containing the human heavy chain J-μ intronic enhancer (Hayday et al., (1984) *Nature* 307:334–340), to it. The resulting plasmid, pMHE1, consists of the mouse and human heavy chain J-μ intron enhancers ligated together into pUC18 such that they can be excised on a single BamHI/HindIII fragment.

Figure 36:
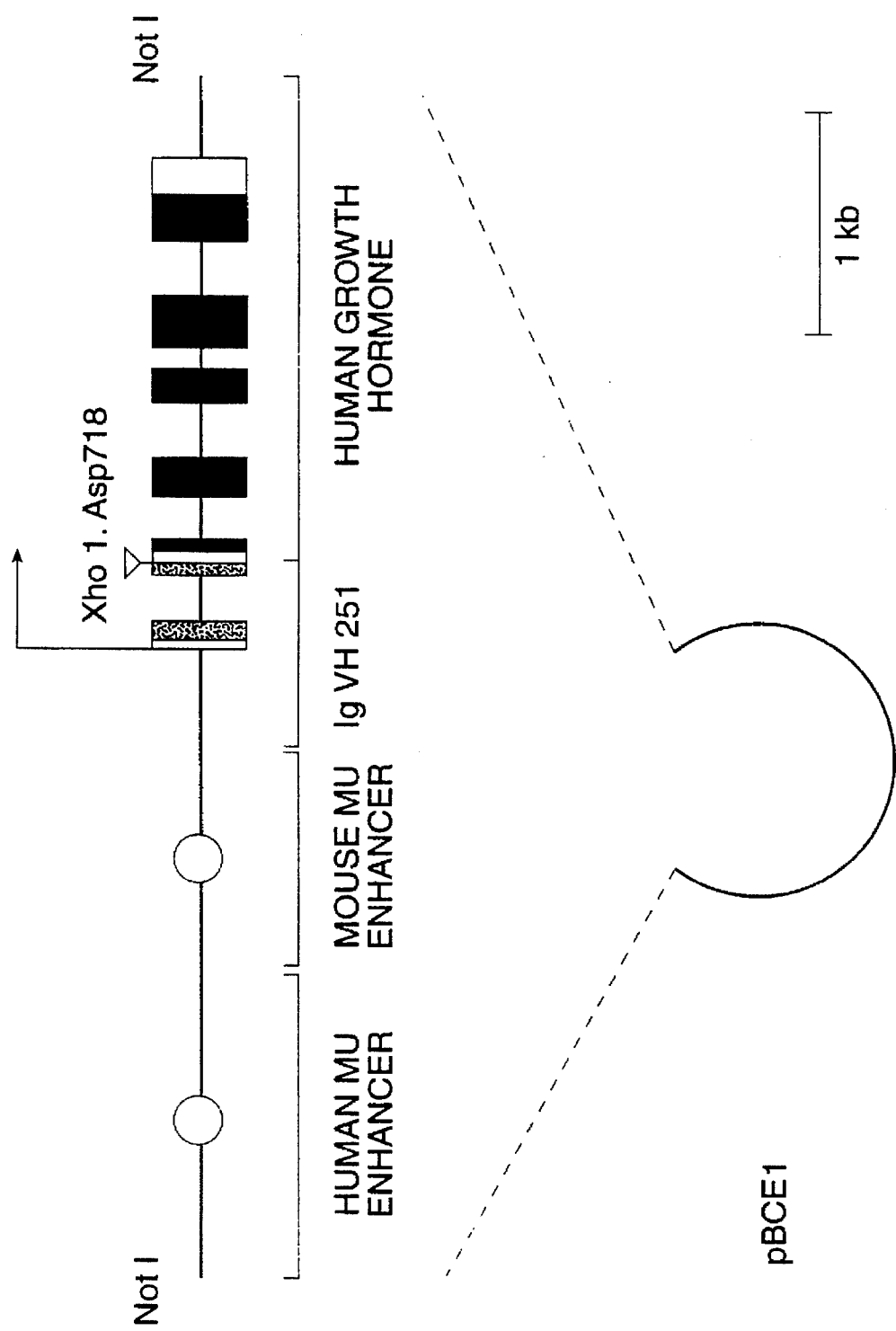
FIG. 36 is a schematic representation of plasmid pBCE1.
Figure 37A:
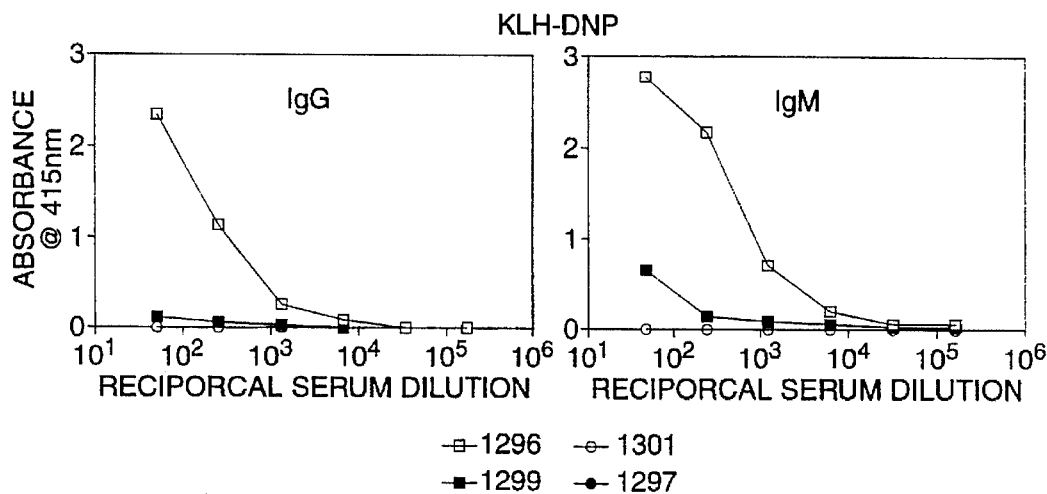
FIGS. 37A–37C depict the immune response of transgenic mice of the present invention against KLH-DNP, by measuring IgG and IgM levels specific for KLH-DNP (37A), KLH (37B) and BSA-DNP (37C).
Figure 37B:
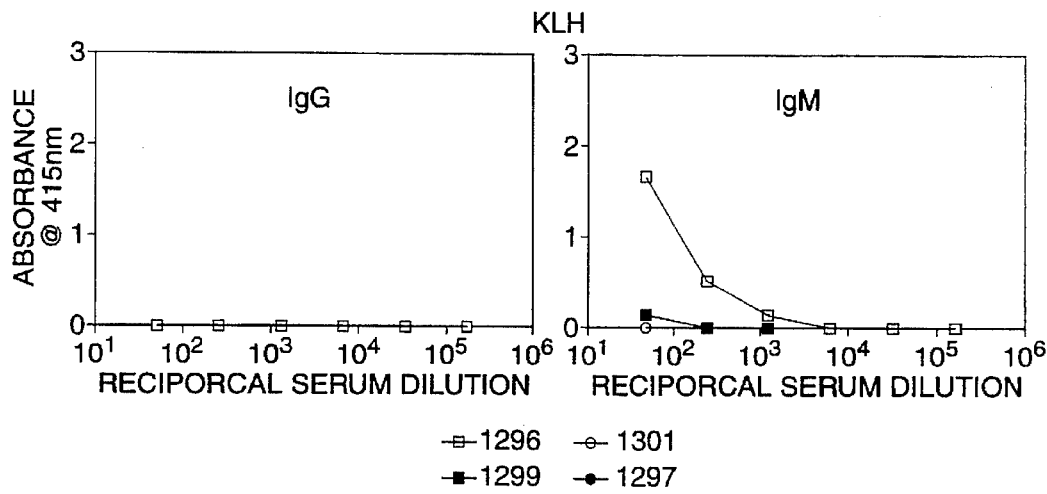
Figure 37C:
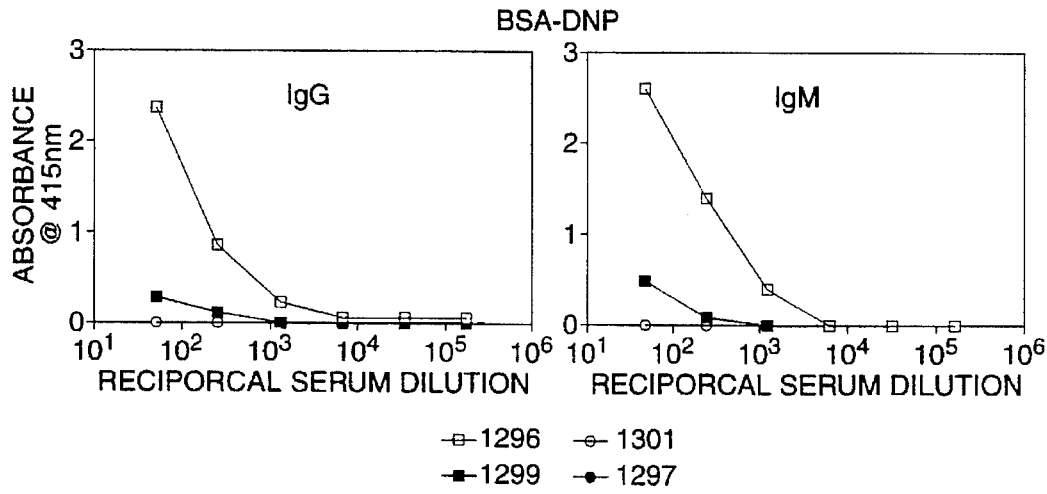

The BamHI/HindIII fragment of pMHE1 is cloned into BamHI/HindIII cut pVhgh to generate the B-cell expression vector pBCE1. This vector, depicted in FIG. 36, contains unique XhoI and Asp718 cloning sites into which antisense DNA fragments can be cloned. The expression of these antisense sequences is driven by the upstream heavy chain promoter-enhancer combination the downstream hGH gene sequences provide polyadenylation sequences in addition to intron sequences that promote the expression of transgene constructs. Antisense transgene constructs generated from pBCE1 can be separated from vector sequences by digestion with NotI.

B. An IgM Antisense Transgene Construct

The following two oligonucleotides:

```
5'- cgc ggt acc gag agt cag tcc ttc cca aat gtc -3'

5'- cgc ctc gag aca gct gga atg ggc aca tgc aga -3'
``` are used as primers for the amplification of mouse IgM constant region sequences by polymerase chain reaction (PCR) using mouse spleen cDNA as a substrate. The resulting 0.3 kb PCR product is digested with Asp718 and XhoI and cloned into Asp718/XhoI digested pBCE1 to generate the antisense transgene construct pMAS1. The purified NotI insert of pMAS1 is microinjected into the pronuclei of half day mouse embryos—alone or in combination with one or more other transgene constructs—to generate transgenic mice. This construct expresses an RNA transcript in B-cells that hybridizes with mouse IgM mRNA, thus down-regulating the expression of mouse IgM protein. Double transgenic mice containing pMAS1 and a human heavy chain transgene minilocus such as pHC1 (generated either by coinjection of both constructs or by breeding of singly transgenic mice) will express the human transgene encoded Ig receptor on a higher percentage of B-cell than mice transgenic for the human heavy chain minilocus alone. The ratio of human to mouse Ig receptor expressing cells is due in part to competition between the two populations for factors and cells that promoter B-cell differentiation and expansion. Because the Ig receptor plays a key role in B-cell development, mouse Ig receptor expressing B-cells that express reduced levels of IgM on their surface (due to mouse Ig specific antisense down-regulation) during B-cell development will not compete as well as cells that express the human receptor.

C. An IgKappa Antisense Transgene Construct

The following two oligonucleotides:

```
5'- cgc ggt acc gct gat gct gca cca act gta tcc -3'

5'- cgc ctc gag cta aca ctc att cct gtt gaa gct -3'
``` are used as primers for the amplification of mouse IgKappa constant region sequences by polymerase chain reaction (PCR) using mouse spleen cDNA as a substrate. The resulting 0.3 kb PCR product is digested with Asp718 and XhoI and cloned into Asp718/XhoI digested pBCE1 to generate the antisense transgene construct pKAS1. The purified NotI insert of pKAS1 is microinjected into the pronuclei of half day mouse embryos—alone or in combination with one or more other transgene constructs—to generate transgenic mice. This construct expresses an RNA transcript in B-cells that hybridizes with mouse IgK mRNA, thus down-regulating the expression of mouse IgK protein as described above for pMAS1.

Example 19

This example demonstrates the successful immunization and immune response in a transgenic mouse of the present invention.

Immunization of Mice

Keyhole limpet hemocyanin conjugated with greater than 400 dinitrophenyl groups per molecule (Calbiochem, La Jolla, Calif.) (KLH-DNP) was alum precipitated according to a previously published method (Practical Immunology, L. Hudson and F. C. Hay, Blackwell Scientific (Pubs.), p. 9, 1980). Four hundred μg of alum precipitated KLH-DNP along with 100 μg dimethyldioctadecyl Ammonium Bromide in 100 μL of phosphate buffered saline (PBS) was injected intraperitoneally into each mouse. Serum samples were collected six days later by retro-orbital sinus bleeding.

Analysis of Human Antibody Reactivity in Serum

Antibody reactivity and specificity were assessed using an indirect enzyme-linked immunosorbent assay (ELISA). Several target antigens were tested to analyze antibody induction by the immunogen. Keyhole limpet hemocyanin (Calbiochem) was used to identify reactivity against the protein component, bovine serum albumin-DNP for reactivity against the hapten and/or modified amino groups, and KLH-DNP for reactivity against the total immunogen. Human antibody binding to antigen was detected by enzyme conjugates specific for IgM and IgG sub-classes with no cross reactivity to mouse immunoglobulin. Briefly, PVC microtiter plates were coated with antigen drying overnight at 37° C. of 5 μg/mL protein in PBS. Serum samples diluted in PBS, 5% chicken serum, 0.5% Tween-20 were incubated in the wells for 1 hour at room temperature, followed by anti-human IgG Fc and IgG F(ab')-horseradish peroxidase or anti-human IgM Fc-horseradish peroxidase in the same diluent. After 1 hour at room temperature enzyme activity was assessed by addition of ABTS substrate (Sigma, St. Louis, Mo.) and read after 30 minutes at 415–490 nm.

Human Heavy Chain Participation in Immune Response in Transgenic Mice

FIGS. 37A–37D illustrate the response of three mouse littermates to immunization with KLH-DNP. Mouse number 1296 carried the human IgM and IgG unrearranged transgene and was homozygous for mouse Ig heavy chain knockout. Mouse number 1299 carried the transgene on a non-knockout background, while mouse 1301 inherited neither of these sets of genes. Mouse 1297, another littermate, carried the human transgene and was hemizygous with respect to mouse heavy chain knockout. It was included as a non-immunized control.

The results demonstrate that both human IgG and IgM responses were developed to the hapten in the context of conjugation to protein. Human IgM also developed to the KLH molecule, but no significant levels of human IgG were present at this time point. In pre-immunization serum samples from the same mice, titers of human antibodies to the same target antigens were insignificant.

Example 20

This example demonstrates the successful immunization with a human antigen and immune response in a transgenic mouse of the present invention, and provides data demonstrating that nonrandom somatic mutation occurs in the variable region sequences of the human transgene.

Demonstration of Antibody Responses Comprising Human Immunoglobulin Heavy Chains Against a Human Glycoprotein Antigen Transgenic mice used for the experiment were homozygous for functionally disrupted murine immunoglobulin heavy chain loci produced by introduction of a transgene at the joining (J) region (supra) resulting in the absence of functional endogenous (murine) heavy chain production. The transgenic mice also harbored at least one complete unrearranged human heavy chain mini-locus transgene, (HC1, supra), which included a single functional $V_H$ gene ($V_H251$), human μ constant region gene, and human γ1 constant region gene. Transgenic mice shown to express human immunoglobulin transgene products (supra) were selected for immunization with a human antigen to demonstrate the capacity of the transgenic mice to make an immune response against a human antigen immunization. Three mice of the HC1-26 line and three mice of the HC1-57 line (supra) were injected with human antigen.

One hundred μg of purified human carcinoembryonic antigen (CEA) insolubilized on alum was injected in complete Freund's adjuvant on Day 0, followed by further weekly injections of alum-precipitated CEA in incomplete Freund's adjuvant on Days 7, 14, 21, and 28. Serum samples were collected by retro-orbital bleeding on each day prior to injection of CEA. Equal volumes of serum were pooled from each of the three mice in each group for analysis.

Figure 38:
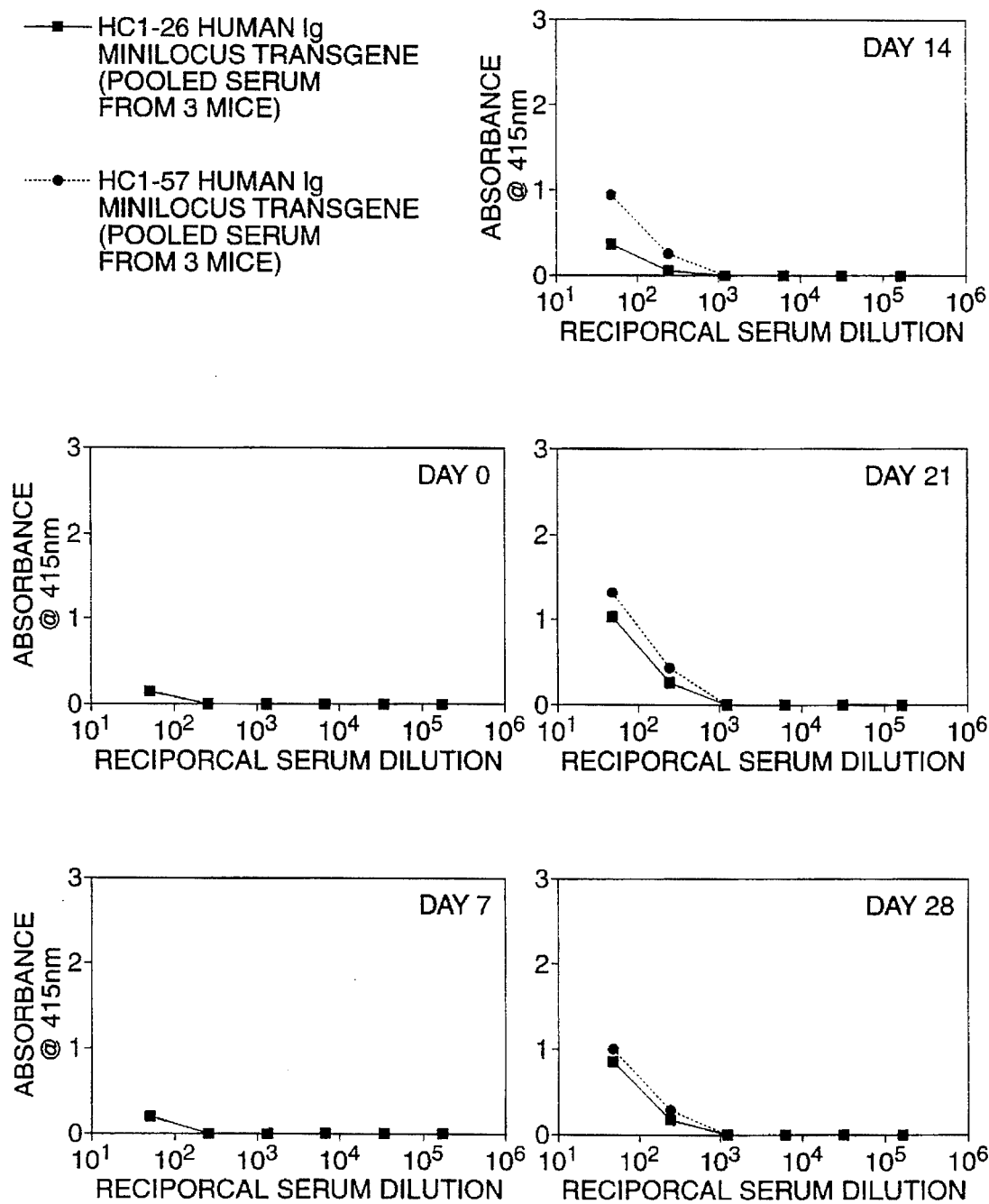
FIG. 38 shows ELISA data demonstrating the presence of antibodies that bind human carcinoembryonic antigen (CEA) and comprise human µ chains; each panel shows reciprocal serial dilutions from pooled serum samples obtained from mice on the indicated day following immunization.
Figure 39:
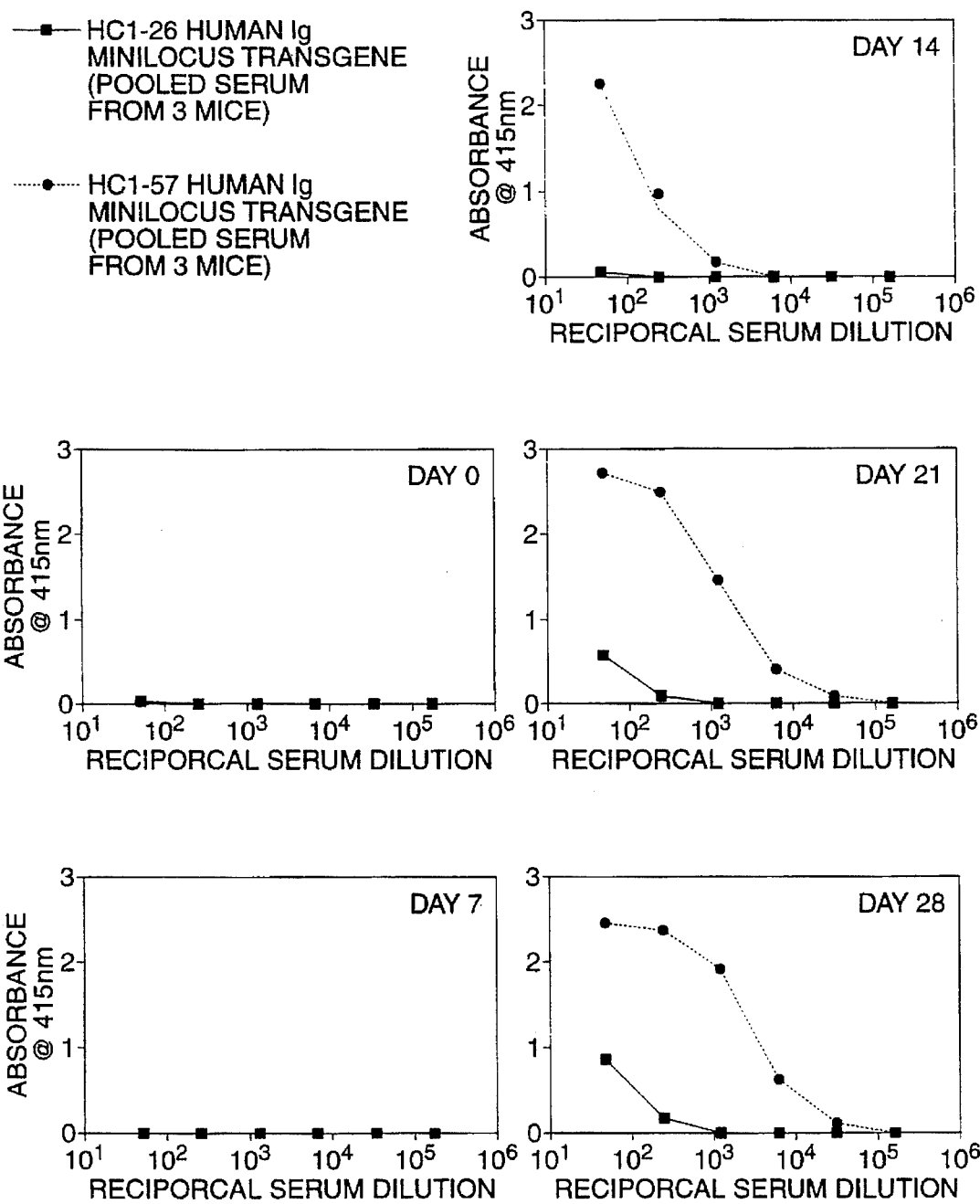
FIG. 39 shows ELISA data demonstrating the presence of antibodies that bind human carcinoembryonic antigen (CEA) and comprise human γ chains; each panel shows reciprocal serial dilutions from pooled serum samples obtained from mice on the indicated day following immunization.

Titers of human μ chain-containing immunoglobulin and human γ chain-containing immunoglobulin which bound to human CEA immobilized on microtiter wells were determined by ELISA assay. Results of the ELISA assays for human μ chain-containing immunoglobulins and human γ chain-containing immmunoglbulins are shown in FIGS. 38 and 39, respectively. Significant human μ chain Ig titers were detected for both lines by Day 7 and were observed to rise until about Day 21. For human γ chain Ig, significant titers were delayed, being evident first for line HC1-57 at Day 14, and later for line HC1-26 at Day 21. Titers for human γ chain Ig continued to show an increase over time during the course of the experiment. The observed human μ chain Ig response, followed by a plateau, combined with a later geveloping γ chain response which continues to rise is characteristic of the pattern seen with affinity maturation. Analysis of Day 21 samples showed lack of reactivity to an unrelated antigen, keyhole limpet hemocyanin (KLC), indicating that the antibody response was directed against CEA in a specific manner.

These data indicate that animals transgenic for human unrearranged immunoglobulin gene loci: (1) can respond to a human antigen (e.g., the human glycoprotein, CEA), (2) can undergo isotype switching ("class switching) as exemplified by the observed μ to γ class switch, and (3) exhibit characteristics of affinity maturation in their humoral immune responses. In general, these data indicate: (1) the human Ig transgenic mice have the ability to induce heterologous antibody production in response to a defined antigen, (2) the capacity of a single transgene heavy chain variable region to respond to a defined antigen, (3) response kinetics over a time period typical of primary and secondary response development, (4) class switching of a transgene-encoded humoral immune response from IgM to IgG, and (5) the capacity of transgenic animal to produce human-sequence antibodies against a human antigen.

Demonstration of Somatic Mutation in a Human Heavy Chain Transgene Minilocus

Line HC1-57 transgenic mice, containing multiple copies of the HC1 transgene, were bred with immunoglobulin heavy chain deletion mice to obtain mice that contain the HC1 transgene and contain disruptions at both alleles of the endogenous mouse heavy chain (supra). These mice express human mu and gammal heavy chains together with mouse kappa and lambda light chains (supra). One of these mice was hyperimmunized against human carcinoembryonic antigen by repeated intraperitoneal injections over the course of 1.5 months. This mouse was sacrificed and lymphoid cells isolated from the spleen, inguinal and mesenteric lymph nodes, and peyers patches. The cells were combined and total RNA isolated. First strand cDNA was synthesized from the RNA and used as a template for PCR amplification with the following 2 oligonucleotide primers:

```
149  5'-cta gct cga gtc caa gga gtc tgt gcc gag gtg cag ctg
     (g/a/t/c)-3'

151  5'-ggc gct cga gtt cca cga cac cgt cac cgg ttc-3'
```

Figure 40:
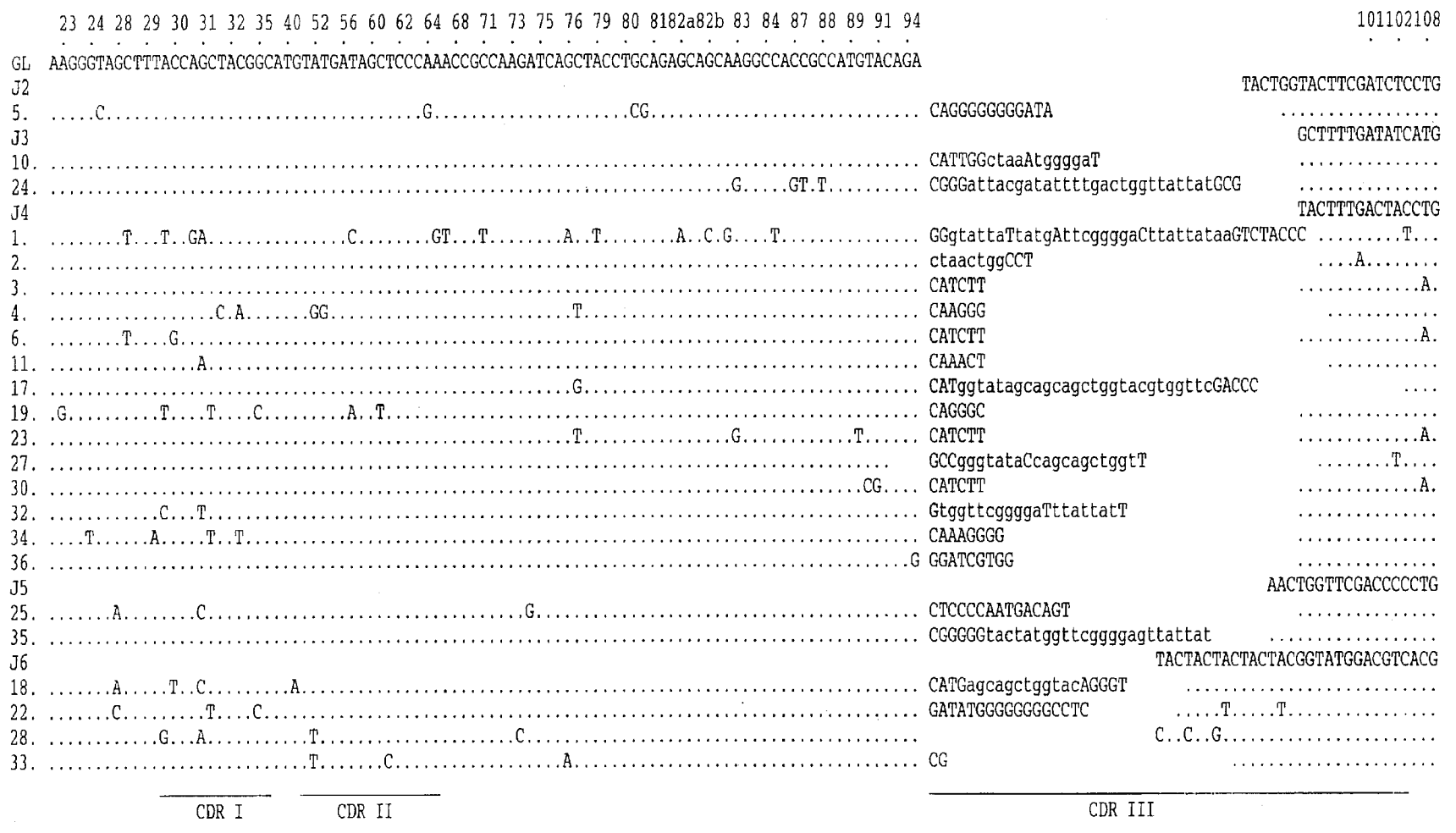

These primers specifically amplify VH251/gammal cDNA sequences. The amplified sequences were digested with XhoI and cloned into the vector pNN03. DNA sequence from the inserts of 23 random clones is shown in FIG. 40; sequence variations from germline sequence are indicated, dots indicate sequence is identical to germline. Comparison of the cDNA sequences with the germline sequence of the VH251 transgene reveals that 3 of the clones are completely unmutated, while the other 20 clones contain somatic mutations. One of the 3 non-mutated sequences is derived from an out-of-frame VDJ joint. Observed somatic mutations at specific positions of occur at similar frequencies and in similar distribution patterns to those observed in human lymphocytes (Cai et al. (1992) J. Exp. Med. 176: 1073, incorporated herein by reference). The overall frequency of somatic mutations is approximately 1%; however, the frequency goes up to about 5% within CDR1, indicating selection for amino acid changes that affect antigen binding.

This demonstrates antigen driven affinity maturation of the human heavy chain sequences.

Example 21

This example demonstrates the successful formation of a transgene by co-introduction of two separate polynucleotides which recombine to form a complete human light chain minilocus transgene.

Generation of an Unrearranged Light Chain Minilocus Transgene by Co-injection of Two Overlapping DNA Fragments 1. Isolation of Unrearranged Functional $V_\kappa$ Gene Segments vk65.3, vk65.5, vk65.8 and vk65.15

The $V_\kappa$ specific oligonucleotide, oligo-65 (5'-agg ttc agt ggc agt ggg tct ggg aca gac ttc act ctc acc atc agc-3'), was used to probe a human placental genomic DNA library cloned into the phage vector λEMBL3/SP6/T7 (Clonetech Laboratories, Inc., Palo Alto, Calif.). DNA fragments containing $V_\kappa$ segments from positive phage clones were subcloned into plasmid vectors. Variable gene segments from the resulting clones are sequenced, and clones that appear functional were selected. Criteria for judging functionality include: open reading frames, intact splice acceptor and donor sequences, and intact recombination sequence. DNA sequences of 4 functional $V_\kappa$ gene segments (vk65.3, vk65.5, vk65.8, and vk65.15) from 4 different plasmid clones isolated by this procedure are shown in FIGS. 41–44. The four plasmid clones, p65.3f, p65.5g1, p65.8, and p65.15f, are described below.

(1 a) p65.3f

A 3 kb Xba fragment of phage clone λ65.3 was subcloned into pUC19 so that the vector derived SalI site was proximal to the 3' end of the insert and the vector derived BamHI site 5'. The 3 kb BamHI/SalI insert of this clone was subcloned into pGP1f to generate p65.3f.

(1 b) p65.5g1

A 6.8 kb EcoRI fragment of phage clone λ65.5 was subcloned into pGP1f so that the vector derived XhoI site is proximal to the 5' end of the insert and the vector derived SalI site 3'. The resulting plasmid is designated p65.5g1.

(1 c) p65.8

A 6.5 kb HindIII fragment of phage clone λ65.8 was cloned into pSP72 to generate p65.8.

(1 d) p65.15f

A 10 kb EcoRI fragment of phage clone λ65.16 was subcloned into pUC18 to generate the plasmid p65.15.3. The $V_\kappa$ gene segment within the plasmid insert was mapped to a 4.6 kb EcoRI/HindIII subfragment, which was cloned into pGP1f. The resulting clone, p65.15f, has unique XhoI and SalI sites located at the respective 5' and 3' ends of the insert.

2. pKV4

The XhoI/SalI insert of p65.8 was cloned into the XhoI site of p65.15f to generate the plasmid pKV2. The XhoI/SalI insert of p65.5g1 was cloned into the XhoI site of pKV2 to generate pKV3. The XhoI/SalI insert of pKV3 was cloned into the XhoI site of p65.3f to generate the plasmid pKV4. This plasmid contains a single 21 kb XhoI/SalI insert that includes 4 functional $V_\kappa$ gene segments. The entire insert can also be excised with NotI.

3. pKC1B (3 a) pKcor

Two XhoI fragments derived from human genomic DNA phage λ clones were subcloned into plasmid vectors. The first, a 13 kb $J_\kappa 2$-$J_\kappa 5$/$C_\kappa$ containing fragment, was treated with Klenow enzyme and cloned into HindIII digested, Klenow treated, plasmid pGP1d. A plasmid clone (pK-31) was selected such that the 5' end of the insert is adjacent to the vector derived ClaI site. The second XhoI fragment, a 7.4 kb piece of DNA containing $J_\kappa 1$ was cloned into XhoI/SalI-digested pSP72, such that the 3' insert XhoI site was destroyed by ligation to the vector SalI site. The resulting clone, p36.2s, includes an insert derived ClaI site 4.5 kb upstream of $J_\kappa 1$ and a polylinker derived ClaI site downstream in place of the naturally occurring XhoI site between $J_\kappa 1$ and $J_\kappa 2$. This clone was digested with ClaI to release a 4.7 kb fragment which was cloned into ClaI digested pK-31 in the correct 5' to 3' orientation to generate a plasmid containing all 5 human $J_\kappa$ segments, the human intronic enhancer human $C_\kappa$, 4.5 kb of 5' flanking sequence, and 9 kb of 3' flanking sequence. This plasmid, pKcor, includes unique flanking XhoI and SalI sites on the respective 5' and 3' sides of the insert.

(3 b) pKcorB

A 4 kb BamHI fragment containing the human 3' kappa enhancer (Judde, J.-G. and Max, E. E. (1992) *Mol. Cell. Biol.* 12: 5206, incorporated herein by reference) was cloned into pGP1f such that the 5' end is proximal to the vector XhoI site. The resulting plasmid, p24Bf, was cut with XhoI and the 17.7 kb XhoI/SalI fragment of pKcor cloned into it in the same orientation as the enhancer fragment. The resulting plasmid, pKcorB, includes unique XhoI and SalI sites at the 5' and 3' ends of the insert respectively.

(3 c) pKC1B

The XhoI/SalI insert of pKcorB was cloned into the SalI site of p65.3f to generate the light-chain minilocus-transgene plasmid pKC1B. This plasmid includes a single functional human $V_\kappa$ segment, all 5 human $J_\kappa$ segments, the human intronic enhancer, human $C_\kappa$, and the human 3' kappa enhancer. The entire 25 kb insert can be isolated by NotI digestion.

4. Co4

Figure 45:
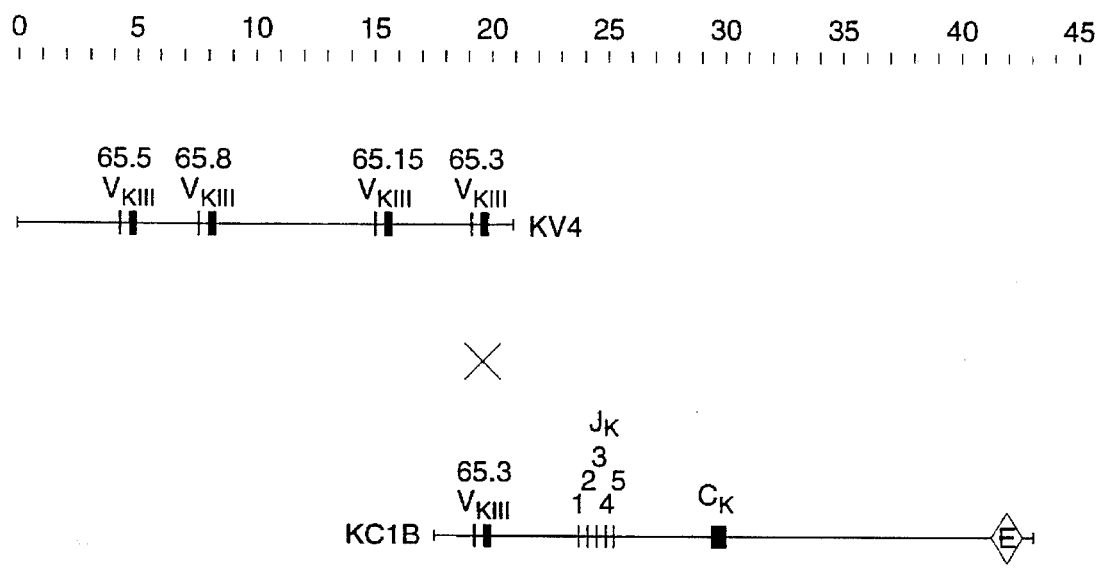
FIG. 45 shows formation of a light chain minilocus by homologous recombination between two overlapping fragments which were co-injected.

The two NotI inserts from plasmids pKV4 and pKC1B were mixed at a concentration of 2.5 µg/ml each in microinjection buffer, and co-injected into the pronuclei of half day mouse embryos as described in previous examples. Resulting transgenic animals contain transgene inserts (designated Co4, product of the recombination shown in FIG. 45) in which the two fragments co-integrated. The 3' 3 kb of the pKV4 insert and the 5'3 kb of the pKC1B insert are identical. Some of the integration events will represent homologous recombinations between the two fragments over the 3 kb of shared sequence. The Co4 locus will direct the expression of a repertoire of human sequence light chains in a transgenic mouse.

Example 22

This example demonstrates the successful production of a murine hybridoma clone secreting a monoclonal antibody reactive with a specific immunogen, wherein the monoclonal antibody comprises a human immunoglobulin chain encoded by a human Ig transgene.

Generation of Monoclonal Antibodies Incorporating Human Heavy Chain Transgene Product 1. Immunization of Mouse Harboring Human Heavy Chain Transgene A mouse containing a human heavy chain encoding transgene and homozygous for knockout (i.e., functional disruption) of the endogenous heavy chain locus (see, EXAMPLE 20, supra) was immunized with purified human CEA, and spleen cells were subsequently harvested after a suitable immune response period. The murine spleen cells were fused with mouse myeloma cells to generate hybridomas using conventional techniques (see, Kohler and Milstein, *Eur. J. Immunol.*, 6:511–519 (1976); Harlow and Lane, *Antibodies: A Laboratory Manual*, Cold Spring Harbor, N.Y. (1988)). The mouse used for immunization contained a human unrearranged heavy chain minilocus transgene which comprised a single functional $V_H$ gene ($V_{H251}$), human D and J segments, human μ constant region, and human γ1 constant region genes. The transgenic line from which it originated was designated HC1-57 (supra).

One hundred μg of purified human carcinoembryonic antigen (CEA) (Cyrstal Chem, Chicago, Ill. or Scripps Labs, San Diego, Calif.) insolubilized on alum was injected in complete Freund's adjuvant on Day 0, followed by further weekly injections of alum-precipitated CEA in incomplete Freund's adjuvant on Days 7, 14, 21, and 28. An additional 20 μg of soluble CEA was administered intravenously on Day 83, followed by 50 μg alum-precipitated CEA in incomplete Freund's adjuvant on Day 92. Human heavy chain responses to CEA were confirmed in serum samples prior to fusion of spleen cells with myleoma cells. The animal was sacrificed on Day 95, the spleen removed and fused with P3×63-Ag8.653 mouse myeloma cells (ATCC CRL 1580, American Type Culture Collection, Rockville, Md.) using polyethylene glycol. Two weeks later, supernates from fusion wells were screened for the presence of antibodies specifically reactive with CEA, and which contained human heavy chain μ or γ constant region epitopes by ELISA. Briefly, purified human CEA was coated onto PVC microtiter plates at 2.5 μg/ml, and incubate with culture supernate diluted 1:4 or 1:5 in PBS, 0.5% Tween-20, 5% chicken serum. Plates were washed, followed by addition of horseradish peroxidase-conjugated goat antiserum specific for human IgG Fc or rabbit antiserum specific for human IgM Fc5Mu (Jackson ImmunoResearch, West Grove, Pa.). Presence of conjugate bound to captured antibody was determined, after further washing, by the addition of ABTS substrate. Two independent fusion wells were found to contain antibody with substantial binding to CEA. After cloning, both hybridomas were found to be positive for the presence of human μ chain and murine κ chain by ELISA. No mouse IgG or IgM were detected using similar assays.

Subcloning of the two independent parent hybridomas resulted in two clones, designated 92-09A-4F7-A5-2 and 92-09A-1D7-1-7-1. Both lines were deposited with the ATCC Patent Culture Depository under the Budapest Treaty and were assigned ATCC Designation HB 11307 and HB 11308, respectively. Culture supernatants from these cell lines were assessed for specificity by testing for reactivity to several purified target proteins using ELISA. As shown in FIG. 46, ELISA assays for determining the reactivity of the monoclonal antibodies to various antigens demonstrate that only CEA and the CEA-related antigen NCA-2 show significant reactivity, indicating the development of a restricted reactivity for the variable regions of the heterohybrid immunoglobulin molecules.

Example 23

This example demonstrates that a rearranged human VDJ gene encoded by a human Ig minilocus transgene may be transcribed as a transcript which includes an endogenous Ig constant region gene, for example by the mechanism of trans-switching, to encode a chimeric human/mouse Ig chain.

Identification of Trans-Switch Transcripts Encoding Chimeric Human-Mouse Heavy Chains RNA was isolated from a hyperimmunized HC1 line 57 transgenic mouse homozygous for the endogenous heavy chain J segment deletion (supra). cDNA was synthesized according to Taylor et al. (1993) *Nucleic Acids Res.* 20: 6287, incorporated herein by reference, and amplified by PCR using the following two primers:

o-149 (human $V_{H251}$): 5'-CTA GCT CGA GTC CAA GGA GTC TGT GCC GAG GTG CAG CTG (G,A,T,C)-3' o-249 (mouse gamma): 5'-GGC GCT CGA GCT GGA CAG GG(A/C) TCC A(G/T)A GTT CCA-3'

Oligonucleotide o-149 is specific for the HC1-encoded variable gene segment $V_{H251}$, while o-249 hybridizes to both mouse and human gamma sequences with the following order of specificities:

mouse γ1=mouse γ2b=mouse γ3>mouse γ2a>>human γ1.

DNA sequences from 10 randomly chosen clones generated from the PCR products was determined and is shown in FIG. 47. Two clones comprised human VDJ and mouse γ1; four clones comprised human VDJ and mouse γ2b; and four clones comprised human VDJ and mouse γ3. These results indicate that in a fraction of the transgenic B cells, the transgene-encoded human VDJ recombined into the endogenous murine heavy chain locus by class switching or an analogous recombination.

Example 24

This example describes a method for screening a pool of hybridomas to discriminate clones which encode chimeric human/mouse Ig chains from clones which encode and express a human Ig chain. For example, in a pool of hybridoma clones made from a transgenic mouse comprising a human Ig heavy chain transgene and homozygous for a J region-disrupted endogenous heavy chain locus, hybridoma clones encoding trans-switched human VDJ-murine constant region heavy chains may be identified and separated from hybridoma clones expressing human VDJ-human constant region heavy chains.

Sceening Hybridomas to Eliminate Chimeric Ig Chains

The screening process involves two stages, which may be conducted singly or optionally in combination: (1) a preliminary ELISA-based screen, and (2) a secondary molecular characterization of candidate hybridomas. Preferably, a preliminary ELISA-based screen is used for initial identification of candidate hybridomas which express a human VDJ region and a human constant region.

Hybridomas that show positive reactivity with the antigen (e.g., the immunogen used to elicit the antibody response in the transgenic mouse) are tested using a panel of monoclonal antibodies that specifically react with mouse μ, γ, κ, and λ, and human μ, γ, and κ. Only hybridomas that are positive for human heavy and light chains, as well as negative for mouse chains, are identified as candidate hybridomas that express human immunoglobulin chains. Thus, candidate hybridomas are shown to have reactivity with specific antigen and to possess epitopes characteristic of a human constant region.

RNA is isolated from candidate hybridomas and used to synthesize first strand cDNA. The first strand cDNA is then ligated to a unique single-stranded oligonucleotide of predetermined sequence (oligo-X) using RNA ligase (which ligates single-stranded DNA). The ligated cDNA is then amplified in two reactions by PCR using two sets of oligonucleotide primers. Set H (heavy chain) includes an oligo that specifically anneals to either human μ or human γ1 (depending on the results of the ELISA) and an oligo that anneals to the oligo-X sequence. This prevents bias against detection of particular V segments, including mouse V segments that may have trans-rearranged into the human minilocus. A second set of primers, Set L (light chain), includes an oligo that specifically anneals to human κ and an oligo that anneals specifically to oligo-X. The PCR products are molecularly cloned and the DNA sequence of several are determined to ascertain whether the hybridoma is producing a unique human antibody on the basis of sequence comparison to human and murine Ig sequences.

Example 25

This example demonstrates production of a transgenic mouse harboring a human light chain (κ) minilocus.
Human κ Minilocus Transgenic Mice
KC1

A 13 kb XhoI Jκ2-Kκ containing fragment from a phage clone (isolated from a human genomic DNA phage library by hybridization to a κ specific oligonucleotide, e.g., supra) was treated with Klenow enzyme and cloned into the Klenow treated HindIII site of pGP1d to produce pK-31. This destroyed the insert XhoI sites and positioned the unique polylinker derived XhoI site at the 5' end next to Jκ2. A unique polylinker derived ClaI site is located between this XhoI site and the inset sequences, while a unique polylinker derived SalI site is located at the 3' end of the insert. A 7.5 kb XhoI fragment, containing Jκ1 and upstream sequences, was also isolated from a human genomic DNA phage clone (isolated from a human genomic DNA phage library by hybridization to a K specific oligonucleotide, e.g. supra). This 7.5 kb XhoI fragment was cloned into the SalI site of pSP72 (Promega, Madison, Wis.), thus destroying both XhoI sites and positioning a polylinker ClaI site 3' of Jκ1. Digestion of the resulting clone with ClaI released a 4.7 kb fragment containing Jk1 and 4.5 kb of upstream sequences. This 4.7 kb fragment was cloned into the ClaI site of pK-31 to create pKcor. The remaining unique 5' XhoI site is derived from polylinker sequences. A 6.5 kb XhoI/SalI DNA fragment containing the unrearranged human VκIII gene segment 65.8 (plasmid p65.8, EXAMPLE 21) was cloned into the XhoI site of pKcor to generate the plasmid pKC1. The NotI insert of pKC1 was microinjected into ½ day mouse embryos to generate transgenic mice. Two independent pKC1 derived transgenic lines were established and used to breed mice containing both heavy and light chain miniloci. These lines, KC1-673 and KC1-674, were estimated by Southern blot hybridization to contain integrations of approximately 1 and 10–20 copies of the transgenes respectively.
KC1e The plasmid pMHE1 (EXAMPLES 13 and 18) was digested with BamHI and HindIII to excise the 2.3 kb insert containing both the mouse and human heavy chain J-μ intronic enhancers. This fragment was Klenow treated, ligated to SalI linkers (New England Biolabs, Beverly, Mass.), and cloned into the unique 3' SalI site of pKC1 to generate the plasmid pKC1e. The NotI insert of pKC1e was microinjected into ½ day mouse embryos to generate transgenic mice. Four independent pKC1e derived transgenic lines were established and used to breed mice containing both heavy and light chain miniloci. These lines, KC1e-1399, KC1e-1403, KC1e-1527, and KC1e-1536, were estimated by Southern blot hybridization to contain integrations of approximately 20–50, 5–10, 1–5, and 3–5 copies of the transgene, respectively.
pKC2

A 6.8 kb XhoI/SalI DNA fragment containing the unrearranged human VκIII gene segment 65.5 (plasmid p65.5g1, EXAMPLE 21) was cloned into the unique 5' XhoI site of pKC1 to generate the plasmid pKC2. This minilocus transgene contains two different functional VκIII gene segments. The NotI insert of pKC2 was microinjected into ½ day mouse embryos to generate transgenic mice. Five independent pKC2 derived transgenic lines were established and used to breed mice containing both heavy and light chain miniloci. These lines, KC2-1573, KC2-1579, KC2-1588, KC2-1608, and KC2-1610, were estimated by Southern blot hybridization to contain integrations of approximately 1–5, 10–50, 1–5, 50–100, and 5–20 copies of the transgene, respectively.

Example 26

This example shows that transgenic mice bearing the human μ transgene can make an antigen-induced antibody response forming antibodies comprising a functional human κ chain.

Antibody Responses Associated with Human Ig κ Light Chain

A transgenic mouse containing the HC1-57 human heavy chain and KC1e human κ transgenes was immunized with purified human soluble CD4 (a human glycoprotein antigen). Twenty μg of purified human CD4 (NEN Research products, Westwood, Mass.) insolublized by conjugation to polystyrene latex particles (Polysciences, Warrington, Pa.) was injected intraperitoneally in saline with dimethyldioctadecyl ammonium bromide (Calbiochem, San Diego, Calif.) on Day 0, followed by further injections on Day 20 and Day 34.

Retro-orbital bleeds were taken on Days 25 and 40, and screened for the presence of antibodies to CD4, containing human IgM or human IgG heavy chain by ELISA. Briefly, purified human CD4 was coated onto PVC microtiter plates at 2.5 μg/ml and incubated with culture supernate diluted 1:4/1:5 in PBS, 0.5% Tween-20, 5% chicken serum. Plates were washed, followed by addition of horseradish peroxidase-conjugated goat antiserum specific for human IgG Fc or rabbit antiserum specific for human IgM Fc5Mu (Jackson ImmunoResearch, Westr Grove, Pa.). Presence of conjugate bound to captured antibody was determined after further washing by addition of ABTS substrate. Human μ reactive with antigen was detected in both bleeds, while there was essentially undetectable κ reactivity. The Day 40 sample was also tested for antigen-reactive human κ chain using the same assay with goat anti-human μ peroxidase conjugate (Sigma, St. Louis, Mo.). CD4-binding κ reactivity was detected at this time point. The assay results are shown in FIG. 48.

Example 27

This example shows the successful generation of mice which are homozygous for functionally disrupted murine heavy and light chain loci (heavy chain and κ chain loci) and which concomitantly harbor a human heavy chain transgene and a human light chain transgene capable of productively rearranging to encode functional human heavy chains and functional human light chains. Such mice are termed "0011" mice, indicating by the two 0's in the first two digits that the mice lack functional heavy and light chain loci and indicating by the 1's in the second two digits that the mice are hemizygous for a human heavy chain transgene and a human light chain transgene. This example shows that such 0011 mice are capable of making a specific antibody response to a predetermined antigen, and that such an antibody response can involve isotype switching.

0011/0012 Mice: Endogenous Ig Knockout+Human Ig Transgenes

Mice which were homozygous for a functionally disrupted endogenous heavy chain locus lacking a functional $J_H$ region (designated JHD++ or JHΔ++) and also harboring the human HC1 transgene, such as the HC1-26 transgenic mouse line described supra, were interbred with mice homozygous for a functionally disrupted endogenous kappa chain locus lacking a functional $J_H$ region (designated here as JKD++ or JKΔ++; see Example 9) to produce mice homozygous for functionally disrupted heavy chain and kappa chain loci (heavy chain/kappa chain knockouts), designated as JHD++/JKD++ and containing a HC1 transgene. Such mice were produced by interbreeding and selected on the basis of genotype as evaluated by Southern blot of genomic DNA. These mice, designated HC1-26+/ JKD++/JHD++ mice, were interbred with mice harboring a human kappa chain transgene (lines KC2-1610, KC1e-1399, and KC1e-1527; see Example 25), and Southern blot analysis of genomic DNA was used to identify offspring mice homozygous for functionally disrupted heavy and light chain loci and also hemizygous for the HC1 transgene and the KC2 or KC1e transgene. Such mice are designated by numbers and were identified as to their genotype, with the following abbreviations: HC1-26+ indicates hemizygosity for the HC1-26 line human heavy chain minilocus transgene integration; JHD++ indicates homozygosity for $J_H$ knockout; JKD++ indicates homozygosity for $J_K$ knockout; KC2-1610+ indicates hemizygosity for a KC2 human κ transgene integrated as in line KC2-1610; KC1e-1527+ indicates hemizygosity for a KC1e human κ transgene integrated as in line KC1e-1527; KC1e-1399+ indicates hemizygosity for a KC1e human κ transgene integrated as in line KC1e-1399.

The resultant individual offspring were each given a numerical designation (e.g., 6295, 6907, etc.) and each was evaluated for the presence of $J_H$ knockout alleles, $J_K$ knockout alleles, HC1-26 transgene, and κ transgene (KC2 or KC1e) and determined to be either hemizygous (+) or homozygous (++) at each locus. Table 10 shows the number designation, sex, and genotypes of several of the offspring mice.

TABLE 10

| ID No. | Sex | Ig Code | Genotype |
|---|---|---|---|
| 6295 | M | 0011 | HC1-26+; JHD++; JKD++; KC2-1610+ |
| 6907 | M | 0011 | HC1-26+; JHD++; JKD++; KC1e-1527+ |
| 7086 | F | 0011 | HC1-26+; JHD++; JKD++; KC1e-1399+ |
| 7088 | F | 0011 | HC1-26+; JHD++; JKD++; KC1e-1399+ |
| 7397 | F | 0011 | HC1-26+; JHD++; JKD++; KC1e-1527+ |
| 7494 | F | 0012 | HC1-26+; JHD++; JKD++; KC2-1610++ |
| 7497 | M | 0011 | HC1-26+; JHD++; JKD++; KC1e-1399+ |
| 7648 | F | 0011 | HC1-26+; JHD++; JKD++; KC2-1610+ |
| 7649 | F | 0012 | HC1-26+; JHD++; JKD++; KC2-1610++ |
| 7654 | F | 0011 | HC1-26+; JHD++; JKD++; KC2-1610+ |
| 7655 | F | 0011 | HC1-26+; JHD++; JKD++; KC2-1610+ |
| 7839 | F | 0011 | HC1-26+; JHD++; JKD++; KC1e-1399+ |
| 7656 | F | 0001 | HC1-26−; JHD++; JKD++; KC2-1610+ |
| 7777 | F | 1100 | Col-2141−; JHD+; JKD+ |

We removed spleens from three 6 week old female mice. Mouse #7655 was determined by Southern blot hybridization to be hemizygous for the HC1 (line 26) and KC2 (line 1610) transgene integrations, and homozygous for the JHΔ and JKΔ targeted deletions of the mouse μ and κJ regions. Mouse #7656 was determined by Southern blot hybridization to be hemizygous for the KC2 (line 1610) transgene integration and homozygous for the JHΔ and JKΔ targeted deletions of the mouse μ and κJ regions. Mouse #7777 was determined by Souther blot hybridization to be hemizygous for the JHΔ and JKΔ targeted deletions of the mouse μ and κJ regions. Because of the recessive nature of these deletions, this mouse should be phenotypically wild-type.

Expression of Endogenous Ig Chains in 0011 Mice

FACS analysis using a panel of antibodies reactive with either human μ, mouse μ, hman κ, mouse κ, or mouse λ was used to sort lymphocytes explanted from (1) a wildtype mouse (7777), (2) a 0001 mouse homozygous for heavy chain and kappa knockout alleles and harboring a human light chain transgene (7656), and (3) a 0011 mouse homozygous for heavy chain and kappa knockout alleles and harboring a human light chain transgene and a human heavy chain transgene (7655).

We prepared single cell suspensions from spleen and lysed the red cells with $NH_4Cl$, as described by Mishell and Shiigi (Mishell, B. B. & Shiigi, S. M. (eds) *Selected Methods in Cellular Immunology*. W. H. Freeman & Co., New York, 1980). The lymphocytes are stained with the following reagents: propidium iodide (Molecular Probes, Eugene, Oreg.), FITC conjugated anti-human IgM (clone G20-127; Pharmingen, San Diego, Calif.), FITC conjugated anti-mouse IgM (clone R6-60.2; Pharmingen, San Diego, Calif.), phycoerythrin conjugated anti-human Igκ (clone HP6062; CalTag, South San Francisco, Calif.), FITC conjugated anti-mouse Igλ (clone R26-46; Pharmingen, San Diego, Calif.) FITC conjugated anti-mouse B220 (clone RA3-6B2; Pharmingen, San Diego, Calif.), and Cy-Chrome conjugated anti-mouse B220 (clone RA3-6B2; Pharmingen, San Diego, Calif.). We analyzed the stained cells using a FACScan flow cytometer and LYSIS II software (Becton Dickinson, San Jose, Calif.). Macrophages and residual red cells are excluded by gating on forward and side scatter. Dead cells are excluded by gating out propidium iodide positive cells. The flow cytometric data in FIGS. 49 and 50 confirms the Southern blot hybridization data and demonstrates that mouse #7655 expresses both human μ and human κ and relatively little if any mouse μ or mouse κ. Nevertheless a significant fraction of the B cells (about 70–80%) appear to express hybrid Ig receptors consisting of human heavy and mouse λ light chains.

Figure 49:
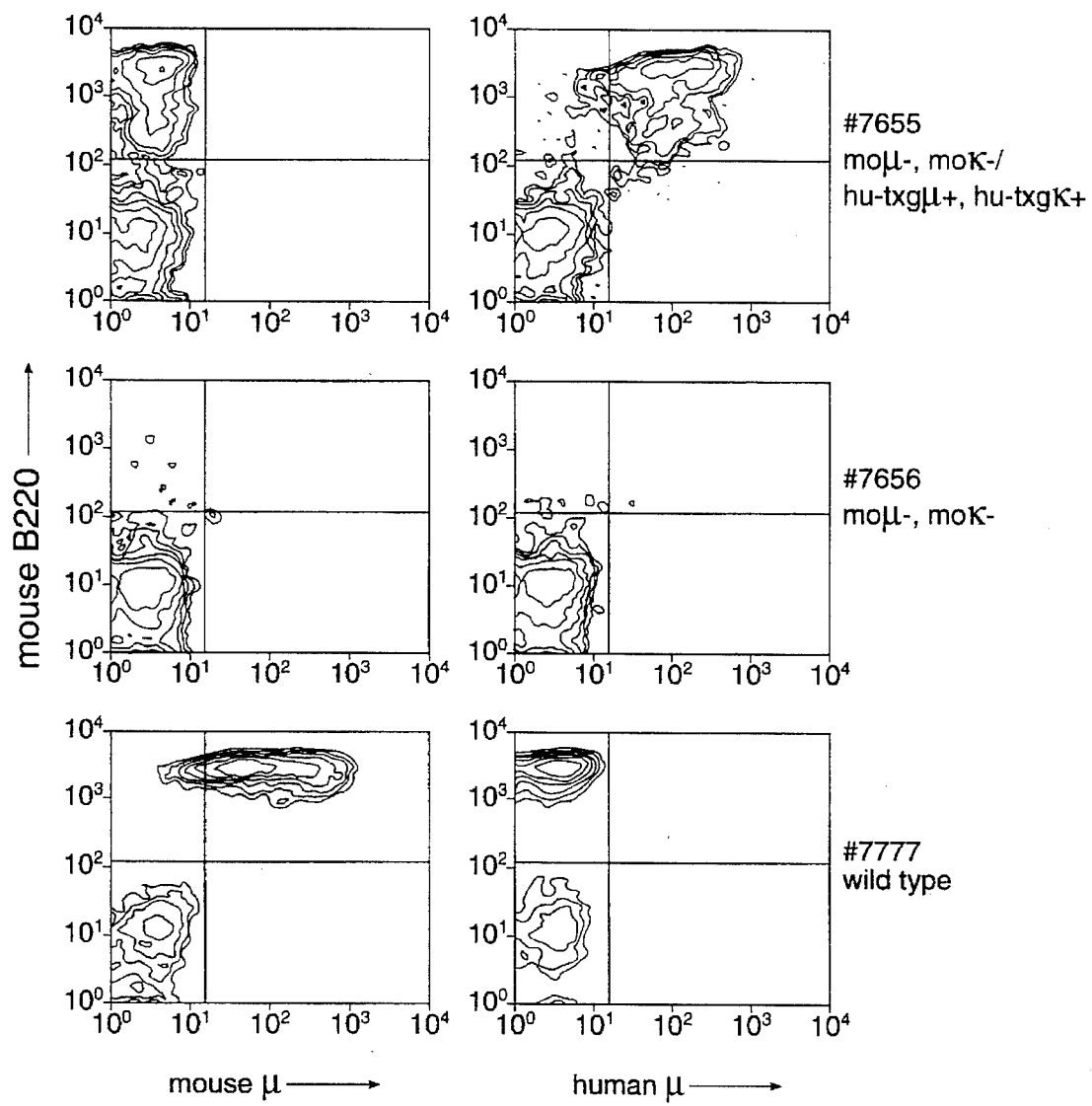
FIG. 49 shows relative distribution of lymphocytes staining for human µ or mouse µ as determined by FACS for three mouse genotypes.

FIG. 49 shows the relative distribution of B cells expressing human μ or mouse μ on the cell surface; 0011 mouse (7655) lymphocytes are positive for human μ but relatively lack mouse μ; 0001 mouse (7656) lymphocytes do not express much human μ or mouse μ; wildtype mouse (7777) lymphocytes express mouse μ but lack human μ.

Figure 50:
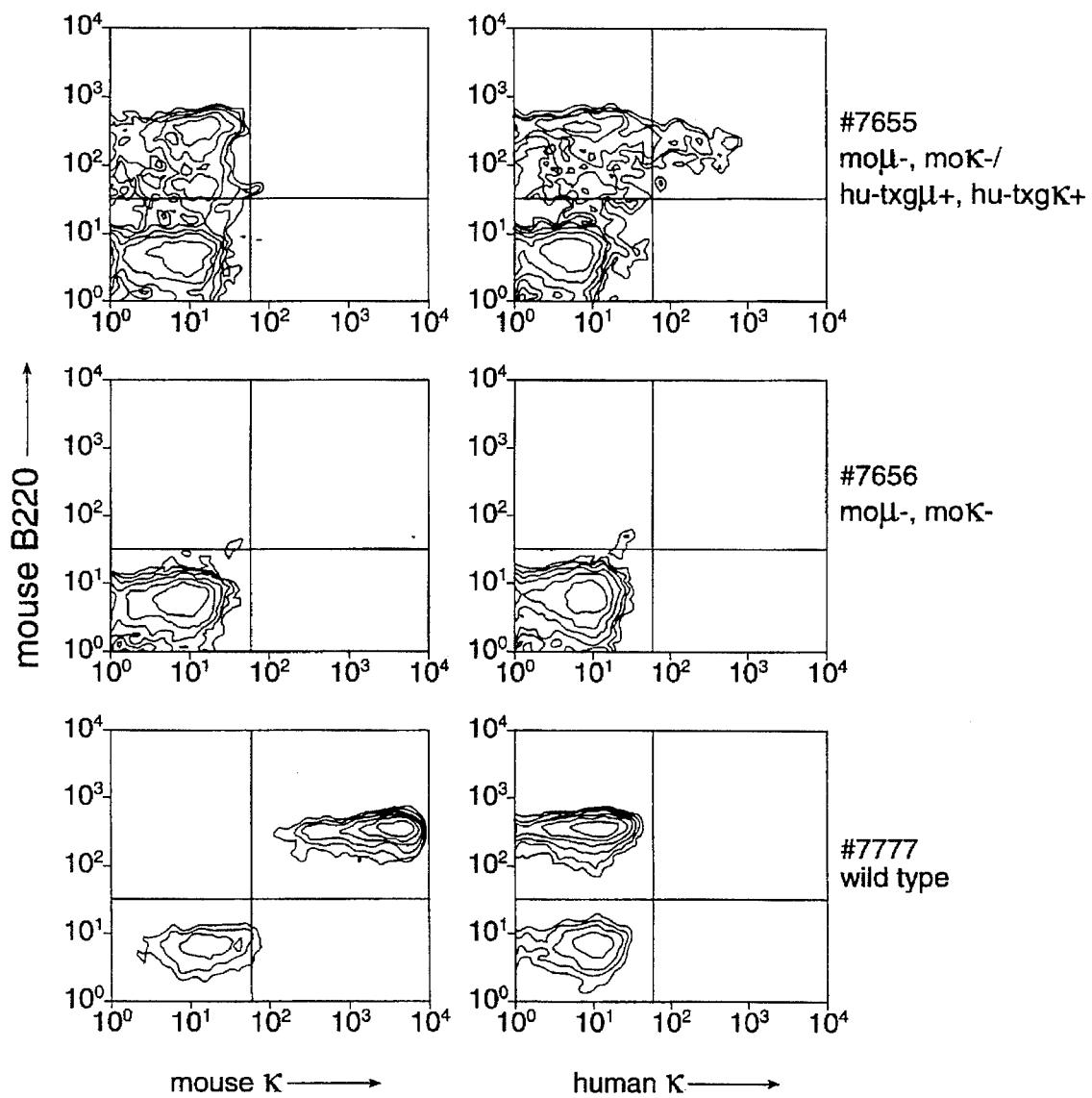
FIG. 50 shows relative distribution of lymphocytes staining for human κ or mouse κ as determined by FACS for three mouse genotypes.

FIG. 50 shows the relative distribution of B cells expressing human κ or mouse κ on the cell surface; 0011 mouse (7655) lymphocytes are positive for human κ but relatively lack mouse κ; 0001 mouse (7656) lymphocytes do not express much human κ or mouse κ; wildtype mouse (7777) lymphocytes express mouse κ but lack human κ.

Figure 51:
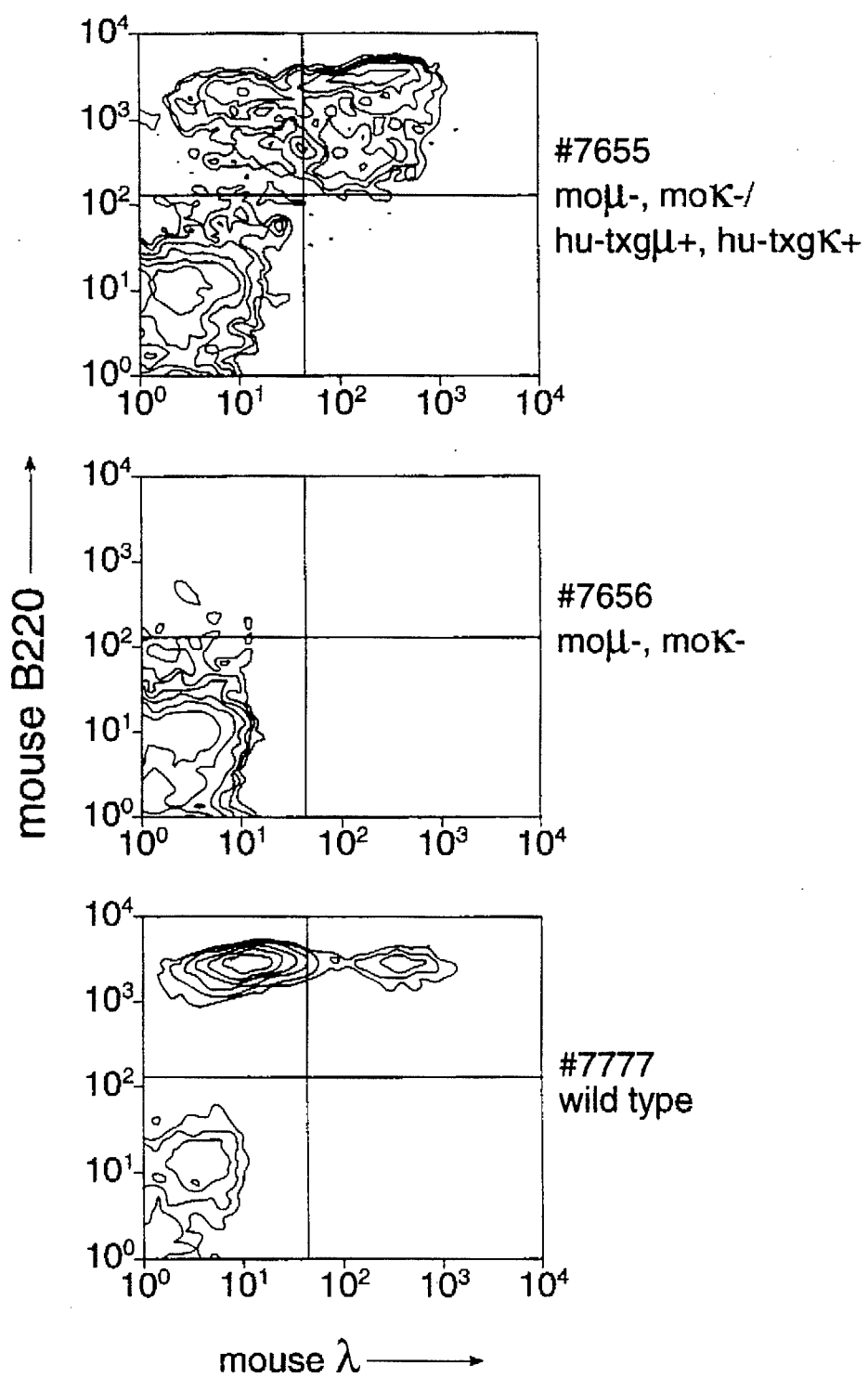
FIG. 51 shows relative distribution of lymphocytes staining for mouse λ as determined by FACS for three mouse genotypes.

FIG. 51 shows the relative distribution of B cells expressing mouse λ on the cell surface; 0011 mouse (7655) lymphocytes are positive for mouse λ; 0001 mouse (7656) lymphocytes do not express significant mouse λ; wildtype mouse (7777) lymphocytes express mouse λ but at a relatively lower level than the 0011 mouse (7655).

Figure 52:
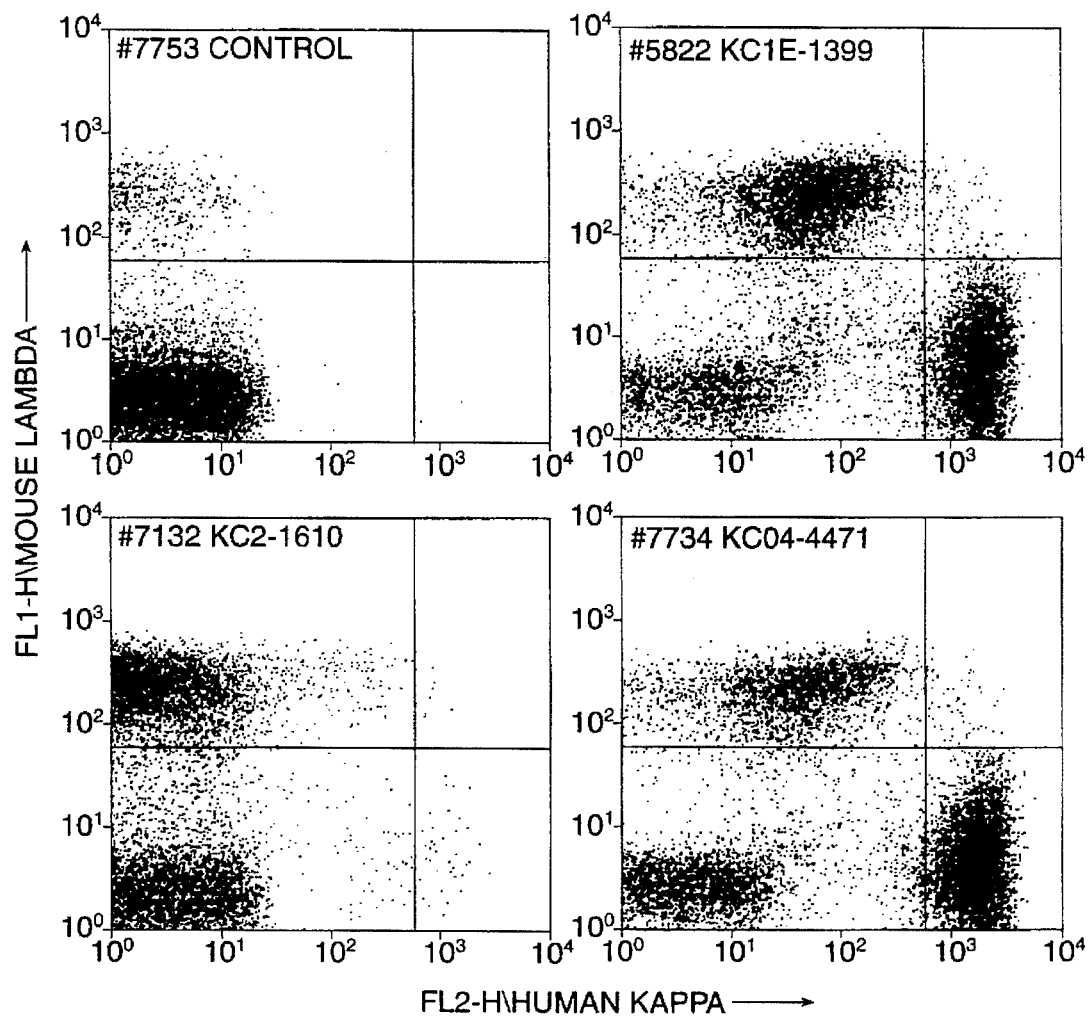
FIG. 52 shows relative distribution of lymphocytes staining for mouse λ or human κ as determined by FACS for four mouse genotypes.

FIG. 52 shows the relative distribution of B cells positive for endogenous mouse λ as compared to human κ (transgene-encoded). The upper left panel shows the results of cells from a wildtype mouse possessing functional endogenous heavy and light chain alleles and lacking human transgene(s); the cells are positive for mouse lambda. The upper right panel shows cells from a mouse (#5822) having a κ knockout background (JKD++) and harboring the human κ transgene intergration of the KC1e-1399 line; the cells are positive for human κ or mouse λ in roughly proportional amounts. The lower left panel shows cells from a mouse (#7132) having a κ knockout background (JKD++) and harboring the human κ transgene intergration of the KC2-1610 line; more cells are positive for mouse λ than for human κ, possibly indicating that the KC2-1610 transgene integration is less efficient than the KC1e-1399 transgene integration. The lower right panel shows cells from a mouse harboring a human κ minilocus transgene (KCo4) and lacking a functional endogenous murine κ allele. The data presented in FIG. 52 also demonstrates the variability of phenotypic expression between transgenes. Such variability indicates the desirability of selecting for individual transgenes and/or transgenic lines which express one or more desired phenotypic features resulting from the integrated transgene (e.g., isotype switching, high level expression, low murine Ig background). Generally, single or multiple transgene species (e.g., pKC1e, pKC2, KCo4) are employed separately to form multiple individual transgenic lines differing by: (1) transgene, (2) site(s) of transgene integration, and/or (3) genetic background. Individual transgenic lines are examined for desired parameters, such as: (1) capability to mount an immune respone to a predetermined antigen, (2) frequency of isotype switching within transgene-encoded constant regions and/or frequency of trans-switching to endogenous (e.g., murine) Ig constant region genes, (3) expression level of transgene-encoded immmunoglobulin chains and antibodies, (4) expression level of endogenous (e.g., murine) immunoglobulin immunoglobulin sequences, and (5) frequency of productive VDJ and VJ rearrangement. Typically, the transgenic lines which produce the largest concentrations of transgene-encoded (e.g., human) immunoglobulin chains are selected; preferably, the selected lines produce about at least 40 μg/ml of transgene-encoded heavy chain (e.g., human μ or human γ) in the serum of the transgenic animal and/or about at least 100 μg/ml of transgene-encoded light chain (e.g., human κ).

Mice were examined for their expression of human and murine immmunoglobulin chains in their unimmunized serum and in their serum following immunization with a specific antigen, human CD4. FIG. 53 shows the relative expression of human μ, human γ, murine μ, murine γ, human κ, murine κ, and murine λ chains present in the serum of four separate unimmunized 0011 mice of various genotypes (nt=not tested); human κ predominates as the most abundant light chain, and human μ and murine γ (putatively a product of trans-switching) are the most abundant heavy chains, with variability between lines present, indicating the utility of a selection step to identify advantageous genotypic combinations that minimize expression of murine chains while allowing expression of human chains. Mice #6907 and 7088 show isotype switching (cis-switching within the transgene) from human μ to human γ.

Figure 54:
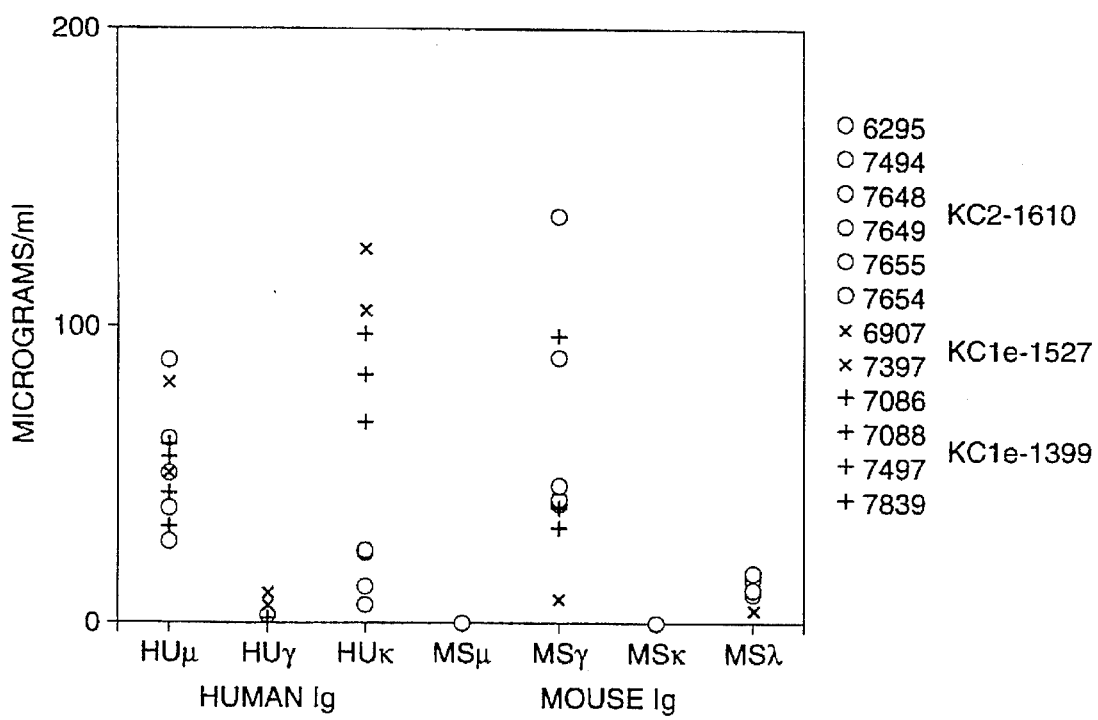
FIG. 54 shows a scatter plot showing the amounts of human µ, human γ, human κ, mouse µ, mouse γ, mouse κ, and mouse λ chains in the serum of unimmunized 0011 mice of various genotypes.

FIG. 54 shows serum immunoglobulin chain levels for human μ (huμ), human γ (huγ), human κ (huκ), murine μ (msμ), murine γ (msγ), murine κ (msκ), and murine λ (msλ) in mice of the various 0011 genotypes.

Specific Antibody Response in 0011 Mice

An 0011 mouse (#6295) was immunized with an immunogenic dose of human CD4 according to the following immunization schedule: Day 0, intraperitoneal injection of 100 μl of CD4 mouse immune serum; Day 1, inject 20 μg of human CD4 (American Bio-Tech) on latex beads with DDA in 100 μl; Day 15 inject 20 μg of human CD4 (American Bio-Tech) on latex beads with DDA in 100 μl; Day 29 inject 20 μg of human CD4 (American Bio-Tech) on latex beads with DDA in 100 μl; Day 43 inject 20 μg of human CD4 (American Bio-Tech) on latex beads with DDA in 100 μl.

Figure 55:
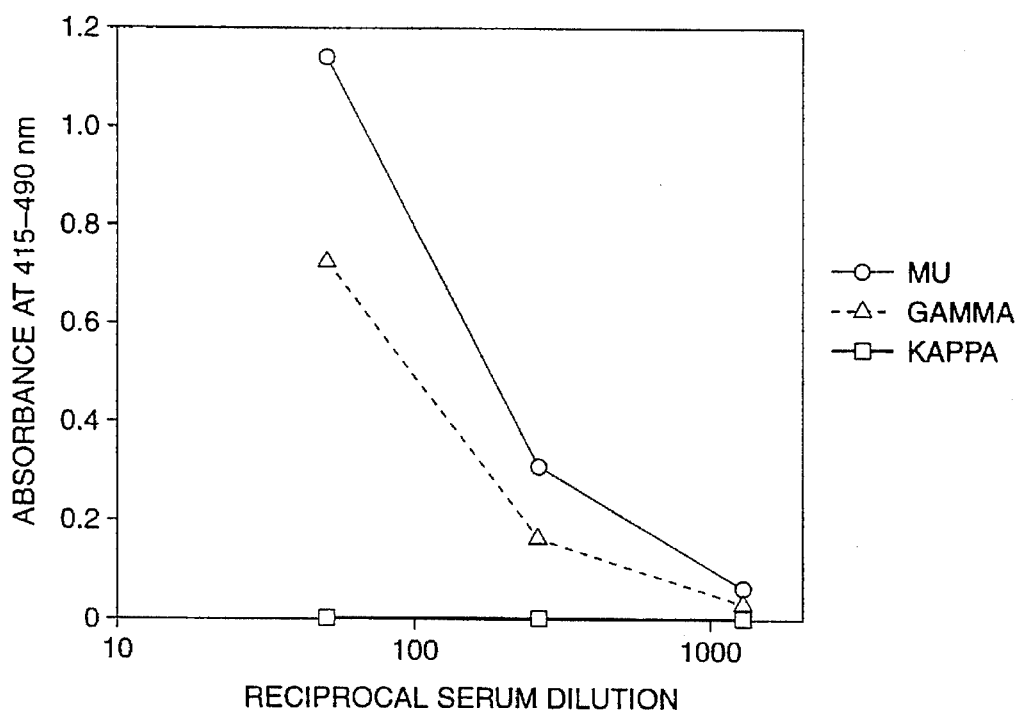
FIG. 55 shows the titers of antibodies comprising human µ, human γ, or human κ chains in anti-CD4 antibodies in the serum taken at three weeks or seven weeks post-immunization following immunization of a 0011 mouse with human CD4.

FIG. 55 shows the relative antibody response to CD4 immunization at 3 weeks and 7 weeks demonstrating the presence of human μ, human κ, and human γ chains in the anti-CD4 response. Human γ chains are present at significantly increased abundance in the 7 week serum, indicating that cis-switching within the heavy chain transgene (isotype switching) is occurring in a temporal relationship similar to that of isotype switching in a wildtype animal.

Figure 56:
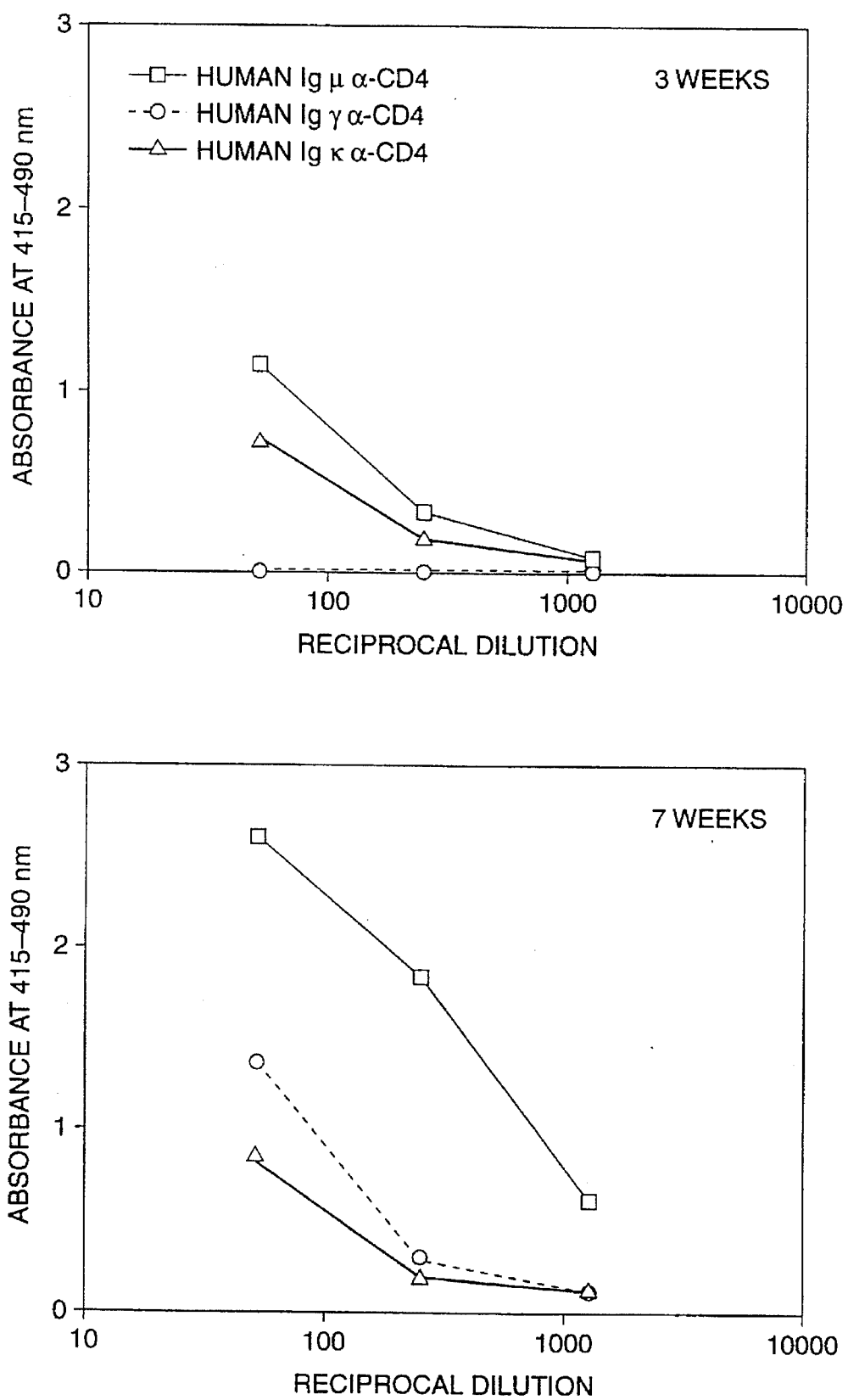
FIG. 56 shows a schematic representation of the human heavy chain minilocus transgenes pHC1 and pHC2, and the light chain minilocus transgenes pKC1, pKC1e, and the light chain minilocus transgene created by homologous recombination between pKC2 and Co4 at the site indicated.

FIG. 56 shows a schematic compilation of various human heavy chain and light chain transgenes.

Example 28

This example provides for the targeted knockout of the murine λ light chain locus.

Targeted Inactivation of the Murine Lambda Light Chain Locus

Unlike the Ig heavy and kappa light chain loci, the murine VλJλ and Cλ gene segments are not grouped into 3 families arranged in a 5' to 3' array, but instead are interspersed. The most 5' portion consists of two V segments (Vλ2 and VλX) which are followed, proceeding in a 3' direction, by two constant region exons, each associated with its own J segment (Jλ2Cλ2 and the pseudogene Jλ4Cλ4). Next is the most extensively used V segment (Vλ1) which is followed by the second cluster of constant region exons (Jλ3Cλ3 and Jλ1Cλ1,). Overall the locus spans approximate 200 kb, with intervals of ~20–90 kb between the two clusters.

Expression of the lambda locus involves rearrangement of Vλ2 or VλX predominantly to Jλ2 and only rarely further 3' to Jλ3 or Jλ1. Vλ1 can recombine with both Jλ3 and Jλ1. Thus the lambda locus can be mutated in order to fully eliminate recombination and expression of the locus.

Figure 57B:
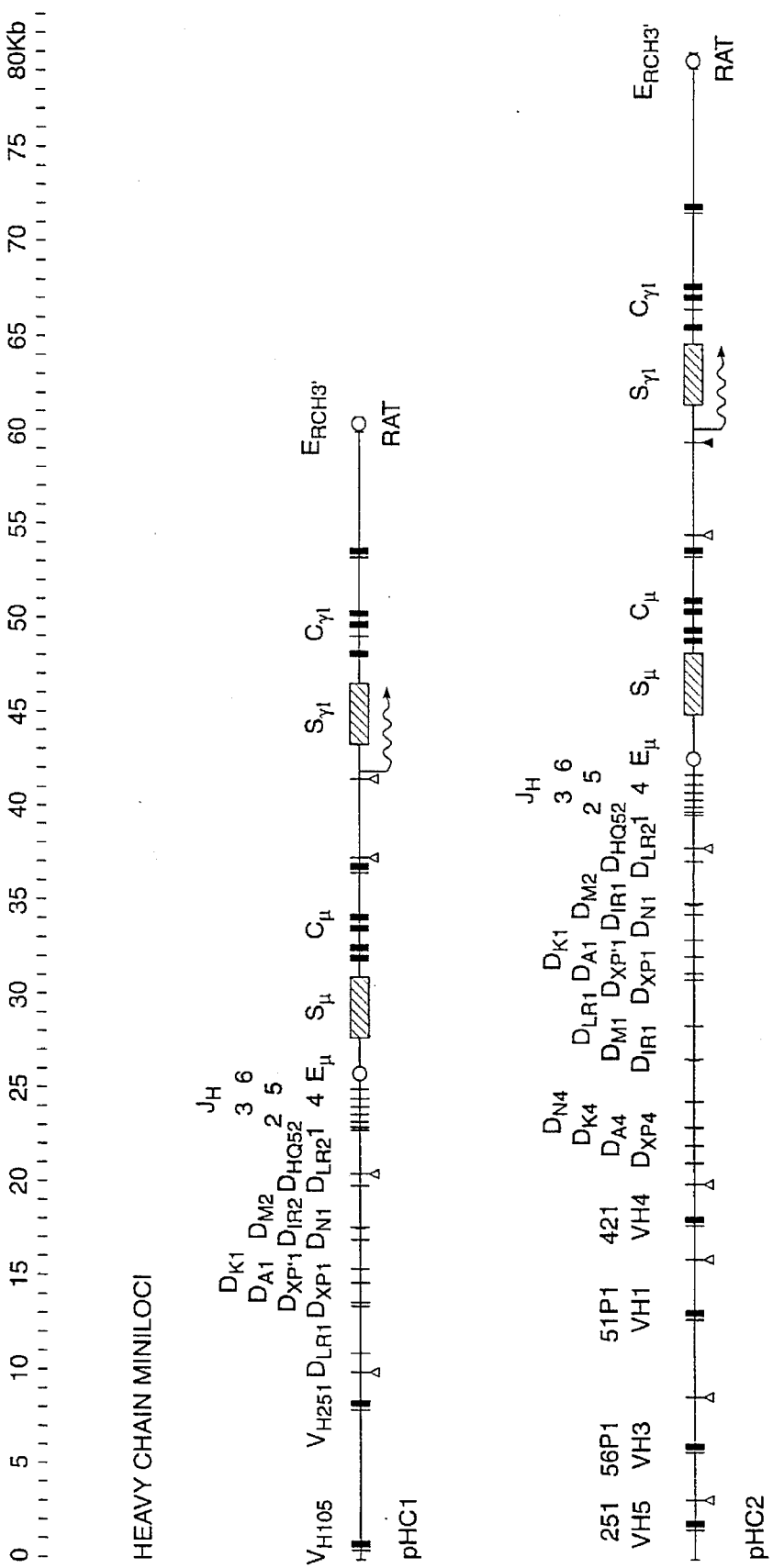
FIG. 57 shows a linkage map of the murine lambda light chain locus as taken from Storb et al. (1989) op.cit.; the stippled boxes represent a pseudogene.

The distance between the two lambda gene clusters makes it difficult to inactivate expression of the locus via the generation of a single compact targeted deletion, as was used in inactivating the murine Ig heavy and kappa light chain loci. Instead, a small single deletion which would eliminate expression lambda light chains spans approximately 120 kb, extending from Jλ2Cλ2 to Jλ1Cλ1 (FIG. 57). This removes all of the lambda constant region exons as well as the Vλ1 gene segment, ensuring inactivation of the locus.

Replacement type targeting vectors (Thomas and Capecchi (1987) op.cit) are constructed in which the deleted 120 kb is replaced with the selectable marker gene, neo, in a PGK expression cassette. The marker is embedded within genomic lambda sequences flanking the deletion to provide homology to the lambda locus and can also contain the HSV-tk gene, at the end of one of the regions of homology, to allow for enrichment for cells which have homologously integrated the vectors. Lambda locus genomic clone sequences are obtained by screening of a strain 129/Sv genomic phage library isogenic to the ES line being targeted, since the use of targeting vectors isogenic to the chromosomal DNA being targeted has been reported to enhance the efficiency of homologous recombination. Targeting vectors are constructed which differ in their lengths of homology to the lambda locus. The first vector (vector 1 in FIG. 58) contains the marker gene flanked by total of approximately 8–12 kb of lambda locus sequences. For targeting events in which replacement vectors mediate addition or detection of a few kb of DNA this has been demonstrated to be a more than sufficient extent of homology (Hasty et al. (1991) op.cit; Thomas et al. (1992) op.cit.). Vectors with an additional approximately 40–60 kb of flanking lambda sequence are also constructed (vector 2 in FIG. 58). Human Ig miniloci of at least 80 kb are routinely cloned and propagated in the plasmid vector pGP1 (Taylor et al. (1993) op.cit).

An alternative approach for inactivation of the lambda locus employs two independent mutations, for example mutations of the two constant region clusters or of the two V region loci, in the same ES cell. Since both constant regions are each contained within ~6 kb of DNA, whereas one of the V loci spans ~19 kb, targeting vectors are constructed to independently delete the Jλ2Cλ2/Jλ4Cλ4 and the Jλ3Cλ3/Jλ1Cλ1 loci. As shown in FIG. 58, each vector consists of a selectable marker (e.g., neo or pac) in a PGK expression cassette, surrounded by a total of ~8–12 kb of lambda locus genomic DNA blanking each deletion. The HSV-tk gene can be added to the targeting vectors to enrich for homologous recombination events by positive-negative selection. ES cells are targeted sequentially with the two vectors, such that clones are generated which carry a deletion of one of the constant region loci; these clones are then targeted sequentially with the two vectors, such that clones will be generated which carry a deletion of one of the constant region loci, and these clones are then targeted to generate a deletion of the remaining functional constant region cluster. Since both targeting events are thus being directed to the same cell, it is preferable to use a different selectable marker for the two targetings. In the schematic example shown in FIG. 58, one of the vectors contains the neogene and the other the pac (puromycin N-acetyl transferase) gene. A third potential dominant selectable marker is the hyg (hygromycin phosphotransferase) gene. Both the pac and hyg genes can be been inserted into the PGK expression construct successfully used for targeting the neogene into the Ig heavy and kappa light chain loci. Since the two lambda constant region clusters are tightly linked, it is important that the two mutations reside on the same chromosome. There preferably is a 50% probability of mutating the same allele by two independent targeting events, and linkage of the mutations is established by their co-segregation during breeding of chimeras derived from the doubly targeted ES cells.

This example provides for the targeted knockout of the murine heavy chain locus.

Targeted Inactivation of the Murine Heavy Chain Locus

Figure 60:
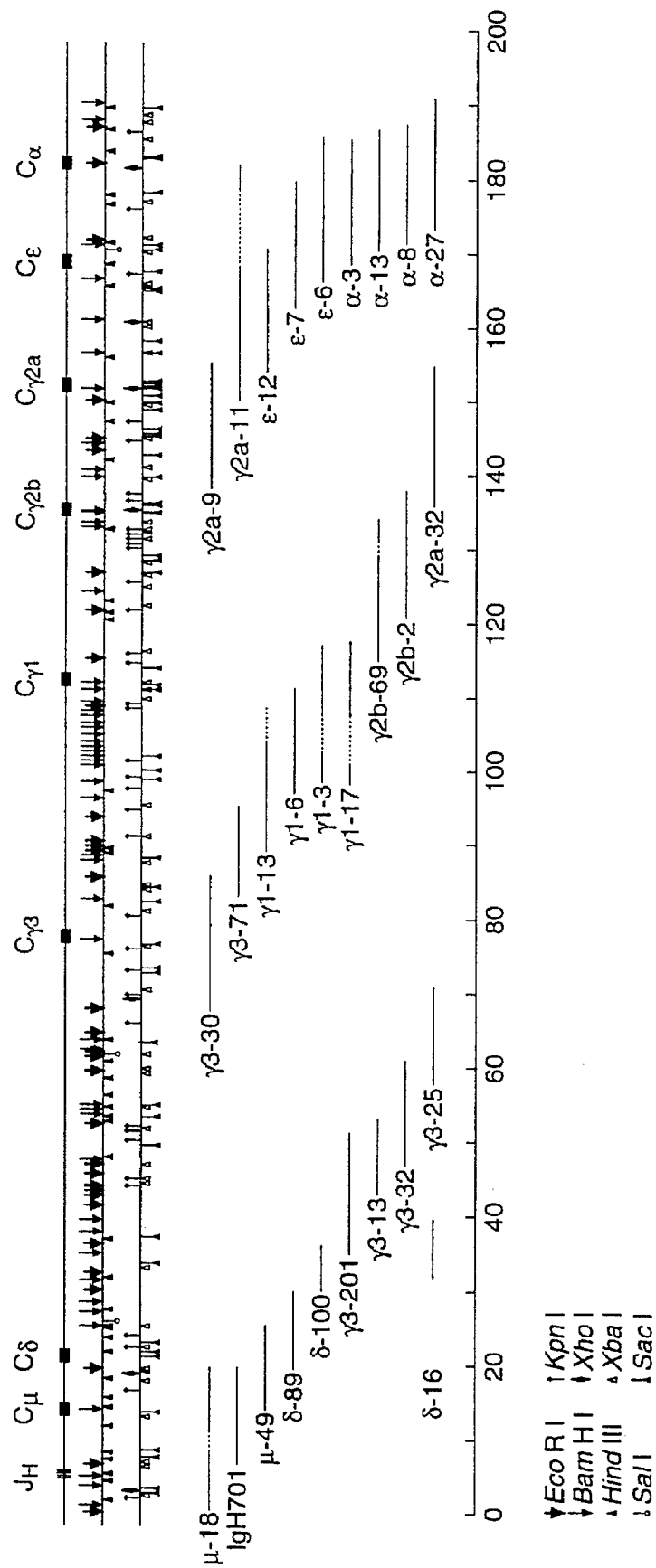
FIG. 60 shows a map of the BALB/c murine heavy chain locus as taken from *Immunoglobulin Genes*, Honjo, T, Alt, F W, and Rabbits T H (eds.) Academic Press, NY (1989) p.

A homologous recombination gene targeting transgene having the structure shown in FIG. 59 is used to delete at least one and preferably substantially all of the murine heavy chain locus constant region genes by gene targeting in ES cells. FIG. 59 shows a general schematic diagram of a targeting transgene. Segment (a) is a cloned genomic DNA sequence located upstream of the constant region gene(s) to be deleted (i.e, proximal to the $J_H$ genes); segment (b) comprises a positive selection marker, such as pgk-neo; segment (c) is a cloned genomic DNA sequence located downstream of the constant region gene(s) to be deleted (i.e, distal to the constan region gene(s) and and $J_H$ genes); and segment (d), which is optional, comprises a negative selection marker gene (e.g., HSV-tk). FIG. 60 shows a map of the murine heavy chain locus as taken from *Immunoglobulin Genes*, Honjo, T, Alt, F W, and Rabbits T H (eds.) Academic Press, NY (1989) p. 129.

A targeting transgene having a structure according to FIG. 59, wherein: (1) the (a) segment is the 11.5 kb insert of clone JH8.1 (Chen et al. (1993) *Int. Immunol.* 5: 647) or an equivalent portion comprising about at least 1–4 kb of sequence located upstream of the murine Cμ gene, (2) the (b) segment is pgk-neo as described supra, (3) the (c) segment comprises the 1674 bp sequence shown in FIG. 61 or a 4–6 kb insert isolated from a phage clone of the mouse Cα gene isolated by screening a mouse genomic clone library with the end-labeled oligonucleotide having the sequence:

5'-gtg ttg cgt gta tca gct gaa acc tgg aaa cag ggt gac cag-3' and (4) the (d) segment comprises the HSV-tk expression cassette described supra.

Alternatively, a stepwise deletion of one or more heavy chain constant region genes is performed wherein a first targeting transgene comprises homology regions, i.e., segments (a) and (c), homologous to sequences flanking a constant region gene or genes, a first species of positive selection marker gene (pgk-neo), and an HSV-tk negative selection marker. Thus, the (a) segment can comprise a sequence of at least about 1–4 kb and homologous to a region located upstream of Cγ3 and the (c) segment can comprise a sequence of at least about 1–4 kb and homologous to a region located upstream of Cγ2a. This targeting transgene deletes the Cγ3, Cγ1, Cγ2b, and Cγ2a genes. This first targeting transgene is introduced into ES cells and correctly targeted recombinants are selected (e.g., with G418), producing a correctly targeted C region deletion. Negative selection for loss of the HSV-tk cassette is then performed (e.g., with ganciclovir or FIAU). The resultant correctly targeted first round C deletion recombinants have a heavy chain locus lacking the Cγ3, Cγ1, Cγ2b, and Cγ2a genes.

A second targeting transgene comprises homology regions, i.e., segments (a) and (c), homologous to sequences flanking a constant region gene or genes, a second species of positive selection marker gene different that the first species (e.g., gpt or pac), and an HSV-tk negative selection marker. Thus, the (a) segment can comprise a sequence of at least about 1–4 kb and homologous to a region located upstream of Cε and the (c) segment can comprise a sequence of at least about 1–4 kb and homologous to a region located upstream of Cα. This targeting transgene deletes the Cε and Cα genes.

This second targeting transgene is introduced into the correctly targeted C-region recombinant ES cells obtained from the first targeting event. Cells which are correctly targeted for the second knockout event (i.e., by homologous recombination with the second targeting transgene) are selected for with a selection drug that is specific for the second species of positive selection marker gene (e.g., mycophenolic acid to select for gpt; puromycin to select for pac). Negative selection for loss of the HSV-tk cassette is then performed (e.g., with ganciclovir or FIAU). These resultant correctly targeted second round C region recombinants have a heavy chain locus lacking the Cγ3, Cγ1, Cγ2b, Cγ2a, Cε, and Cα genes.

Correctly targeted first-round or second-round recombinant ES cells lacking one or more C region genes are used for blastocyst injections as described (supra) and chimeric mice are produced. Germline transmission of the targeted heavy chain alleles is established, and breeding of the resultant founder mice is performed to generate mice homozygous for C-region knockouts. Such C-region knockout mice have several advantages as compared to $J_H$ knockout mice; for one example, C-region knockout mice have diminished ability (or completely lack the ability) to undergo trans-switching between a human heavy chain transgene and an endogenous heavy chain locus constant region, thus reducing the frequency of chimeric human/mouse heavy chains in the transgenic mouse. Knockout of the murine gamma genes is preferred, although μ and delta are frequently also deleted by homologous targeting. C-region knockout can be done in conjunction with other targeted lesions int he endogenous murine heavy chain locus; a C-region deletion can be combined with a $J_H$ knockout to preclude productive VDJ rearrangement of the murine heavy chain locus and to preclude or reduce trans-switching between a human heavy chain transgene and the murine heavy chain locus, among others. For some embodiments, it may be desirable to produce mice which specifically lack one or more C-region genes of the endogenous heavy chain locus, but which retain certain other C-region genes; for example, it may be preferable to retain the murine Cα gene to allow to production of chimeric human/mouse IgA by trans-switching, if such IgA confers an advantageous phenotype and does not substantially interfere with the desired utility of the mice.

Example 29

This example demonstrates ex vivo depletion of lymphocytes expressing an endogenous (murine) immunoglobulin from a lymphocyte sample obtained from a transgenic mouse harboring a human transgene. The lymphocytes expressing murine Ig are selectively depleted by specific binding to an anti-murine immunoglobulin antibody that lacks substantial binding to human immunoglobulins encoded by the transgene(s).

Ex Vivo Depletion of Murine Ig-Expressing B-cells

A mouse homozygous for a human heavy chain minilocus transgene (HC2) and a human light chain minilocus transgene (KCo4) is bred with a C57BL/6 (B6) inbred mouse to obtain 2211 mice (i.e., mice which: are homozygous for a functional endogenous murine heavy chain locus, are homozygous for a functional endogenous murine light chain locus, and which possess one copy of a human heavy chain transgene and one copy of a human light chain transgene). Such 2211 mice also express B6 major and minor histocompatibility antigens. These mice are primed with an immunogenic dose of an antigen, and after approximately one week spleen cells are isolated. B cells positive for murine Ig are removed by solid phase-coupled antibody-dependent cell separation according to standard methods (Wysocki et al. (1978) Proc. Natl. Acad. Sci. (U.S.A.) 75: 2844; MACS magnetic cell sorting, Miltenyi Biotec Inc., Sunnyvale, Calif.), followed by antibody-dependent complement-mediated cell lysis (*Selected Methods in Cellular Immunology*, Mishell B B and Shiigi S M (eds.), W. H. Freeman and Company, New York, 1980, pp.211–212) to substantially remove residual cells positive for murine Ig. The remaining cells in the depleted sample (e.g., T cells, B cells positive for human Ig) are injected i.v., preferably together with additional anti-murine Ig antibody to deplete arising B cells, into a SCID/B6 or RAG/B6 mouse. The reconstitutued mouse is then further immunized for the antigen to obtain antibody and affinity matured cells for producing hybridoma clones.

Example 30

Production of Fully Human Antibodies in Somatic Chimeras

A method is described for producing fully human antibodies in somatic chimeric mice. These mice are generated by introduction of embryonic stem (ES) cells, carrying human immunoglobulin (Ig) heavy and light chain transgenes and lacking functional murine Ig heavy and kappa light chain genes, into blastocysts from RAG-1 or RAG-2 deficient mice.

RAG-1 and RAG-2 deficient mice (Mombaerts et al. (1992) *Cell* 68: 869; Shinkai et al. (1992) *Cell* 68: 855) lack murine B and T cells due to an inability to initiate VDJ rearrangement and to assemble the gene segments encoding Igs and T cell receptors (TCR). This defect in B and T cell production can be complemented by injection of wild-type ES cells into blastocysts derived from RAG-2 deficient animals. The resulting chimeric mice produce mature B and T cells derived entirely from the injected ES cells (Chen et al. (1993) *Proc. Natl. Acad. Sci. USA* 90: 4528).

Genetic manipulation of the injected ES cells is used for introducing defined mutations and/or exogenous DNA constructs into all of the B and/or T cells of the chimeras. Chen et al. (1993), *Proc. Natl. Acad. Sci. USA* 90:4528–4532) generated ES cells carrying a homozygous inactivation of the Ig heavy chain locus, which, when injected into RAG blastocysts, produced chimeras which made T cells in the absence of B cells. Transfection of a rearranged murine heavy chain into the mutant ES cells results in the rescue of B cell development and the production of both B and T cells in the chimeras.

Chimeric mice which express fully human antibodies in the absence of murine Ig heavy chain or kappa light chain synthesis can be generated. Human Ig heavy and light chain constructs are introduced into ES cells homozygous for inactivation of both the murine Ig heavy and kappa light chain genes. The ES cells are then injected into blastocysts derived from RAG2 deficient mice. The resulting chimeras contain B cells derived exclusively from the injected ES cells which are incapable of expressing murine Ig heavy and kappa light chain genes but do express human Ig genes.

Generation of ES cells Homozygous for Inactivation of the Immunoglobulin Heavy and Kappa Light Chain Genes Mice bearing inactivated Ig heavy and kappa light chain loci were generated by targeted deletion, in ES cells, of Ig $J_H$ and $J_K/C_K$ sequences, respectively according to known procedures (Chen et al. (1993) *EMBO J.* 12: 821; and Chen et al. (1993) *Int. Immunol.* op.cit). The two mutant strains of mice were bred together to generate a strain homozygous for inactivation of both Ig loci. This double mutant strain was used for derivation of ES cells. The protocol used was essentially that described by Robertson (1987, in Teratocarcinomas and Embryonic Stem Cells: A Practical Approach, p. 71–112, edited by E. J. Robertson, IRL Press). Briefly, blastocysts were generated by natural matings of homozygous double mutant mice. Pregnant females were ovariectomized on day 2.5 of gestation and the "delayed" blastocysts were flushed from the uterus on day 7 of gestation and cultured on feeder cells, to help maintain their undifferentiated state. Stem cells from the inner cell mass of the blastocysts, identifiable by their morphology, were picked, dissociated, and passaged on feeder cells. Cells with a normal karyotype were identified, and male cell lines will be tested for their ability to generate chimeras and contribute to the germ cells of the mouse. Male ES cells are preferable to female lines since a male chimera can produce significantly more offspring.

Introduction of Human Ig Genes into Mouse Ig Heavy and Kappa Light Chain Deficient ES cells Human immunoglobulin heavy and light chain genes are introduced into the mutant ES cells as either minilocus constructs, such as HC2 and KC-C04, or as YAC clones, such as J1.3P. Transfection of ES cells with human Ig DNAs is carried out by techniques such as electroporation or lipofection with a cationic lipid. In order to allow for selection of ES cells which have incorporated the human DNA, a selectable marker either is ligated to the constructs or is co-transfected with the constructs into ES cells. Since the mutant ES cells contain the neomycin phosphotransferse (neo) gene as a result of the gene targeting events which generated the Ig gene inactivations, different selectable markers, such as hygromycin phosphotransferase (hyg) or puromycin N-acetyl transferase (pac), are used to introduce the human Ig genes into the ES cells.

The human Ig heavy and light chain genes can be introduced simultaneously or sequentially, using different selectable markers, into the mutant ES cells. Following transfection, cells are selected with the appropriate selectable marker and drug-resistant colonies are expanded for freezing and for DNA analysis to verify and analyze the integration of the human gene sequences.

Generation of Chimeras

ES clones containing human Ig heavy and light chain genes are injected into RAG-2 blastocysts as described (Bradley, A. (1987), in Teratocarcinomas and Embryonic Stem Cells: A Practical Approach, p. 113–151, edited by E. J. Robertson, IRL Press) and transferred into the uteri of pseudopregnant females. Offspring are screened for the presence of human antibodies by ELISA assay of serum samples. Positive animals are used for immunization and the production of human monoclonal antibodies.

Example 31

This example describes the introduction, via homologous recombination in ES cells, of a targeted frameshift mutation into the murine heavy chain locus leading to a deletion of B cells which undergo switch recombination. The frameshifted mice are suitable hosts for harboring non-murine (e.g., human) transgenes encoding human sequence immunoglobulins.

The novel frameshifted mice can be used for expressing non-murine (e.g., human) sequence immunoglobulins encoded by heavy chain transgene(s) and/or light chain transgene(s), and for the isolation of hybridomas expressing class-switched, affinity matured, human sequence antibodies from introduced transgenes, among other uses. A frameshift is introduced into one of the four mouse JH gene segments and into the first exon of the mouse μ gene. The two introduced frameshift mutations compensate for each other thus allowing for the expression of fully functional murine μ heavy chain when a B cell uses the frameshifted JH for a functional VDJ joint. None of the other three JH segments can be used for functional VDJ joining because of the frameshift in μ, which is not compensated in the remaining JH genes. Alternatively, compensating frameshifts can be engineered into multiple murine JH genes.

A mouse homozygous for a compensated, frameshifted immunoglobulin heavy chain allele has an approximately physiological level of peripheral B cells, and an approximately physiological level of serum IgM comprising both murine and human μ. However, B cells recruited into germinal centers frequently undergo a class switch to a non-μ isotype. Such a class switch in B cells expressing the endogenous murine μ chain leads to the expression of a non-compensated frameshift mRNA, since the remaining non-μ $C_H$ genes do not possess a compensating frameshift. The resulting B cells do not express a B cell receptor and are deleted. Hence, B cells expressing a murine heavy chain are deleted once they reach the stage of differentiation where isotype switching occurs. However, B cells expressing heavy chains encoded by a non-murine (e.g., human) transgene capable of isotype switching and which does not contain such isotype-restrictive frameshifts are capable of further development, including isotype switching and/or affinity maturation, and the like.

Therefore, the frameshifted mouse has an impaired secondary response with regard to murine heavy chain (μ) but a significant secondary response with regard to transgene-encoded heavy chains. If a heavy chain transgene that is capable of undergoing class switching is introduced into this mutant background, the non-IgM secondary response is dominated by transgene expressing B cells. It is thus possible to isolate affinity matured human sequence immunoglobulin expressing hybridomas from these frameshifted mice. Moreover, the frameshifted mice generally possess immunoprotective levels of murine IgM, which may be advantageous where the human heavy chain transgene can encode only a limited repertoire of variable regions.

For making hybridomas secreting human sequence monoclonal antibodies, transgenic mutant mice are immunized; their spleens fused with a myeloma cell line; and the resulting hybridomas screened for expression of the transgene encoded human non-μ isotype. Further, the frameshifted mouse may be advantageous over a JH deleted mouse because it will contain a functional μ switch sequence adjacent to a transcribed VDJ which serves as an active substrate for cis-switching (Gu et al. (1993) *Cell* 73: 1155); thus reducing the level of trans-switched B cells that express chimeric human/mouse antibodies.

Construction of Frameshift Vectors

Two separate frameshift vectors are built. One of the vectors is used to introduce 2 nucleotides at the 3' end of the mouse J4 gene segment, and one of the vectors is used to delete those same two nucleotides from the 5' end of exon 1 of the mouse μ gene.

1. JH Vector

A 3.4 kb XhoI/EcoRI fragment covering the mouse heavy chain J region and the μ intronic enhancer is subcloned into a plasmid vector that contains a neomycin resistance gene as well as a herpes thymidine kinase gene under the control of a phosphoglycerate kinase promoter (tk/neo cassette; Hasty et al., (1991) *Nature* 350: 243). This clone is then used as a substrate for generating 2 different PCR fragments using the following oligonucleotide primers:

o-A1  5'- cca cac tct gca tgc tgc aga agc ttt tct gta -3' o-A2  5'- ggt gac tga ggt acc ttg acc cca gta gtc cag -3' o-A3  5'- ggt tac ctc agt cac cgt ctc ctc aga ggt aag aat ggc ctc -3' o-A4  5'- agg ctc cac cag acc tct cta gac agc aac tac -3'

Oligonucleotides o-A1 and o-A2 are used to amplify a 1.2 kb fragment which is digested with SphI and KpnI. Oligonucleotides o-A3 and o-A4 are used to amplify a 0.6 kb fragment which is digested with KpnI and XbaI. These two digested fragments are then cloned into SphI/XbaI digested plasmid A to produce plasmid B.

Plasmid B contains the 2 nucleotide insertion at the end of the J4 and, in addition, contains a new KpnI site upstream of the insertion. The KpnI site is used as a diagnostic marker for the insertion.

Additional flanking sequences may be cloned into the 5' XhoI site and the 3' EcoRI site of plasmid B to increase its homologous recombination efficiency. The resulting plasmid is then digested with SphI, or another restriction enzyme with a single site within the insert, and electroporated into embryonic stem cells which are then selected with G418 as described by Hasty et al. (1991) op.cit. Homologous recombinants are identified by Southern blot hybridization and then selected with FIAU as described by Hasty et al. to obtain deleted subclones which contain only the 2 base pair insertion and the new KpnI site in JH4. These are identified by Southern blot hybridization of KpnI digested DNA and confirmed by DNA sequence analysis of PCR amplified JH4 DNA.

The resulting mouse contains a JH4 segment that has been converted from the unmutated sequence:

... TGGGGTCAAGGAACCTCAGTCACCGTCTCCTCAG_gtaagaatggcctctcc ...
   Trp Gly Gln Gly Thr Ser Val Thr VAl Ser Ser Glu to the mutant sequence:

... TGGGGTCAAGGTACCTCAGTCACCGTCTCCTCAGAGgtaagaatggcctctcc ...
   Trp Gly Gln Gly Thr Ser Val Thr VAl Ser Ser Glu μ Exon 1 Vector Using similar in vitro mutagenesis methodology described above to engineer a two base pair insertion into the JH4 gene segment, PCR products and genomic subclones are assembled to create a vector containing a two base pair deletion at the 5' end of the first μ exon. In addition, to mark the mutation, a new XmnI site is also introduced downstream by changing an A to a G.

The sequence of the unmutated μ gene is:

... ctggtcctcagAGAGTCAGTCCTTCCCAAATGTCTTCCCCCTCGTC ...
              Glu Ser Gln Ser Phe Pro Asn Val Phe Pro Leu Val The sequence of the mutated μ gene is:

XmnI

... ctggtcctcag_AGTCAGTCCTTCCCGAATGTCTTCCCCCTCGTC ...
              Ser Gln Ser Phe Pro Asn Val Phe Pro Leu Val The homologous recombination vector containing the mutant sequence is linearized and electroporated into an ES cell line containing the JH4 insertion. Homologous recombinants are identified from neomycin-resistant clones. Those homologous recombinants that contain the frameshift insertion on the same chromosome as the JH4 insertion are identified by Southern blot hybridization of KpnI/BamHI digested DNA. The JH4 insertion is associated with a new KpnI site that reduces the size of the J-μ intron containing KpnI/BamHI fragment from the wild type 11.3 kb to a mutant 9 kb. The resulting clones are then selected for deletion of the inserted tk/neo cassette using FIAU. Clones containing the mutant μ exon are identified by Southern blot hybridization of XmnI digested DNA. The mutation is confirmed by DNA sequence analysis of PCR amplified μ exon1 DNA.

Generation of Frameshifted Mice

The ES cell line containing both the two base pair insertion in JH4, and the two base pair deletion in μ exon 1, is then introduced into blastocyst stage embryos which are inserted into pseudopregnant females to generate chimeras. Chimeric animals are bred to obtain germline transmission, and the resulting animals are bred to homozygosity to obtain mutant animals homozygous for compensated frameshifted heavy chain loci and having impaired secondary humoral immune responses in B cells expressing murine heavy chains.

A human heavy chain transgene, such as for example pHC1 or pHC2 and the like, may be bred into the murine heavy chain frameshift background by crossbreeding mice harboring such a human transgene into mice having the frameshifted murine IgH locus. Via interbreeding and backcrossing, mice homozygous at the murine IgH locus for μ-compensated frameshifted murine IgH alleles (i.e., capable of compensated in-frame expression of only murine μ and not murine non-μ chains) and harboring at least one integrated copy of a functional human heavy chain transgene (e.g., pHC1 or pHC2) are produced. Such mice may optionally contain knockout of endogenous murine κ and/or λ loci as described supra, and may optionally comprise a human or other non-murine light chain transgene (e.g., pKC1e, pKC2, and the like).

Alternatively, the human transgene(s) (heavy and/or light) may comprise compensating frameshifts, so that the transgene J gene(s) contain a frameshift that is compensated by a frameshift in the transgene constant region gene(s). Trans-switching to the endogenous constant region genes is uncompensated and produces a truncated or nonsense product; B cells expressing such uncompensated trans-switched immunoglobulins are selected against and depleted.

Example 32

Endogenous Heavy Chain Inactivation by D Region Ablation

This example describes a positive-negative selection homologous recombination vector for replacing the mouse germline immunoglobulin heavy chain D region with a nonfunctional rearranged VDJ segment. The resulting allele functions within a B cell as a normal non-productive allele, with the allele undergoing intra-allele heavy chain class switching, thereby reducing the level of trans-switching to an active transgene locus.

D Region Targeting Construct

An 8–15 kb DNA fragment located upstream of the murine D region is isolated and subcloned from a mouse strain 129 phage library using an oligonucleotide probe comprising approximately 50 consecutive nucleotides of the published sequence for the DFL16.1 segment listed in GenBank. DFL16.1 is the upstream D segment (i.e., proximal to the V region gene cluster and distal to the constant region gene cluster).

Similarly, a 9.5 kb BamHI fragment containing JH3, JH4, Eμ, Sμ, and the first two coding exons of the μ constant region is isolated and subcloned from a mouse strain 129 genomic phage library.

A 5–10 kb rearranged VDJ is then isolated from a mouse hybridoma (any strain) and a synthetic linker containing a stop codon is inserted into the J segment. The stop linker within the J is preferable to an out-of-frame VDJ junction because of the possibility of V replacement rearrangements.

These three fragments are assembled together with a PGKneo positive selection cassette and a PGKHSVtk negative selection cassette to form a positive-negative selection vector for eliminating the mouse D region in 129-derived ES cells (e.g., AB1) by homologous recombination. The targeting vector is formed by ligating the 8–15 kb DNA fragment to the positive selection cassette (e.g., PGKneo), which is itself ligated to the rearranged 5–10 kb rearranged VDJ, which is itself ligated to the 9.5 kb BamHI fragment; the negative selection cassette (e.g., PGKHSVtk) is then ligated at either end of the targeting construct. The construction of such a D region targeting vector is shown schematically in FIG. 63.

The D region targeting construct is transferred into AB1 ES cells, positive and negative selection is performed as described above, and correctly targeted ES cells are cloned. The correctly targeted ES cell clones are used for blastocyst injections and chimeric mice are produced. The chimeric mice are bred to produce founder mice harboring a D-region inactivated heavy chain allele. Interbreeding of offspring is performed to produce homozygotes lacking a functional endogenous heavy chain locus. Such homozygotes are used to crossbreed to mice harboring human Ig transgenes (e.g., pHC1, pHC2, pKC2, pKC1e, KCo4) to yield (by further backcrossing to the homozygotes lacking a functional D-region) mice lacking a functional endogenous heavy chain locus and harboring a human heavy transgene (and preferably also a human light chain transgene). In embodiments where some functional endogenous light chain loci remain (e.g., λ loci), it is generally preferred that transgenes contain transcriptional control sequences that direct high level expression of human light chain (e.g., κ) polypeptides, and thus allow the transgene locus to compete effectively with the remaining endogenous light chain (e.g., λ) loci. For example, the Co4 kappa light chain transgene is generally preferred as compared to pKC1 with regard to the ability to compete effectively with the endogenous λ loci in the transgenic animal.

Example 33

This example describes expansion of the human light chain transgene V gene repertoire by co-injection of a human κ light chain minilocus and a yeast artificial chromosome comprising a portion of the human Vκ locus.
Introduction of Functional Human Light Chain V Segments by Co-Injection of Vκ-Containing YAC DNA and a κ Minilocus An approximately 450 kb YAC clone containing part of the human Vκ locus was obtained as a non-amplified YAC DNA from clone 4×17E1 of the publicly available ICRF YAC library (Larin et al. (1991) *Proc. Natl. Acad. Sci. (U.S.A.)* 88: 4123; Genome Analysis Laboratory, Imperial Cancer Research Fund, London, UK). The 450 kb YAC clone was isolated without prior amplification by standard pulsed-field gel electrophoresis as per the manufacturer's specifications (CHEF DR-II electrophoresis cell, Bio-Rad Laboratories, Richmond, Calif.). Six individual pulse field gels were stained with ethidium bromide and the gel material containing the YAC clone DNA was excised from the gel and then embedded in a new (low melting point agarose in standard gel buffer) gel cast in a triangular gel tray. The resulting triangular gel (containing the six excised YAC-containing gel blocks) was extended at the apex with a narrow agarose gel with 2M NaOAc in addition to the standard electrophoresis buffer. The gel was then placed in an electrophoresis chamber immersed in standard gel buffer. The Y-shaped gel former rises above the surface of the buffer so that current can only flow to the narrow high salt gel portion. A plexiglas block was placed over the high salt gel slice to prevent diffusion of the NaOAc into the buffer. The YAC DNA was then electrophoresed out of the original excised gel sliced (embedded) and into the narrow high salt gel portion. At the point of transition from the low salt gel to the high salt gel, there is a resistance drop that effectively halts the migration of the DNA at the apex of the triangular gel.

Following electrophoresis and staining with ethidium bromide, the concentrated YAC DNA was cut away from the rest of the gel and the agarose was digested with GELase (EpiCentre Technologies, Madison, Wis.). Cesium chloride was then added to the resultant YAC-containing liquid to obtain a density of 1.68 g/ml. This solution was centrifuged at 37,000 rpm for 36 hours to separate the YAC DNA from any contaminating material. 0.5 ml fractions of the resulting density gradient were isolated and the peak DNA fraction was dialyzed against 5 mM Tris (pH 7.4), 5 mM NaCl, 0.1M EDTA. Following dialysis, the concentration of the resulting 0.65 ml solution of YAC DNA was found to contain 2 µg/ml of DNA. This YAC DNA was mixed with purified DNA insert from plasmids pKC1B and pKV4 at a ratio of 20:1:1 (micrograms YAC4×17E1:KC1B:KV4). The resulting 2 µg/ml solution was injected into the pronuclei of half-day B6CBF2 embryos, and 95 surviving microinjected embryos were transferred into the oviducts of pseudopregnant females. Twelve mice which developed from the microinjected embryos were born.

Example 34

This example describes class-switching, somatic mutation, and B cell development in immunized transgenic mice homozygous for an inactivated endogenous immunoglobulin locus and containing the HC1 or HC2 heavy chain transgene(s).

To demonstrate that a human sequence germline configuration minilocus can functionally replace the authentic locus, we bred a mouse strain lacking endogenous IgH with strains containing human germline-configuration IgH transgenes. The two transgene miniloci, HC1 and HC2, include one and four functional variable (V) segments respectively 10 and 16 diversity (D) segments respectively, all six joining (JH) segments, and both the µ and γ1 constant region segments. The miniloci include human cis-acting regulatory sequences—such as the JH-µ intronic enhancer and the µ and γ1 switch sequences—that are closely linked to the coding segments. They also include an additional enhancer element derived from the 3' end of the rat IgH locus. We crossed HC1 and HC2 transgenic mice with stem-cell derived mutant mice that lack JH segments (JHD mice) as described (supra) and cannot therefore undergo functional heavy chain rearrangements. The resulting transgenic-JHD mice contain B cells that are dependent on the introduced heavy chain sequences.
Immunizations and Hybridomas We immunized mice by intraperitoneal injections of 50–100 µg of antigen. Antigens included human carcinoembryonic antigen (CEA; Crystal Chem, chicago, Ill.), hen eggwhite lysozyme (HEL; Pierce, Rockford, Ill.), and keyhole limpet hemocyanin (KLH; Pierce, Rockford, Ill.). For primary injections we mixed the antigen with complete Freund's adjuvant, for subsequent injections we used incomplete Freund's adjuvant (Gibco BRL, Gaithersburg, Md.). We fused spleen cells with the non-secreting mouse myeloma P3×63-Ag8.653 (ATCC, CRL1580). We assayed serum samples and hybridoma supernatants for the presence of specific and non-specific antibody comprising human heavy chain sequences by ELISA. For detection of non-specific antibodies we coated microtiter wells with human heavy chain isotype specific antibody (mouse MAb α human IgG1, clone HP6069, Calbiochem, La Jolla, Calif.; mouse MAb α human IgM, clone CH6, The Binding Site, Birmingham, UK) and developed with peroxidase conjugated antisera (horseradish peroxidase conjugated affinity purified fab fragment from polyclonal goat α human IgG (fc), cat #109-036-098; affinity purified horseradish peroxidase conjugated polyclonal rabbit α human IgM(fc), cat #309-035-095. Jackson Immuno Research, West Grove, Pa.). For detection of antigen-specific antibodies we coated microtiter wells with antigen and developed with peroxidase-conjugated human heavy chain isotype specific antisera. We detected bound peroxidase by incubation with hydrogen peroxide and 2,2'-Azino-bis-(3-Ethylbenzthiazoline-6-Sulfonic Acid, Sigma Chem. Co., St. Louis, Mo.). The reaction product is measured by absorption at 415 nm, and corrected for absorption at 490 nm.

Flow Cytometry

We prepared single cell suspensions from spleen, bone marrow, and peritoneal cavity, and lysed red cells with NH$_4$Cl, as described by Mishell and Shiigi. The lymphocytes are stained with the following reagents: Phycoerythrin conjugated anti-mouse Igκ (clone X36; Becton Dickinson, San Jose, Calif.), FITC conjugated anti-mouse IgD (clone SBA 1, Southern Biotech, Ala.), FITC conjugated anti-mouse CD5 (clone 53-7.3; Becton Dickinson, San Jose, Calif.), FITC conjugated anti-mouse Igλ (clone R26-46; Pharmingen, San Diego, Calif.), and Cy-Chrome conjugated anti-mouse B220 (clone RA3-6B2; Pharmingen, San Diego, Calif.). We analyzed the stained cells using a FACScan flow cytometer and LYSIS II software (Becton Dickinson, San Jose, Calif.). Most macrophages, neutrophils, and residual red cells are excluded by gating on forward and side scatter.

Rescue of B cell Compartment

In the peritoneal cavity of HC1 transgenic-JHD animals we find normal levels of CD5$^+$ B cells and approximately one-quarter the normal level of conventional CD5$^-$ B cells. The transgenic peritoneal CD5$^+$ B cells are similar to the so-called B-1 cells described in normal animals: they are larger than conventional B and T lymphocytes, they express lower levels of B220 than the conventional B cells found in the spleen, and they include a higher proportion of λ light chain expressing cells. Over 90% of the splenic B cells express κ, while up to 50% of the peritoneal B cells express λ. Thus, while the level of conventional B cells is uniformly reduced in all tissues, the level of B-1, which are reported to have a much greater capacity for self-renewal, appears to be normal in the HC1 transgenic-JHD animals.

Class Switching

In transgenic-JHD mice, repeated exposure to antigen results in the production of human γ1 antibodies as well as μ antibodies. We injected human CEA into transgenic-JHD mice at weekly intervals and monitored the serum levels of antigen-specific IgM and IgG1 over a period of four weeks (FIG. 63). At one week there is a detectable IgM response but no IgG1 response. However, the IgG1 response is greater than the IgM response after two weeks, and it continues to increase while the IgM response remains relatively constant. This pattern—an initial IgM reaction followed by an IgG reaction—is typical of a secondary immune response; and it suggests that cis-acting sequences included in the transgene may be responding to cytokines that direct class switching. We have considered three possible mechanisms for expression of non-μ isotypes, each of which have been discussed in the literature. These mechanisms are: alternative splicing, which does not involve deletion of the μ gene; "δ-type" switching, which involved deletion of the μ gene via homologous recombination between flanking repeat sequences; and non-homologous recombination between switch regions. The results of our experiments, described below, are indicative of a switch region recombination model.

Two types of non-deletional alternative splicing mechanisms can be invoked to explain an isotype shift. First, it is possible that a single transcript covering both μ and γ1 is expressed from the transgene; this transcript could be alternatively spliced in response to cytokines induced by exposure to antigen. Alternative, a cytokine induced sterile transcript initiating upstream of γ1 could be trans-spliced to the μ transcript. If either of these mechanisms were responsible for the expression of human γ1 sequences, then we would expect to be able to isolate hybridomas that express both μ and γ1. However, although we have screened several hundred hybridomas expressing either human μ or human γ1, we have not found any such double producer ($\mu^+$, $\gamma1^+$) hybridomas. This indicates that expression of γ1 is accompanied by deletion of the μ gene.

Deletion of the μ gene can be mediated by non-homologous recombination between the μ and γ1 switch regions, or by homologous recombination between the two flanking 400 bp direct repeats (σμ and Σμ) that are included in the HC1 and HC2 transgenes. Deletional recombination between σμ and Σμ has been reported to be responsible for the IgD$^+$, IgM$^-$ phenotype of some human B cells. While the first mechanism, non-homologous switch recombination, should generate switch products of varying lengths, the second mechanism, σμ/Σμ recombination, should always generate the same product. We performed a Southern blot analysis of genomic DNA isolated from three hybridomas (FIG. 64A), one expressing μ and two expressing γ1. We find genomic rearrangements upstream of the transgene γ1 only in the two the γ1 switch regions (FIG. 64B). Furthermore, neither of the observed structures is compatible with homologous recombination between σμ and Σμ. Our results are therefore consistent with a model for γ1 isotype expression mediated by deletional non-homologous recombination between the transgene encoded μ and γ1 switch regions.

Trans-Switching

In addition to human γ1, we find mouse γ in the serum of HC1 and HC2 transgenic-JHD mice. We have also obtained mouse γ expressing hybridomas from these animals. Because the non-transgenic homozygous JHD animals do not express detectable levels of mouse immunoglobulins, we attribute the expression of mouse γ in the HC1 and HC2 transgenic-JHD animals to the phenomenon of trans-switching. All of the transgenic hybridomas that we have analyzed express either mouse or human constant region sequences, but not both. It is therefore unlikely that a trans-splicing mechanism is involved. We used PCR amplification to isolate cDNA clones of trans-switch products, and determined the nucleotide sequence of 10 of the resulting clones (FIG. 65). The 5' oligonucleotide in the PCR amplification is specific for the transgene encoded VH251, and the 3' oligonucleotide is specific for mouse γ1, γ2b, and γ3 sequences. We find examples of trans-switch products incorporating all three of these mouse constant regions.

Somatic Mutation

Figure 7:
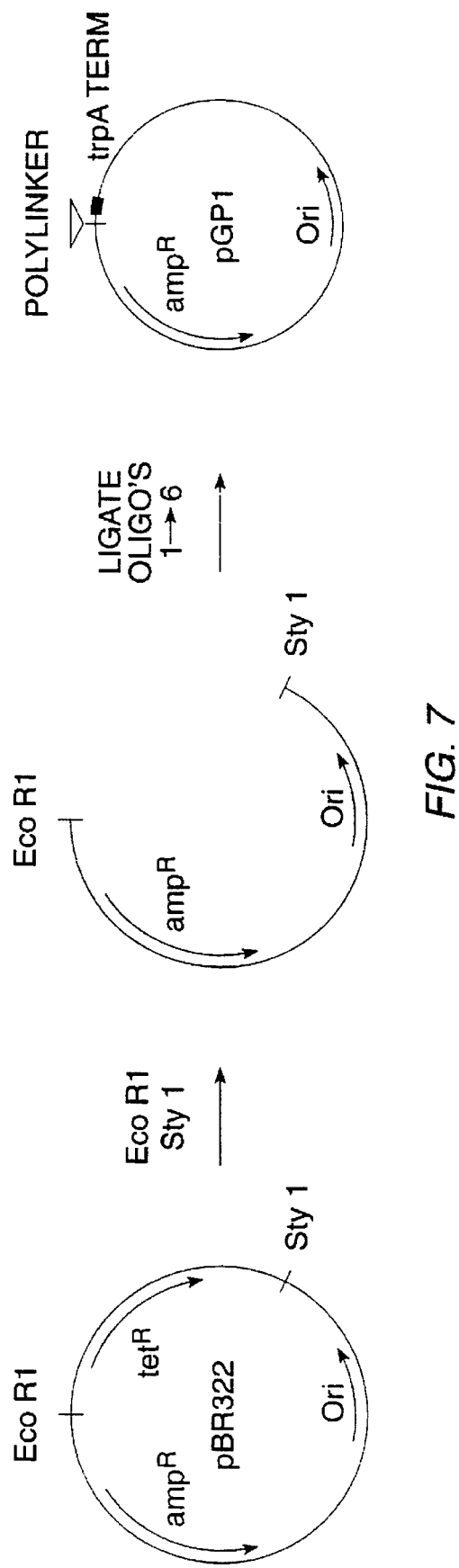
FIG. 7 depicts the construction of pGP1.

Approximately 1% of the nucleotides within the variable regions of the trans-switch products shown in FIG. 7 are not germline encoded. This is presumably due to somatic mutation. Because the mutated sequence has been translocated to the endogenous locus, the cis-acting sequences directing these mutations could be located anywhere 3' of the mouse γ switch. However, as we discuss below, we also observe somatic mutation in VDJ segments that have not undergone such translocations; and this result indicates that sequences required by heavy chain somatic mutation are included in the transgene.

To determine if the HC1 and HC2 constructs include sufficient cis-acting sequences for somatic mutation to occur in the transgenic-JHD mice, we isolated and partially sequenced cDNA clones derived from two independent HC1 transgenic lines and one HC2 line. We find that some of the γ1 transcripts from transgenic-JHD mice contain V regions with extensive somatic mutations. The frequency of these mutated transcripts appears to increase with repeated immunizations. FIGS. 66A and 66B show two sets of cDNA sequences: one set is derived form an HC1 (line 26) transgenic-JHD mouse that we immunized with a single injection of antigen 5 days before we isolated RNA; the second set is derived from an HC1 (line 26) transgenic-JHD mouse that we hyperimmunized by injecting antigen on three different days beginning 5 months before we isolated RNA; the second set is derived from an HC1 (line 26) transgenic-JHD mouse that we hyperimmunized by injecting antigen on three different days beginning 5 months before we isolated RNA. Only 2 of the 13 V regions from the 5 day post-exposure mouse contain any non-germline encoded nucleotides. Each of these V's contains only a single nucleotide change, giving an overall somatic mutation frequency of less than 0.1% for this sample. In contrast, none of the 13 V sequences from the hyperimmunized animal are completely germline, and the overall somatic mutation frequency is 1.6%.

Comparison of µ and γ1 transcripts isolated from a single tissue sample shows that the frequency of somatic mutations is higher in transgene copies that have undergone a class switch. We isolated and partially sequenced 47 independent µ and γ1 cDNA clones from a hyperimmunized CH1 line 57 transgenic-JHD mouse (FIG. 67A and 67B). Most of the µ cDNA clones are unmodified relative to the germline sequence, while over half of the γ1 clones contain multiple non-germline encoded nucleotides. The γ1 expressing cells are distinct from the µ expressing cells and, while the two processes are not necessarily linked, class switching and somatic mutation are taking place in the same subpopulation of B cells.

Although we do not find extensive somatic mutation of the VH251 gene in non-hyperimmunized CH1 transgenic mice, we have found considerable somatic mutation in VH56p1 and VH51p1 genes in a naive HC2 transgenic mouse. We isolated spleen and lymph node RNA from an unimmunized 9 week old female HC2 transgenic animal. We individually amplified γ1 transcripts that incorporate each of the four V regions in the HC2 transgene using V and γ1 specific primers. The relative yields of each of the specific PCR products were VH56p1>>VH51p1>VH4.21>VH251. Although this technique is not strictly quantitative, it may indicate a bias in V segment usage in the HC2 mouse. FIG. 68 shows 23 randomly picked γ1 cDNA sequences derived from PCR amplifications using an equimolar mix of all four V specific primers. Again we observe a bias toward VH56p1 (19/23 clones). In addition, the VH56p1 sequences show considerable somatic mutation, with an overall frequency of 2.1% within the V gene segment. Inspection of the CDR3 sequences reveals that although 17 of the 19 individual VH56p1 clones are unique, they are derived from only 7 different VDJ recombination events. It thus appears that the VH56p1 expressing B cells are selected, perhaps by an endogenous pathogen or self antigen, in the naive animal. It may be relevant that this same gene is over-represented in the human fetal repertoire.

Summary

Upstream cis-acting sequences define the functionality of the individual switch regions, and are necessary for class switching. Our observation—that class switching within the HC1 transgene is largely confined to cells involved in secondary response, and does not occur randomly across the entire B cell population—suggests that the minimal sequences contained with the transgene are sufficient. Because the γ sequences included in this construct begin only 116 nucleotides upstream of the start site of the γ1 sterile transcript, the switch regulatory region is compact.

Our results demonstrate that these important cis-acting regulatory elements are either closely linked to individual γ genes, or associated with the 3' heavy chain enhancer included in the HC1 and HC2 transgenes. Because the HC1 and HC2 inserts undergo transgene-autonomous class switching—which can serve as a marker for sequences that are likely to have been somatically mutated—we were able to easily find hypermutated transcripts that did not originate from translocations to the endogenous locus. We found somatically mutated γ transcripts in three independent transgenic lines (two HC1 lines and one HC2 line). It is therefore unlikely that sequences flanking the integration sites of the transgene affect this process; instead, the transgene sequences are sufficient to direct somatic mutation.

Example 35

This example describes the generation of hybridomas from mice homozygous for an inactivated endogenous immunoglobulin locus and containing transgene sequences encoding a human sequence heavy chain and human sequence light chain. The hybridomas described secrete monoclonal antibodies comprising a human sequence heavy chain and a human seqeunce light chain and bind to a predetermined antigen expressed on T lymphocytes. The example also demonstrates the capacity of the mice to make a human sequence antibody in response to a human-derived immunogen, human CD4, and the suitability of such mice as a source for making hybridomas secreting human sequence monoclonal antibodies reactive with human antigens.

A. Generation of Human Ig Monoclonal Antibodies Derived from HC1 Transgenic Mice Immunized with a Human CD4 Antigen A transgenic mouse homozygous for a functionally disrupted $J_H$ locus and harboring a transgene capable of rearranging to encode a human sequence heavy chain and a transgene capable of rearranging to encode a human sequence light chain was immunized. The genotype of the mouse was HC1-26$^+$ KC1e-1536$^+$ $J_H D^{+/+}$ $J_K D^-$, indicating homozygosity for murine heavy chain inactivation and the presence of germline copies of the HC1 human sequence heavy chain transgene and the KC1e human sequence light chain transgene.

The mouse was immunized with a variant of the EL4 cell line (ATCC) expressing a mouse-human hybrid CD4 molecule encoded by a stably transfected polynucleotide. The expressed CD4 molecule comprises a substantially human-like CD4 sequence. Approximately 5×10$^6$ cells in 100 µl of PBS accompanied by 100 µl of Complete Freund's Adjuvant (CFA) were introduced into the mouse via intraperitoneal injection on Day 0. The inoculation was repeated on Days 7, 14, 21, 28, 60, and 77, with test bleeds on Days 18, 35, and 67. The spleen was removed on Day 81 and approximately 7.2×10$^7$ spleen cells were fused to approximately 1.2×10$^7$ fusion partner cells (P3×63Ag8.653 cell line; ATCC) by standard methods (PEG fusion) and cultured in RPMI 1640 15% FCS, 4 mM glutamine, 1 mM sodium pyruvate plus HAT and PSN medium. Multiple fusions were performed.

Hybridomas were grown up and supernatants were tested with ELISA for binding to a commercial source of purified recombinant soluble human sequence CD4 expressed in CHO cells (American Bio-Technologies, Inc. (ABT), Cambridge, Mass.) and/or CD4 obtained from NEN-DuPont. The ABT sample contained a purified 55 kD human CD4 molecule comprised the $V_1$ through $V_3$ domains of human CD4. The recombinant human sequence CD4 (produced in CHO-K1 cells) was adsorbed to the assay plate and used to capture antibody from hybridoma supernatants, the captured antibodies were then evaluated for binding to a panel of antibodies which bind either human μ, human κ, human γ, murine μ, or murine κ.

One hybridoma was subcloned from its culture plate well, designated 1F2. The 1F2 antibody bound to the ABT CD4 preparation, was positive for human μ and human κ, and was negative for human γ, mouse γ, and mouse κ.

B. Generation of Human Ig Monclonal Antibodies Derived from HC2 Transgenic Mice Immunized with Human CD4 and Human IgE The heavy chain transgene, HC2, is shown in FIG. 56 and has been described supra (see, Example 34).

The human light chain transgene, KCo4, depicted in FIG. 56 is generated by the cointegration of two individually cloned DNA fragments at a single site in the mouse genome. The fragments comprise 4 functional Vκ segments, 5J segments, the Cκ exon, and both the intronic and downstream enhancer elements (see Example 21) (Meyer and Neuberger (1989), *EMBO J.* 8:1959–1964; Judde and Max (1992), *Mol. Cell Biol.* 12:5206–5216). Because the two fragments share a common 3 kb sequence (see FIG. 56), they can potentially integrate into genomic DNA as a contiguous 43 kb transgene, following homologous recombination between the overlapping sequences. It has been demonstrated that such recombination events frequently occur upon microinjection of overlapping DNA fragments (Pieper et al. (1992), *Nucleic Acids Res.* 20:1259–1264). Co-injected DNA's also tend to co-integrate in the zygote, and the sequences contained within the individually cloned fragments would subsequently be jointed by DNA rearrangement during B cell development. Table 11 shows that transgene inserts from at least 2 of the transgenic lines are functional. Examples of VJ junctions incorporating each of the 4 transgene encoded V segments, and each of the 5J segments, are represented in this set of 36 clones.

TABLE 11

Human light chain V and J segment usage in KCo4 transgenic mice. The table shows the number of PCR clones, amplified from cDNA derived from two transgenic lines, which contain the indicated human kappa sequences. cDNA was synthesized using spleen RNA isolated from w individual KCo4 transgenic mice (mouse #8490, 3 mo., male, KCo4 line 4437; mouse #8867, 2.5 mo., female, KCo4 line 4436). The cDNA was amplified by PCR using a $C_κ$ specific oligonucleotide, 5'TAG AAG GAA TTC AGC AGG CAC ACA ACA GAG GCA GTT CCA 3', AND A 1:3 mixture of the following 2 $V_κ$ specific oligonucleotides: 5' AGC TTC TCG AGC TCC TGC TGC TCT GTT TCC CAG GTG CC 3' and 5' CAG CTT CTC GAC CTC CTG CTA CTC TGG CTC (C,A)CA GAT ACC 3'. The PCR product was digested with XhoI and EcoRI, and cloned into a plasmid vector. Partial nucleotide sequences were determined by the dideoxy chain termination method for 18 randomly picked clones from each animal. The sequences of each clone were compared to the germline sequence of the unrearranged transgene.

| line | $V_κ65.5$ | $V_κ65.8$ | $V_κ65.15$ | $V_κ65.3$ | $J_κ1$ | $J_κ2$ | $J_κ3$ | $J_κ4$ | $J_κ5$ |
|---|---|---|---|---|---|---|---|---|---|
| #4436 | 0 | 11 | 4 | 3 | 14 | 1 | 0 | 2 | 1 |
| #4437 | 1 | 3 | 7 | 7 | 5 | 2 | 1 | 7 | 3 |

Twenty-three light chain minilocus positive and 18 heavy chain positive mice developed from the injected embryos. These mice, and their progeny, were bred with mice containing targeted mutations in the endogenous mouse heavy (strain JHD) and κ light chain loci (strain JCKD) to obtain mice containing human heavy and κ light chain in the absence of functional mouse heavy and κ light chain loci. These mice contain only λB cells.

Table 13 show that somatic mutation occurs in the variable regions of the transgene-encoded human heavy chain transcripts of the transgenic mice. Twenty-three cDNA clones from a HC2 transgenic mouse were partially sequenced to determine the frequency of non-germline encoded nucleotides within the variable region. The data include only the sequence of V segment codons 17–94 from each clone, and does not include N regions. RNA was isolated from the spleen and lymph node of mouse 5250 (HC2 line 2550 hemizygouc, JHD homozygous). Single-stranded cDNA was synthesized and γ transcripts amplified by PCR as described [references]. The amplified cDNA was cloned into plasmid vectors, and 23 randomly picked clones were partially sequenced by the dideoxy chain-termination method. The frequency of PCR-introduced nucleotide changes is estimated from constant region sequence as <0.2%.

TABLE 12

The Variable Regions of Human γ Transcripts in HC2 Transgenic Mice Contain Non-Germline-Encoded Nucleotides

| VH Segment | Number of clones | Number of non-germline encoded nucleotides | Frequency of non-germline-encoded nucleotides (%) |
|---|---|---|---|
| VH251 | 0 | — | — |
| VH56P1 | 10 | 100 | 2.1 |
| VH51P1 | 1 | 5 | 2.0 |
| VH4.21 | 3 | 0 | 0.0 |

Flow Cytometry

We analyzed the stained cells using a FACScan flow cytometer and LYSIS II software (Becton Dickinson, San Jose, Calif.). Spleen cells were stained with the following reagents: propidium iodide (Molecular Probes, Eugene, Oreg.), phycoerythrin conjugated α-human Igκ (clone HP6062; Caltag, S. San Francisco, Calif.), phycoerythrin conjugated α-mouse Igκ (clone X36; Becton Dickinson, San Jose, Calif.), FITC conjugated α-mouse Igλ (clone R26-46; Pharmingen, San diego, Calif.), FITC conjugated α-mouse Igμ (clone R6-60.2; Pharmingen, San Diego, Calif.), FITC conjugated α-human Igμ (clone G20-127; Pharmingen, San Diego, Calif.), and Cy-Chrome conjugated α-mouse B220 (clone RA3-6B2; Pharmingen, San Diego, Calif.).

Expression of Human Ig Transgenes

FIG. 69 shows a flow cytometric analysis of spleen cells from KCo4 and HC2 mice that are homozygous for both the JHD and JCKD mutations. The human sequence HC2 transgene rescued B cell development in the JHD mutant background, restoring the relative number of B220$^+$ cells in the spleen to approximately half that of a wild type animal. These B cells expressed cell surface immunoglobulin receptors that used transgene encoded heavy chain. The human KCo4 transgene was also functional, and competed successfully with the intact endogenous λ light chain locus. Nearly 95% of the splenic B cells in JHD/JCKD homozygous mutant mice that contain both heavy and light chain human transgenes (double transgenic) expressed completely human cell surface IgMκ.

Serum Ig levels were determined by ELISA done as follows: human μ: microtiter wells coated with mouse Mab α human IgM (clone CH6, The Binding Site, Birmingham, UK) and developed with peroxidase conjugated rabbit α human IgM(fc) (cat #309-035-095, Jackson Immuno Research, West Grove, Pa.). Human γ: microtiter wells coated with mouse MAb α human IgG1 (clone HP6069, Calbiochem, La Jolla, Calif.) and developed with peroxidase conjugated goat e human IgG(fc) (cat #109-036-098, Jackson Immuno Research, West Grove, Pa.). Human κ: microtiter wells coated with mouse Mab α human Igκ (cat #0173, AMAC, Inc. Igκ (cat#A7164, Sigma Chem. Co., St. Louis, Mo.). Mouse γ: microtiter wells coated with goat α mouse IgG (cat #115-006-071, Jackson Immuno Research, West Grove, Pa.). Mouse λ: microtiter wells coated with rat MAb α mouse Igλ (cat #02171D, Pharmingen, San Diego, Calif.) and developed with peroxidase conjugated rabbit α mouse IgM(fc) (cat #309-035-095, Jackson Immuno Research, West Grove, Pa.). Bound peroxidase is detected by incubation with hydrogen peroxide and 2,2'-Azino-bis-)3-Ethylbenzthiazoline-6-Sulfonic Acid, Sigma Chem. Co., St. Louis, Mo.). The reaction product is measured by absorption at 415 nm.

The double transgenic mice also express fully human antibodies in the serum. FIG. 70 shows measured serum levels of immunoglobulin proteins for 18 individual double transgenic mice, homozygous for endogenous heavy and kappa light chain inactivations, derived from several different transgenic founder animals. We found detectable levels of human μ, γ1, and κ. We have shown supra that the expressed human γ1 results from authentic class switching by genomic recombination between the transgene μ and γ1 switch regions. Furthermore, we have found that intra-transgene class switching was accompanied by somatic mutation of the heavy chain variable regions. In addition to human immunoglobulins, we also found mouse γ and λ in the serum. The present of mouse λ protein is expected because the endogenous locus is completely intact. We have shown elsewhere that the mouse γ expression is a consequence of trans-switch recombination of transgene VDJ segments into the endogenous heavy chain locus. This trans-switching phenomenon, which was originally demonstrated for wild-type heavy chain alleles and rearranged VDJ transgenes (Durdik et al. (1989), Proc. Natl. Acad. Sci. USA 86:2346–2350; Gerstein et al. (1990), Cell 63:537–548), occurs in the mutant JHD background because the downstream heavy chain constant regions and their respective switch elements are still intact.

The serum concentration of human IgMκ in the double transgenic mice was approximately 0.1 mg/ml, with very little deviation between animals or between lines. However, human γ1, mouse γ, and mouse λ levels range from 0.1 to 10 micrograms/mi. The observed variation in γ levels between individual animals may be a consequence of the fact that γ is an inducible constant region. Expression presumably depends on factors such as the health of the animal, exposure to antigens, and possibly MHC type. The mouse λ serum levels are the only parameter that appears to correlate with individual transgenic lines. KCo4 line 4436 mice which have the fewest number of copies of the transgene per integration (approximately 1–2 copies) have the highest endogenous λ levels, while KCo4 line 4437 mice (~10 copies per integration) have the lowest λ levels. This is consistent with a model in which endogenous λ rearranges subsequent to the κ transgene, and in which the serum λ level is not selected for, but is instead a reflection of the relative size of the precursor B cell pool. Transgene loci containing multiple light chain inserts may have the opportunity to undergo more than one V to J recombination event, with an increased probability that one of them will be functional. Thus high copy lines will have a smaller pool of potential λ cells.

Immunizations with Human CD4 and IgE

To test the ability of the transgenic B cells to participate in an immune response, we immunized double transgenic mice with human protein antigens, and measured serum levels of antigen specific immunoglobulins by ELISA. Mice were immunized with 50 μg recombinant sCD4 (cat. #013101, American Bio-Technologies Inc., Cambridge, Mass.) covalently linked to polystyrene beads (cat #08226, Polysciences Inc., Warrington, Pa.) in complete Freund's adjuvant by intraperitoneal injection. Each of the mice are homozygous for disruptions of the endogenous μ and κ loci, and hemizygous for the human heavy chain transgene HC2 line 2500 and human κ light chain transgene KCo4 line 4437.

Methods

Serum samples were diluted into microtiter wells coated with recombinant sCD4. Human antibodies were detected with peroxidase conjugated rabbit α human IgM(fc) (Jackson Immuno Research, West Grove, Pa.) or peroxidase conjugated goat anti-human Igκ (Sigma, St. Louis, Mo.).

FIG. 71A shows the primary response of transgenic mice immunized with recombinant human soluble CD4. All four of the immunized animals show an antigen-specific human IgM response at one week. The CD4-specific serum antibodies comprise both human μ heavy chain and human κ light chain.

To evaluate the ability of the HC2 transgene to participate in a secondary response, we hyperimmunized the transgenic mice by repeated injection with antigen, and monitored the heavy chain isotype of the induced antibodies. Mice homozygous for the human heavy chain transgene HC2 and human κ light chain transgene KCo4 were immunized with 25 μg of human IgEκ (The Binding Site, Birmingham, UK)

in complete Freund's adjuvant on day=0. Thereafter, animals were injected with IgEκ in incomplete Freund's adjuvant at approximately weekly intervals. Serum samples were diluted 1:10, and antigen-specific ELISAs were performed on human IgE, λ coated plates.

FIG. 71B shows a typical time course of the immune response from these animals: we injected double transgenic mice with human IgE in complete Freund's adjuvant, followed by weekly boosts of IgE in incomplete Freund's adjuvant. The initial human antibody response was IgMκ, followed by the appearance of antigen specific human IgGκ. The induced serum antibodies in these mice showed no cross-reactivity to human IgM or BSA. The development, over time, of a human IgG We have also tested the ability of the heavy chain transgene to undergo class switching in vitro: splenic B cells purified form animals hemizygous for the same heavy chain construct (HC2, line 2550) switch from human IgM to human IgG1 in the presence of LPS and recombinant mouse IL-4. However, in vitro switching did not take place in the presence of LPS and recombinant mouse IL-2, or LPS alone.

We find human IgM-expressing cells in the spleen, lymph nodes, peritoneum, and bone marrow of the double-transgenic/double-knockout (0011) mice. Although the peritoneal cavity contains the normal number of B cells, the absolute number of transgenic B cells in the bone marrow and spleen is approximately 10–50% of normal. The reduction may result from a retardation in transgene-dependent B cell development. The double-transgenic/double-knockout (0011) mice also express fully human antibodies in the serum, with significant levels of human μ, γ1, and κ in these mice. The expressed human γ1 results from authentic class switching by genomic recombination between the transgene μ and γ1 switch regions. Furthermore, the intratransgene class switching is accompanied by somatic mutation of the heavy chain variable regions encoded by the transgene. In addition to human immunoglobulins, we find mouse μ and mouse λ in these mice. The mouse μ expression appears to be a result of trans-switching recombination, wherein transgene VDJ gene is recombined into the endogenous mouse heavy chain locus. Trans-switching, which was originally observed in the literature for wild-type heavy chain alleles and rearranged VDJ transgenes, occurs in our $J_H^{-/-}$ background because the mouse downstream heavy chain constant regions and their respective switch elements are still intact.

To demonstrate the ability of the transgenic B cells to participate in an immune response, we immunized the 0011 mice with human protein antigens, and monitored serum levels of antigen-specific immunoglobulins. The initial human antibody response is IgM, followed by the expression of antigen-specific human IgG (FIG. 71B and FIG. 73). The lag before appearance of human IgG antibodies is consistent with an association between class-switching and a secondary response to antigen.

In a transgenic mouse immunized with human CD4, human IgG reactivity to the CD4 antigen was detectable at serum concentrations ranging from $2 \times 10^{-2}$ to $1.6 \times 10^{-4}$.

Identification of Anti-Human CD4 Hybridomas

A transgenic mouse homozygous for the human heavy chain transgene HC2 and human κ light chain transgene KCo4 were immunized with 20 μg of recombinant human CD4 in complete Freund's adjuvant on day 0. Thereafter, animals were injected with CD4 in incomplete Freund's adjuvant at approximately weekly intervals. FIG. 73 shows human antibody response to human CD4 in serum of the transgenic mouse. Serum samples were diluted 1:50, and antigen-specific ELISAs were performed on human CD4 coated plates. Each line represents individual sample determinations. Solid circles represent IgM, open squares represent IgG.

A mouse of line #7494 (0012; HC1-26+; JHD++; JKD++; KC2-1610++) was immunized on days 0, 13, 20, 28, 33, and 47 with human CD4, and produced anti-human CD4 antibodies comprised of human κ and human μ or γ.

By day 28, human μ and human κ were found present in the serum. By day 47, the serum response against human CD4 comprised both human μ and human γ, as well as human κ. On day 50, splenocytes were fused with P3×63-Ag8.653 mouse myeloma cells and cultured. Forty-four out of 700 wells (6.3%) contained human γ and/or κ anti-human CD4 monoclonal antibodies. Three of these wells were confirmed to contain human γ anti-CD4 monoclonal antibodies, but lacked human κ chains (presumably expressing mouse λ). Nine of the primary wells contained fully human IgMκ anti-CD4 monoclonal antibodies, and were selected for further characterization. One such hybridoma expressing fully human IgMκ anti-CD4 monoclonal antibodies was designated 2C11-8.

Primary hybridomas were cloned by limiting dilution and assessed for secretion of human μ and κ monoclonal antibodies reactive against CD4. Five of the nine hybridomas remained positive in the CD4 ELISA. The specificity of these human IgMκ monoclonal antibodies for human CD4 was demonstrated by their lack of reactivity with other antigens including ovalbumin, bovine serum albumin, human serum albumin, keyhole limpet hemacyanin, and carcinoembryonic antigen. To determine whether these monoclonal antibodies could recognize CD4 on the surface of cells (i.e., native CD4), supernatants from these five clones were also tested for reactivity with a CD4+ T cell line, Sup T1. Four of the five human IgMκ monoclonal antibodies reacted with these CD4+ cells. To further confirm the specificity of these IgMκ monoclonal antibodies, freshly isolated human peripheral blood lymphocytes (PBL) were stained with these antibodies. Supernatants from clones derived from four of the five primary hybrids bound only to CD4+ lymphocytes and not to CD8+ lymphocytes (FIG. 72).

FIG. 72 shows reactivity of IgMκ anti-CD4 monoclonal antibody with human PBL. Human PBL were incubated with supernatant from each clone or with an isotype matched negative control monoclonal antibody, followed by either a mouse anti-human CD4 monoclonal antibody conjugated to PE (top row) or a mouse anti-human CD8 Ab conjugated to FITC (bottom row). Any bound human IgMκ was detected with a mouse anti-human μ conjugated to FITC or to PE, respectively. Representative results for one of the clones, 2C11-8 (right side) and for the control IgMκ (left side) are shown. As expected, the negative control IgMκ did not react with T cells and the goat anti-human μ reacted with approximately 10% of PBL, which were presumably human B cells.

Good growth and high levels of IgMκ anti-CD4 monoclonal antibody production are important factors in choosing a clonal hybridoma cell line for development. Data from one of the hybridomas, 2C11-8, shows that up to 5 pg/cell/d can be produced (FIG. 74). Similar results were seen with a second clone. As is commonly observed, production increases dramatically as cells enter stationary phase growth. FIG. 74 shows cell growth and human IgMκ anti-CD4 monoclonal antibody secretion in small scale cultures. Replicate cultures were seeded at $2 \times 10^5$ cells/ml in a total volume of 2 ml. Every twenty-four hours thereafter for four days, cultures were harvested. Cell growth was determined by counting viable cells and IgMκ production was quantitated by an ELISA for total human μ (top panel). The production per cell per day was calculated by dividing the amount of IgMκ by the cell number (bottom panel).

FIG. 75 shows epitope mapping of a human IgMκ anti-CD4 monoclonal antibody. Competition binding flow cytometric experiments were used to localize the epitope recognized by the IgMκ anti-CD4 monoclonal antibody, 2C11-8. For these studies, the mouse anti-CD4 monoclonal antibodies, Leu3a and RPA-T4, which bind to unique, nonoverlapping epitopes on CD4 were used. PE fluorescence of CD4+ cells preincubated with decreasing concentrations of either RPA-TA or Leu-3a followed by staining with 2C11-8 detected with PE-conjugated goat anti-human IgM. 1There was concentration-dependent competition for the binding of the human IgMκ anti-CD4 monoclonal antibody 2C11-8 by Leu3a but not by RPA-T4 (FIG. 75). Thus, the epitope recognized by 2C11-8 was similar to or identical with that recognized by monoclonal antibody Leu3a, but distinct from that recognized by RPA-T4.

In summary, we have produced several hybridoma clones that secrete human IgMκ monoclonal antibodies that specifically react with native human CD4 and can be used to discriminate human PBLs into CD4$^+$ and CD4$^-$ subpopulations. At least one of these antibodies binds at or near the epitope defined by monoclonal antibody Leu3a. Monoclonal antibodies directed to this epitope have been shown to inhibit a mixed leukocyte response (Engleman et al., J. Exp. Med. (1981) 153:193). A chimeric version of monoclonal antibody Leu3a has shown some clinical efficacy in patients with mycosis fungoides (Knox et al. (1991) Blood 77:20).

We also isolated hybridoma cell lines from one of the mice that responded to human CD4 immunization. Five of the cloned hybridomas secrete human IgGκ (human γ1/human κ) antibodies that bind to recombinant human CD4 and do not crossreact (as measured by ELISA) with a panel of other glycoprotein antigens. The association and dissociation rates of the immunizing human CD4 antigen for the monoclonal antibodies secreted by two of the IgGκ hybridomas, 4E4.2 and 2C5.1, were determined. The experimentally-derived binding constants ($K_a$) were approximately $9 \times 10^7$ M$^{-1}$ and $8 \times 10^7$ M$^{-1}$ for antibodies 4E4.2 and 2C5.1, respectively. These $K_a$ values fall within the range of murine IgG anti-human CD4 antibodies that have been used in clinical trials by others (Chen et al. (1993) Int. Immunol. 6: 647).

We conclude that human immunoglobulin-expressing B cells undergo development and respond to antigen in the context of a mouse immune system. Antigen responsivity leads to immunoglobulin heavy chain isotype switching and variable region somatic mutation. We has also demonstrated that conventional hybridoma technology can be used to obtain monoclonal human sequence antibodies from these mice. Therefore, these transgneic mice represent a source of human antibodies against human target antigens.

Example 36

This example describes the generation of transgenic mice homozygous for an inactivated endogenous heavy chain and κ chain locus and harboring a transgene capable of isotype switching to multiple downstream human $C_H$ genes. The example also demonstrates a cloning strategy for assembling large transgenes (e.g., 160 kb) by co-microinjection of multiple DNA fragments comprising overlapping homologous sequence joints (see FIG. 76), permitting construction of a large transgene from more than two overlapping fragments by homologous recombination of a plurality of homology regions at distal ends of the set of fragments to be assembled in vivo, such as in a microinjected ES cell or its clonal progeny. The example also shows, among other things, that isolated lymphocytes from the transgenic animals can be induced to undergo isotype switching in vitro, such as with IL-4 and LPS.

A set of five different plasmid clones was constructed such that the plasmid inserts could be isolated, substantially free of vector sequences; and such that the inserts together form a single imbricate set of overlapping sequence spanning approximately 150 kb in length. This set includes human V, D, J, μ, γ3, and γ1 coding sequences, as well as a mouse heavy chain 3' enhancer sequence. The five clones are, in 5' to 3' order: pH3V4D, pCOR1xa, p11-14, pP1-570, and pHP-3a (FIG. 76). Several different cloning vectors were used to generate this set of clones. Some of the vectors were designed specifically for the purpose of building large transgenes. These vectors (pGP1a, pGP1b, pGP1c, pGP1d, pGP1f, pGP2a, and pGP2b) are pBR322-based plasmids that are maintained at a lower copy number per cell than the pUC vectors (Yanisch-Perron et al. (1985) Gene 33: 103–119). The vectors also include trpA transcription termination signals between the polylinker and the 3' end of the plasmid β-lactamase gene. The polylinkers are flanked by restriction sites for the rare-cutting enzyme NotI; thus allowing for the isolation of the insert away from vector sequences prior to embryo microinjection. Inside of the NotI sites, the polylinkers include unique XhoI and SalI sites at either end. The pGP1 vectors are described in Taylor et al. (1992) Nucleic Acids Res. 23: 6287. To generate the pGP2 vectors, pGP1f was first digested with AlwNI and ligated with the synthetic oligonucleotides o-236 and o-237 (o-236, 5'- ggc gcg cct tgg cct aag agg cca -3'; o-237, 5'- cct ctt agg cca agg cgc gcc tgg -3') The resulting plasmid is called pGP2a. Plasmid pGP2a was then digested with KpnI and EcoRI, and ligated with the oligonucleotides o-288 and o-289 (o-288, 5'- aat tca gta tcg atg tgg tac -3'; o-289, 5'- cac atc gat act g -3') to create pGP2b (FIGS. 77A and FIG. 77B).

The general scheme for transgene construction with the pGP plasmids is outlined in FIG. 78 (paths A and B). All of the component DNA fragments are first cloned individually in the same 5' to 3' orientation in pGP vectors. Insert NotI, XhoI and SalI sites are destroyed by oligonucleotide mutagenesis or if possible by partial digestion, polymerase fill-in, and blunt end ligation. This leaves only the polylinker derived XhoI and SalI sites at the 5' and 3' ends of each insert. Individual inserts can then be combined stepwise by the process of isolating XhoI/SalI fragments from one clone and inserting the isolated fragment into either the 5' XhoI or 3' SalI site of another clone (FIG. 78, path A). Transformants are then screened by filter hybridization with one or more insert fragments to obtain the assembled clone. Because XhoI/SalI joints cannot be cleaved with either enzyme, the resulting product maintains unique 5' XhoI and 3' SalI sites, and can be used in the step of the construction. A variation of this scheme is carried out using the vectors pGP2a and pGP2b (FIG. 78, path B). These plasmids includes an SfiI site between the ampicillin resistance gene and the plasmid origin of replication. By cutting with SfiI and XhoI or SalI, inserts can be isolated together with either the drug resistance sequence or the origin of replication. One SfiI/XhoI fragment is ligated to one SfiI/SalI fragment in each step of the synthesis. There are three advantages to this scheme: (i) background transformants are reduced because sequences from both fragments are required for plasmid replication in the presence of ampicillin; (ii) the ligation can only occur in a single 5' to 3' orientation; and (iii) the SfiI ends are not self-compatible, and are not compatible with SalI or XhoI, thus reducing the level of non-productive ligation. The disadvantage of this scheme is that insert SfiI sites must be removed as well as NotI, XhoI, and SalI sites. These medium copy vectors are an improvement over the commonly used pUC derived cloning vectors. To compare the ability of these vectors to maintain large DNA inserts, a 43 kb XhoI fragment comprising the human JH/Cμ region was ligated into the SalI site of pSP72 (Promega, Madison, Wis.), pUC19 (BRL, Grand Island, N.Y.), and pGP1f. Transformant colonies were transferred to nitrocellulose and insert containing clones were selected by hybridization with radiolabeled probe. Positive clones were grown overnight in 3 ml media and DNA isolated: EcoRI digestion of the resulting DNA reveals that all the pSP72 and pUC19 derived clones deleted the insert (FIG. 79); however, 12 of the 18 pGP1f derived clones contained intact inserts. Both orientations are represented in these 12 clones.

The construction and isolation of the five clones (pH3V4D, pCOR1xa, p11-14, pP1-570, and pHP-3a) used to generate the HCo7 transgene is outlined below.

pH3V4D

Germline configuration heavy chain variable gene segments were isolated from phage 1 genomic DNA libraries using synthetic oligonucleotide probes for VH1 and VH3 classes. The VH1 class probe was o-49:

5'- gtt aaa gag gat ttt att cac ccc tgt gtc ctc tcc aca ggt gtc -3'

The VH3 class probe was o-184:

5'- gtt tgc agg tgt cca gtg t(c,g)a ggt gca gct g(g,t)t gga gtc (t,c)(g,c)g -3'

Positively hybridizing clones were isolated, partially restriction mapped, subcloned and partially sequenced. From the nucleotide sequence it was determined that one of the VH1 clones isolated with the o-49 probe encoded a VH gene segment, 49.8, comprising an amino acid sequence identical to that contained in the published sequence of the hv1263 gene (Chen et al. (1989) Arthritis Rheum. 32: 72). Three of the VH3 genes, 184.3, 184.14, and 184.17, that were isolated with the o-184 probe contained sequences encoding identical amino acid sequences to those contained in the published for the VH genes DP-50, DP-54, and DP-45 (Tomlinson et al. (1992) J. Mol. Biol. 227: 776). These four VH genes were used to build the pH3V4D plasmid.

The 184.3 gene was found to be contained within a 3 kb BamHI fragment. This fragment was subcloned into the plasmid vector pGP1f such that the XhoI site of the polylinker is 5' of the gene, and the SalI site is 3'. The resulting plasmid is called p184.3.36f. The 184.14 gene was found to be contained within a 4.8 kb HindIII fragment. This fragment was subcloned into the plasmid vector pUC19 in an orientation such that the gene could be further isolated as a 3.5 kb fragment by XhoI/SalI digestion at a genomic XhoI site 0.7 kb upstream of the gene and a polylinker derived SalI site 3' of the gene. The resulting plasmid is called p184.14.1. The 184.17 gene was found to be contained within a 5.7 kb HindIII fragment. This fragment was subcloned into the plasmid vector pSP72 (Promega, Madison, Wis.) in an orientation such that the polylinker derived XhoI and SalI sites are, respectively, 5' and 3' of the gene. The insert of this plasmid includes an XhoI site at the 3' end of the gene which was eliminated by partial digestion with XhoI, Klenow fragment filling-in, and religation. The resulting plasmid is called p184.17SK. The 49.8 gene was found to be contained within 6.3 kb XbaI fragment. This fragment was subcloned into the plasmid vector pNN03, such that the polylinker derived XhoI and ClaI sites are, respectively, 5' and 3' of the gene, to create the plasmid pV$_H$49.8 (Taylor et al. (1994) International Immunol. 6: 579). The XhoI/ClaI insert of pVH49.8 was then subcloned into pGP1f to create the plasmid p49.8f, which includes unique XhoI and SalI sites respectively at the 5' and 3' end of the 49.8 gene.

The 3.5 kb XhoI/SalI fragment of p184.14.1 was cloned into the XhoI site of p184.3.36f to generate the plasmid pRMV$_H$1, which includes both the 184.14 and the 184.3 genes in the same orientation. This plasmid was digested with XhoI and the 5.7 kb XhoI/SalI fragment of p184.17SK was inserted to create the plasmid pRMVH2, which contains, from 5' to 3', the three VH genes 184.17, 184.14, and 184.3, all in the same orientation. The plasmid pRMVH2 was then cut with XhoI, and the 6.3 kb XhoI/SalI insert of p49.8f inserted to create the plasmid pH3VH4, which contains, from 5' to 3', the four VH genes 49.8, 184.17, 184.14, and 184.3, all in the same orientation.

The 10.6 kb XhoI/EcoRV insert of the human D region clone pDH1 (described supra; e.g., in Example 12) was cloned into XhoI/EcoRV digested pGPe plasmid vector to create the new plasmid pDH1e. This plasmid was then digested with EcoRV and ligated with a synthetic linker fragment containing a SalI site (5'- ccg gtc gac ccg -3'). The resulting plasmid, pDH1es, includes most of the human D1 cluster within an insert that can be excised with XhoI and SalI, such that the XhoI site is on the 5' end, and the SalI site is on the 3' end. This insert was isolated and cloned into the SalI site of pH3VH4 to create the plasmid pH3VH4D, which includes four germline configuration human VH gene segments and 8 germline configuration human D segments, all in the same 5' to 3' orientation. The insert of this clone can be isolated, substantially free of vector sequences, by digestion with NotI.

pCOR1xa

The plasmid pCOR1 (described supra) which contains a 32 kb XhoI insert that includes 9 human D segments, 6 human J segments, the Jμ intronic heavy chain enhancer, the μ switch region, and the Cμ coding exons—was partially digested with XhoI, Klenow treated, and a synthetic SalI linker ligated in to produce the new plasmid pCOR1xa, which has a unique XhoI site at the 5' end and a unique SalI site at the 3' end. Both pCOR1 and pCOR1xa contain a 0.6 kb rat heavy chain 3' enhancer fragment at the 3' end, which is included in the insert if the plasmid is digested with NotI instead of XhoI or XhoI/SalI.

pP1-570

A phage P1 library (Genome Systems Inc., St. Louis, Mo.) was screened by PCR using the oligonucleotide primer pair:

5'- tca caa gcc cag caa cac caa g -3'
5'- aaa agc cag aag acc ctc tcc ctg -3'

This primer pair was designed to generate a 216 bp PCR product with a human γ gene template. One of the P1 clones identified was found to contain both the human γ3 and γ1 genes within an 80 kb insert. The insert of this clone, which is depicted in FIG. 80, can be isolated, substantially free of vector sequences, by digestion with NotI and SalI.

p11-14

Restriction mapping of the human γ3/γ1 clone P1-570 revealed a 14 kb BamHI fragment near the 5' end of the insert. This 14 kb fragment was subcloned into the plasmid vector pGP1f such that the polylinker derived SalI site is adjacent to the 5' end of the insert. The resulting plasmid is called pB14. Separately, an 11 kb NdeI/SpeI genomic DNA fragment covering the 3' end of the human μ gene and the 5' end of the human δ gene, derived from the plasmid clone pJ1NA (Choi et al. (1993) *Nature Genetics* 4: 117), was subcloned into the SalI site of pBluescript (Stratagene, LaJolla, Calif.) using synthetic oligonucleotide adapters. The resulting SalI insert was then isolated and cloned into the SalI site of pB14 such that the relative 5' to 3' orientation of the μ fragment from pJ1NA is the same as that of the γ fragment from P1-570. The resulting clone is called p11-14. The insert of this clone can be isolated, substantially free of vector sequences, by digestion with NotI.

pHP-3a

The mouse heavy chain 3' enhancer (Dariavach et al. (1991) *Eur. J. Immunol.* 21: 1499; Lieberson et al. (1991) *Nucleic Acids Res.* 19: 933) was cloned from a balb/c mouse genomic DNA phage λ library. To obtain a probe, total balb/c mouse thymus DNA was used as a template for PCR amplification using the following two oligonucleotides:

```
cck76:  5'- caa tag ggg tca tgg acc c   -3' cck77:  5'- tca ttc tgt gca gag ttg gc  -3'
```

The resulting 220 bp amplification product was cloned using the TA Cloning™ Kit (Invitrogen, San Diego, Calif.) and the insert used to screen the mouse phage library. A positively hybridizing 5.8 kb HindIII fragment from one of the resultant phage clones was subcloned into pGP1f. The orientation of the insert of this subclone, pHC3'ENfa, is such that the polylinker XhoI site is adjacent to the 5' end of the insert and the SalI site adjacent to the 3' end. Nucleotide sequence analysis of a portion of this HindII fragment confirmed that it contained the 3' heavy chain enhancer. The insert of pHC3' ENfa includes an XhoI site approximately 1.9 kb upstream of the EcoR1 site at the core of the enhancer sequence. This XhoI site was eliminated by partial digestion, Klenow fill-in, and religation, to create the clone pH3'Efx, which includes unique XhoI and SalI sites, respectively, at the 5' and 3' ends of the insert.

The 3' end of the human γ3/γ1 clone P1-570 was subcloned as follows: P1-570 DNA was digested with NotI, klenow treated, then digested with XhoI; and the 13 kb end fragment isolated and ligated to plasmid vector pGP2b which had been digested with BamHI, klenow treated, and then digested with XhoI. The resulting plasmid, pPX-3, has lost the polylinker NotI site adjacent to the polylinker XhoI site at the 5' end of the insert; however, the XhoI site remains intact, and the insert can be isolated by digestion with NotI and XhoI, or SalI and XhoI. The 3' enhancer containing XhoI/SalI insert of pH3'Efx was isolated and ligated into the 3' SalI site of pPX-3 to create the plasmid pHP-3a. The enhancer containing fragment within the pHP-3a insert is ligated in the opposite orientation as the 3' end of the P1-570 clone. Therefore, pHP-3a contains an internal SalI site, and the insert is isolated by digestion with XhoI and NotI. Because this is an enhancer element, 5' to 3' orientation is generally not critical for function.

HCo7

To prepare the HCo7 DNA mixture for pronuclear microinjection, DNA from each of the five plasmids described above was digested with restriction enzymes and separated on an agarose gel. Clone pH3V4D was cut with NotI; pCOR1xa was cut with NotI; p11-14 was cut with NotI; pP1-570 was cut with NotI and SalI; and pHP-3a was cut with NotI and XhoI. The DNA inserts were electroeluted and further purified on an equilibrium CsCl gradient without EtBr. The inserts were dialyzed into injection buffer and mixed as follows: 50 microliters of pH3V4D insert @ 20.4 ng/microliter; 50 microliters of pCOR1xa insert @ 20.8 ng/microliter; 50 microliters of p11-14 insert @ 15.6 ng/microliter; 300 microliters of pP1-570 insert @ 8.8 ng/microliter; 60 microliters of pHP-3a insert @ 10.8 ng/microliter; and 1.49 ml injection buffer.

HCo7 Transgenic Animals

The HCo7 DNA mixture was microinjected into the pronuclei of one-half day old embryos, and the embryos transferred into the oviducts of pseudopregnant females, as described by Hogan et al. (Manipulating the mouse embryo, Cold Spring Harbor laboratories, Cold Spring Harbor N.Y.).

Tail tip DNA was isolated from 202 animals that developed from microinjected embryos. Southern blot analysis of this DNA, using a probe comprising human μ and DH sequences, revealed 22 founder animals that had incorporated at least a portion of the HCo7 transgene. FIG. 81 shows an analysis of the expression of human μ and human γ1 in the serum of 6 G0 animals that developed from embryos microinjected with HCo7 DNA. Serum levels of human immunoglobulin proteins were measured by ELISA as described in Lonberg et al. (1994) *Nature* 368: 856. Four of these six mice showed evidence of incorporation of the transgene by Southern blot analysis, and three of these mice expressed both human μ and human γ1 proteins in their serum. The single transgenic mouse that did not express human immunoglobulin proteins was determined by Southern blot analysis to contain only a low number of copies of the transgene, and it is possible that the entire transgene was not incorporated, or that this mouse was a genetic mosaic. Two of the founder HCo7 mice, #11952 and #11959, were bred with human κ minilocus (KCo4 line 4436) transgenic mice that were also homozygous for disruptions of the endogenous heavy, and κ light chain loci (Lonberg et al. op.cit), to generate mice that were homozygous for the two endogenous locus disruptions and hemizygous for the two introduced human miniloci, KCo4 and HCo7. Five of these so-called double-transgenic/double-deletion mice were analyzed for expression of human IgM, human IgG1, and human IgG3. As a control, three HC2/KCo4 double-transgenic/double-deletion mice were included in the analysis. This experiment is presented in FIG. 82. The ELISA data in this figure was collected as in Lonberg et al. (op.cit), except that for detection of human IgG3, the coating antibody was a specific mAb directed against human IgG3 (cat. #08041, Pharmingen, La Jolla, Calif.); the other details of the IgG3 assay were identical to those published for IgG1. While the HC2/KCo4 mice express only human IgM and human IgG1, the HCo7/KCo4 mice also express human IgG3 in addition to these two isotypes. Expression of human γ3 and γ1 in the HCo7 mice has also been detected by PCR amplification of cDNA synthesized from RNA isolated from the spleen of a transgenic mouse. FIG. 83 depicts PCR amplification products synthesized using spleen cDNA from three different lines of transgenic mice: line 2550 is an HC2 transgenic line, while lines 11959 and 11952 are HCo7 transgenic lines. Single stranded cDNA was synthesized from spleen RNA as described by Taylor et al. (1992) *Nucleic Acid Res.* 20: 6287. The cDNA was then PCR amplified using the following two oligonucleotides:

```
o-382:  5'- gtc cag aat tcg gt(c,g,t) cag ctg gtg (c,g)ag
            tct gg -3' o-383:  5'- ggt ttc tcg agg aag agg aag act gac ggt cc  -3'
```

This primer pair directs the synthesis of PCR products that spans the hinge region of human γ transcripts. Because of differences in the structures of the human γ1 and γ3 hinge regions, PCR amplification distinguishes between these two transcripts. A human γ1 template will direct the synthesis of a 752 bp PCR product, while human γ3 directs the synthesis of a 893 bp product. While only human γ1 template is detectable in the HC2 line 2550 and HCo7 line 11959 spleens, both γ1 and γ3 transcripts are detectable in the HCo7 line 11952 spleen. Because of the non-quantitative nature of this assay, and because of differences in γ3 expression between individual animals (shown by ELISA in FIG. 82), the inability to observe γ3 in the HCo7 line 11959 spleen in FIG. 83 does not indicate that γ3 is not expressed in this line. Isolated spleen cells from the HCo7/KCo4 mice can also be induced to express both IgG1 and IgG3 in vitro by stimulation with LPS and IL4. This experiment is shown in FIG. 84. Spleen cells from a 7 week old male HCo7/KCo4 double-transgenic/double-deletion mouse (#12496; line 11959/4436) tested for immunoglobulin secretion in response to the thymus-independent B cell mitogen, LPS, alone and in conjunction with various cytokines. Splenocytes were enriched for B cells by cytotoxic elimination of T cells. B-enriched cells were plated in 24 well plates at $2 \times 10^6$ cells per well in 2 ml of 10% FCS in RPMI-1640. LPS was added to all wells at 10 micrograms/ml. IL-2 was added at 50 units/ml, IL-4 was added at 15 ng/ml, IL-6 was added at 15 ng/ml, γIFN was added at 100 units/ml. Cultures were incubated at 37° C., 5% $CO_2$ for 10 days, then supernatants were analyzed for human IgG1 and IgG3 by ELISA. All reagents for ELISA were polyclonal anti-serum from Jackson Immunologicals (West Grove, Pa.), except the capture anti-human IgM, which was a monoclonal antibody from The Binding Site (Birmingham, UK).

The foregoing description of the preferred embodiments of the present invention has been presented for purposes of illustration and description. They are not intended to be exhaustive or to limit the invention to the precise form disclosed, and many modifications and variations are possible in light of the above teaching. It will be apparent that certain changes and modifications may be practiced within the scope of the claims.

All publications and patent applications herein are incorporated by reference to the same extent as if each individual publication or patent application was specifically and individually indicated to be incorporated by reference. Commonly assigned applications U.S. Ser. No. 08/209,741 filed 9 Mar. 1994, U.S. Ser. No. 08/165,699 filed 10 Dec. 1993 and U.S. Ser. No. 08/161,739 filed 03 Dec. 1993, which is a continuation-in-part of U.S. Ser. No. 08/155,301 filed 18 Nov. 1993, WO92/03918, U.S. Ser. No. 07/810,279 filed 17 Dec. 1991, U.S. Ser. No. 07/853,408 filed 18 Mar. 1992, U.S. Ser. No. 07/904,068 filed 23 Jun. 1992, U.S. Ser. No. 07/990,860 filed 16 Dec. 1992, WO93/12227, and U.S. Ser. No. 08/053,131 filed 26 Apr. 1993 are each incorporated herein by reference.

What is claimed is:

1. A transgenic mouse containing in its genome a transgene comprising in operable linkage a plurality of human V genes, a plurality of human D genes, a plurality of human J genes, a human μ $C_H$ gene, at least two different non-μ human $C_H$ genes and associated isotype switching sequences, wherein human μ and human γ switch sequences are located in closer proximity to each other than in the naturally occurring human immunoglobulin locus; and wherein in lymphocytes of said mouse the transgene undergoes productive VDJ rearrangement and μ to γ isotype switching by recombination between the human μ and human γ switch sequences such that the mouse produces a serum containing immunoglobulins of at least three human heavy chain isotypes in response to antigenic stimulation.

2. A transgenic mouse of claim 1, wherein the lymphocytes further have integrated a human light chain transgene.

3. A transgenic mouse of claim 2, wherein the serum comprises a population of IgG comprising a subpopulation of IgG composed of human γ1 and human κ and a subpopulation of IgG composed of human γ3 and human κ.

4. The transgenic mouse of claim 1, wherein the human γ switch sequences is contained within an approximately 5.3 kb HindIII fragment.

5. The transgenic mouse of claim 1, wherein the human γ switch sequences is contained within an approximately 4 kb HindIII fragment.

* * * * *